US008547536B2

(12) United States Patent
D'Ascenzi et al.

(10) Patent No.: US 8,547,536 B2
(45) Date of Patent: Oct. 1, 2013

(54) ANALYSIS OF MIXTURES INCLUDING PROTEINS

(75) Inventors: Sandro D'Ascenzi, Siena (IT); Giuseppe De Conciliis, Colle di Val D'Elsa (IT); Claudia Magagnoli, Monteriggioni (IT); Giovanni Luigi Mattioli, Castelnuovo Berardenga (IT)

(73) Assignee: Novartis AG, Basel (CH)

( * ) Notice: Subject to any disclaimer, the term of this patent is extended or adjusted under 35 U.S.C. 154(b) by 431 days.

(21) Appl. No.: 12/746,830

(22) PCT Filed: Dec. 9, 2008

(86) PCT No.: PCT/IB2008/003678
§ 371 (c)(1),
(2), (4) Date: Jun. 8, 2010

(87) PCT Pub. No.: WO2009/074867
PCT Pub. Date: Jun. 18, 2009

(65) Prior Publication Data
US 2010/0253934 A1    Oct. 7, 2010

(30) Foreign Application Priority Data

Dec. 10, 2007 (GB) .................................. 0724103.7
Jul. 21, 2008 (GB) .................................. 0813345.6

(51) Int. Cl.
*G01N 21/00* (2006.01)
(52) U.S. Cl.
USPC .............. 356/51; 356/326; 356/432; 436/164
(58) Field of Classification Search
USPC ..................... 356/51, 326, 432; 436/164, 86, 436/95
See application file for complete search history.

(56) References Cited

U.S. PATENT DOCUMENTS

| 4,921,841 | A | 5/1990 | Obrig |
| 6,342,259 | B1 | 1/2002 | Wesley |
| 6,611,777 | B2 * | 8/2003 | Samsoondar ................ 702/104 |
| 7,303,922 | B2 * | 12/2007 | Jeng et al. .................... 436/164 |
| 7,570,357 | B2 * | 8/2009 | Tsenkova ...................... 356/326 |
| 7,623,234 | B2 * | 11/2009 | Puzey ............................ 356/326 |

OTHER PUBLICATIONS

Anthony J. Owen, Uses of Derivative Spectroscopy, 1995, Agilent Technology.*
Torres, J. et al. "Spectroscopic studies of bacteriorhodopsin fragments dissolved in organic solution," Biophysical Journal USA, vol. 68, No. 5, 1995, pp. 2049-2055.
Sabes, M. et al. "Spectrophotometric studies on the tryptophan residues of bacteriorhodopsin during the photocycle," Photobiochemistry and Photobiophysics Netherlands, vol. 8, No. 2, 1984, pp. 97-101.

* cited by examiner

*Primary Examiner* — Layla Lauchman
(74) *Attorney, Agent, or Firm* — Helen Lee; Otis Littlefield

(57) ABSTRACT

The quality control of vaccines is an important step in the release of vaccines to patients. Problems when dealing with vaccines include stability, batch-to-batch consistency and contamination. The invention provides a method of analyzing the composition of a protein-containing sample by electromagnetic spectroscopy, and derivatizing the obtained spectrum to obtain a derivative spectrum of the sample. The derivative spectrum may optionally be compared to a reference spectrum, to assess stability, contamination etc. relative to the reference. The derivative analysis technique allows the separation and discrimination between the spectral contributions of different components, thereby allowing differences in the spectra to be assigned to particular groups of the protein, or particular contaminants etc.

15 Claims, 142 Drawing Sheets

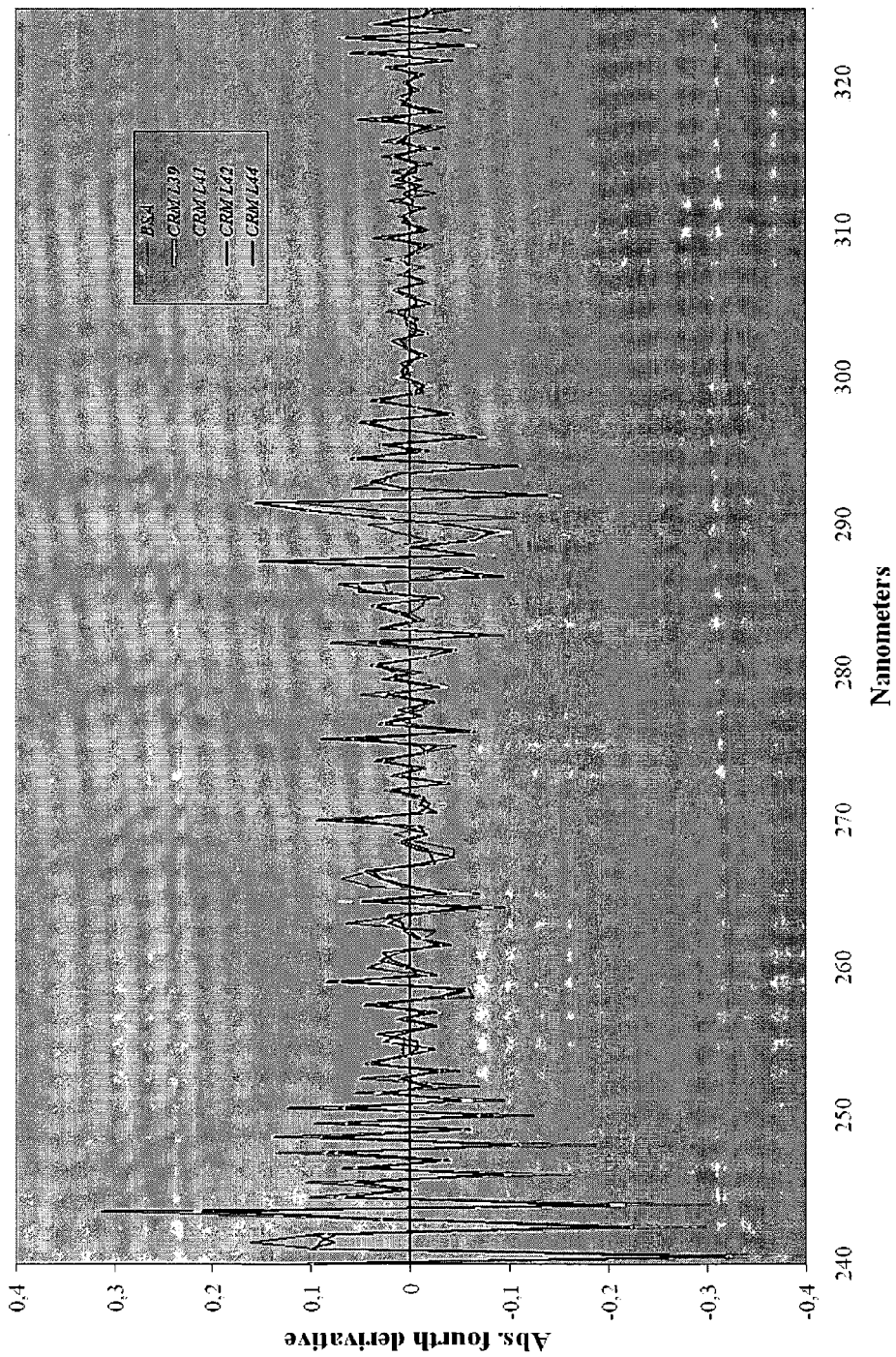

Figure 30
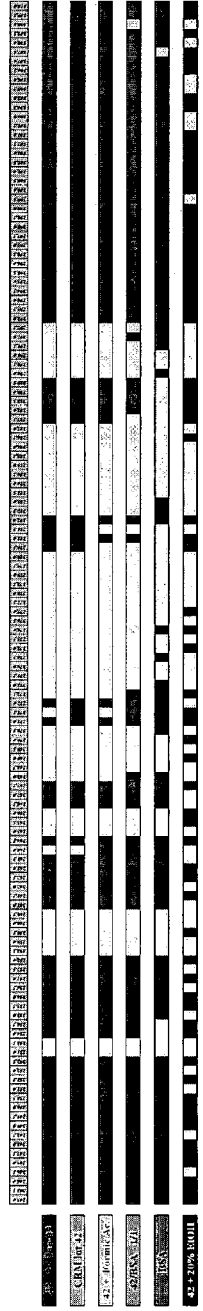
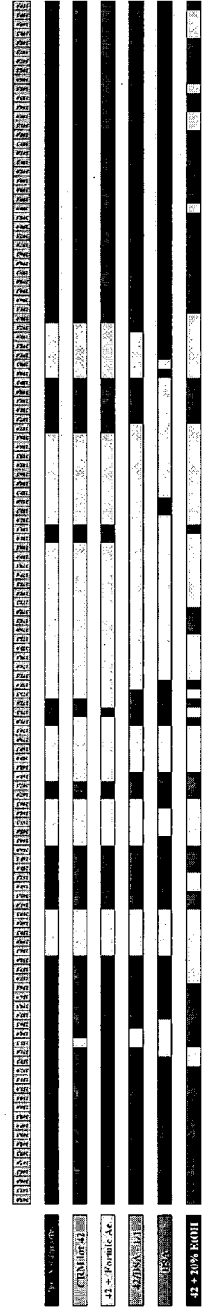
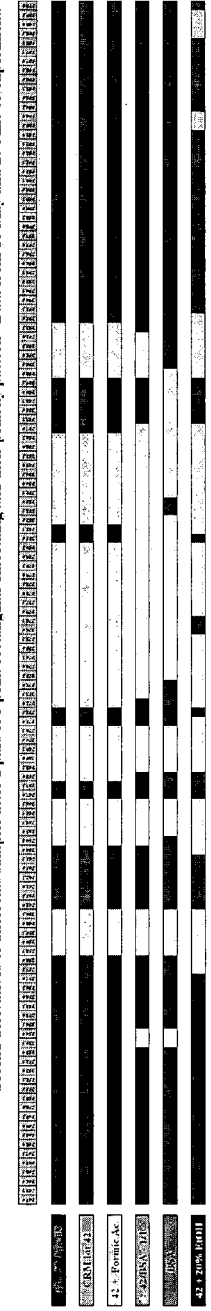
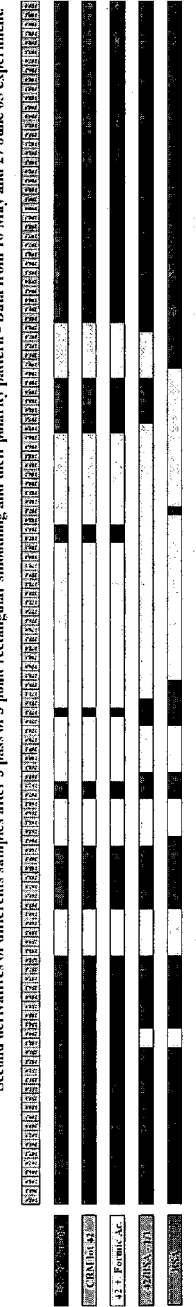

Figure 34

```
          1          11          21          31          41          51
  1  MASPDVKSAD  TLSKPAAPVV  SEKETEAKED  APQAGSQGQG  APSAQGGQDM  AAVSEENTGN   60
 61  GGAAATDKPK  NEDEGAQNDM  PQNAADTDSL  TPNHTPASNM  PAGNMENQAP  DAGESEQPAN  120
121  QPDMANTADG  MQGDDPSAGG  ENAGNTAAQG  TNQAENNQTA  GSQNPASSTN  PSATNSGGDF  180
181  GRTNVGNSVV  IDGPSQNITL  THCKGDSCSG  NNFLDEEVQL  KSEFEKLSDA  DKISNYKKDG  240
241  KNDGKNDKFV  GLVADSVQMK  GINQYIIFYK  PKPTSFARFR  RSARSRRSLP  AEMPLIPVNQ  300
301  ADTLIVDGEA  VSLTGHSGNI  FAPEGNYRYL  TYGAEKLPGG  SYALRVQGEP  SKGEMLAGTA  360
361  VYNGEVLHFH  TENGRPSPSR  GRFAAKVDFG  SKSVDGIIDS  GDGLHMGTQK  EKAAIDGNGF  420
421  KGTWTENGGG  DVSGKFYGPA  GEEVAGKYSY  RPTDAEKGGF  GVFAGKKEQD  GGSGGGATYK  480
481  VDEYHANARF  AIDHFNTSTN  VGGFYGLTGS  VEFDQAKRDG  KIDITIPVAN  LQSGSQHFTD  540
541  HLKSADIFDA  AQYPDIRFVS  TKFNFNGKKL  VSVDGNLTMH  GKTAPVKLKA  EKFNCYQSPM  600
601  AKTEVCGGDF  STTIDRTKWG  VDYLVNVGMT  KSVRIDIQIE  AAKQ
```

*Figure 52*

```
      1           11          21          31          41          51
      |           |           |           |           |           |
  1   MVSAVIGSAA  VGAKSAVDRR  TTGAQTDDNV  MALRIETTAR  SYLRQNNQTK  GYTPQISVVG    60
 61   YNRHLLLLGQ  VATEGEKQFV  GQIARSEQAA  EGVYNYITVA  SLPRTAGDIA  GDTWNTSKVR   120
121   ATLLGISPAT  QARVKIVTYG  NVTYVMGILT  PEEQAQITQK  VSTTVGVQKV  ITLYQNYVQR   180
181   GSGGGGVAAD  IGAGLADALT  APLDHKDKGL  QSLTLDQSVR  KNEKLKLAAQ  GAEKTYGNGD   240
241   SLNTGKLKND  KVSRFDFIRQ  IEVDGQLITL  ESGEFQVYKQ  SHSALTAFQT  EQIQDSEHSG   300
301   KMVAKRQFRI  GDIAGEHTSF  DKLPEGGRAT  YRGTAFGSDD  AGGKLTYTID  FAAKQGNGKI   360
361   EHLKSPELNV  DLAAADIKPD  GKRHAVISGS  VLYNQAEKGS  YSLGIFGGKA  QEVAGSAEVK   420
421   TVNGIRHIGL  AAKQ
```

```
              1          11         21         31         41         51
              |          |          |          |          |          |
  1    ATNDDDVKKA ATVAIAAAYN NGQEINGFKA GETIYDIDED GTITKKDATA ADVEADDFKG
 61    LGLKKVVTNL TKTVNENKQN VDAKVKAAES EIEKLTTKLA DTDAALADTD AALDATTNAL
121    NKLGENITTF AEETKTNIVK IDEKLEAVAD TVDKHAEAFN DIADSLDETN TKADEAVKTA
181    NEAKQTAEET KQNVDAKVKA AETAAGKAEA AAGTANTAAD KAEAVAAKVT DIKADIATNK
241    DNIAKKANSA DVYTREESDS KFVRIDGLNA TTEKLDTRLA SAEKSIADHD TRLNGLDKTV
301    SDLRKETRQG LAEQAALSGL FQPYNVG
```

B

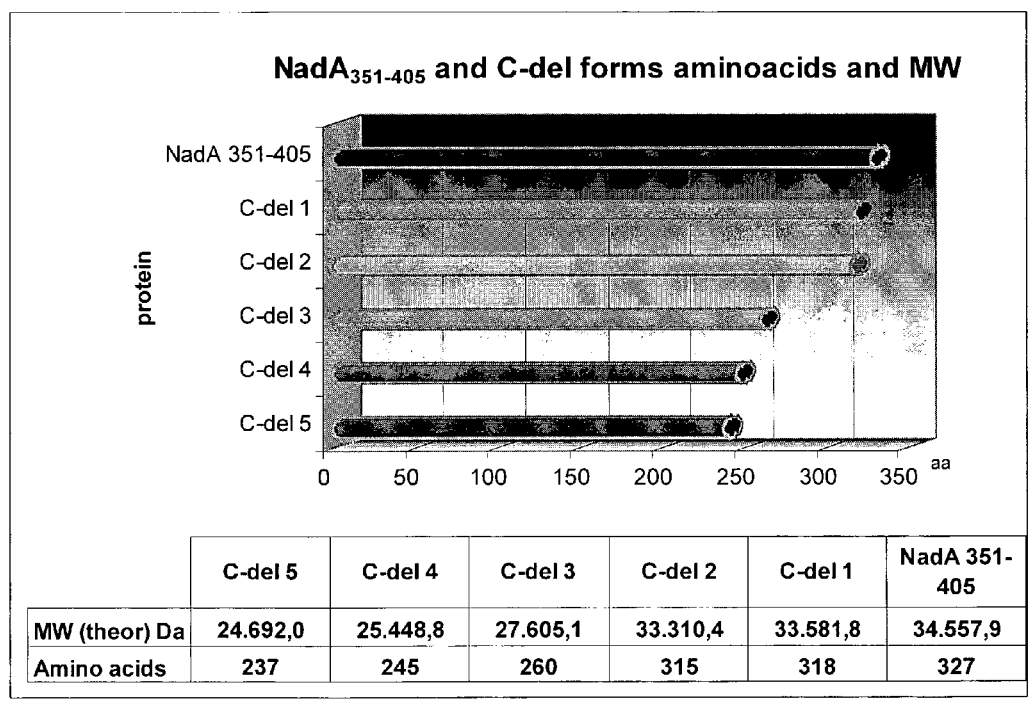

| | C-del 5 | C-del 4 | C-del 3 | C-del 2 | C-del 1 | NadA 351-405 |
|---|---|---|---|---|---|---|
| MW (theor) Da | 24.692,0 | 25.448,8 | 27.605,1 | 33.310,4 | 33.581,8 | 34.557,9 |
| Amino acids | 237 | 245 | 260 | 315 | 318 | 327 |

Figure 86
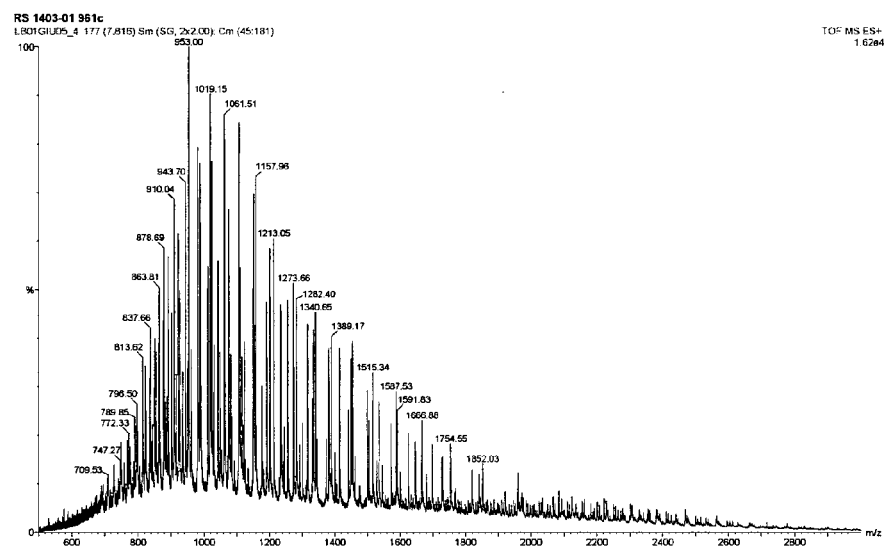
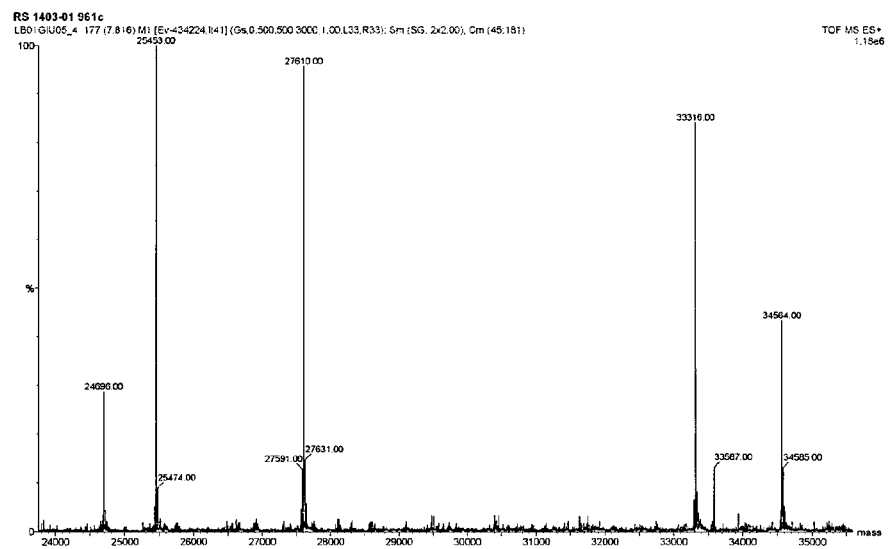

Figure 87
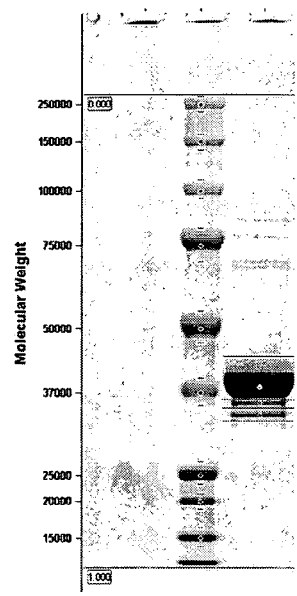
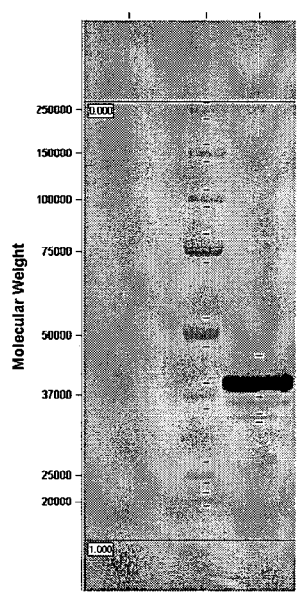
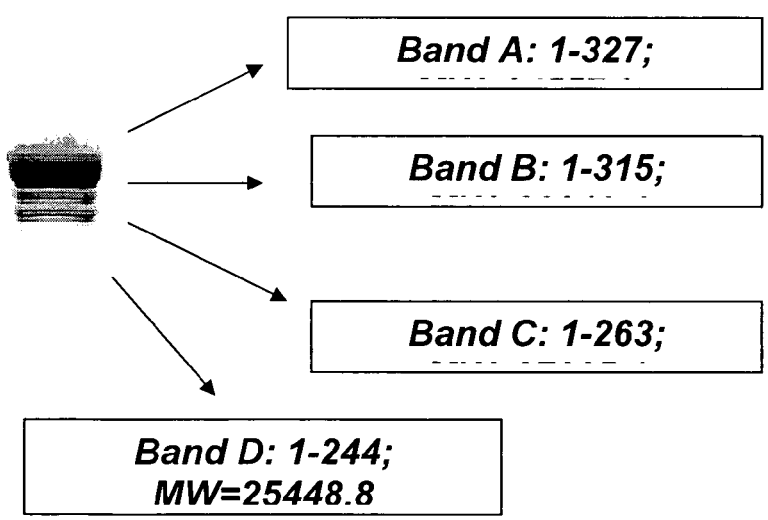

*Figure 92*
A
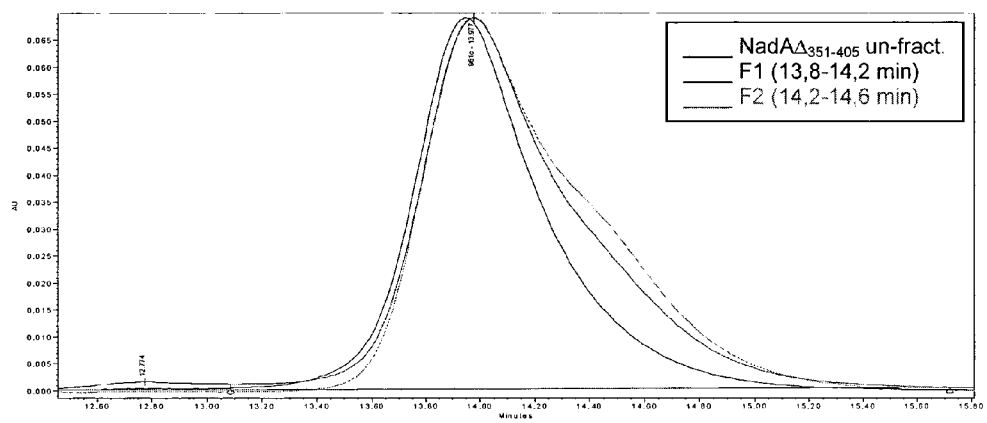
B
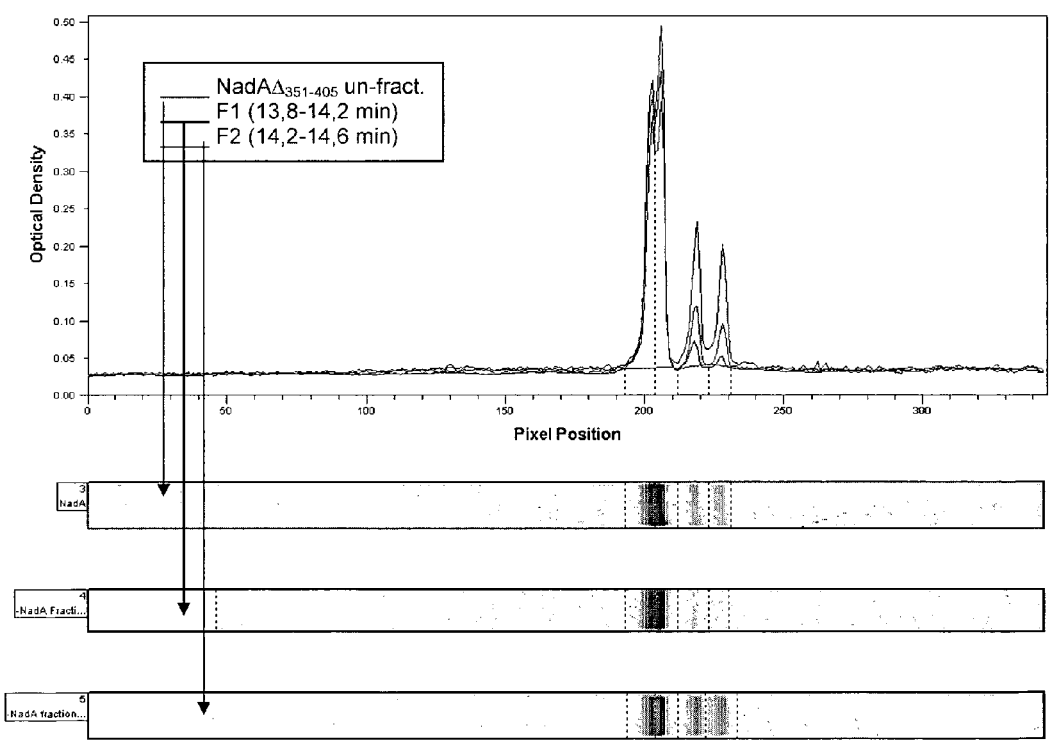

A

B

| Sample | Mw (KDa) | Mw/Mn | Rh avg. (nm) |
|---|---|---|---|
| trimer (1) | 91,840 | 1.007 | 7,0 |
| trimer (2) | 95,640 | 1.006 | 7,5 |
| monomer | 33,720 | 1.001 | 5.2 |
| C-del monomer | 26,750 | 1.008 | 5.1 |
| BSA | 68,470 | 1.005 | 3.9 |

*Figure 96*
A
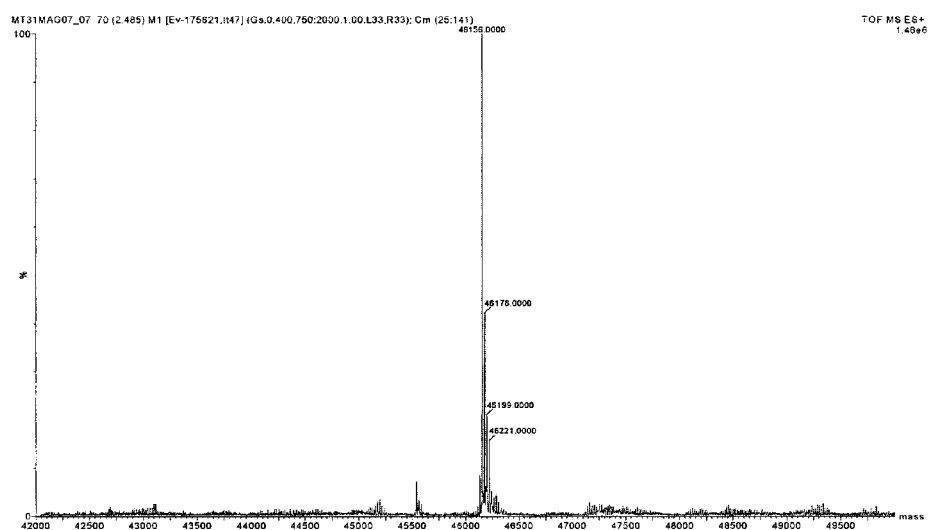
B
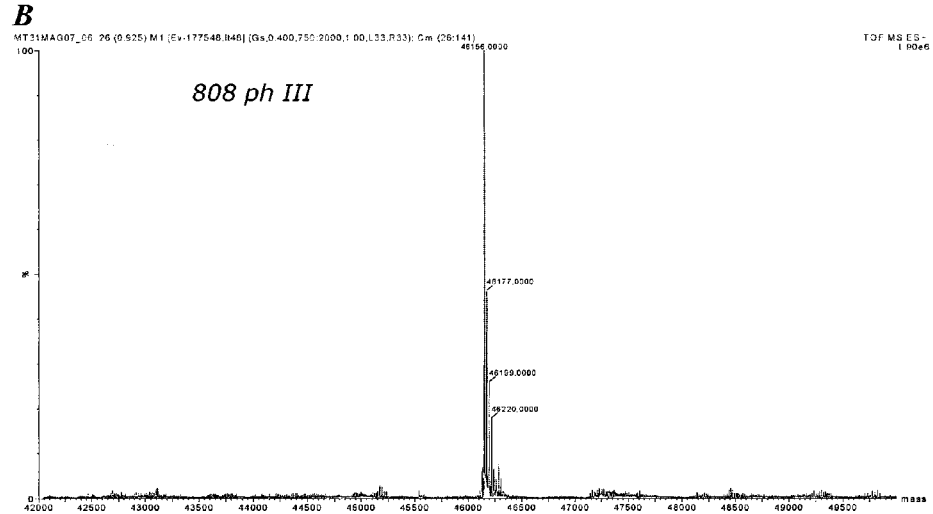
808 ph III

*Figure 96 cont.*
A
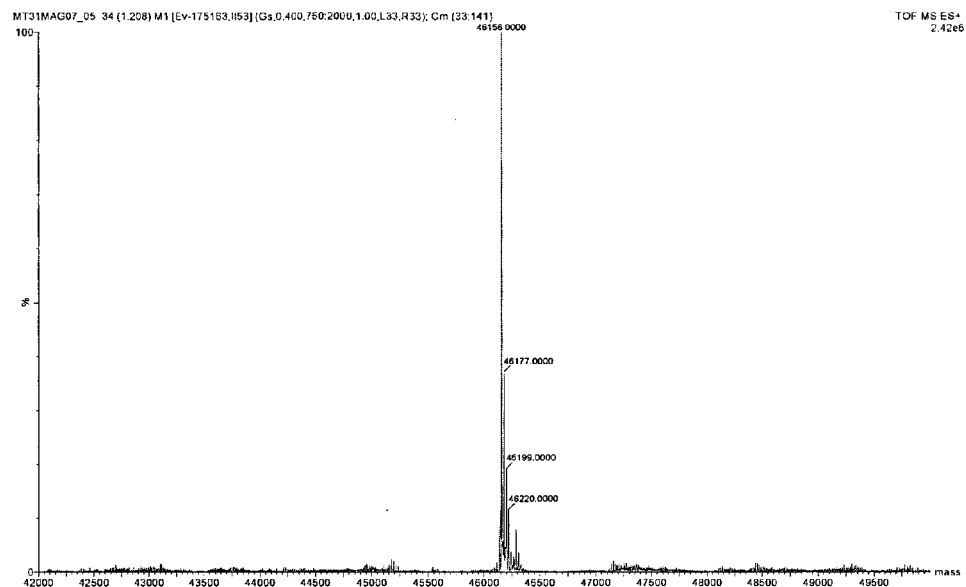
B
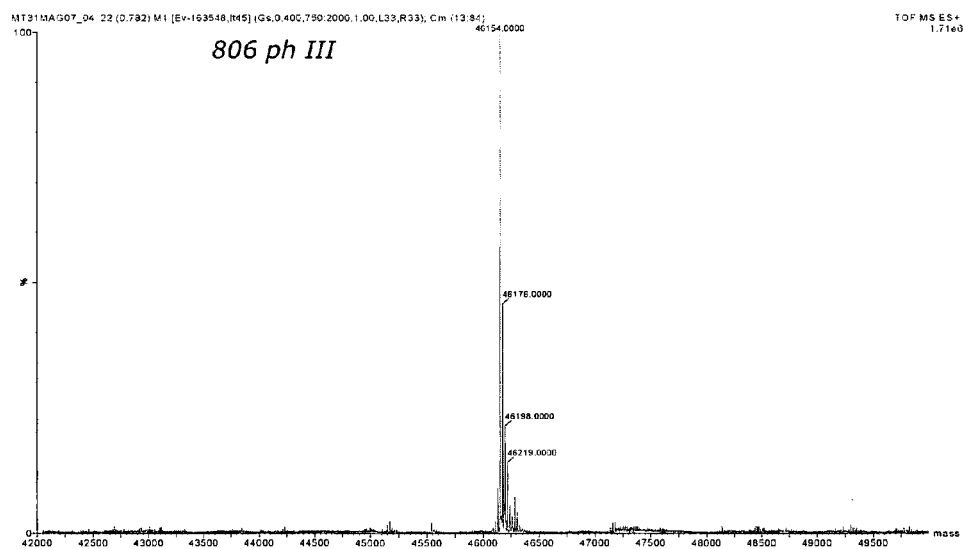

| lot | Crossover nm | max/min [mdeg] | |
|---|---|---|---|
| | | 189*/190 nm | 208 nm |
| ph II | 198,7 | 17,44 | -9,73 |
| ph III 806 | 198,7 | 15,07 | -9,13 |
| ph III 807 | 198,7 | 16,92* | -10,49 |
| ph III 808 | 198,8 | 14,95 | -9,45 |

A

B

| | | D1 0 crossing (nm) | |
|---|---|---|---|
| | | 280 nm exc | 295 nm exc |
| Sample description | lot | average 3 det. | average 3 det. |
| 936-741 Novartis phase II | RS15-03-01 | 341,06 | 343,81 |
| 936-741 PB Sandoz phase III | CON 806 | 341,01 | 344,22 |
| | CON 807 | 341,33 | 343,86 |
| | CON 808 | 340,18 | 343,94 |
| | average all lots | 340,90 | 343,96 |
| | std.dev. | 0,50 | 0,18 |
| | RSD% | 0,15 | 0,05 |

| | Lot | % Area 936-741 |
|---|---|---|
| 1 | RS15-03-01 (phase II) | 94,80 |
| 2 | Sandoz 806 | 97,80 |
| 3 | Sandoz 807 | 96,86 |
| 4 | Sandoz 808 | 97,91 |

| | Lane % | Lane % average |
|---|---|---|
| Lane 3 std RS 15-03-01 | 9 0 , 4 1 | 9 0 , 4 |
| Lane 4 PB 806 | 9 4 , 4 7 | 9 4 , 5 |
| Lane 5 PB 806 | 9 4 , 5 3 | |
| Lane 6 PB 807 | 9 3 , 9 6 | 9 3 , 9 |
| Lane 7 PB 807 | 9 3 , 7 8 | |
| Lane 8 PB 808 | 9 4 , 8 3 | 9 4 , 8 |
| Lane 9 PB 808 | 9 4 , 8 6 | |

ANALYSIS OF MIXTURES INCLUDING PROTEINS

All documents cited herein are incorporated by reference in their entirety.

RELATED APPLICATIONS

This application is the U.S. National Phase of International Application No. PCT/IB2008/003678, filed Dec. 9, 2008 and published in English, which claims priority to Great Britain Application No. 0724103.7, filed Dec. 10, 2007 and Great Britain Application No. 0813345.6, filed Jul. 21, 2008. The teachings of the above applications are incorporated herein in their entirety by reference.

TECHNICAL FIELD

This invention concerns the analysis and quality control of mixtures including proteins, e.g. vaccines. In particular, the invention concerns the analysis and quality control of glycoconjugate vaccines and other protein antigen-containing vaccines.

BACKGROUND ART

Immunogens comprising capsular saccharide antigens conjugated to carrier proteins are well known in the art. Conjugation converts T-independent antigens into T-dependent antigens, thereby enhancing memory responses and allowing protective immunity to develop, and the prototype conjugate vaccine was for *Haemophilus influenzae* type b (Hib) [e.g. see chapter 14 of ref. 1]. Since the Hib vaccine, conjugated saccharide vaccines for protecting against *Neisseria meningitidis* (meningococcus) and against *Streptococcus pneumoniae* (pneumococcus) have been developed. Other organisms where conjugate vaccines are of interest are *Streptococcus agalactiae* (group B streptococcus) [2], *Pseudomonas aeruginosa* [3] and *Staphylococcus aureus* [4].

Conjugate vaccines for *N. meningitidis* serogroup C have been approved for human use, and include Menjugate™ [5], Meningitec™ and NeisVac-C™. Mixtures of conjugates from each of serogroups A, C, W135 and Y have been reported [e.g. refs. 6-9], including the Menactra™ product. Other mixtures of conjugated antigens include: (i) meningococcal A/C mixtures [10, 11]; (ii) the PrevNar™ product [12] containing seven pneumococcal conjugates; (iii) mixed meningococcal and Hib conjugates [13, 14]; and (iv) combined meningococcal, pneumococcal and Hib conjugates [15].

Problems when dealing with conjugate vaccines include stability, batch-to-batch consistency and contamination. In Hib vaccines, for instance, catalytic depolymerisation of the saccharide has been reported [16], and conjugates of the serogroup A meningococcus capsule are readily hydrolyzed [17]. Instability of conjugates undesirably leads to a reduction in effective dose of immunogenic conjugate over time, variation between batches, and increased levels of uncharacterized breakdown products. References 18 & 19 discuss issues concerning stability testing of Hib conjugate vaccines.

Furthermore, quality control of glycoconjugate vaccines typically requires monitoring of impurities in the vaccine and monitoring of the protein integrity (i.e. denaturation).

In addition to glycoconjugate vaccines, other protein antigen-containing vaccines are also known, e.g. serogroup meningococcus B, hepatitis B virus, diphtheria, tetanus, and acellular pertussis vaccines.

Consequently, vaccines are frequently monitored after manufacture, during storage, and/or prior to administration to ensure their suitability for administration to a patient.

It is an object of the invention to provide modifications and improvements in the quality control of vaccines for assessing their stability, integrity and/or contamination.

DISCLOSURE OF THE INVENTION

UV absorption spectroscopy and fluorescence spectroscopy are known techniques for analyzing protein structure [20]. Proteins contain several chromophores that absorb light in the UV region, most importantly the aromatic rings of Phe, Tyr and Trp. These techniques are particularly useful for probing protein structure because they are sensitive not only to the presence of each chromophore, but also their nearby environment, e.g. local secondary and tertiary protein structure. The techniques have been used for quantifying UV absorbent groups in proteins, and determining the exposure of specific amino acids in proteins to various solvents [20].

The inventors have discovered that information hidden in conventional (underivatized) UV absorption spectra and fluorescence spectra of proteins allows the analysis of small changes in the compositions of protein-containing mixtures (e.g. vaccines). The inventors employ a derivative analysis of the underivatized spectra which reveals secondary and tertiary structure of the protein analyte, and allows the separation and discrimination between the spectral contributions of different components (e.g. different amino acids). Because contamination of the mixture and denaturation/hydrolysis of the protein etc. have an impact on the secondary and tertiary structure of the protein (and therefore the spectral contributions of different amino acids), following changes in the spectra by this technique allows analysis of the stability and integrity of the protein and impurities in the protein-containing mixtures, e.g. vaccines. The inventors have found that this technique is reliable and repeatable, and provides results which cannot be obtained by classical spectral analysis (i.e. by comparison of underivatized spectra). The results can also be easily represented as a "finger-print" representation of the composition of the sample.

Accordingly, there is provided a method of analyzing the composition of a test sample including a protein comprising the steps of (i): analyzing the sample by electromagnetic spectroscopy to obtain a spectrum of response intensity versus wavelength and (ii) derivatising the spectrum with respect to wavelength to obtain a derivative spectrum of the test sample.

Typically, the invention further comprises the step of (iii) comparing the derivative spectrum of the test sample with a derivative spectrum of a reference sample. The comparison step thereby allows analysis of any difference in the composition of the test sample compared with the composition of the reference sample.

Many types of electromagnetic spectroscopy are known, such as absorption spectroscopy (e.g. UV/vis spectroscopy, infra-red (vibrational) spectroscopy), fluorescence spectroscopy (e.g. X-ray fluorescence spectroscopy, UV fluorescence spectroscopy), NMR etc. Each type of spectroscopy provides a spectrum of a characteristic response at given wavelengths. For example, the response of UV absorption spectroscopy is absorption intensity, and therefore the spectrum provided is of absorption intensity versus wavelength. The response of UV fluorescence spectroscopy is emission intensity, and therefore the spectrum provided is of emission intensity versus wavelength.

Preferably, the electromagnetic spectroscopy is UV spectroscopy, preferably UV absorption spectroscopy or UV fluorescence spectroscopy.

Accordingly, in one embodiment of the invention, there is provided a method of analyzing the composition of a test sample including a protein comprising the steps of (i): analyzing the test sample by UV absorption spectroscopy to obtain a spectrum of absorption intensity versus wavelength; (ii) derivatising the spectrum with respect to wavelength to obtain a derivative spectrum of the test sample; and (iii) comparing the derivative spectrum of the test sample with a derivative spectrum of a reference sample.

Further in another embodiment of the invention, there is provided a method of analyzing the composition of a test sample including a protein comprising the steps of (i): analyzing the sample by fluorescence spectroscopy to obtain a spectrum of emission intensity versus wavelength; (ii) derivatising the spectrum with respect to wavelength to obtain a derivative spectrum of the test sample; and (iii) comparing the derivative spectrum of the test sample with a derivative spectrum of a reference sample.

Comparison & Analysis

The underivatized UV spectrum is an additive product of all the exposed groups of a protein: each UV absorbent group and its nearby environment (local secondary and tertiary structure) gives its contribution to the overall absorbance spectrum of the protein. Similarly, the underivatized fluorescence spectrum is an additive product of all the contributions UV fluorescing groups and their nearby local environments. Accordingly, these spectral techniques may in principle be used to explore not only the proteins themselves, but also the environment in which the protein is found (e.g. the presence of solvents, impurities, and other components in the sample). However, the spectral contributions frequently overlap in the underivatized spectra, causing difficulties in assigning changes to a particular group of the protein or its environment.

The derivative analysis technique of the invention allows the separation and discrimination between the spectral contributions of different components (e.g. different amino acids) of the protein, other components in the test sample, and/or denaturation/hydrolysis of the protein. The invention may be used to follow changes in the composition of a test sample over time by monitoring changes in the derivatized spectra. The derivative analysis allows changes in the spectra to be assigned to changes in the particular groups of a protein (e.g. for stability or/and integrity) and/or changes in other particular components in the sample, e.g. contaminants. Alternatively, the invention may be used to compare differences in the composition of a test sample with the composition of known, theoretical or standard (i.e. reference) sample.

Therefore, the invention is particularly useful in monitoring changes in the protein and its environment, or differences between the composition of a sample and another sample, i.e. the invention is particular concerned with comparison. Accordingly, in order to make comparisons, the invention preferably involves the step (iii) of comparing the derivative spectrum of the test sample with a derivative spectrum of a reference sample.

The Derivative Spectrum of the Reference Sample

Preferably, the invention involves comparing the derivative spectrum of the test sample with a derivative spectrum of a reference sample.

In order to compare the differences in the compositions of the test sample and the reference sample, the derivative spectrum of the test sample and the derivative spectrum of the reference sample generally should have been derivatized the same number of times, i.e. both spectra must be of the same order (preferably between first to fourth order, preferably second or fourth order). As an exception, a resolution-enhanced spectrum (as discussed in the section entitled "Resolution enhancement") may be compared directly with the underivatised spectrum.

Moreover, the range of wavelengths of the derivative spectrum of the test sample should at least partially overlap with, and preferably be the same as, the range of wavelengths of the derivative spectrum of the reference sample, in order that the derivative spectra can be compared in wavelengths of overlap.

The derivative spectrum of the reference sample may be obtained before, after, or simultaneously with the derivative spectrum of the test sample. The derivative spectra of the reference sample include, but are limited to, empirically determined spectra or theoretical spectra based on predictions or theoretical calculations. In some embodiments, the derivative spectra are known standards with which the derivative spectrum of the sample may be compared, i.e. the composition of the reference sample is known, or substantially known (e.g. known except for insignificant or minor contaminants etc).

The reference sample is any product with which it is desired to compare the test sample. Typically, the reference sample is a pharmaceutical product. By way of Example, samples may be compared with reference samples in the following ways:

The reference sample is a standard pharmaceutical product of purity known to be suitable for administration to patients. The test sample is compared with the reference sample to determine whether the sample is suitable for administration to patients.

The reference sample is drawn from a pharmaceutical product at time $t_1$ and the test sample is drawn from the pharmaceutical product drawn at a time $t_2$, where $t_2 > t_1$. The test sample is compared with the reference sample to analyse changes in the integrity of the protein and/or changes in contaminants.

The reference sample is a degraded pharmaceutical product. The test sample is compared with the reference sample to determine whether the test sample has degraded to the same extent as the reference sample.

The reference sample is a pharmaceutical product having known impurities. The sample is compared with the reference sample to determine whether the sample contains the same impurities as the reference sample.

Preferably, a database containing n derivative spectra of different reference samples may be compiled, where $n > 2$, preferably $n > 10$. Such a database allows the derivative spectrum of the test sample to be compared simultaneously with the derivative spectra of the many different reference samples. Typically, the step of comparing the derivative spectrum of the test sample with spectra of the database would include determining which spectrum in the database most closely matches the derivative spectrum of the test sample (usually over a particular range of wavelengths).

Comparing Derived Spectra

For UV absorbance spectroscopy, the main characteristics of the underivatized spectrum are the whole characteristic shape, the peak of maximum absorbance ($\lambda_{max}$ abs.), the molar extinction coefficient at $\lambda_{max}$ and the wavelength of minimum absorbance ($\lambda_{min}$). For fluorescence spectroscopy, the main characteristics of the underivatized spectrum and the whole characteristic shape and the peak of maximum emission ($\lambda_{max}$ em.).

Local absorbance peaks and valleys (or troughs), as well as curve inflection, are important, but because they typically overlap despite high resolution scans, characterization is only possible after derivatization (usually between first to fourth order (see "Derivative technique" below). Using the derivatization technique, it is possible to enhance the resoluteness power of the original spectra to better determinate the edges of peaks and troughs, and to separate and discriminate between the spectral contributions of different components.

Accordingly, the derivative spectra of the test sample and the derivative spectra of the reference sample can be compared in a number of ways. For example, specific features of the derivative spectra may be compared, e.g. analyzing changes in the position (i.e. wavelength) of a particular peak (e.g. maximum absorbance in UV absorbance spectroscopy of maximum emission in fluorescence spectroscopy), valley, or curve inflection. Alternatively, the shape of the spectra may be compared over a range of wavelengths, e.g. the preferred wavelength ranges used in analysis as described in "Electromagnetic spectroscopy" below.

Additionally, the derivative spectra may be processed to represent the data contained in the derivative spectra in different ways.

For example, a preferred use of the second derivative is for studying of the convexity pattern of the underivatized spectrum, which may advantageously be used for sample fingerprinting. A curve is defined convex in an interval if all of the points lie below any of its tangents in that part and the second derivative will be negative in the same interval. On the other hand, a curve is defined concave if all the points lie above any of its tangents in that interval, and the second derivative will be positive in the same interval. In practice, the convexity of a spectra is generally analysed over about 0.5 nm intervals. Therefore, in one preferred embodiment, the convexity pattern of the underivatized spectrum may be represented by the polarity of the second derivative against wavelength for form a "polarity spectra". The polarity spectra of the test sample may be compared with the polarity spectra of the reference sample at a specific wavelength, or over a range of wavelengths.

The derivative spectra (particularly the second derivative spectra) may also be combined with the underivatised spectra to provide a resolution-enhanced spectra. Techniques for achieving this are discussed below in the section entitled "Resolution enhancement"

Electromagnetic Spectroscopy

UV Absorption Spectroscopy

In one embodiment, the electromagnetic spectroscopy is UV absorption spectroscopy.

UV protein absorbance is due mainly to the presence of Cysteine and to the aromatic side chains of Tryptophan, Tyrosine and Phenylalanine, as can be seen in FIG. 1. $CRM_{197}$ amino acidic composition, for example, includes several UV absorbent residues, namely 5 Trp, 18 Tyr, 18 Phe, 16 His and 4 Cys residues.

Histidine also absorbs UV, but generally absorbance from the aromatic side chains of Trp, Tyr, and Phe, and Cys residues is more useful because the $\lambda_{max}$ of His lies at about 211 nm, in the far UV range (190 to 240 nm), where substantial absorbance occurs due to other aromatic rings, some buffers and others stabilizing agents. If necessary, the spectral contribution of His can be determined on a more dilute sample in a separate scan.

Consequently, spectral analysis of at least part of the near-UV region (about 240 to about 340 nm) is preferred, and preferably at least part of the region of 240 to 325 nm (245 to 310 nm, preferably 250 to 310 nm, for convexity studies). It is particularly preferred, however, for the analysis to include about 274 nm or 280 nm (preferably both), which correspond to the peaks for Tyrosine and Tryptophan, respectively. However, spectral analysis of the entire near-UV region is particularly preferred for the initial recognition of a molecule (i.e. using the whole spectrum between 240 to 325 nm (preferably about 240 to about 340 nm) as a signature of all the groups). For convexity studies, it is preferred to analyse the whole of the range from 245 to 310 nm, preferably 250 to 310 nm.

Preferably, prior to analysis, the autozero of the UV spectrometer is conducted against air (no cuvette). Analysis is preferably conducted with the cuvette sample in the main beam holder and nothing on the secondary beam, and preferably with a Peltier option enabled. Scan rates are typically around 7.5 nm/min.

Preferably, each sample or blank mean spectra should be the point to point average of at least 3 scans, and each net spectra should preferably be the point to point difference between mean sample spectra and its mean blank spectra.

Fluorescence Spectroscopy

In another embodiment, the electromagnetic spectroscopy is fluorescence spectroscopy.

Fluorescence spectroscopy is a useful probe of secondary structure and structural changes because chromophores display shifted spectra upon increasing or decreasing polarity of their environment, and changes in wavelength of maximum emission ($\lambda_{max}$ em.).

Protein fluorescence is mainly due to the presence of aromatic amino acids, principally Trp and Tyr and, to a lesser extent, Phe. Excitation at a wavelength of 280 nm provides emission due to both Trp and Tyr residues, while excitation at a wavelength of 295 nm allows the preferential emission by Trp residues alone. The emission maximum of Trp is highly sensitive to its structural position and to environmental conditions, and therefore it is a valuable reporter group of protein conformational state. For a valid comparison, the test sample and the reference sample should be excited at the same wavelength (preferably 280 nm or 295 nm).

Preferably, the emission spectrum is analysed in at least part (and optionally all) of the region of 300 to 390 nm. However, it is particularly preferred to include the wavelength of maximum emission ($\lambda_{max}$ em.) of the sample.

The Sample

The invention is useful for analyzing any sample containing a protein analyte. However, when the invention further comprises the step of (iii) comparing the derivative spectrum of the test sample with a derivative spectrum of a reference sample, it is not essential to the invention that the sample contains protein, as the invention may be usefully employed to determine the presence or absence of protein relative to the reference sample. Nevertheless, it is preferred that the sample is suspected to contain (and preferably contains) a protein analyte.

As well as containing a protein, samples to be analysed can include other materials. The sample will generally be in aqueous solution.

The sample may be drawn from a pharmaceutical product to be tested prior to release (e.g. during manufacture or quality control testing), or from a pharmaceutical product to be tested after release (e.g. to assess stability, shelf-life, etc.).

In the methods of analysis of the invention, the sample is typically drawn from, but is not limited to, a protein-containing mixture to be analysed, such as a packaged pharmaceutical product (e.g. a packaged vaccine), a bulk pharmaceutical product prior to packaging (e.g. bulk vaccine) or intermediates in the pharmaceutical product's manufacture. However, the sample may be drawn from any source of protein, e.g. blood etc. The sample may be analysed immediately after being drawn from the source, or the sample may be stored and/or pre-treated before analysis.

The invention is particularly useful for analysing proteins used in vaccines and particularly protein antigens.

For example, glycoconjugate vaccines, which may be single or combined (e.g. a combined glycoconjugate vaccine comprising more than one type of glycoconjugate immunogen), contain protein glycoconjugates and these vaccines may advantageously be analysed by the invention.

Other protein-containing vaccines are also known, such as serogroup meningococcus B, hepatitis B virus, diphtheria, tetanus, and acellular pertussis vaccines.

Glycoconjugates

Typically, glycoconjugates for use in vaccines comprise capsular saccharide antigens covalently linked to carrier proteins. Covalent conjugation is used to enhance immunogenicity of saccharides by converting them from T-independent antigens to T-dependent antigens, thus allowing priming for immunological memory. Conjugation is particularly useful for paediatric vaccines and is a well known technique [e.g. reviewed in refs. 21 to 30]. Saccharides may be linked to the protein carrier directly [31, 32], but a linker or spacer is generally used e.g. adipic acid, β-propionamido [33], nitrophenyl-ethylamine [34], haloacyl halides [35], glycosidic linkages [36], 6-aminocaproic acid [37], ADH [38], $C_4$ to $C_{12}$ moieties [39], etc.

1 Carrier Proteins in Conjugates

Typical carrier proteins in conjugates are bacterial toxins or toxoids, such as diphtheria toxoid or tetanus toxoid. The $CRM_{197}$ diphtheria toxin derivative [40-42] is the carrier protein in Menjugate™, Prevnar™ and Meningitec™, whereas tetanus toxoid is used in NeisVac™. Diphtheria toxoid is used as the carrier in Menactra™. Other known carrier proteins include the *N. meningitidis* outer membrane protein [43], synthetic peptides [44, 45], heat shock proteins [46, 47], pertussis proteins [48, 49], cytokines [50], lymphokines [50], hormones [50], growth factors [50], artificial proteins comprising multiple human $CD4^+$ T cell epitopes from various pathogen-derived antigens [51] (e.g. N19 [52]), protein D from *H. influenzae* [53, 54], pneumococcal surface protein PspA [55], iron-uptake proteins [56], toxin A or B from *C. difficile* [57], etc. Compositions may use more than one carrier protein e.g. to reduce the risk of carrier suppression, and a single carrier protein might carry more than one saccharide antigen [58]. Conjugates generally have a saccharide:protein ratio (w/w) of between 1:5 (i.e. excess protein) and 5:1 (i.e. excess saccharide).

2 Saccharides in Conjugates

The conjugate saccharides may be polysaccharides (e.g. with a degree of polymerisation of >10, e.g. 20, 30, 40, 50, 60 or more) or oligosaccharides (e.g. with a degree of polymerisation of from about 4 to about 10). Oligosaccharides may be the result of depolymerisation and/or hydrolysis of a parent polysaccharide e.g. the analyte may be a saccharide-containing fragment of a larger saccharide. Preferred conjugate saccharides are capsular saccharides.

Even more preferred conjugate saccharides are bacterial capsular saccharides e.g. from *Neisseria meningitidis* (serogroups A, B, C, W135 or Y), *Streptococcus pneumoniae* (serotypes 4, 6B, 9V, 14, 18C, 19F, or 23F), *Streptococcus agalactiae* (types Ia, Ib, II, III, IV, V, VI, VII, or VIII), *Haemophilus influenzae* (typeable strains: a, b, c, d, e or f), *Pseudomonas aeruginosa, Staphylococcus aureus*, etc.

Other saccharides in conjugates can include glucans (e.g. fungal glucans, such as those in *Candida albicans*), and fungal capsular saccharides e.g. from the capsule of *Cryptococcus neoformans*. Other preferred conjugate saccharide antigens are eukaryotic saccharides e.g. fungal saccharides, plant saccharides, human saccharides (e.g. cancer antigens), etc. Other conjugate saccharides are lipopolysaccharides and lipooligosaccharides.

Vaccines

Preferred samples analysed in the present invention are vaccines comprising protein.

1 Conjugate Vaccines

Preferred conjugate vaccines comprise immunogens protecting against:

*Haemophilus influenzae* type b (Hib);
*Neisseria meningitidis* (meningococcus) of serogroups A, C W135 and/or Y;
*Streptococcus pneumoniae* (pneumococcus);
*Streptococcus agalactiae* (group B *streptococcus*);
*Pseudomonas aeruginosa*; or
*Staphylococcus aureus*, either singly or in combination.

Preferred combination conjugate vaccines comprise:
mixtures of conjugates from each of meningococcal serogroups C and Y;
mixtures of conjugates from each of meningococcal serogroups C, W135 and Y;
mixtures of conjugates from each of meningococcal serogroups A, C, W135 and Y;
mixtures of conjugates from meningococcal serogroups A and C;
mixtures of pneumococcal conjugates;
mixed meningococcal and Hib conjugates (e.g. mixtures of Hib conjugates and conjugates from each of meningococcal serogroups A and C, or mixtures of Hib conjugates and conjugates from each of meningococcal serogroups C and Y); or
combined meningococcal, pneumococcal and Hib conjugates.

Vaccines comprising CRM-Hib (i.e. Hib saccharide conjugated to a $CRM_{197}$ carrier) and/or CRM-MenA are particularly preferred. Other preferred vaccines are those containing:
a conjugate of diphtheria toxoid and a *N. meningitidis* serogroup A, C, W135 and/or Y saccharide;
a conjugate of tetanus toxoid and Hib saccharide; or
a conjugate of tetanus toxoid and a *N. meningitidis* serogroup A, C, W135 and/or Y saccharide.

In addition to the conjugate, the vaccine may contain one or more of:
a protein antigen from serogroup B of *N. meningitidis*;
preparations of vesicles prepared from *N. meningitidis* serogroup B;
an antigen from hepatitis A virus, such as inactivated virus [e.g. 59, 60];
an antigen from hepatitis B virus, such as the surface and/or core antigens [e.g. 60, 61];
an antigen from *Bordetella pertussis*, such as pertussis holotoxin (PT) and filamentous haemagglutinin (FHA) from *B. pertussis*, optionally also in combination with pertactin and/or agglutinogens 2 and 3. Cellular pertussis antigens may be used instead;
a diphtheria antigen, such as a diphtheria toxoid [e.g. chapter 13 of ref. 1];
a tetanus antigen, such as a tetanus toxoid [e.g. chapter 27 of ref. 1]; or
polio antigen(s), e.g. IPV.

Such antigens may be adsorbed to an aluminium salt adjuvant (e.g. a hydroxide or a phosphate). Any further saccharide antigens are preferably included as conjugates.

2 Other Protein-Containing Vaccines

Other protein-containing vaccines are known, e.g. serogroup meningococcus B, hepatitis B virus, diphtheria, tetanus, and acellular pertussis vaccines.

Use of the Invention in the Production and Quality Control of Vaccines

The invention may be used at several stages in the production and quality control of vaccines. The invention not only allows the integrity of the protein itself to be monitored, but also the environment of protein, thereby facilitating the monitoring of other components in the vaccines (e.g. caused by contamination by unwanted products).

For example, after the conjugation step during production of a conjugate vaccine, samples can be analysed using the invention in two ways: first, the integrity (i.e. denaturation) of the protein can be monitored e.g. prior to mixing of different conjugates, or prior to release of a vaccine (for regulatory or quality control purposes); second, degradation of the glycoconjugate (e.g. caused by unconjugated saccharide which has depolymerised from the glycoconjugate) can be monitored e.g. to check for incomplete conjugation, or to follow conjugate hydrolysis by monitoring changes due to increasing free saccharide over time; third, contamination by unwanted components can be monitored.

The invention also provides a method of releasing a vaccine for use by physicians, comprising the steps of: (a) manufacturing a vaccine comprising a protein; (b) analysing the vaccine's composition by a method of analysis of the invention; and, if the results from step (b) indicate that the vaccine is acceptable for clinical use, (c) releasing the vaccine for use by physicians. Step (a) may be performed on a packaged vaccine or on a bulk vaccine prior to packaging etc. Step (b) may involve assessment of protein integrity, degradation of the glycoconjugate (where the vaccine is a glycoconjugate vaccine), impurities in the vaccine, etc.

The invention also provides a batch of vaccines, wherein one vaccine within the batch has been analysed using a method of the invention.

The invention also provides a method of monitoring the stability of a vaccine in storage, comprising the steps of: (a) analysing the vaccine as described herein; and, if the results from step (a) indicate that the vaccine is acceptable for clinical use, (b) either (i) continuing to store the vaccine or (ii) releasing the vaccine for use by physicians. Step (a) may be performed on a packaged vaccine, on a bulk vaccine prior to packaging, on saccharides prior to conjugation, etc.

The method of analysis of the invention allows the comparison of the same vaccine under different conditions, or different vaccines under the same conditions.

Thus, the invention provides a method of comparing different vaccines, comprising the steps of: (a) treating a plurality of different vaccines under substantially identical environmental conditions; (b) analysing the treated vaccines as described herein; (c) comparing the results of step (b); and, optionally, (d) selecting a vaccine, e.g. a vaccine stable under the at least one environmental condition from the plurality of different vaccines. Step (d) may, for example, comprise selecting the most stable vaccine under the at least one environmental condition. Thus, uses for this method include comparing the stability of different vaccines, e.g. under storage conditions. The environmental condition can be a chemical condition (e.g. exposure to a chemical component, e.g. a solvent, carrier etc.), pH, temperature, humidity etc. or a combination thereof. The plurality of different vaccines can typically differ in their composition, e.g. presence of other vaccine components, concentration of components, excipients, adjuvants, pH, osmolarity, ionic strength etc., or, where a conjugate vaccine, the length of the saccharide, linker between the saccharide and the carrier, the carrier, etc.

The invention also provides a method of comparing the effect of different environmental conditions on a vaccine, comprising the steps of: (a) treating a plurality of substantially identical samples of a vaccine under a plurality of different environmental conditions; (b) analysing the treated samples as described herein; and (c) comparing the results of step (b); and, optionally, (d) selecting an environmental condition, e.g. an environmental condition under which the vaccine is stable from the plurality of different environmental conditions. Step (d) may, for example, comprise selecting the environmental condition under which the vaccine is most stable. Uses for this method include optimizing the storage conditions of a vaccine. The environmental condition can be a chemical condition (e.g. exposure to a chemical component, e.g. a solvent, carrier etc.), pH, temperature, humidity etc. or a combination thereof.

The invention also provides a bulk pharmaceutical composition comprising as an active ingredient a protein, wherein a sample of the bulk pharmaceutical composition has been analysed using a method of the invention. The invention also provides a pharmaceutical composition drawn from the bulk pharmaceutical composition. A preferred pharmaceutical composition is an immunogenic composition, such as a vaccine, comprising a protein.

Derivative Spectroscopy

The derivatization (or differentiation) of spectra is known as derivative spectroscopy. Derivative spectroscopy may be used in the invention in the following ways: (i) spectral discrimination as a qualitative fingerprinting technique to accentuate small structural differences between nearly identical spectra (see below); (ii) spectral resolution enhancement as a technique for increasing the apparent resolution of overlapping spectral bands in order to more easily determine the number of bands and their wavelengths (see "Resolution enhancement" below); and/or (iii) quantitative analysis as a technique for the correction for irrelevant background absorption and as a way to facilitate multicomponent analysis (see "Trace analysis" below).

Basic spectral discrimination involves comparison of the shape of derivative spectra (typically between the first to fourth derivative) of the test sample and reference sample and, optionally, comparison of the underivatized spectra. Advanced spectral discrimination involves the analysis and comparison of important characteristics of the spectral function, such as peaks, troughs, and points of inflection and zero crossing. However, because raw (i.e. underivatized) spectra are usually too smooth to achieve a very sharp determination of these points, first to second derivative analysis may be used to confirm raw absorbance data. Features in the derived and underivatized spectra can be used as a qualitative fingerprint of the reference sample. For example, broad patterns can be recognized in the spectra of the reference sample, or the positions of specific peaks and troughs etc.

Different derivative levels may be used in different ways, and the choice of derivative levels allows the analysis of different peaks and troughs and other points of interest in the underivatized spectra. In general, first to fourth, preferably first, second and fourth derivative, levels are preferred in the invention. The derivative level may be chosen to allow appropriate analysis of different features of the spectrum. The first derivative of any curve goes through zero at the curve's maxima and minima and shows peaks and troughs at its inflection points. The second derivative has a strong minimum at the point of maximum of the original spectrum. Moreover overlapping peaks from the original spectrum starts to be resolved as local minimums in second derivatives, in which case, instead of a correspondence between a peak in the main spectrum and a local minimum in second derivative, a pattern of nearby small troughs is observed.

Another use of the second derivative is for studying the convexity pattern of the original spectrum, which may advantageously be used for sample fingerprinting (see "Comparison & analysis").

When a deeper peak separation of the spectra is needed (particularly for quantitative analysis), analysis of higher derivatives is possible. For example, fourth derivative analysis may be used to discriminate between the spectral contributions of tryptophan and tyrosine groups (e.g. FIG. 2).

In fourth derivative analysis of UV absorbance spectra, tryptophan exhibits a unique trough at 292 nm, and this property can be used on an unfolded sample, with the help of a calibration curve, to determinate the number of residues in a protein. On the other hand, tyrosine does not exhibit an absolutely unique peak or trough in fourth derivative analysis. The peak at 282 nm has a small contribution due to tryptophan, and the contribution can be taken into account by comparison with the standard curve of a tryptophan-containing model compound at 282 nm. A correction factor can then be used to determine tyrosine concentration from the peak at 282 nm, which is usually achieved by standard addition of tyrosine model compound to a solution of the sample.

Because the amplitude of the nth derivative of a peak-shaped signal is inversely proportional to the nth power of the width of the peak, differentiation may be employed as a general way to discriminate against broad spectral features in favor of narrow components. This principle is the basis for the application of differentiation as a method of correction for background signals in quantitative analysis. Frequently in the analysis of complex samples, the spectral bands caused by the analyte of interest (i.e. the protein in the composition) are superimposed on a broad, gradually curved background. Background of this type can be reduced by differentiation.

An example of reducing the effect of the background is illustrated by FIG. 3. FIG. 3A shows a simulated UV spectrum (absorbance vs. wavelength in nm), with the green (lower) curve representing the spectrum of the pure analyte and the red (upper) line representing the spectrum of a mixture containing the analyte plus other compounds that give rise to the large sloping background absorption. The first derivatives of these two signals are shown in FIG. 3B. It can be seen that the difference between the pure analyte spectrum (green, upper) and the mixture spectrum (red, lower) is reduced. The effect is considerably enhanced in the second derivative, shown in FIG. 3C. In this case the spectra of the pure analyte and of the mixture are almost identical. In order for the technique to work, it is necessary that the background absorption be broader (i.e. have lower curvature) than the analyte spectral peak, but fortunately this situation frequently occurs. Because of their greater discrimination against broad background, second (and sometimes even higher-order) derivatives are often used for such purposes.

Derivative Technique

The derivative technique of the invention provides two advantages for analyzing unprocessed spectra: (i) separation of the spectral contributions of different chemical components in solution and (ii) enhancement of vibrionic structure. These advantages mean the derivative spectra represent better "fingerprints" of the sample composition than the underivatized spectra.

The derivative of a particular point on a curve represents the slope of the tangent line at that point (FIG. 4A) and may be determined by techniques well-known to the skilled person. For practical purposes, however, the derivative is typically approximated by use of the secant line formed from two close points (FIG. 4B). This is a valid approximation because, as the two points used for the secant line get closer one to one another, the average rate of change becomes the instantaneous rate of change and the secant line becomes the tangent line.

The interval for the formation of the secant line (i.e. the distance between the two close points) is typically the spectral resolution of the spectrometer. The spectral resolution influences spectral distortion and becomes one of the key factors for the success of the derivative process. For example, limitations on the derivative technique arise from instrumental noise and background structure. All devices for obtaining the derivative of a real spectrum must effectively average over a finite "wavelength range" ($\lambda R$), because the "real" instant derivative is usually dominated by noise. $\lambda R$ should be chosen experimentally in order to obtain the best compromise between curve distortion and signal-to-noise ratio.

Each derivation of the spectrum enhances the small fluctuations to the spectrum caused by individual components of the sample, and allows the increased separation of the contributions to the spectrum from the components. However, because instrumental noise also causes small fluctuations in the spectrum, this noise will increase through each derivation, and therefore the better the signal to noise ratio of the original spectra, the better the derivative analysis of the invention.

Signal to noise ratio can be increased during data acquisition simply by reducing the spectrometer's scan speed, because the slower the instrument operates, the higher will be the precision on wavelength shift and the longer the time that will be spent sampling each acquired point. Each acquired point is an average value of different absorbance readings. Therefore, a longer sampling time spent at each wavelength means that each point will result from an increasing number of absorbance readings at that point, thereby reducing background noise.

Another way to reduce instrumental noise without affecting signal ratio is by averaging different spectra from the same sample. Single readings can be affected by random events or time-dependent (periodic) fluctuations. Mean spectra, on the other hand, retain all the signal information from the sample but noise fluctuation is reduced.

The noise may also be significantly cut by accepting the loss of some spectral information. The signal-to-noise ratio may be increased and the resulting spectrum will be clearer to understand, even if some spectral details are lost in the process. The smoothing of spectra is one of the preferred approaches for this type of noise reduction.

Smoothing

In many experiments in physical science, the true signal amplitudes (y-axis values) generally change smoothly as a function of the x-axis values, whereas many kinds of noise are seen as rapid, random changes in amplitude from point to point within the signal. In such situations, it is common practice to attempt to reduce the noise by a process called smoothing. In smoothing, the data points of a signal are modified so that individual points that are higher than the immediately adjacent points (presumably because of noise) are reduced, and points that are lower than the adjacent points are increased, thereby leading to a smoother signal. Provided the true underlying signal is smooth, then the true signal will not be much distorted by smoothing, but the noise will be reduced. Where necessary, smoothing may be used in the present invention to reduce noise.

Accordingly, in a preferred embodiment, the invention further comprises the step of smoothing the spectrum before or after the step of derivatising the spectrum. Because it makes no difference whether the smooth operation is applied before or after differentiation, the smoothing may be applied to the spectrum prior to the step of derivatising or on the derivative spectrum.

The simplest smoothing algorithm is the rectangular or unweighted sliding-average smooth; it simply replaces each point in the signal with the average of m adjacent points, where m is a positive integer called the smooth width. For example, for a 3-point smooth (m=3):

$$S_j = \frac{Y_{j-1} + Y_j + Y_{j+1}}{3}$$

for j=2 to n−1, where Sj is the jth point in the smoothed signal, $Y_j$ is the jth point in the original signal, and n is the total number of points in the signal. Similar smooth operations can be constructed for any desired smooth width, m. Usually m is an odd number. The reduction in random noise is approximately the square root of m. The simplest rectangular smooth, with m=3, is also described as quadratic smooth. The triangular smooth is like the rectangular smooth, above, except that it implements a weighted smoothing function. For a 5-point smooth (m=5):

$$S_j = \frac{Y_{j-2} + 2Y_{j-1} + 3Y_j + 2Y_{j+1} + Y_{j+2}}{9}$$

for j=3 to n−2, and similarly for other smooth widths. This is equivalent to two passes of a 3-point rectangular smooth. For peak-type signals, the triangular smooth is better than the rectangular, in that it produces less peak distortion (attenuation and broadening) for a given degree of noise reduction. Smoothing operations can be applied more than once: that is, a previously-smoothed signal can be smoothed again. In some cases this can be useful; however, the noise reduction is much less in each successive smooth. An Example of smoothing is shown in FIG. 5. The left half of this signal is a noisy peak. The right half is the same peak after undergoing a triangular smoothing algorithm. The noise is greatly reduced while the peak itself is hardly changed. Smoothing increases the signal-to-noise ratio and allows the signal characteristics (peak position, height, width, area, etc.) to be measured more accurately, especially when computer-automated methods of locating and measuring peaks are being employed.

The larger the smooth width, the greater the noise reduction, but also the possibility that the signal could be distorted by the smoothing operation. The optimum choice of smooth width depends upon the width and shape of the signal and the digitization interval. For peak-type signals, the critical factor is the smoothing ratio, the ratio between the smooth width m and the number of points in the half-width of the peak. In general, increasing the smoothing ratio improves the signal-to-noise ratio but causes a reduction in amplitude and an increase in the bandwidth of the peak.

FIG. 6 shows a comparison between different noisy gaussian peaks (FIGS. 6A and 6B) smoothed with same incremental smooth width. Narrow peaks show an increased sensitivity for height reduction and, in general, peak distortion, since smoothing ratios (smoothing points/points at half with of the peaks) become higher. In red: FIG. 6A shows a noisy peak with a height of 2.0 (Abs) and a half-with of 80 points and FIG. 6B shows a noisy peak with a height of 1.0 (Abs) and a half-with of 33 points. In green, three curves obtained with increasing levels of triangular smoothing (7.25 and 51 points).

Each of FIGS. 6A and 6B also shows examples of the effect of three different smooth widths on noisy gaussian-shaped peaks. In FIG. 6A, the peak has a (true) height of 2.0 and there are 80 points in the half-width of the peak. The red line is the original unsmoothed peak. The three superimposed green lines are the results of smoothing this peak with a triangular smooth of width (from top to bottom) 7, 25, and 51 points. Because the peak width is 80 points, the smooth ratios of these three smooths are 7/80=0.09, 25/80=0.31, and 51/80=0.64, respectively. As the smooth width increases, the noise is progressively reduced but the peak height also is reduced slightly. For the largest smooth, the peak width is slightly increased. In FIG. 6B, the original peak (in red) has a true height of 1.0 and a half-width of 33 points. The three superimposed green lines are the results of the same three triangular smooths of width (from top to bottom) 7, 25 and 51 points. However, because the peak width in this case is only 33 points, the smooth ratios of these three smooths are larger 0.21, 0.76 and 1.55, respectively. It can be seen that the peak distortion effect (reduction of peak height and increase in peak width) is greater for the narrower peak (FIG. 6B) because the smooth ratios are higher. Smooth ratios of greater than 1.0 are seldom used because of excessive peak distortion.

The optimum smooth ratio depends on the purpose of the peak measurement. If the objective of the measurement is to measure the true peak height and width, then smooth ratios below 0.2 should be used. (In FIG. 6A, the original peak (red line) has a peak height greater than the true value 2.0 because of the noise, whereas the smoothed peak with a smooth ratio of 0.09 has a peak height that is much closer to the correct value). However, if the objective of the measurement is to measure the peak position (x-axis value of the peak), much larger smooth ratios can be employed if desired, because smoothing has no effect at all on the peak position (unless the increase in peak width is so much that it causes adjacent peaks to overlap).

In quantitative analysis applications, the peak height reduction caused by smoothing is not so important, because in most cases calibration is based on the signals of reference samples. If the same signal processing operations are applied to the test sample and to the reference sample, the peak height reduction of the reference signal will be exactly the same as that of the test signal and the effect will cancel out exactly. In such cases smooth widths from 0.5 to 1.0 can be used if necessary to further improve the signal-to-noise ratio, since the noise is reduced by approximately the square root of the smooth width.

In practical analytical chemistry, absolute peak height measurements are seldom required because calibration against reference samples is typically employed (the objective of a quantitative spectrophotometric procedure is not to measure absorbance but rather to measure concentrations in the test sample). It is important, however, to apply exactly the same signal processing steps to the test signal as to the reference signal, otherwise a large systematic error may result.

The Importance of Smoothing Derivatives in Quantitative Analytical Applications

In application of differentiation in quantitative analytical applications, it is preferable to use differentiation in combination with smoothing, in order to optimize the signal-to-noise ratio.

The technique is illustrated in FIG. 7. Window 1 shows a Gaussian band with a small amount of added noise. Windows 2, 3, and 4, show the first derivative of that signal with increasing smooth widths. It can be seen that, without sufficient smoothing, the signal-to-noise ratio of the derivative can be substantially poorer than the original signal. However, with adequate amounts of smoothing, the signal-to-noise ratio of the smoothed derivative can be better than that of the unsmoothed original. This effect is even more striking in the second derivative of the signal, as shown on FIG. 8. In this case, the signal-to-noise ratio of the unsmoothed second derivative (Window 2) is so poor that it is not possible to see the signal visually.

It makes no difference whether the smooth operation is applied before or after the differentiation. What is important, however, is the nature of the smooth, its smooth ratio (ratio of the smooth width to the width of the original peak), and the number of times the signal is smoothed. The optimum value range of smooth ratio that has to be used on derivative spectra is between about 0.5 and about 1.0. For a first derivative, two applications of a simple rectangular smooth or one application of a triangular smooth is adequate. For a second derivative, three applications of a simple rectangular smooth or two applications of a triangular smooth is adequate. The general rule is: for the nth derivative, use at least n+1 applications of rectangular smooth (or half that number of triangular smooths). Such heavy amounts of smoothing result in substantial attenuation of the derivative amplitude. In both FIGS. 7 and 8, the amplitude of the most heavily smoothed derivative (Window 4, bottom right) is much less than its less-smoothed version (Window 3, bottom left). However, this does not present a problem, provided the reference spectra is prepared using the same derivative, smoothing, and measurement procedure as is applied to the test spectra.

In fingerprint analysis, i.e. where the whole spectrum is considered for identification of a sample, N−1 (where N is the derivative degree) quadratic smoothing operations are generally preferred.

In characterization analysis, i.e. where specific features of the spectrum are considered for identification of specific features of the sample, N+1 (where N is the derivative degree) quadratic smoothing operations are generally preferred.

Trace Analysis

The invention is particularly useful for the analysis of a small amount of protein analyte in the presence of a large amount of potentially interfering material. For example, where the sample is a pharmaceutical product, fillers, emulsifiers, flavoring or coloring agents, buffers, stabilizers, or excipients etc. may act to interfere with the signal from the active ingredient.

In such applications, it is common that the signal from the protein analyte is weak, noisy, and superimposed on large background signals. For example, measurement precision may be degraded by sample-to-sample baseline shifts due to non-specific broadband interfering absorption, non-reproducible cuvette positioning, dirt or fingerprints on the cuvette walls, imperfect cuvette transmission matching, and solution turbidity. Baseline shifts from these sources are usually either wavelength-independent (light blockage caused by bubbles or large suspended particles) or exhibit weak wavelength dependence (small-particle turbidity).

The derivative technique of the invention (typically with 4th derivative analysis) allows the discrimination of the absorption by the analyte from these sources of baseline shift. A particular benefit of the suppression of broad background by differentiation is that variations in the background amplitude from sample to sample are also reduced. Suppression provides improved precision or measurement of the analyte, especially when the analyte signal is small compared to the background. An Example of the improved ability to detect trace component in the presence of strong background interference is shown in FIG. 9.

FIG. 9A shows a weak shoulder near the center due to the analyte. The signal-to-noise ratio is very good in this spectrum, but in spite of that the broad, sloping background obscures the peak and makes quantitative measurement difficult. The fourth derivative of this spectrum is shown in FIG. 9B. The background has been almost completely suppressed and the analyte peak now stands out clearly, facilitating measurement.

An alternative example, showing further improvement, is shown in FIG. 10. The spectrum shown in FIG. 10 is the same spectrum as in FIG. 9, except that the concentration of the analyte is lower. It can be seen that it is not possible to determine from the underivatized spectrum whether there is any protein analyte present, but inspection of the fourth derivative spectrum shows clearly that protein analyte is present. Although some noise is evident, the signal-to-noise ratio is sufficiently good for a quantitative measurement.

Resolution Enhancement

The invention may also be advantageously used for resolution enhancement of an underivatized spectrum.

Overlap of bands in the spectrum makes the accurate measurement of their intensities and positions difficult, even if the signal-to-noise ratio is good. The invention may be used to resolve the bands, i.e. to make the bands narrower.

For example, one of the simplest resolution algorithms is based on the weighted sum of the original signal and the negative of its second derivative:

$$R_j = Y_j - kY_j^*$$

where $R_j$ is the resolution-enhanced signal, $Y_j$ is the original signal, $Y_j''$ is the second derivative of $Y_j$, and k is a selected weighting factor. The weighting factor k is selected to optimise the balance between resolution enhancement, signal-to-noise degradation, and baseline undershoot. The optimum choice depends upon the width, shape, and digitization interval of the signal.

FIG. 11A shows a spectrum that consists of several poorly-resolved (partly overlapping) bands, and FIG. 11B shows the application of the above resolution algorithm. The component bands have been artificially narrowed so that the intensities and positions can be measured, albeit with a degradation in the signal-to-noise ratio.

FIG. 12A shows a computer-generated peak with a Lorentzian shape (in red) superimposed on the negative of its second derivative (in green). The second derivative is amplified (by multiplying it by an adjustable constant) so that the negative sides of the inverted second derivative (from approximately X=0 to 100 and from X=150 to 250) are a mirror image of the sides of the original peak over those regions. In this way, when the original peak is added to the inverted second derivative, the two signals will approximately cancel out in the two side regions but will reinforce each other in the central region (from X=100 to 150). The result, shown in FIG. 12B, is a substantial (about 50%) reduction in the width, and an increase in height, of the peak so that the intensities and positions can be more easily measured. The algorithm works best with Lorentzian-shaped peaks; while with Gaussian-shaped peaks the resolution enhancement is still useful but less extensive (only about 20% reduction in the width). A property of this procedure is that it does not change the total peak area (that is, the area under the peak) because the total area under the curve of the derivative of a peak-shaped signal is zero (the area under the negatives lobes cancels the area under the positive lobes).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

The methods of the invention can be used for analytical and/or preparative purposes. References to "analysing", "analysis", etc. should not be construed as excluding preparative methods.

BRIEF DESCRIPTION OF DRAWINGS

Figures Referred to in the Description

FIG. 2 shows the derivatization of a UV absorbence curve as a way to separate components of its overlapping peaks.

FIG. 3 shows the derivatization of a curve in presence of broad background noise.

FIG. 7 shows a noisy spectrum and its first derivative, with or without different degrees of smoothing.

FIG. 8 shows the same noisy spectrum as FIG. 7, with or without different degrees of smoothing.

UV Absorbance Spectroscopy

Figures of Example 2A

Figure 13:
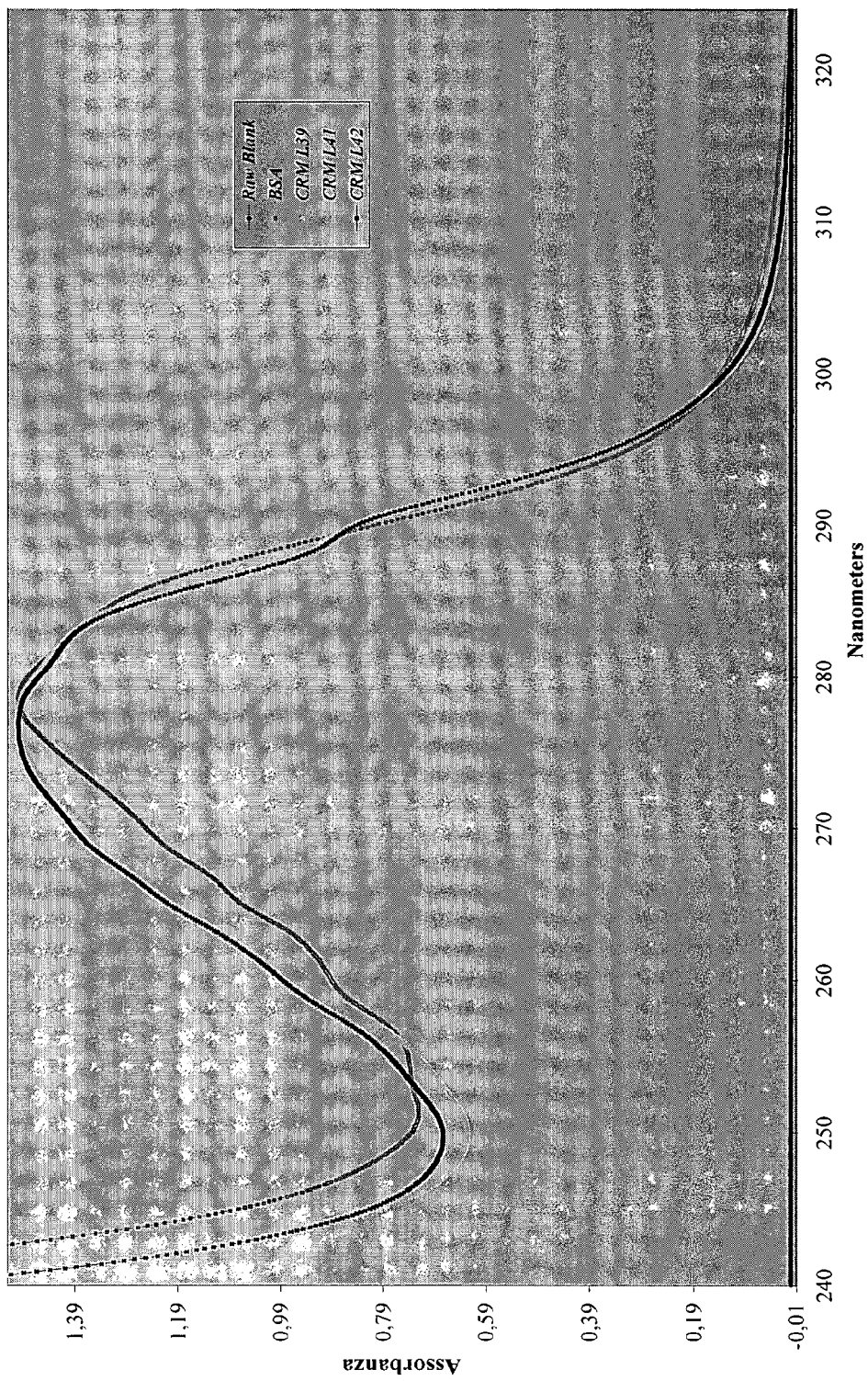

FIG. 13 shows the absorbance normalized spectra (i.e. underivatized) from the analysis of Example 1A.

Figure 14:
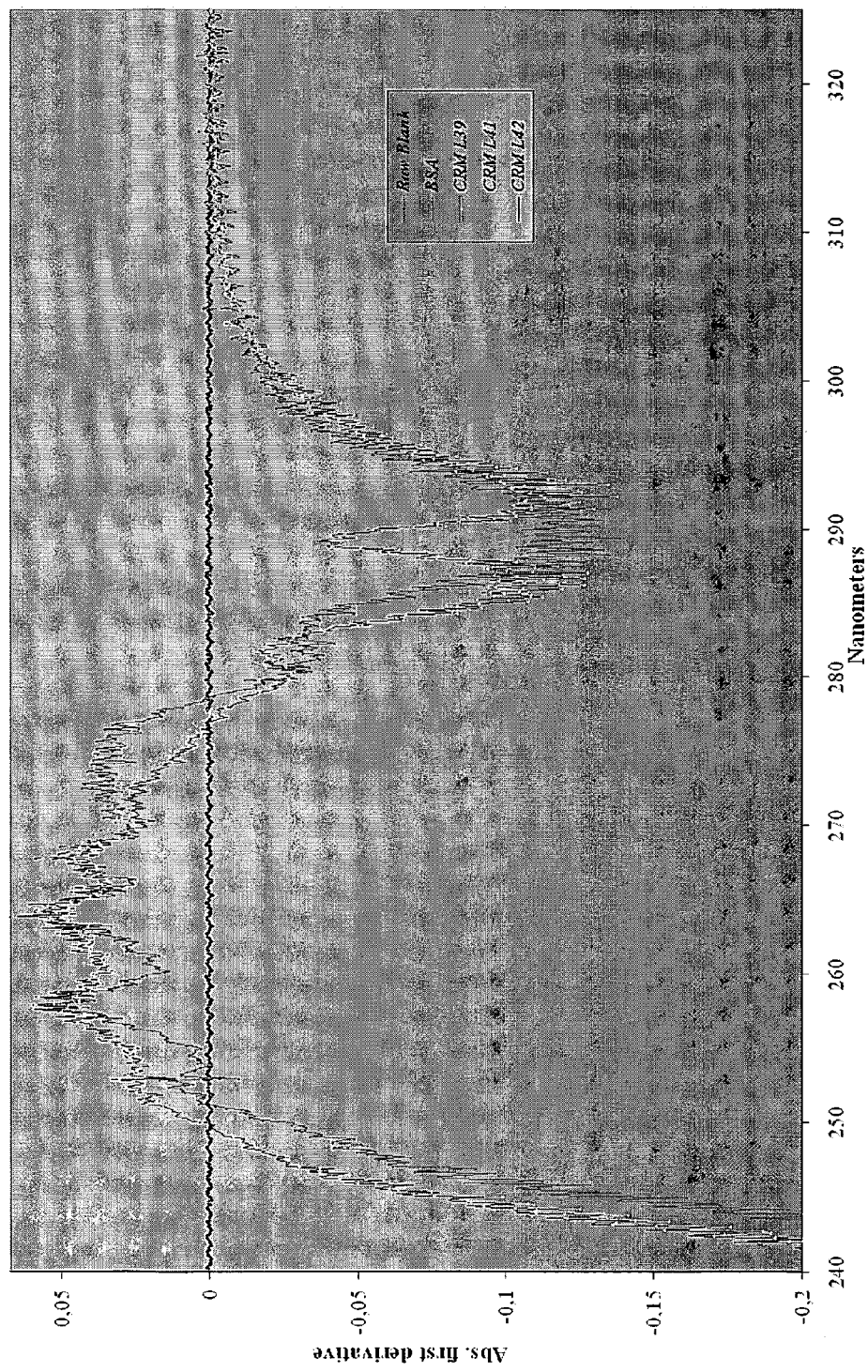

FIG. 14 shows the first order derivatives of the spectra of FIG. 13.

Figure 15:
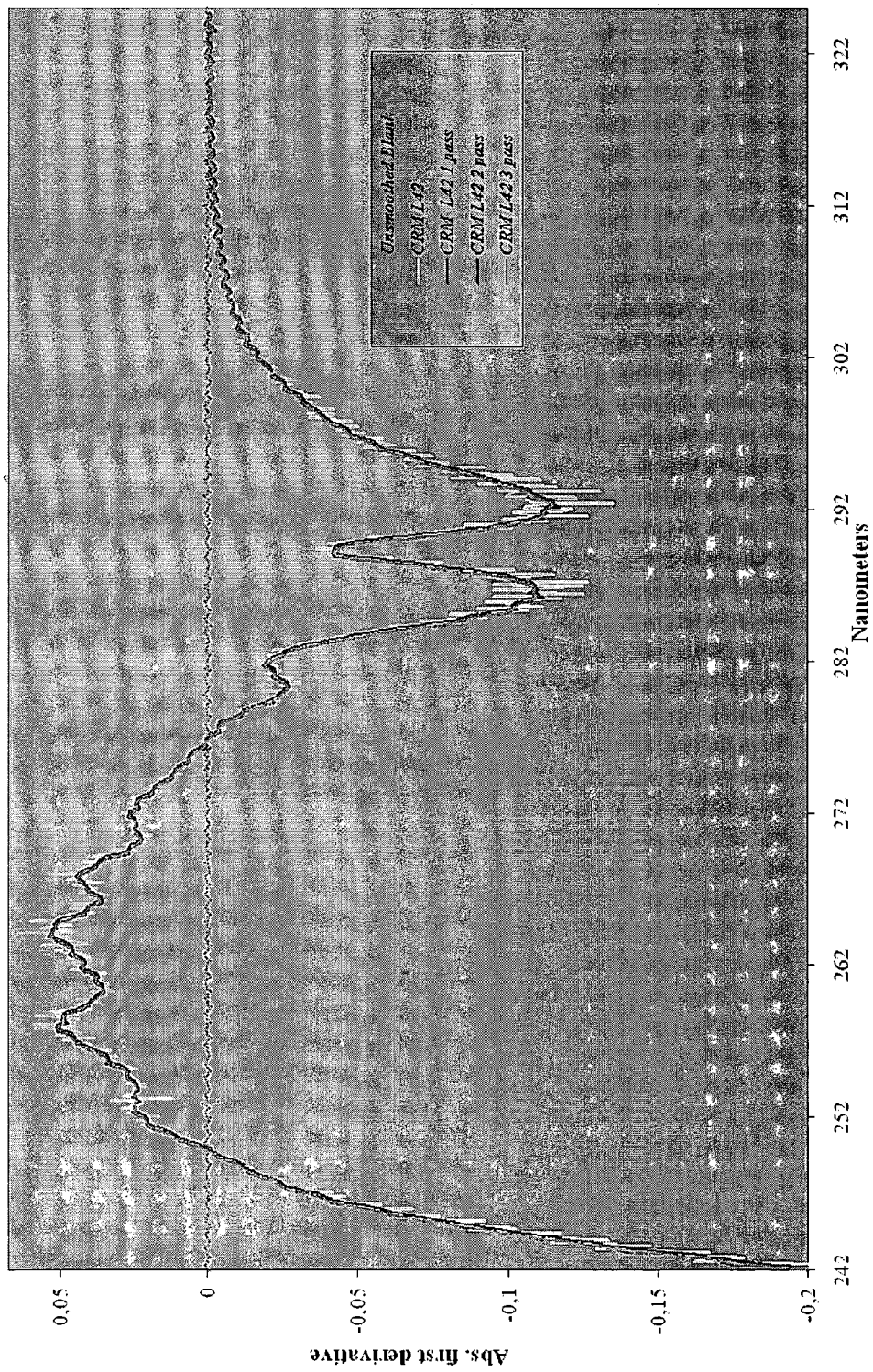

FIG. 15 shows various depths of smoothing on a first derivative of a reference sample (lot 42) from Example 1A.

Figure 16:
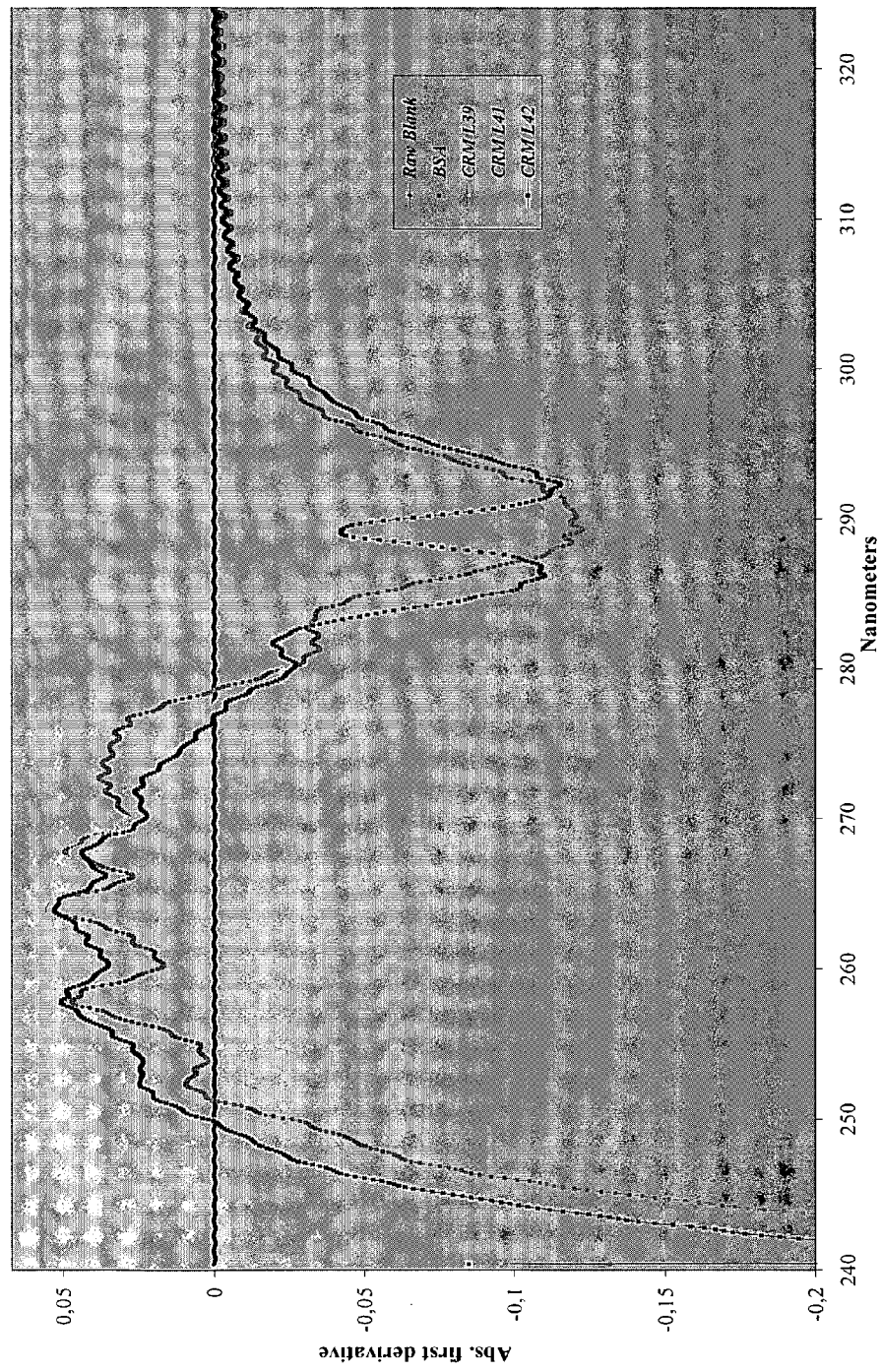

FIG. 16 shows the first order derivatives obtained from the spectra acquired from the samples of Example 1A using 2 passes of a 5-point triangular smooth.

Figures of Example 2B

Figure 17A:
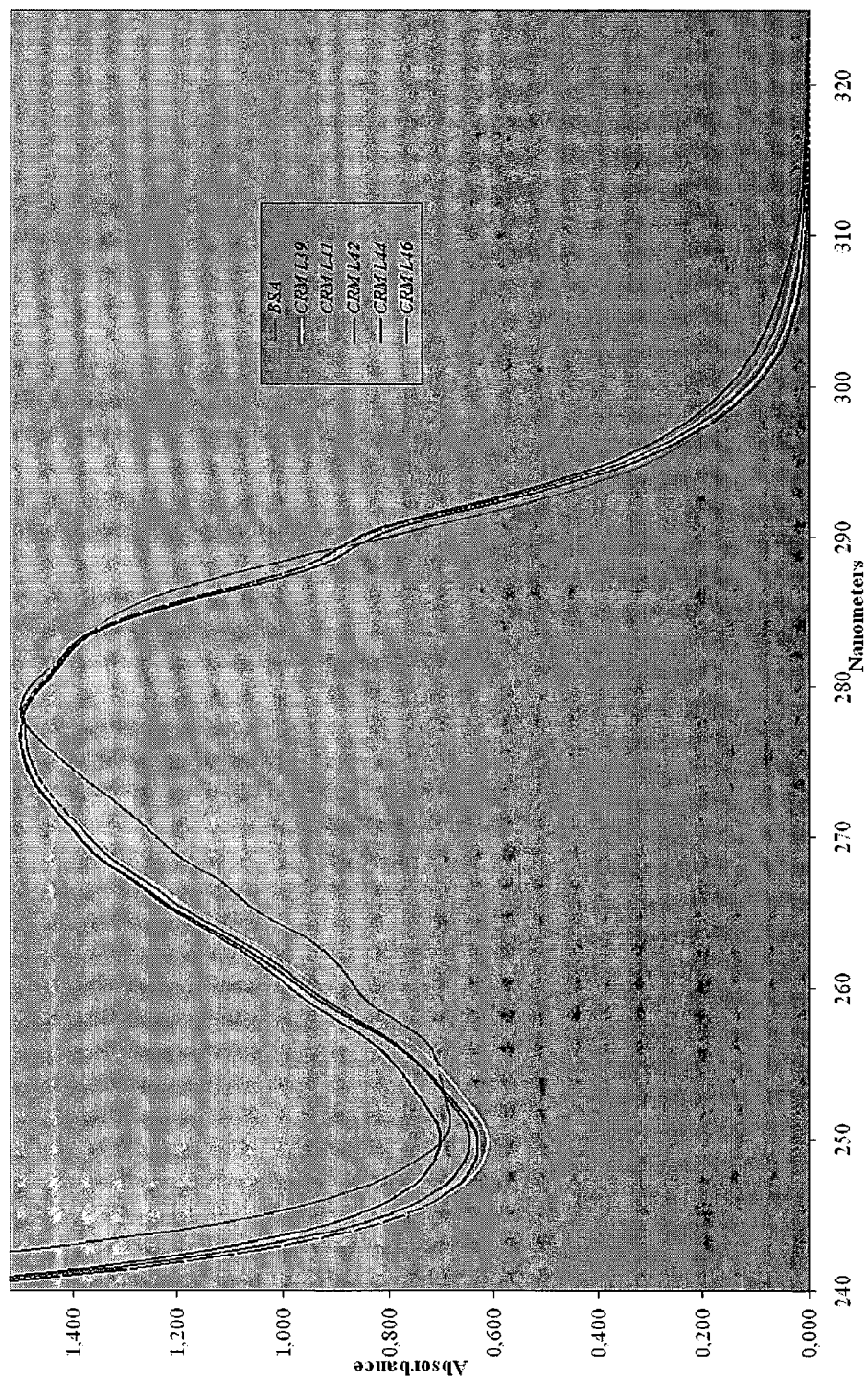
Figure 17B:
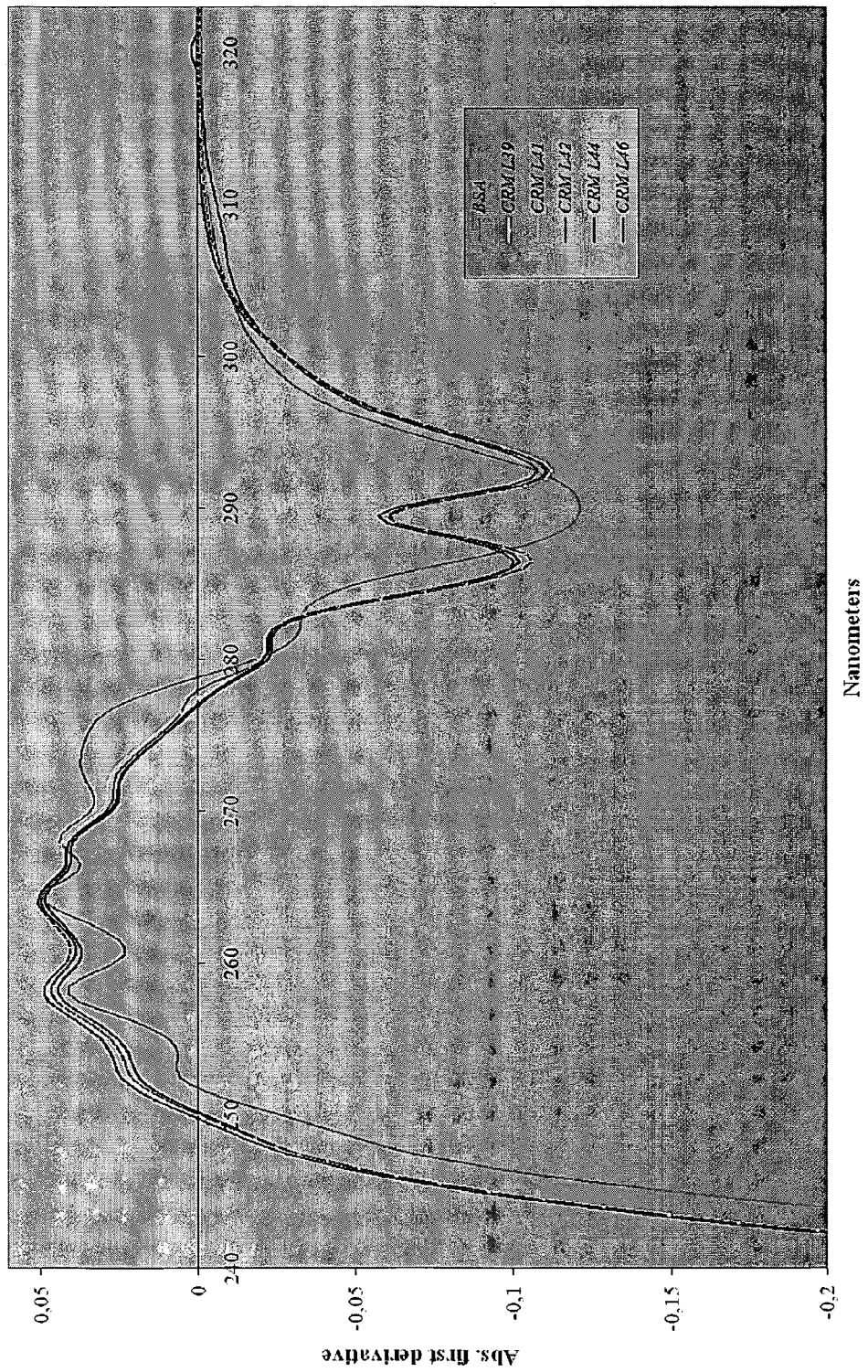
Figure 18A:
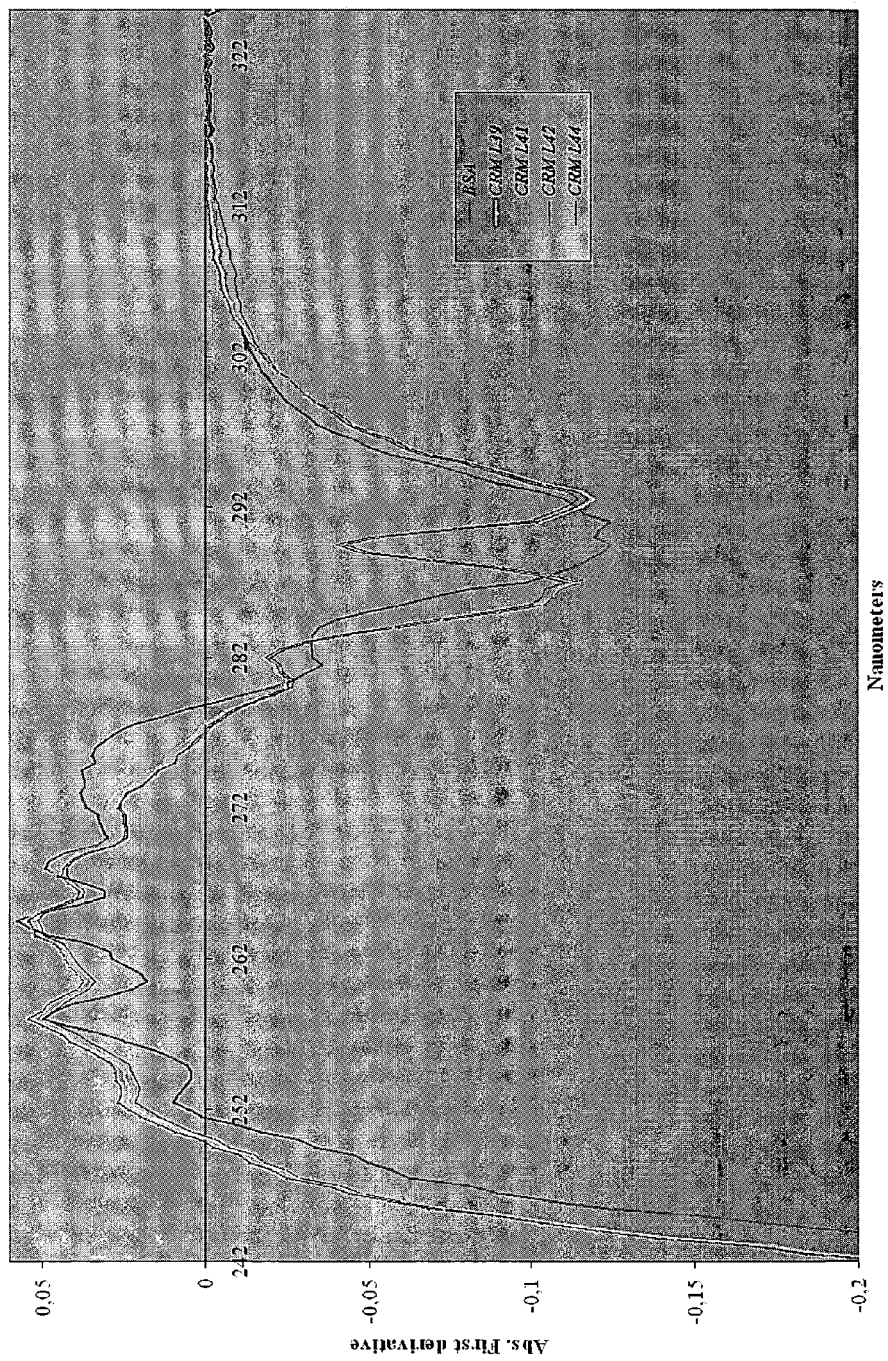
Figure 18B:
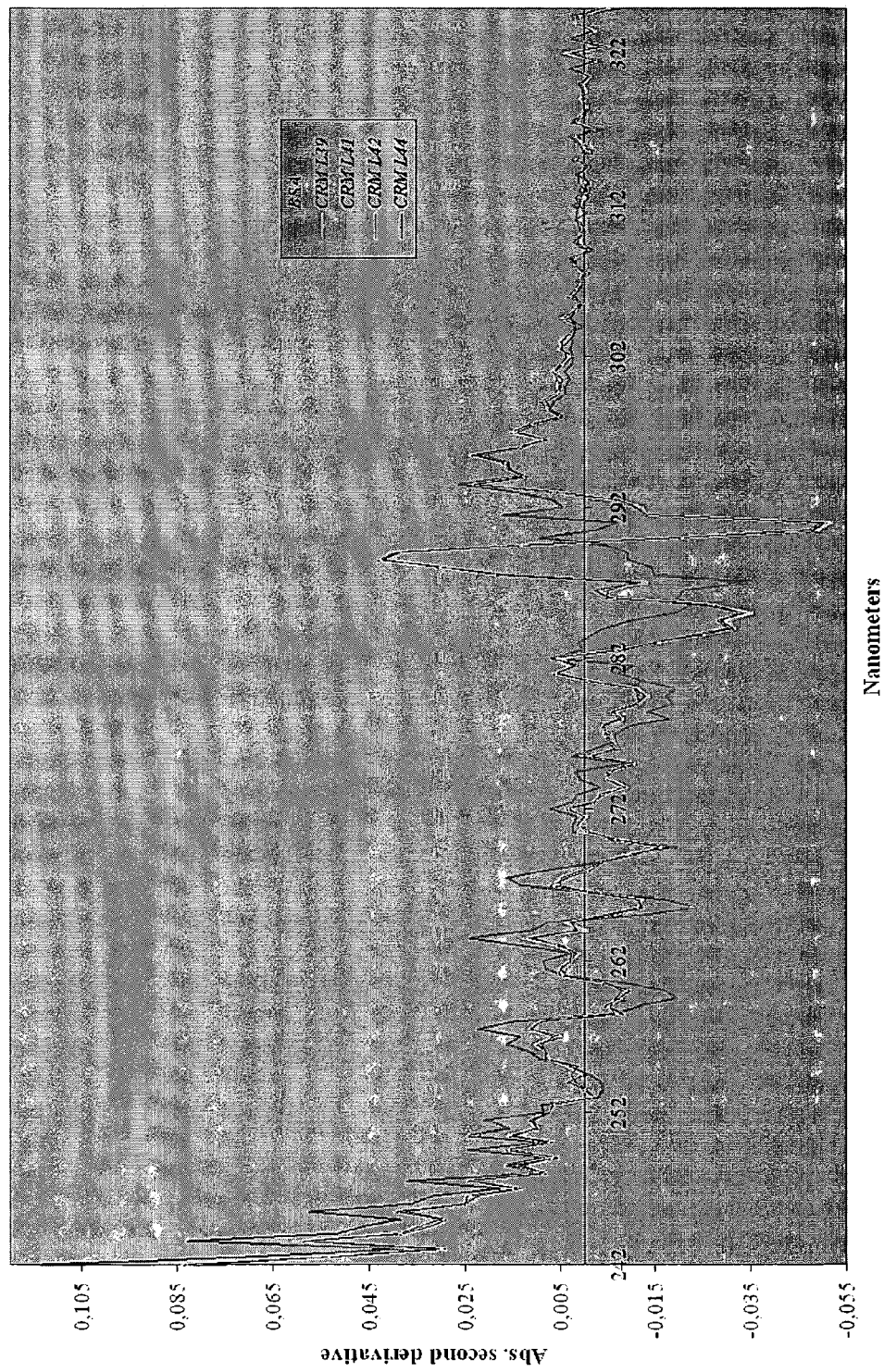
Figure 18C:
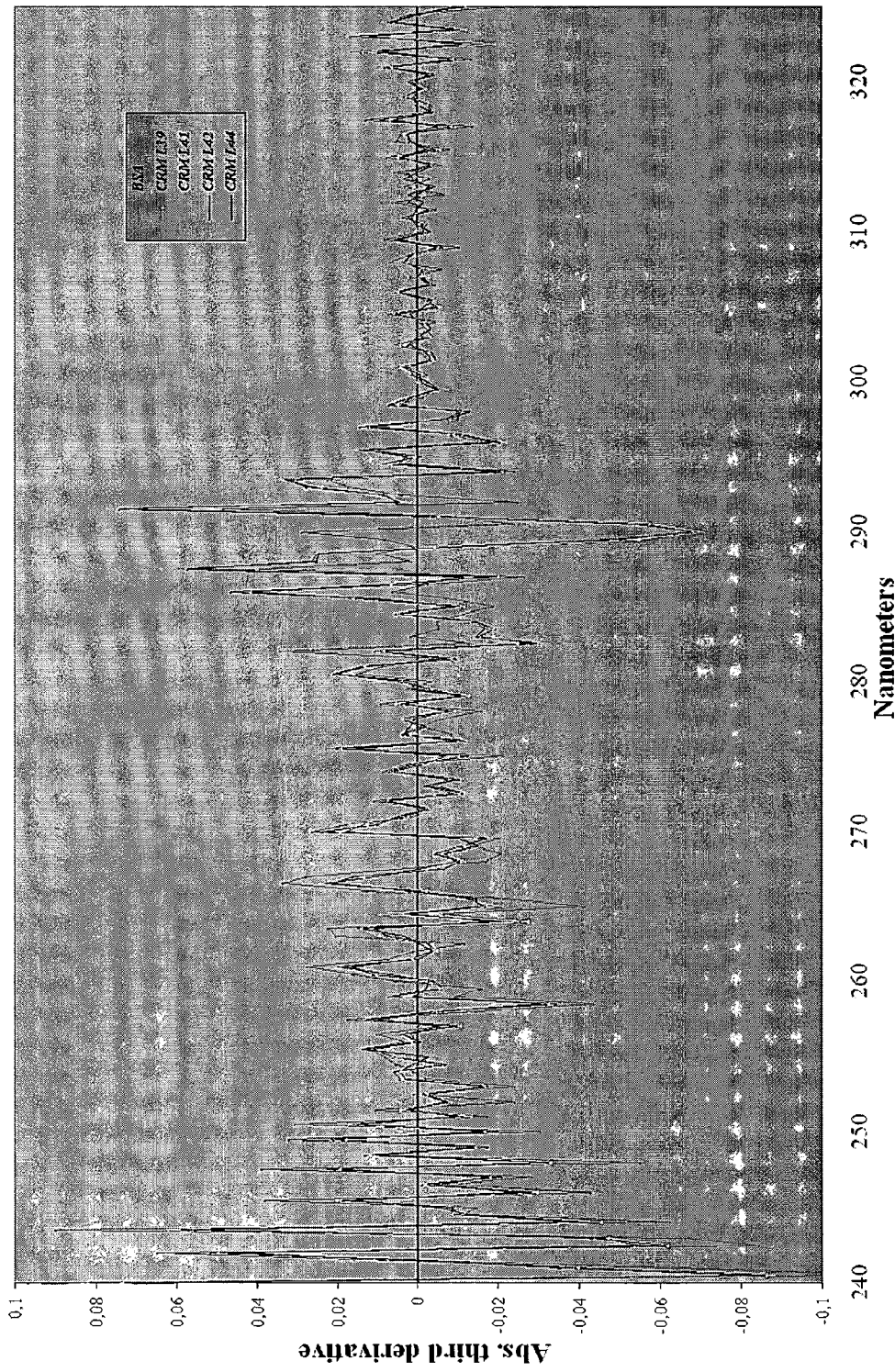
Figure 18D:
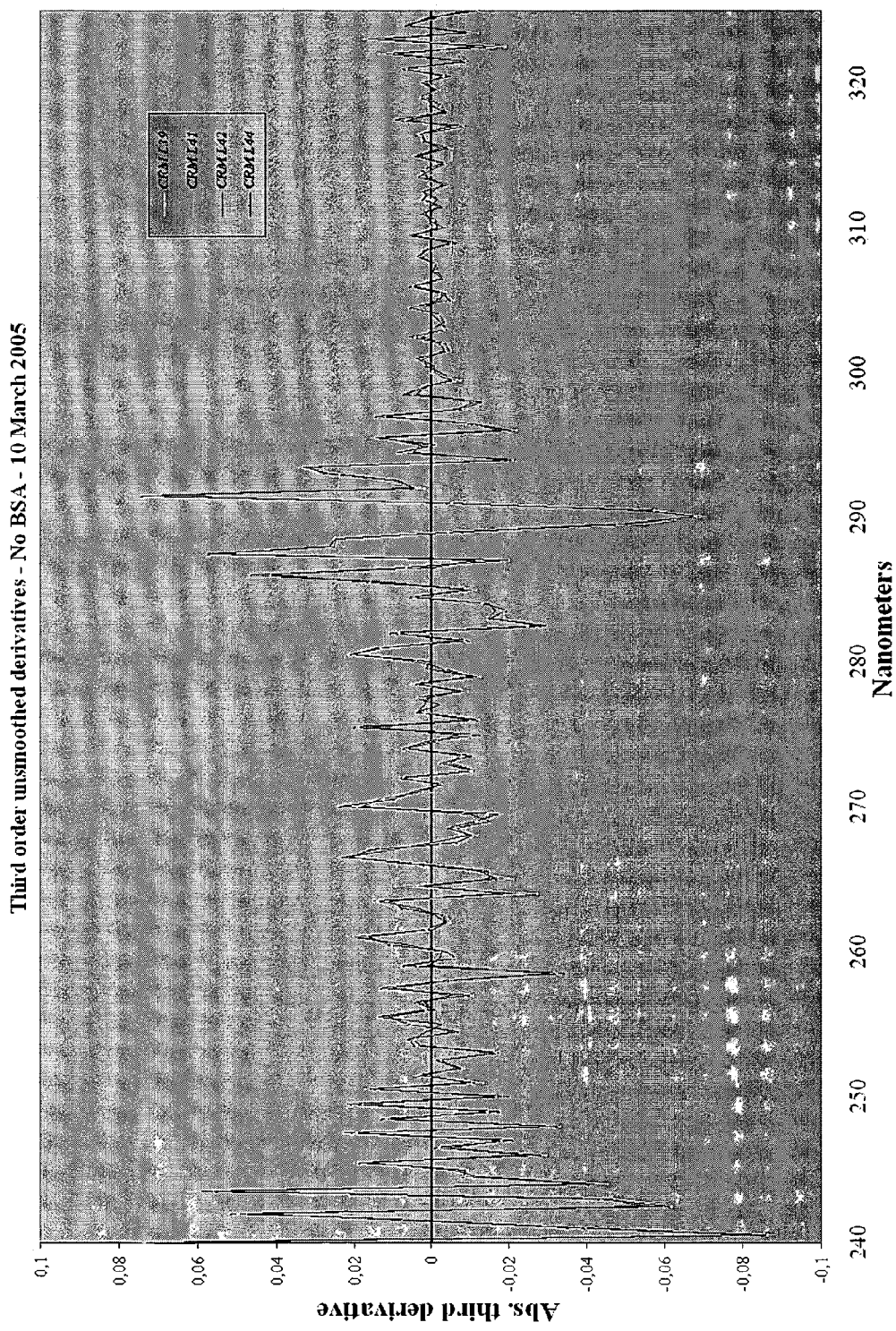
Figure 18F:
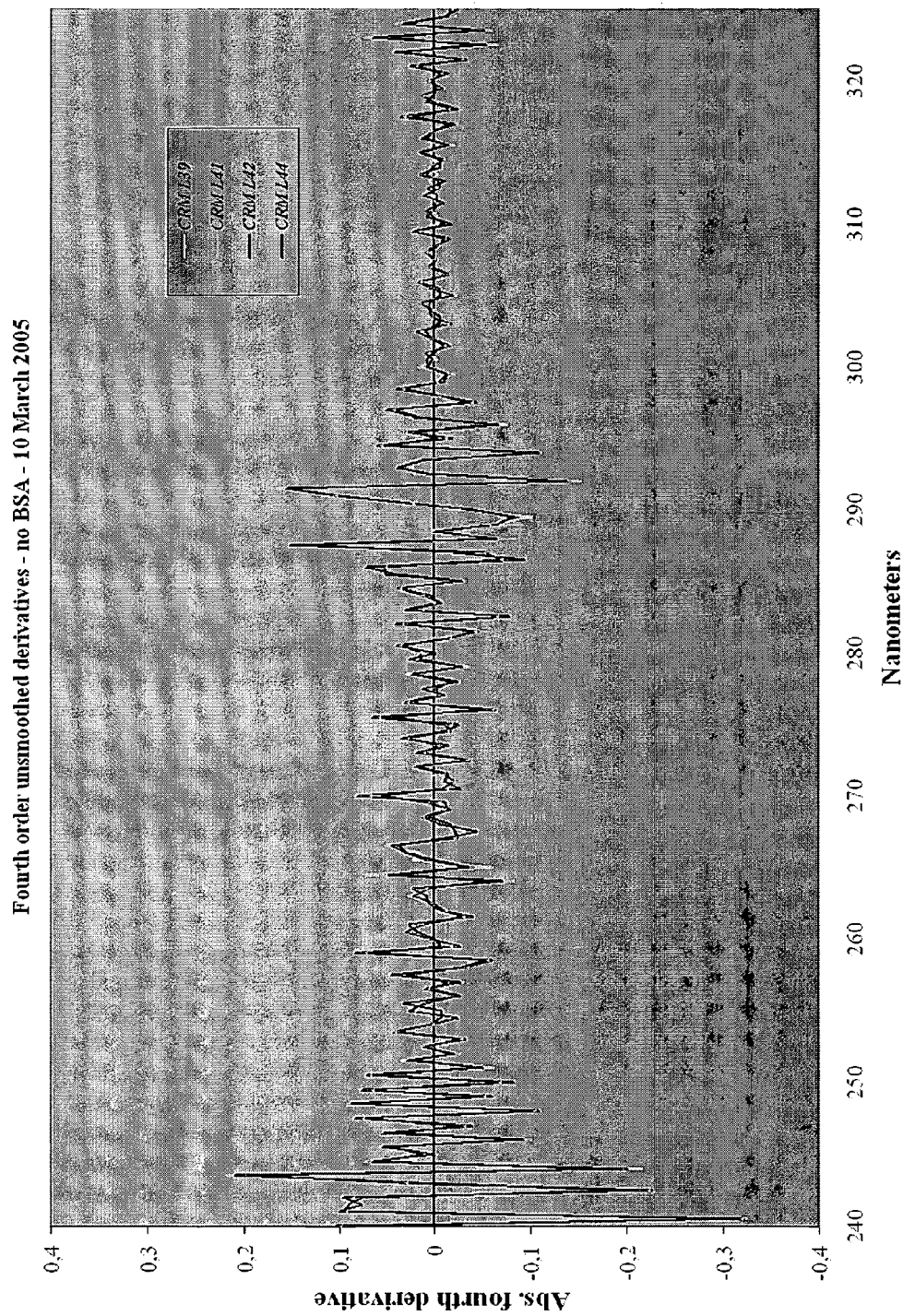

FIG. 17A shows the absorbance normalized spectra (i.e. underivatized) from the analysis of Example 2A. FIG. 17B shows the first order derivatives after light background reduction.

1 BSA and CRM lots 39, 41, 42 and 44 (Session 1)

FIG. 18 shows the fingerprint data from the samples of Example 1B. FIG. 18A shows the unsmoothed first order derivatives. FIG. 18B shows the unsmoothed second order derivatives. FIG. 18C shows the unsmoothed third order derivatives. FIG. 18D shows the unsmoothed third order derivatives, without the derivative for BSA. FIG. 18E shows the unsmoothed fourth order derivatives. FIG. 18F shows the unsmoothed fourth order derivatives, without the derivative for BSA.

Figure 19A:
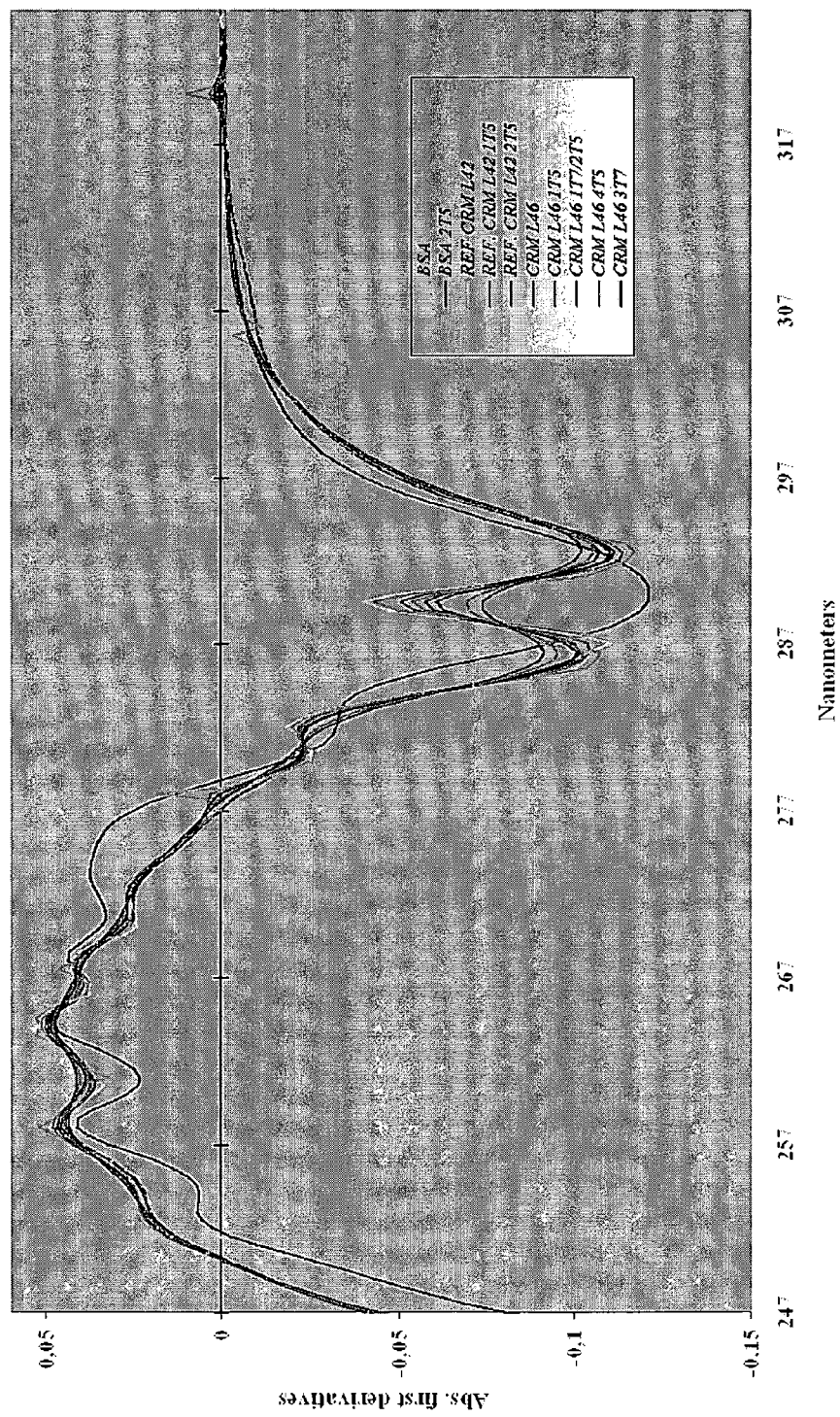
Figure 19B:
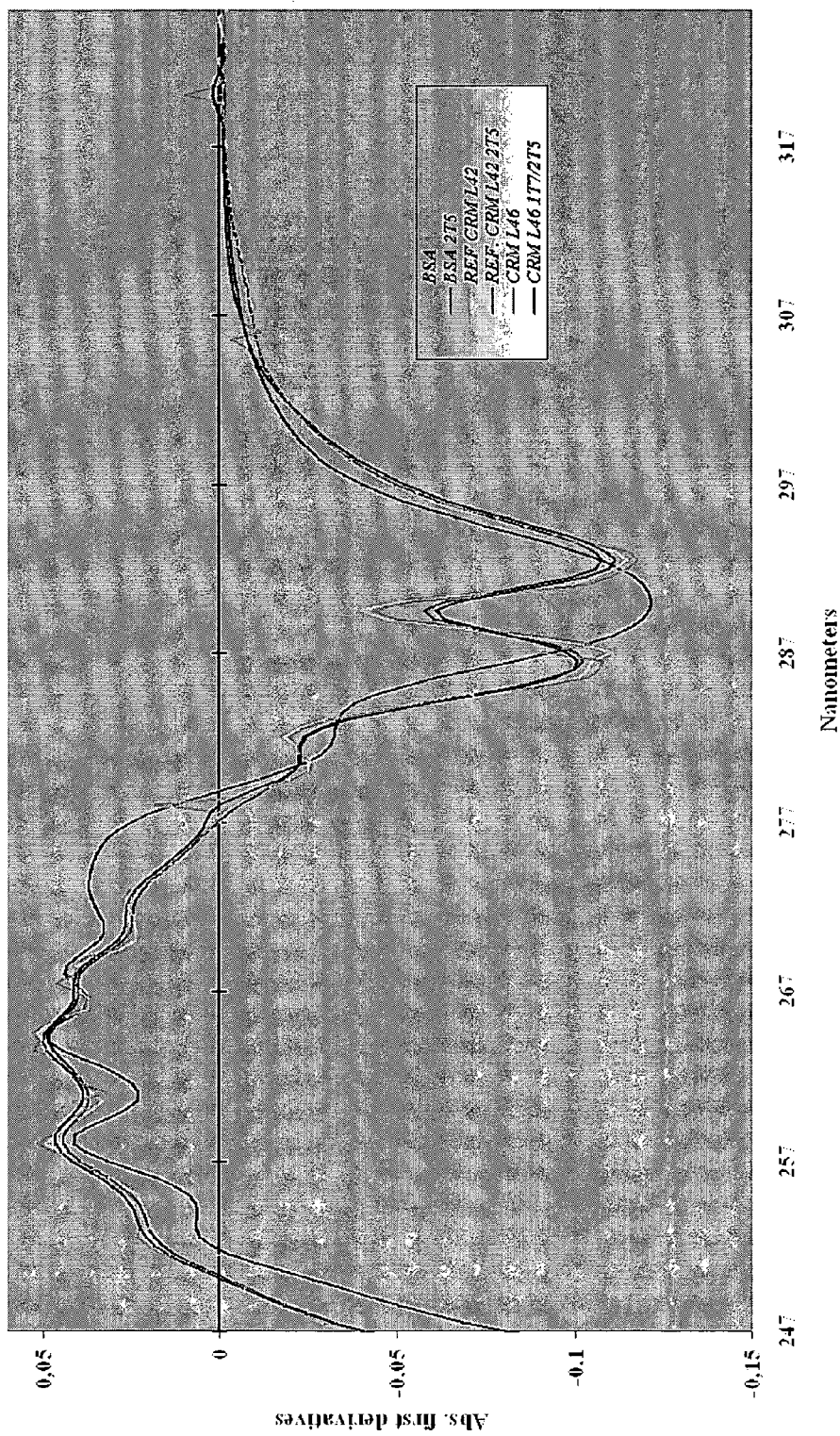

FIG. 19A shows various levels of smoothing of the first order derivative ("2T5" means two 5-point triangular smooths for example) of FIG. 18. FIG. 19B shows a selected sub-set of the first order derivatives after various levels of smoothing; FIG. 19C shows a further sub-set and specifically compares data from Example 2A with data from Example 2B.

2 CRM lot 46 (Session 2)

Figure 20:
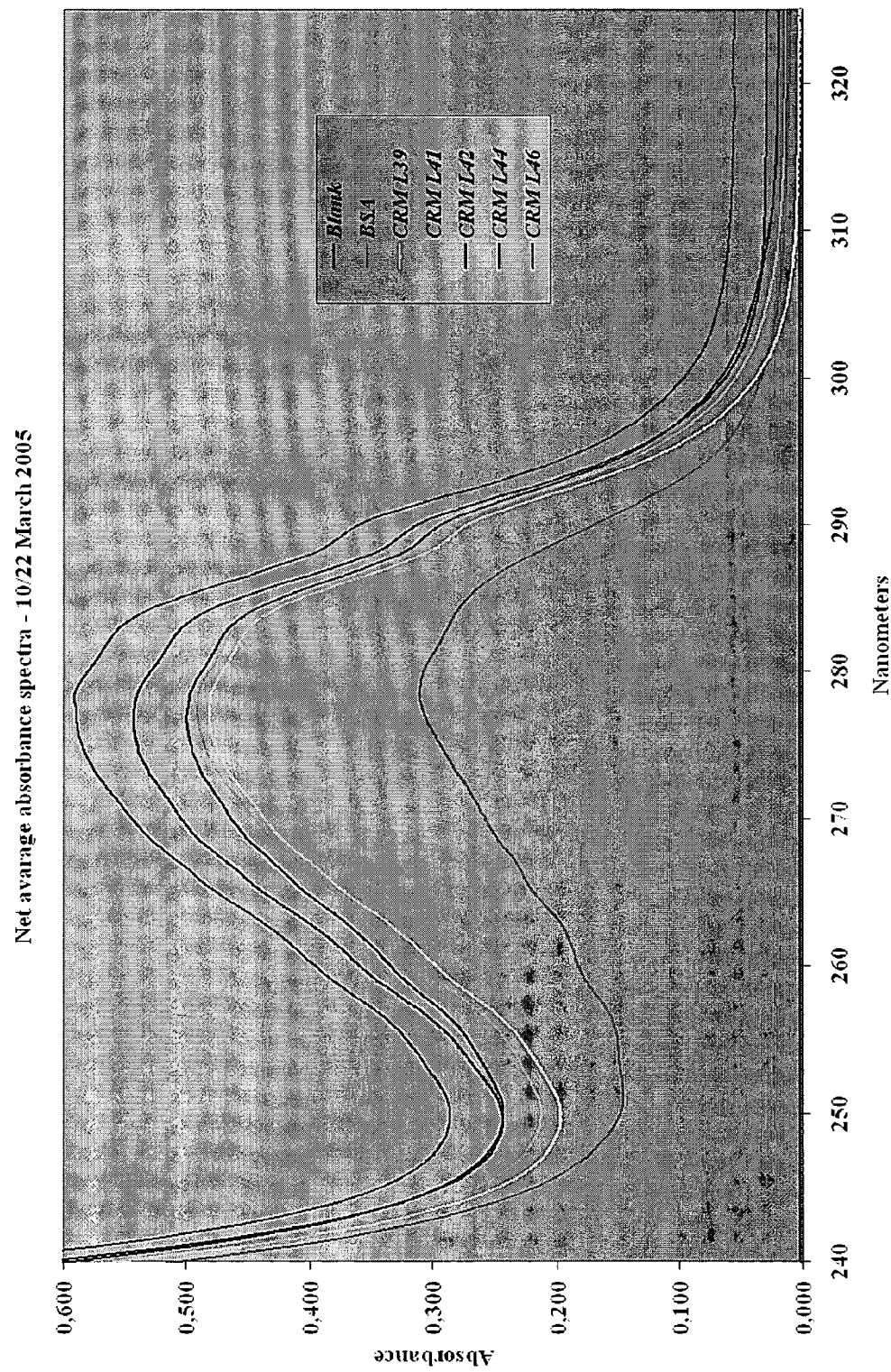

FIG. 20 shows the CRM lot 46 absorbance spectrum of Example 2B.

Figure 21:
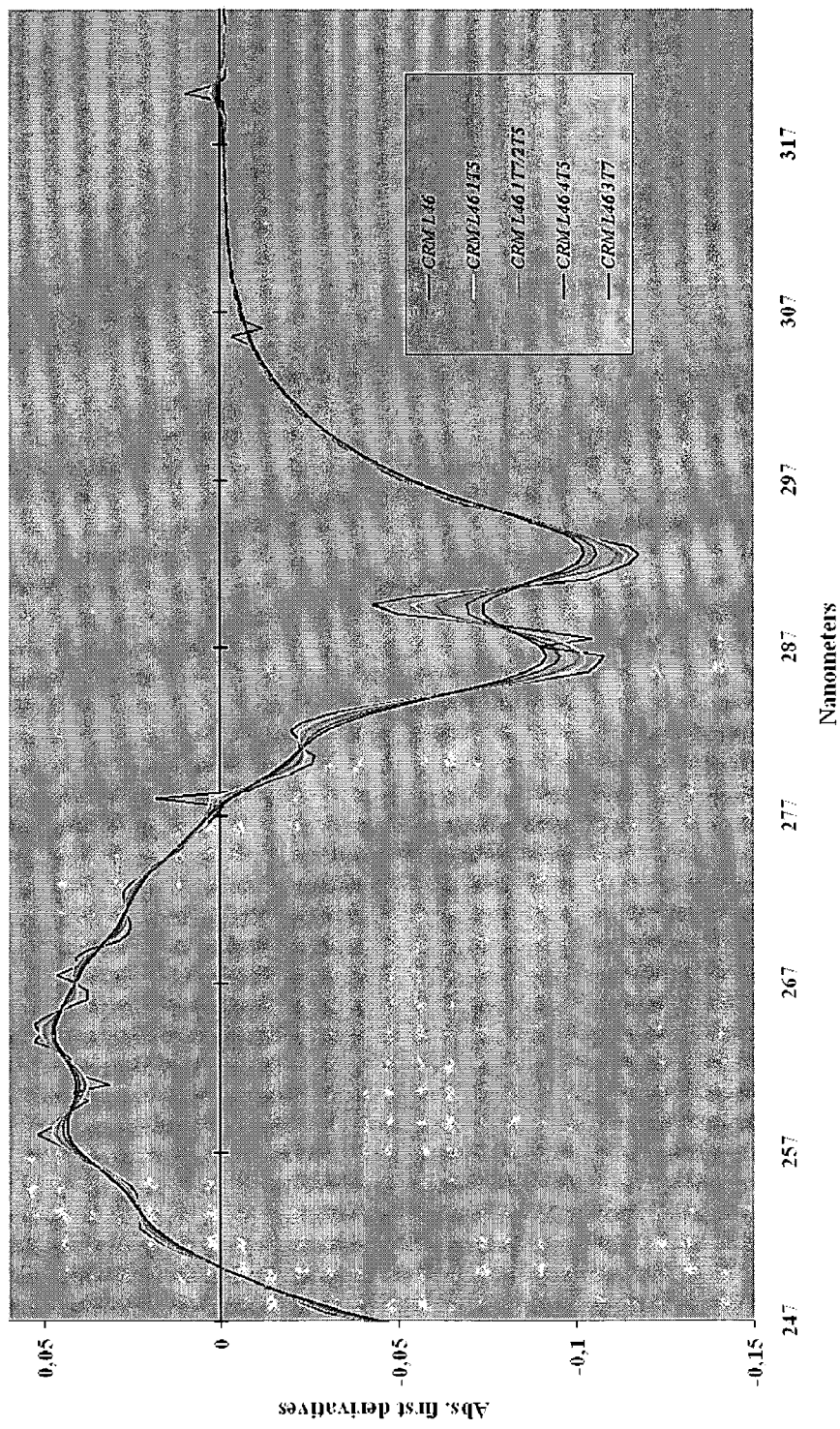

FIG. 21 shows various smoothing levels of the first derivative spectrum of FIG. 20.

Figures of Example 2C

Figure 22A:
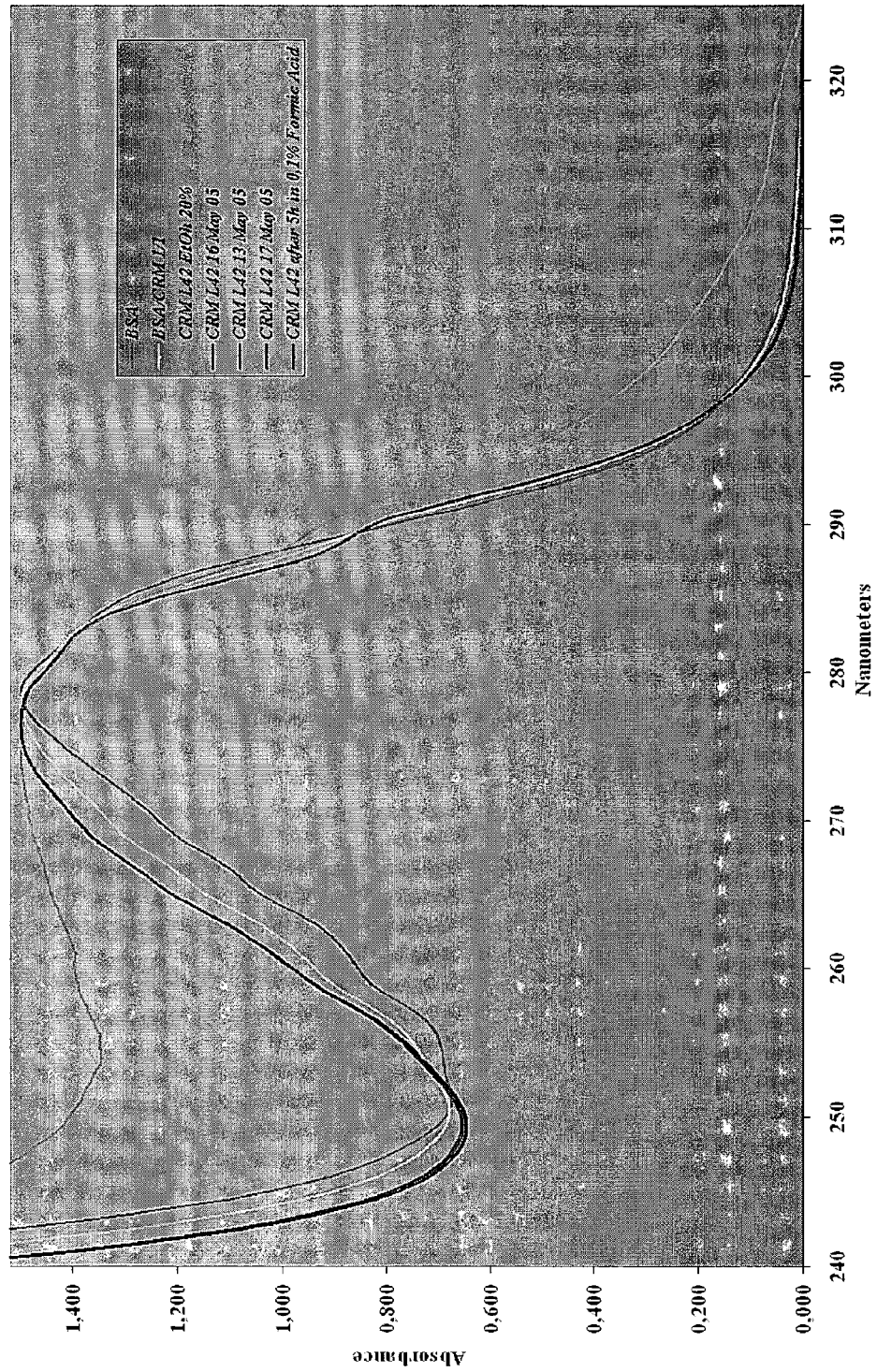
Figure 22B:
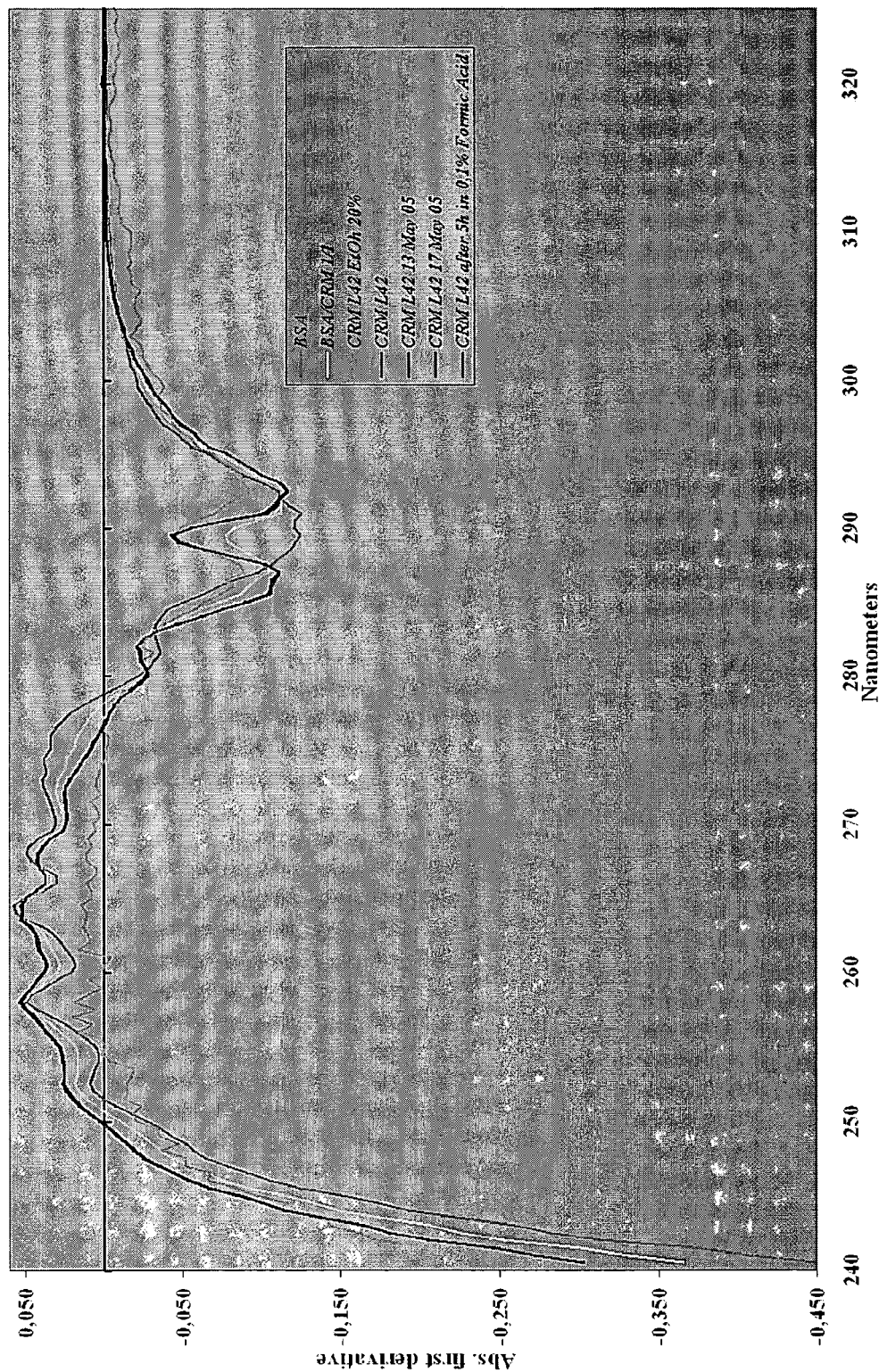
Figure 22C:
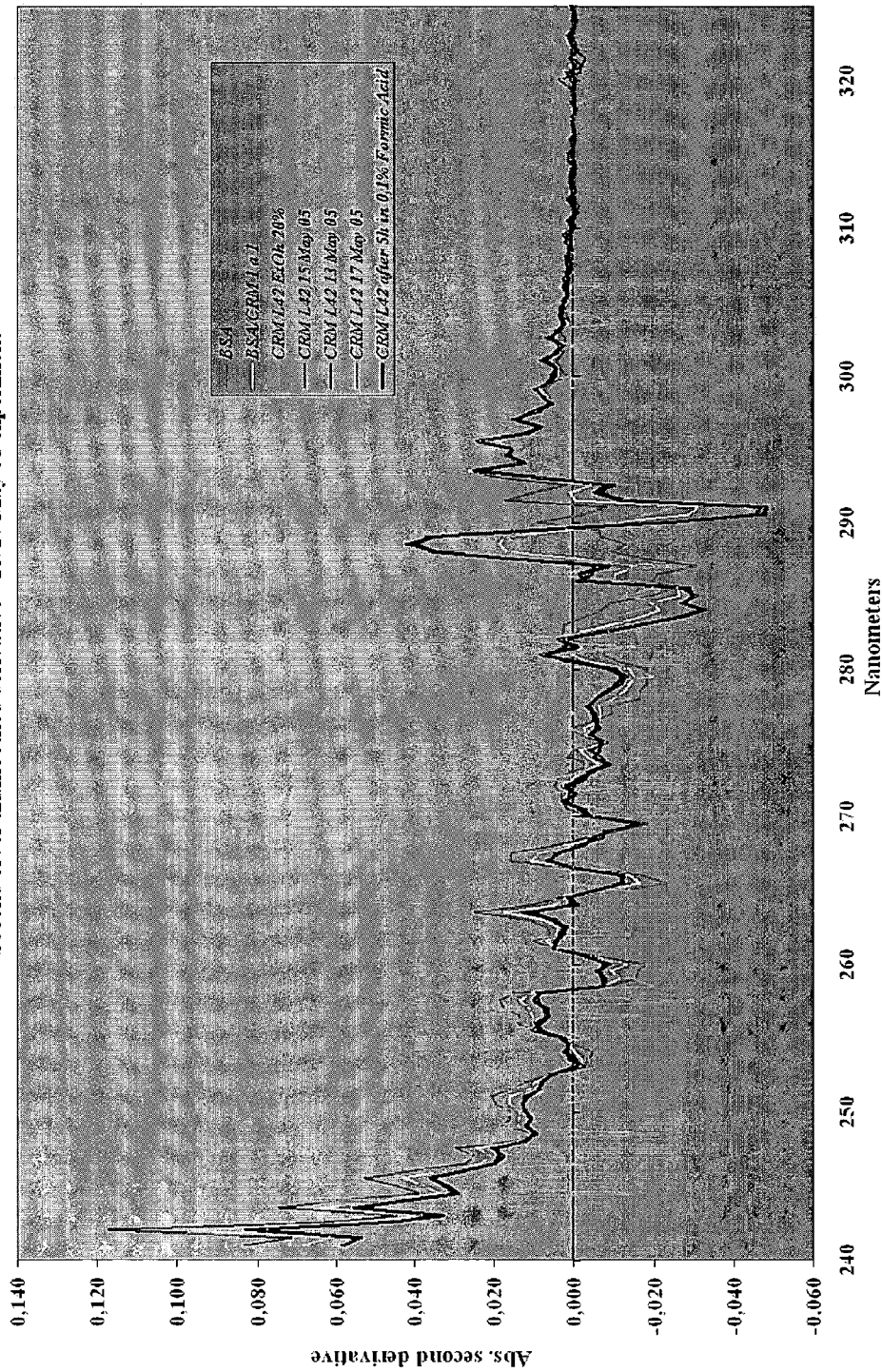
Figure 22D:
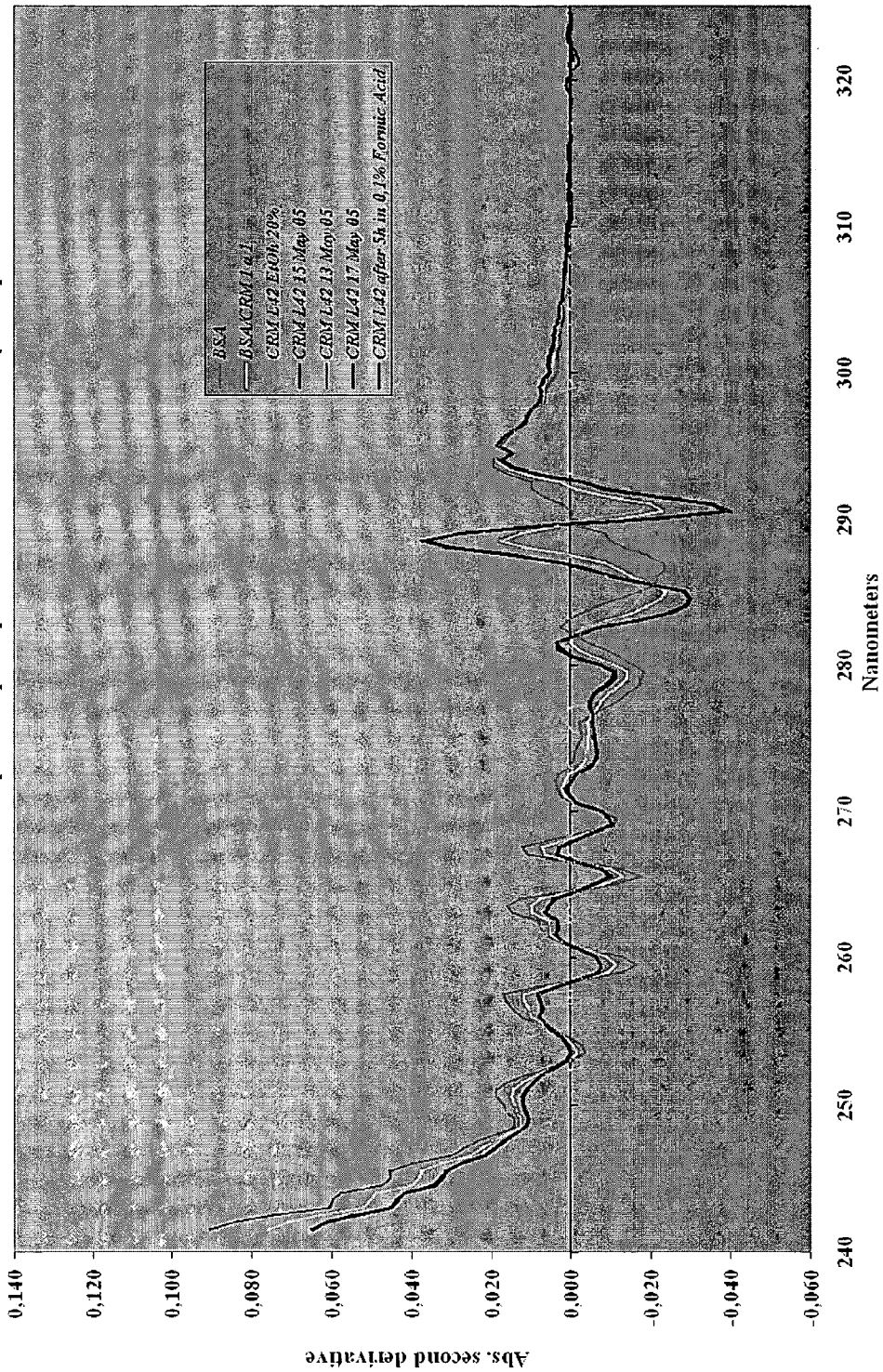
Figure 22E:
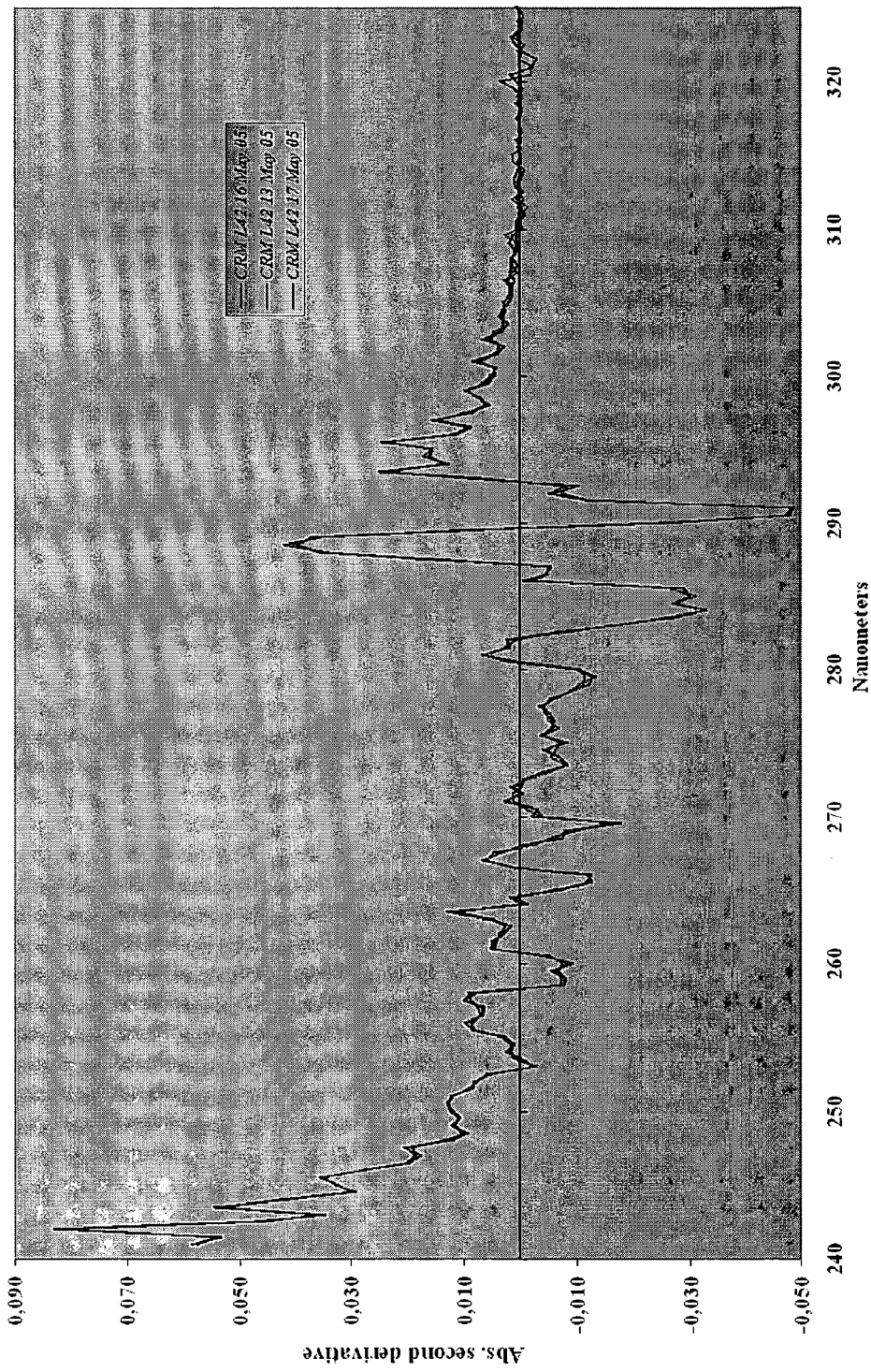
Figure 22F:
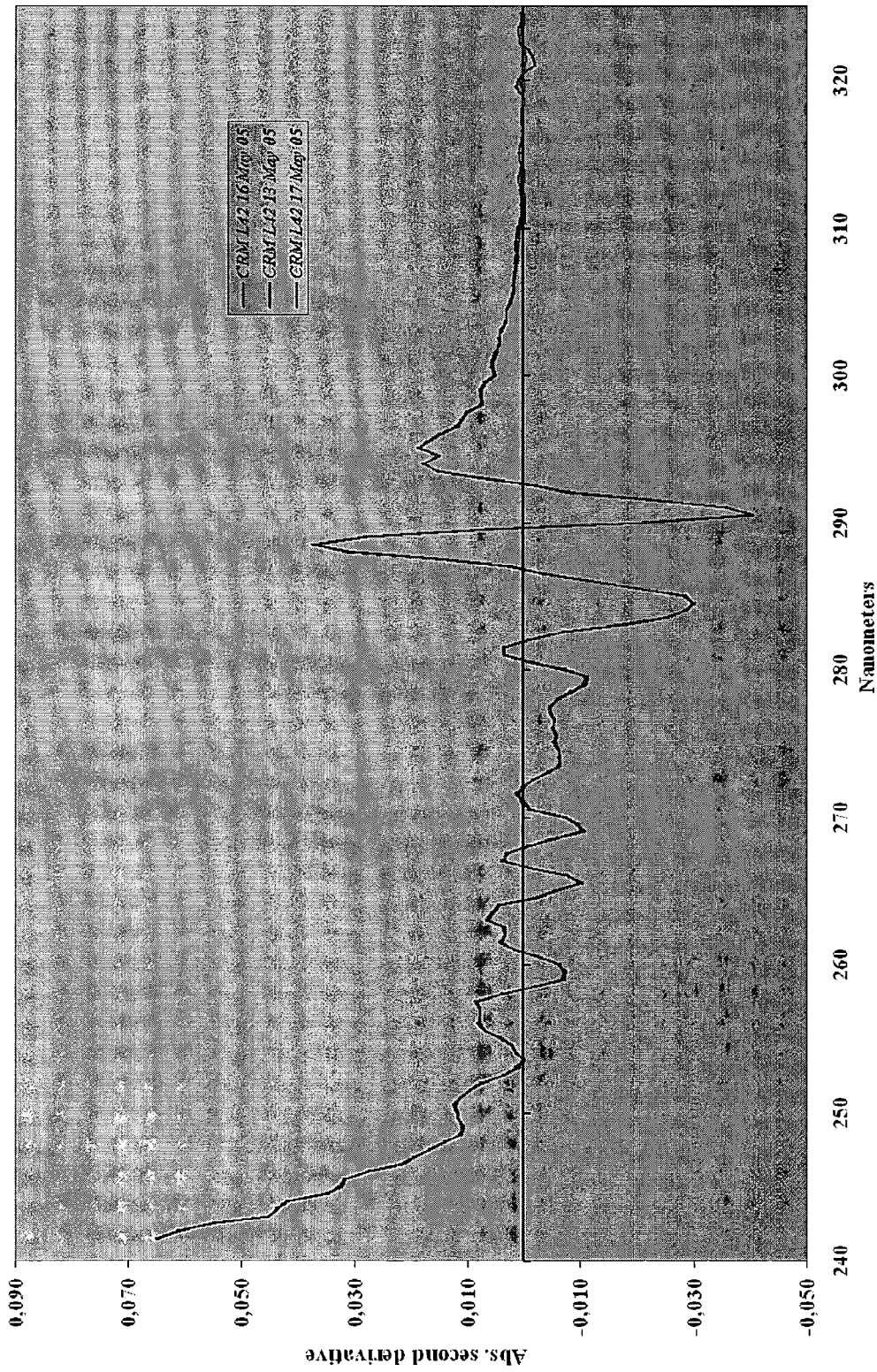

FIG. 22A shows the normalized absorbance spectra. FIG. 22B shows the unsmoothed first order derivative spectra. FIG. 22C shows the unsmoothed second order derivative spectra. FIG. 22D shows the second order derivative spectra after one pass of 3-point quadratic smooth. FIG. 22E shows the unsmoothed second order derivative spectra for the CRM reproducibility experiment. FIG. 22F shows the second order derivative spectra for the CRM reproducibility experiment after one pass of 3-point quadratic smooth.

Figure 23A:
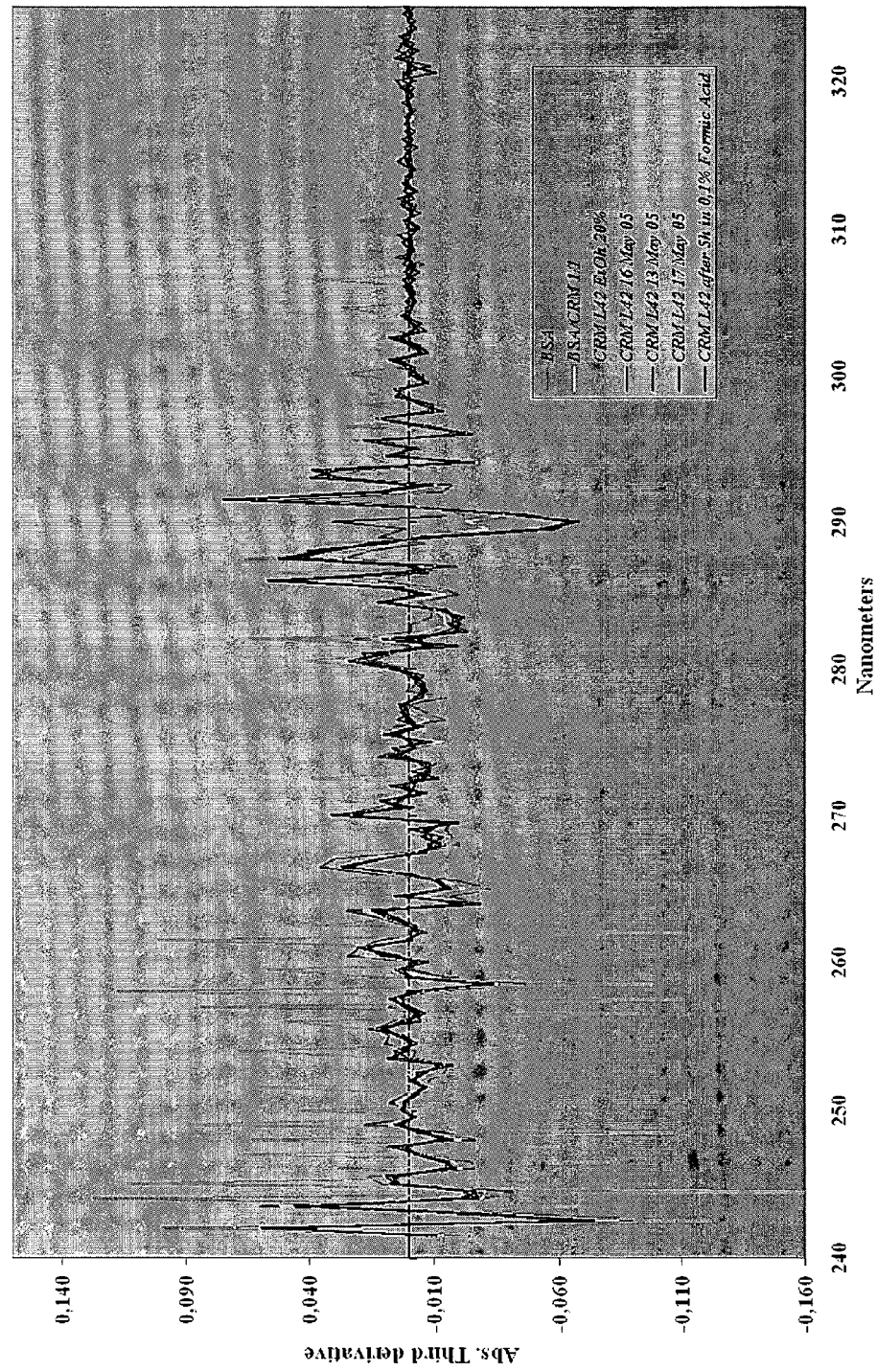
Figure 23B:
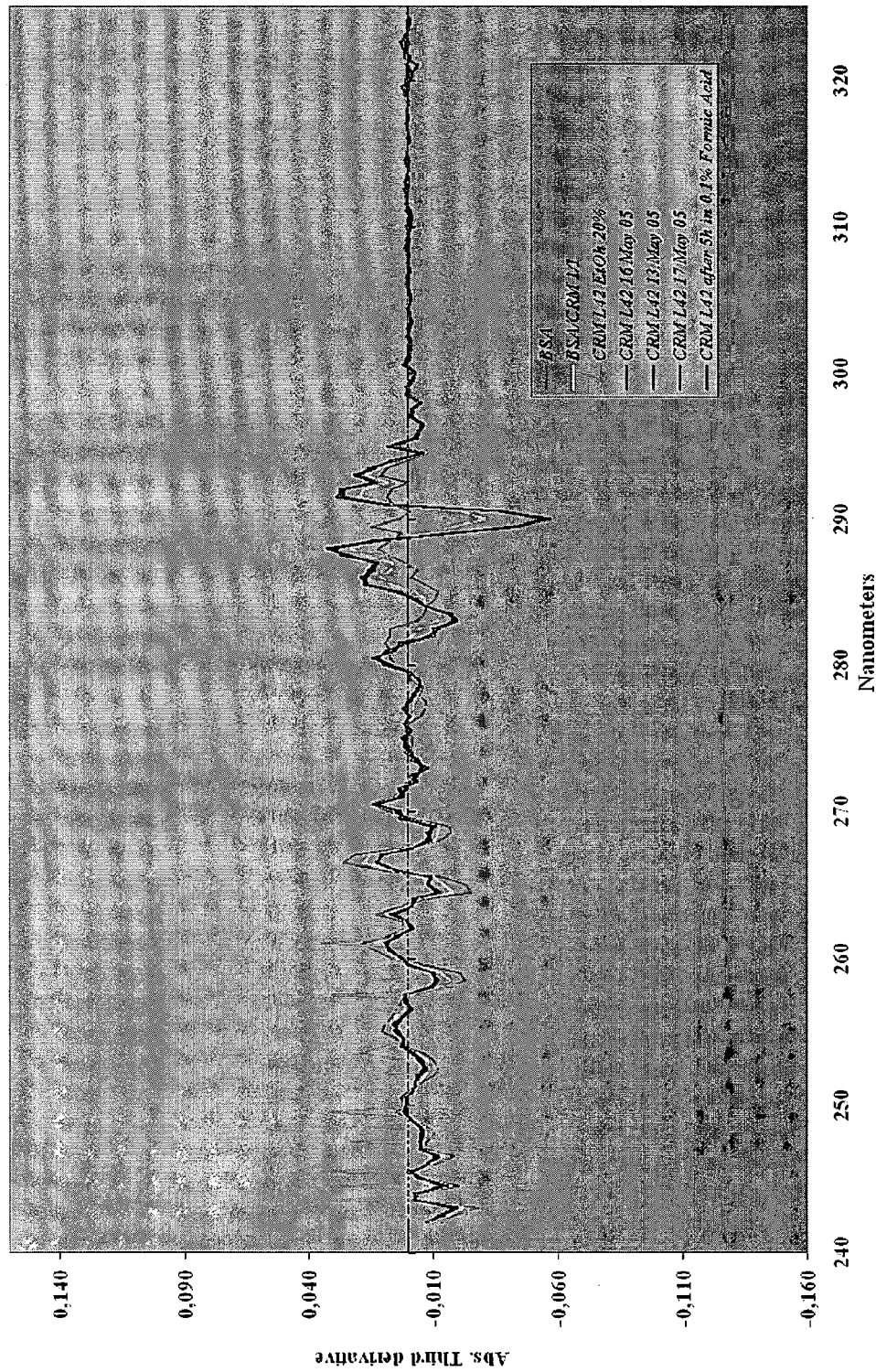
Figure 23C:
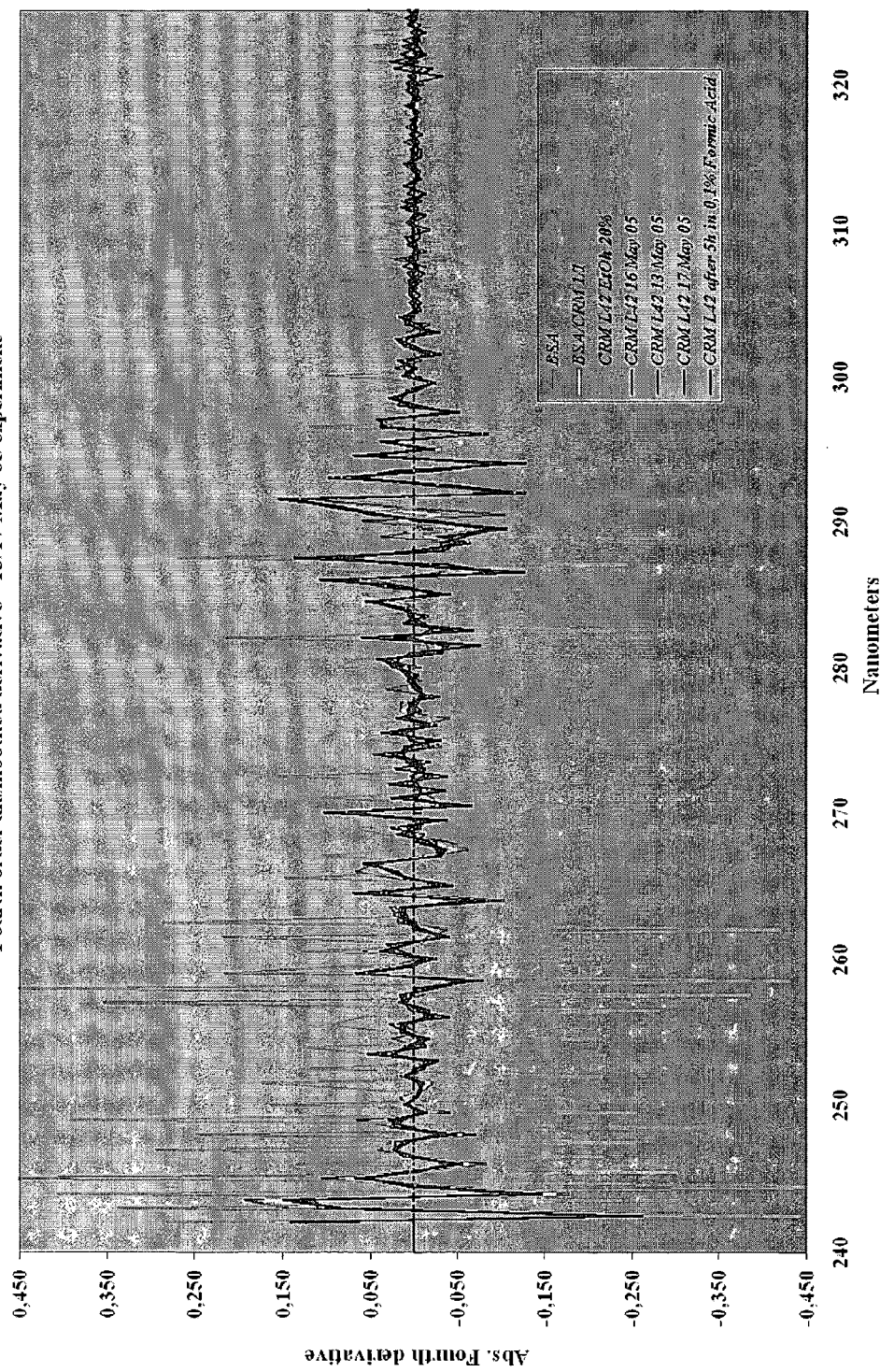
Figure 23D:
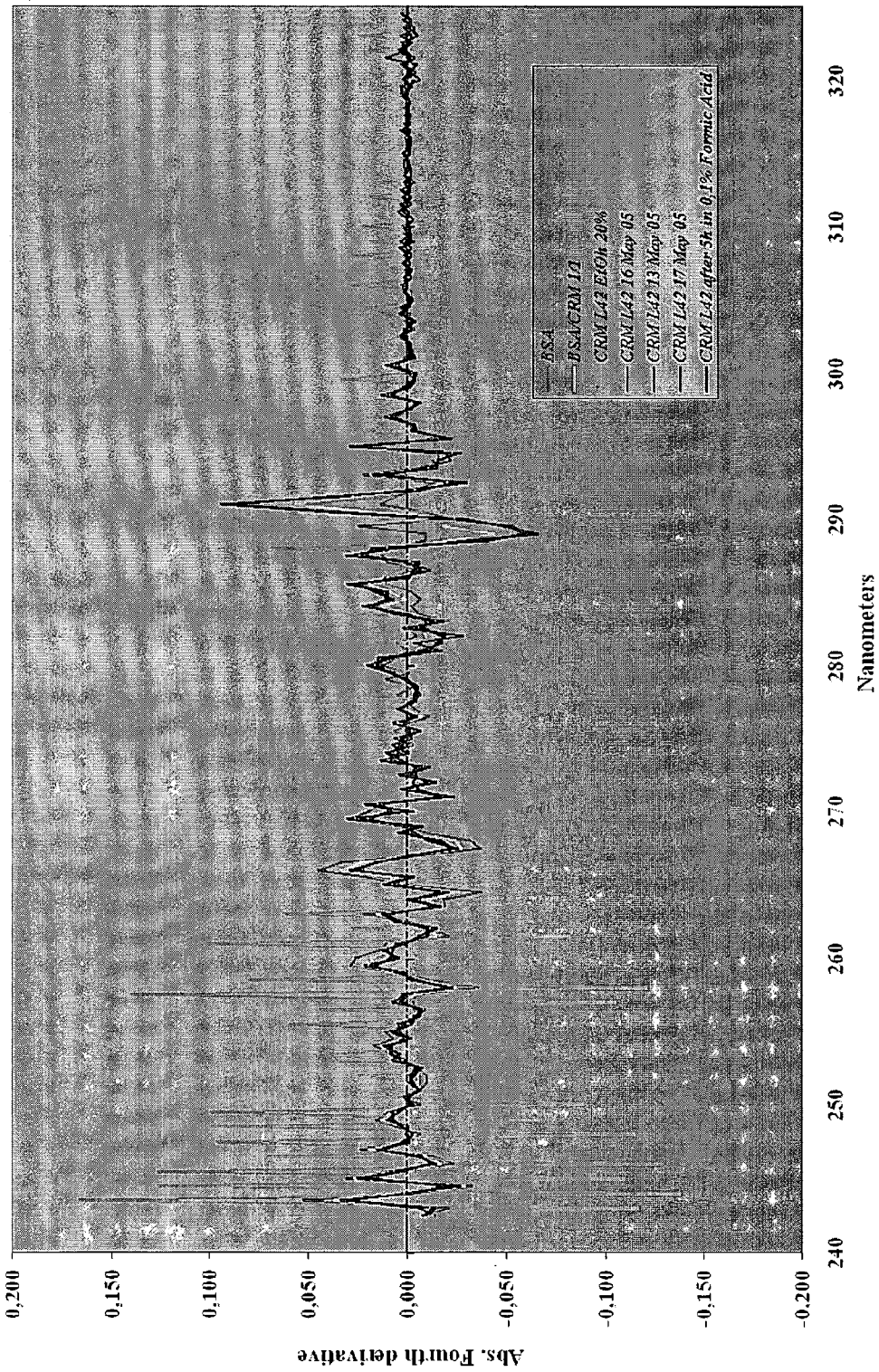
Figure 23E:
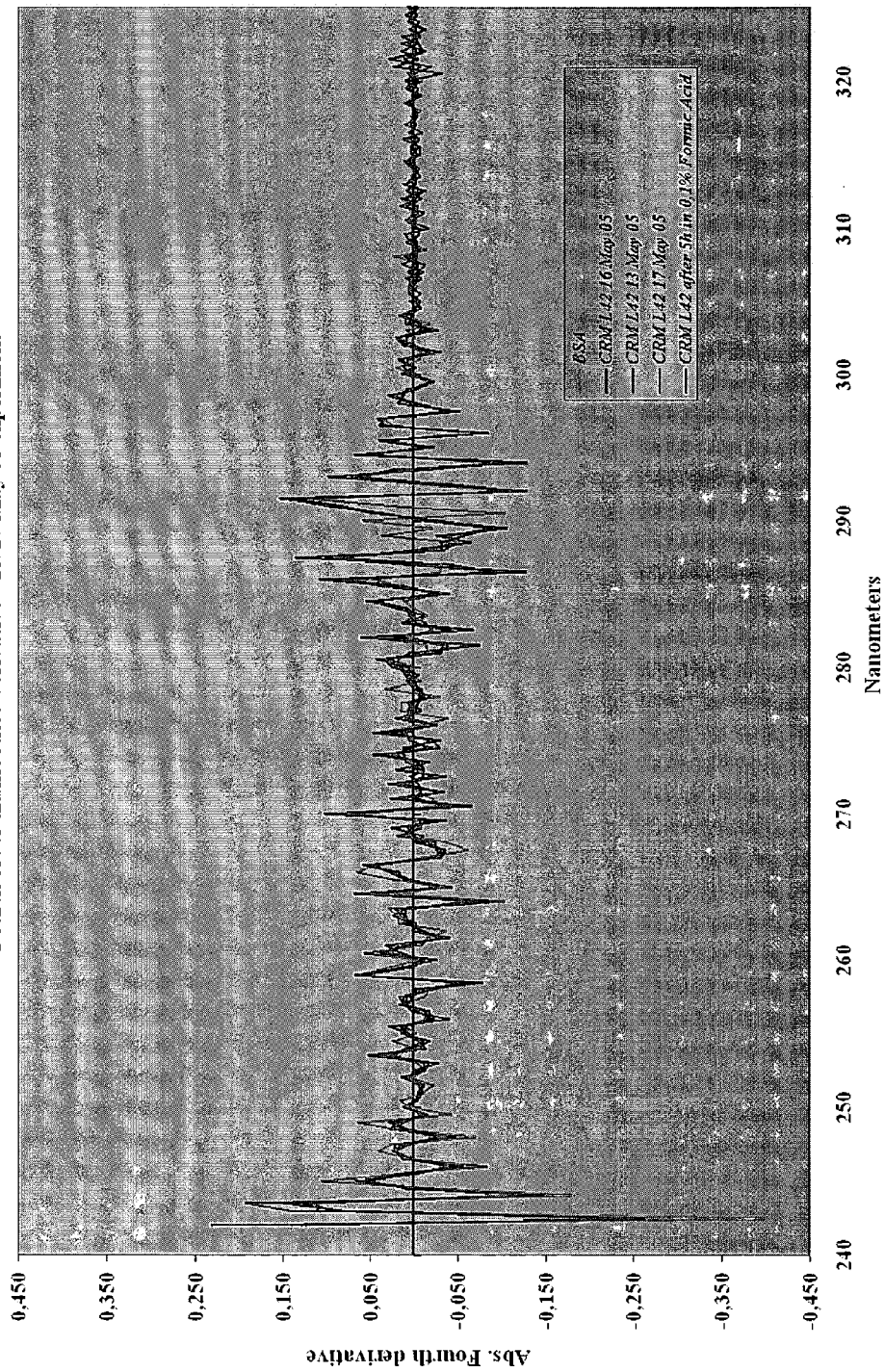
Figure 23F:
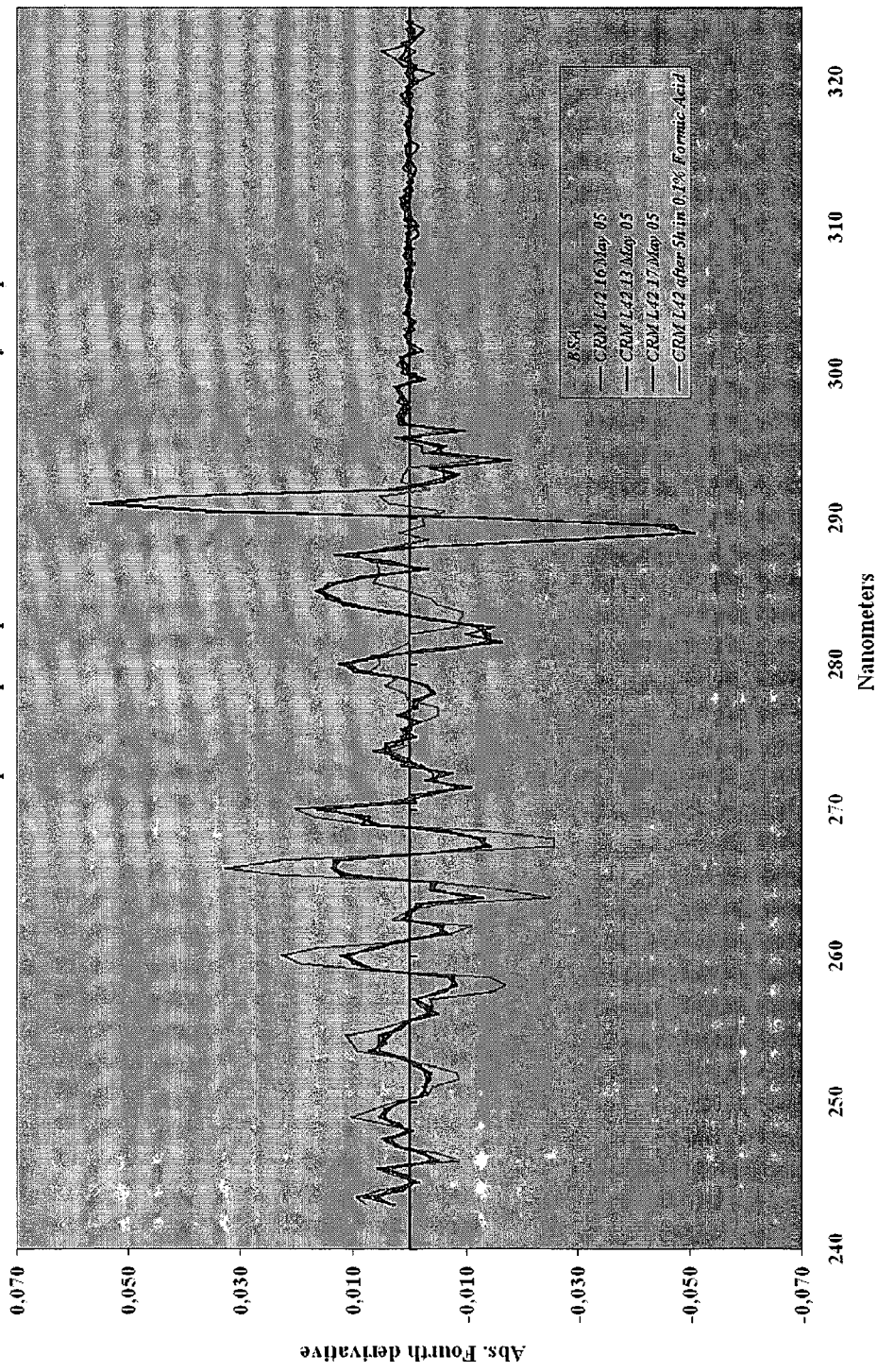

FIG. 23A shows the unsmoothed third order derivative spectra. FIG. 23B shows the third order derivative spectra after one pass of 3-point quadratic smooth. FIG. 23C shows the unsmoothed third order derivative spectra. FIG. 23D shows the fourth order derivative spectra after one pass of 3-point quadratic smooth. FIG. 23E shows the unsmoothed fourth order derivative spectra for the CRM reproducibility experiment. FIG. 23F shows the fourth order derivative spectra for the CRM reproducibility experiment after one pass of 3-point quadratic smooth.

Figure 24A:
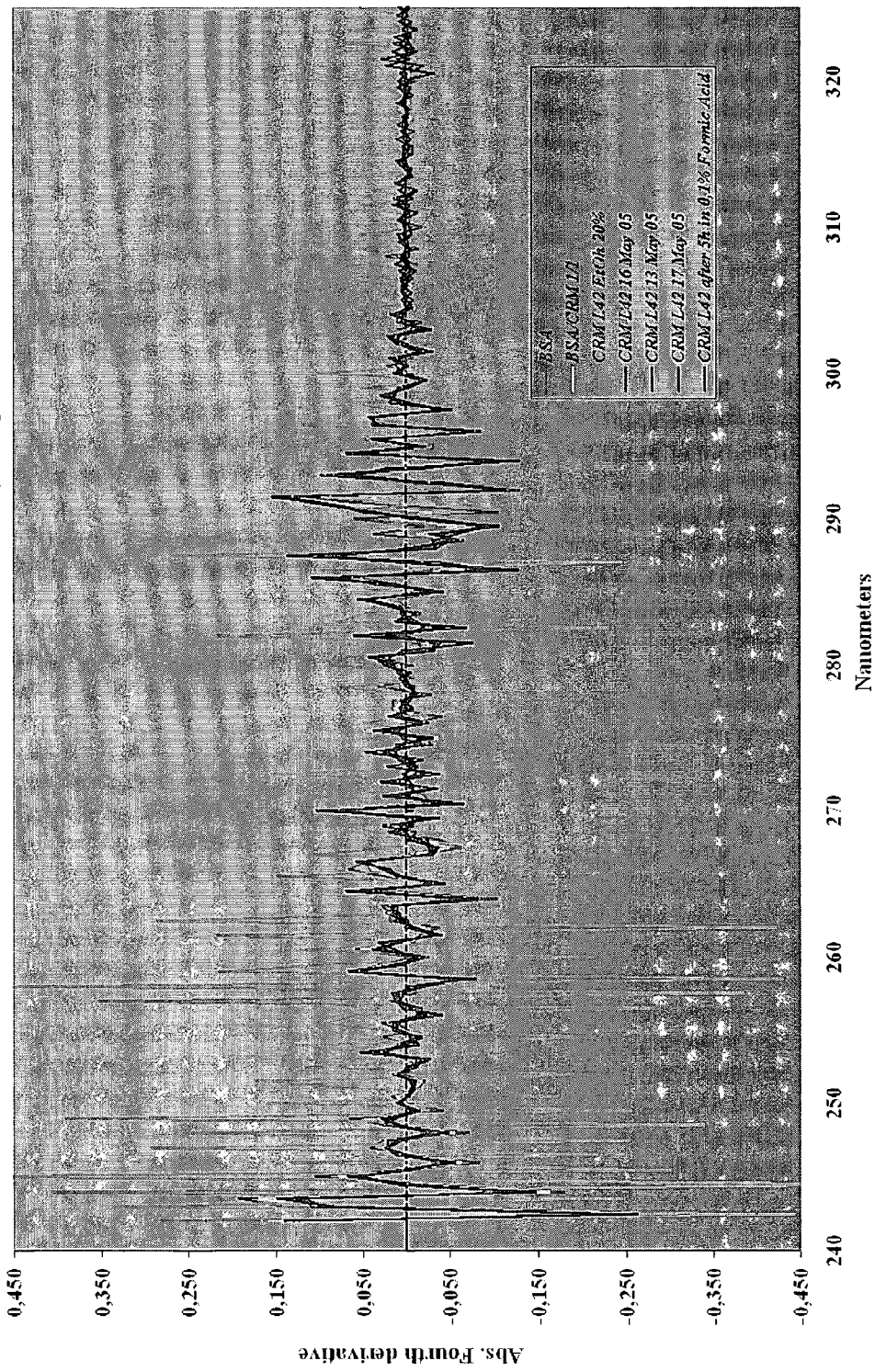
Figure 24B:
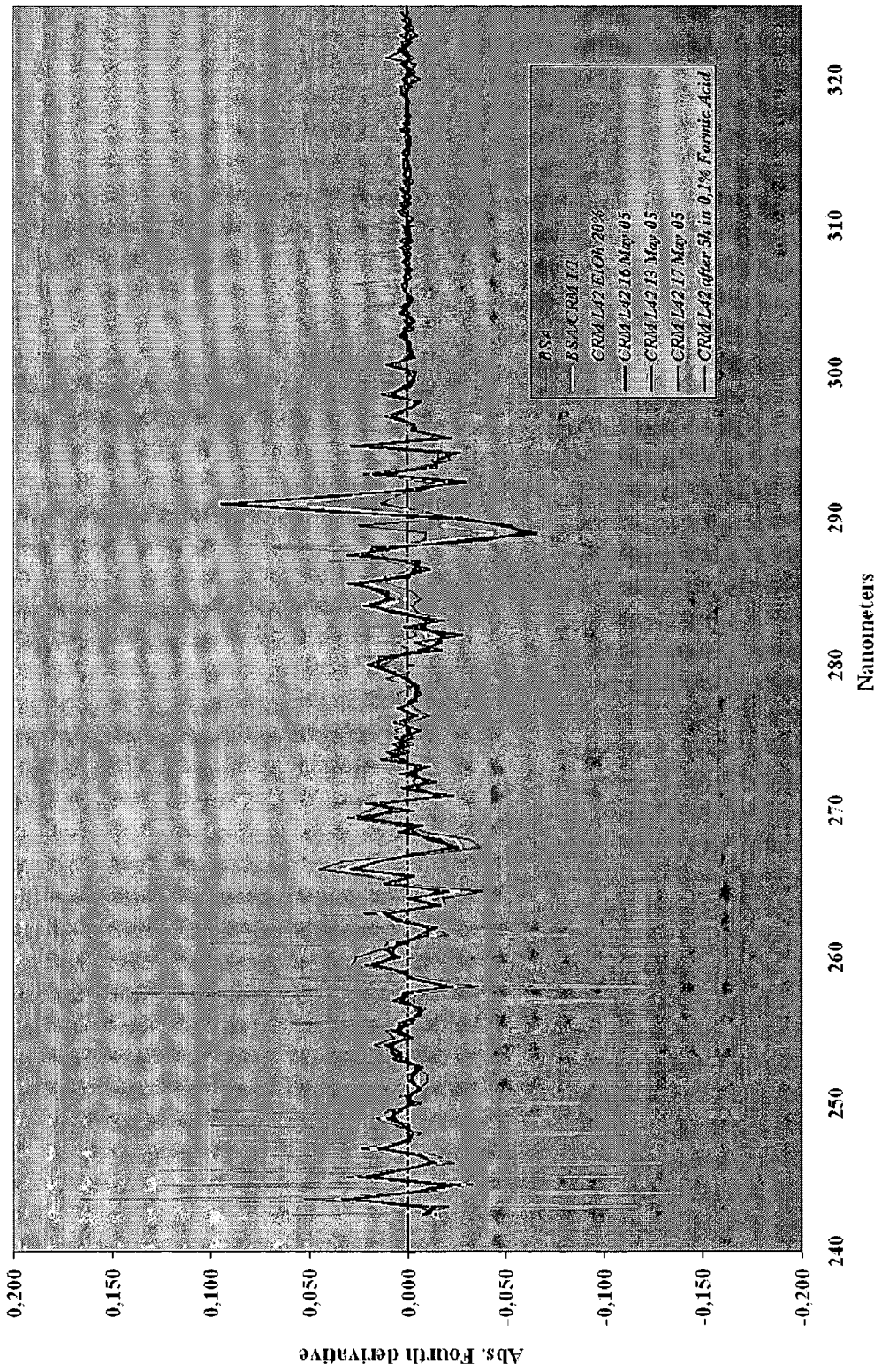
Figure 24C:
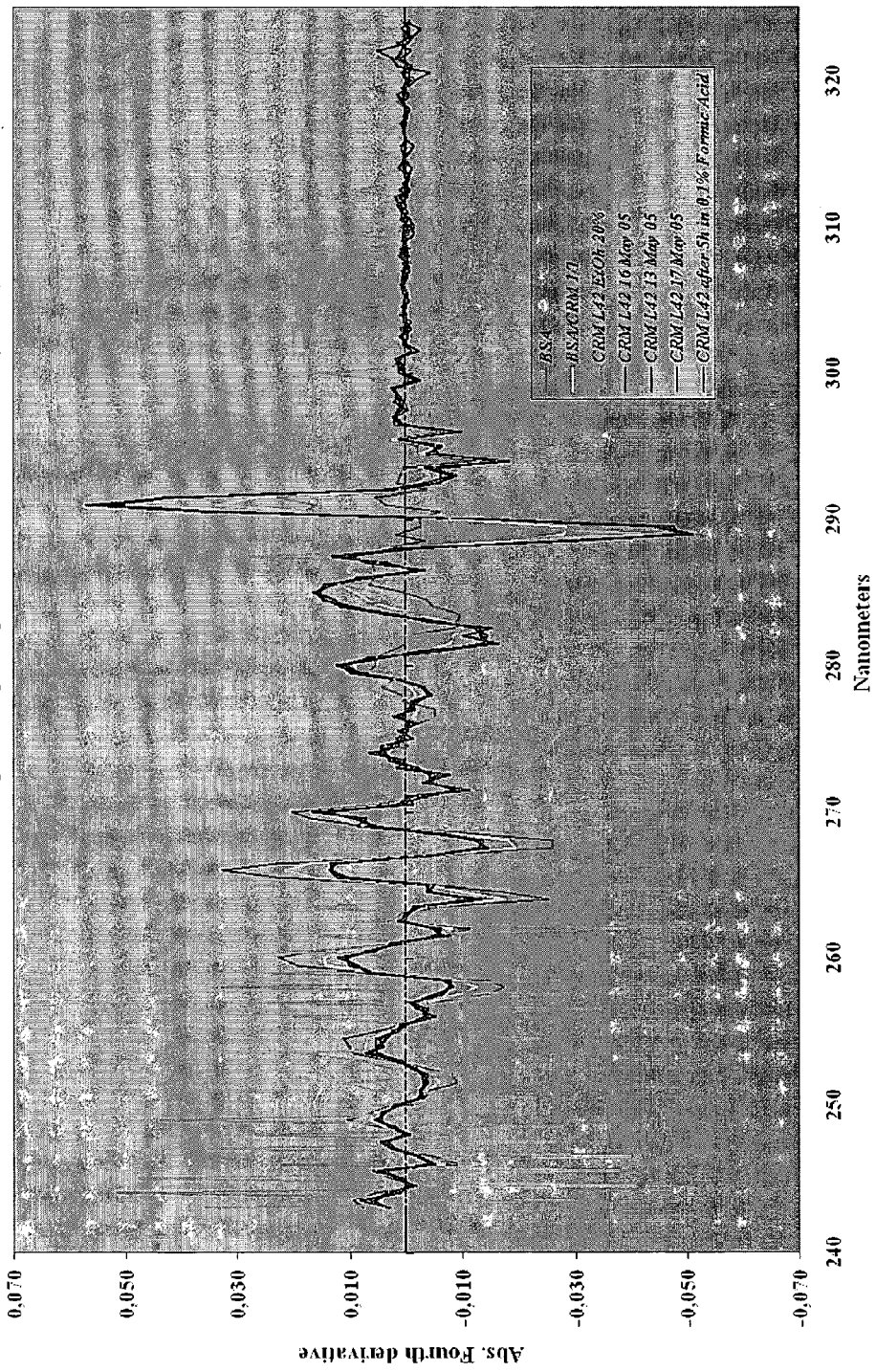
Figure 24D:
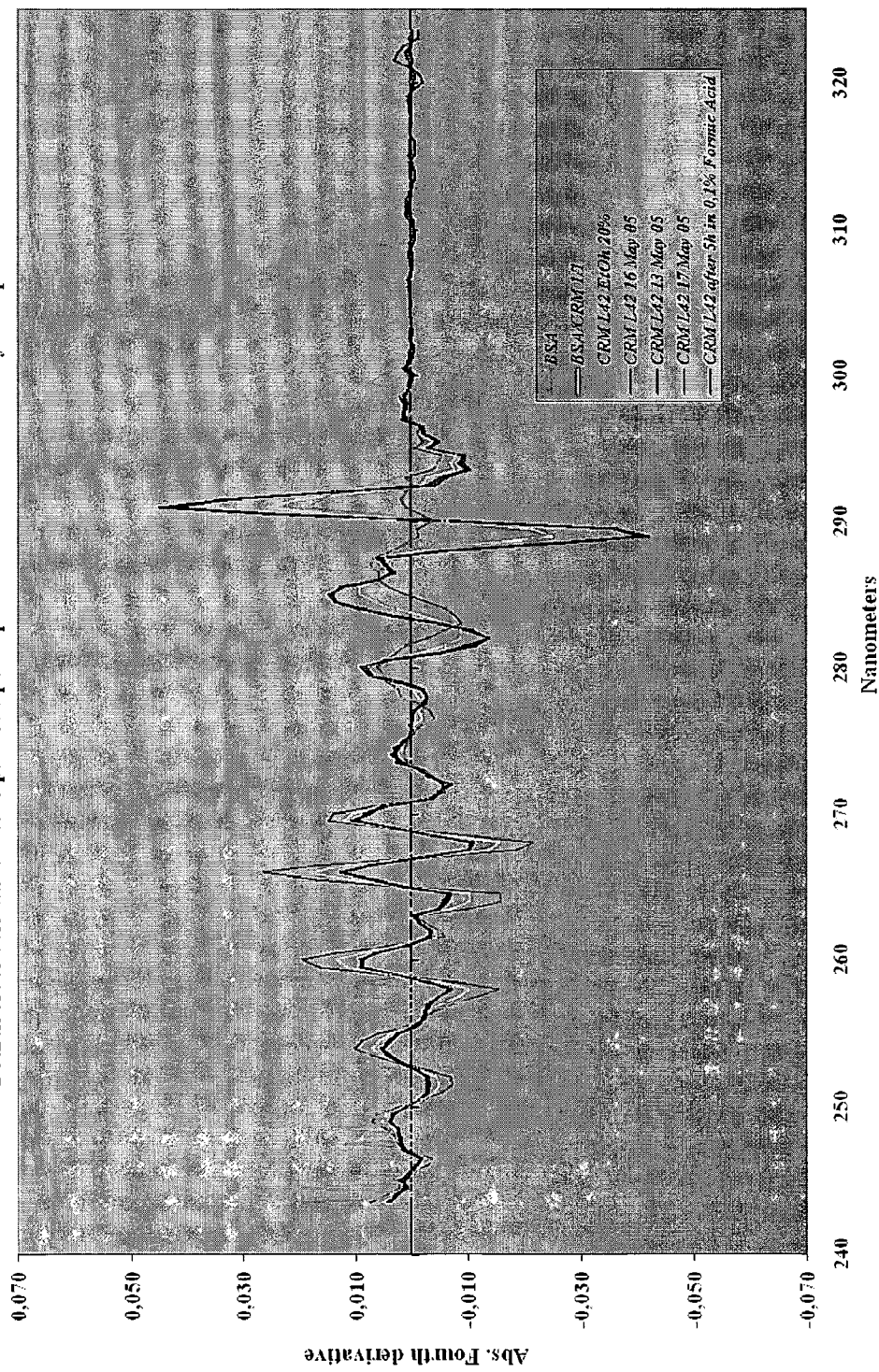

FIG. 24A shows the unsmoothed fourth order derivative spectra. FIG. 24B shows the shows the fourth order derivative spectra after one pass of 3-point quadratic smooth. FIG. 24C shows the shows the fourth order derivative spectra after two passes of 3-point quadratic smooth. FIG. 24D shows the fourth order derivative spectra after three passes of 3-point quadratic smooth.

Figures of Example 2D

FIG. 25 shows the derivative spectra of Nth degree with N−1 passes of a 3-point quadratic smooth. FIG. 25A shows the normalized absorbance spectra of the different CRM lots. FIG. 25B shows the underivatized and second derivative enhanced spectra for lot 42. FIG. 25C shows the unsmoothed first derivative spectra. FIG. 25D shows the second order derivative after 1 pass of a 3-point quadratic smooth. FIG. 25E shows the third order derivative after 2 passes of a 3-point quadratic smooth. FIG. 25F shows the fourth order derivative after 3 passes of a 4-point quadratic smooth.

FIG. 26 shows derivative spectra of Nth degree before and after (N−1) passes of a 3-point quadratic smoothing. The highlighted box in red shows the spectral zone where little differences emerged between TRUN06 and other CRM lots. FIG. 26A shows the unsmoothed second order derivative while FIG. 26B shows the second order derivative after 1 pass of a 3-point quadratic smooth. FIG. 26C shows the unsmoothed third order derivative while FIG. 26D shows the third order derivative after 2 passes of a 3-point quadratic smooth. FIG. 26E shows the unsmoothed fourth order derivative while FIG. 26F shows the fourth order derivative after 3 passes of a 3-point quadratic smooth.

Figures of Example 3

Figure 27A:
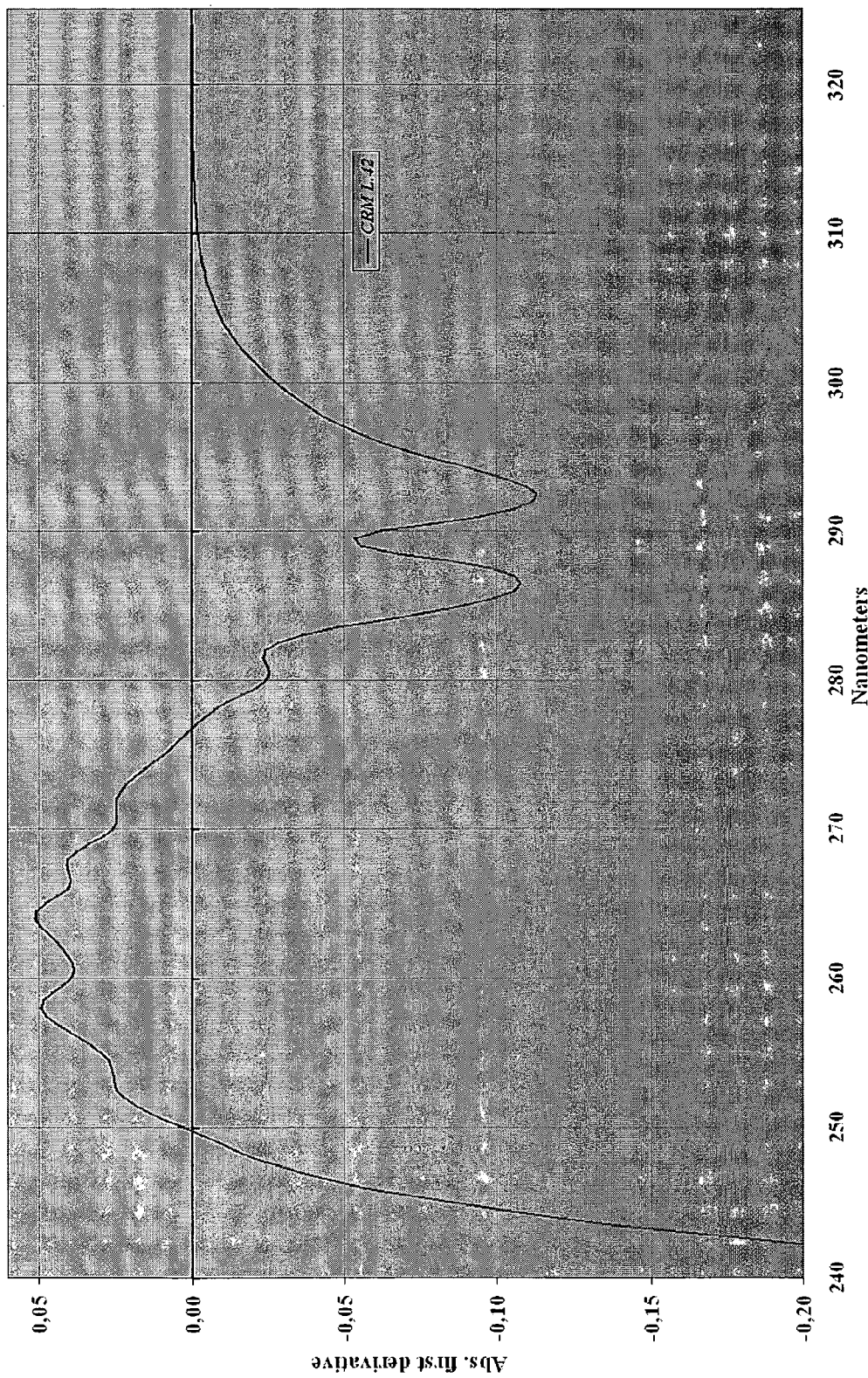
Figure 27B:
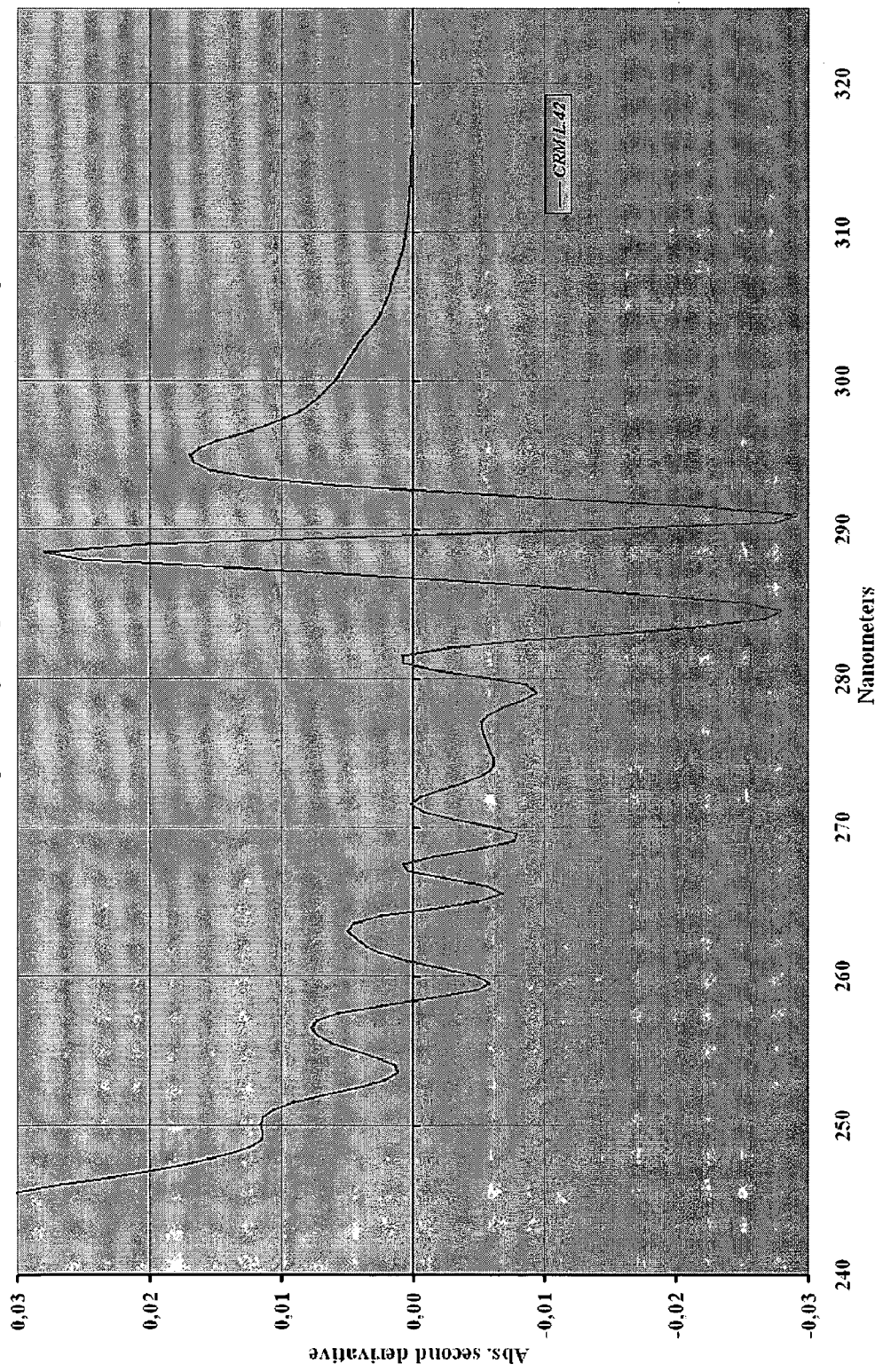
Figure 27C:
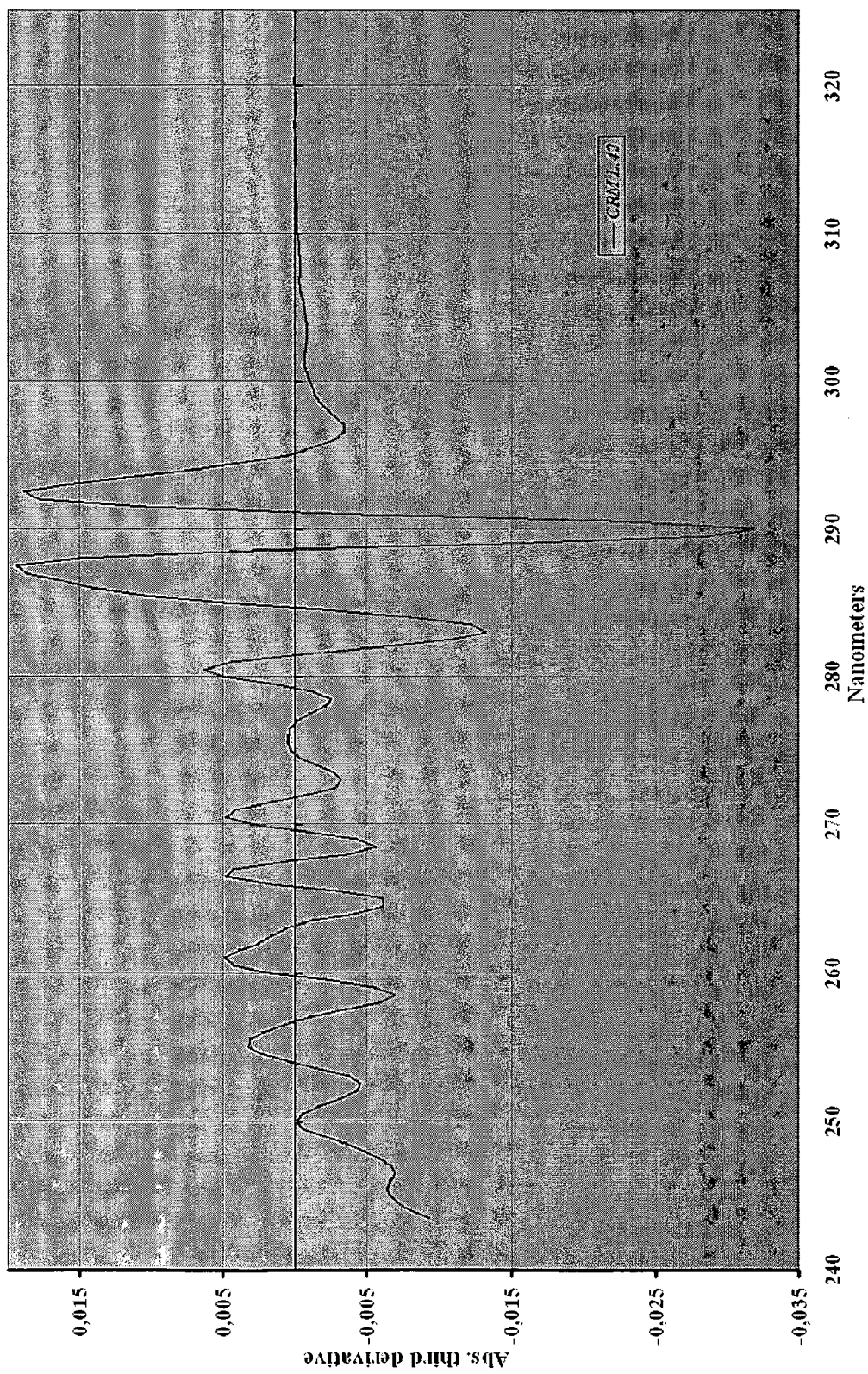
Figure 27D:
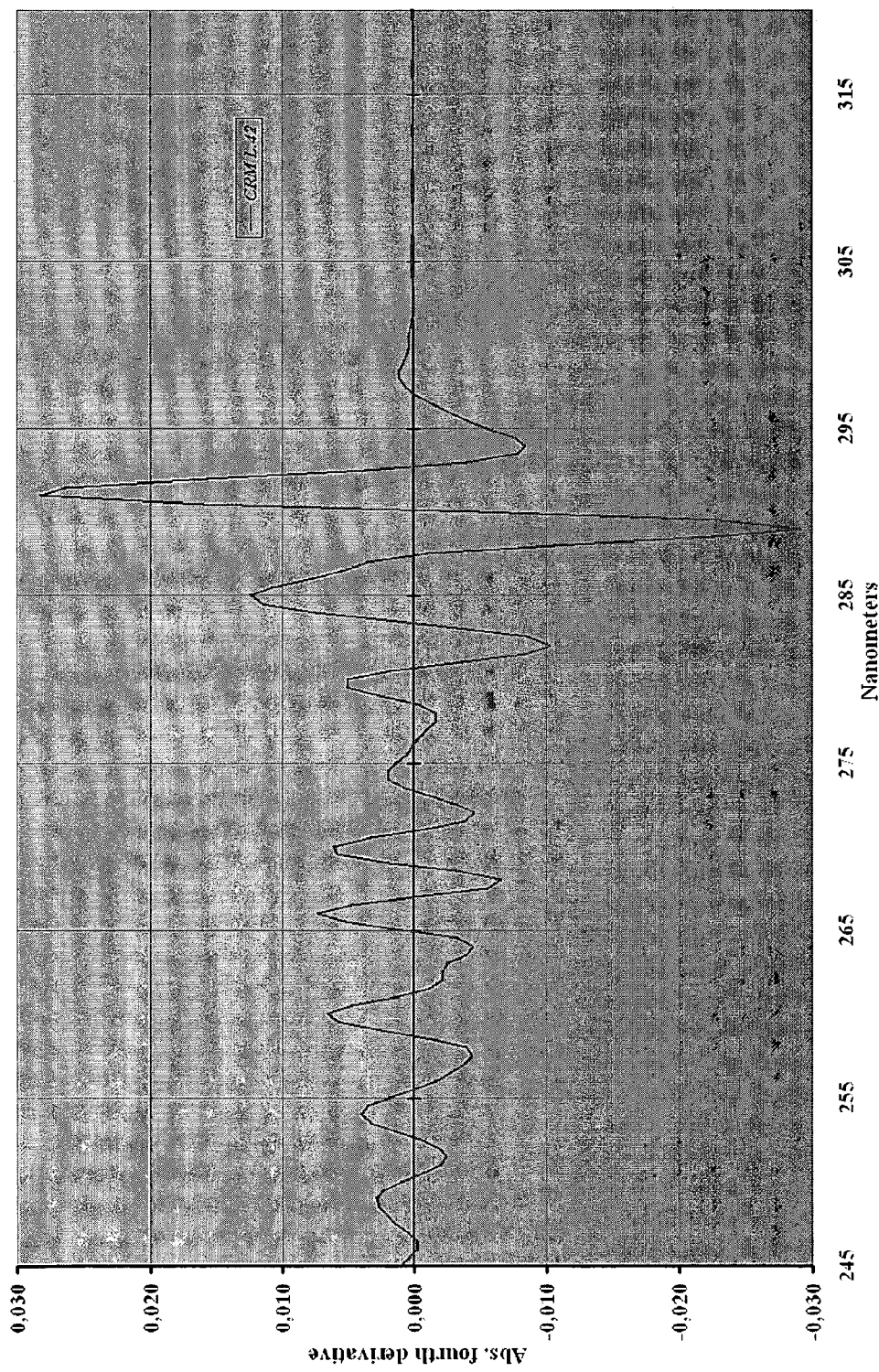

FIG. 27A shows the first order derivative spectra for lot 42 after 2 passes of a 3 point quadratic smooth. FIG. 27B shows the second order derivative spectra for lot 42 after 3 passes of a 3 point quadratic smooth. FIG. 27C shows the third order derivative spectra for lot 42 after 4 passes of a 3 point quadratic smooth. FIG. 27D shows the fourth order derivative spectra for lot 42 after 5 passes of a 3 point quadratic smooth.

Figure 28:
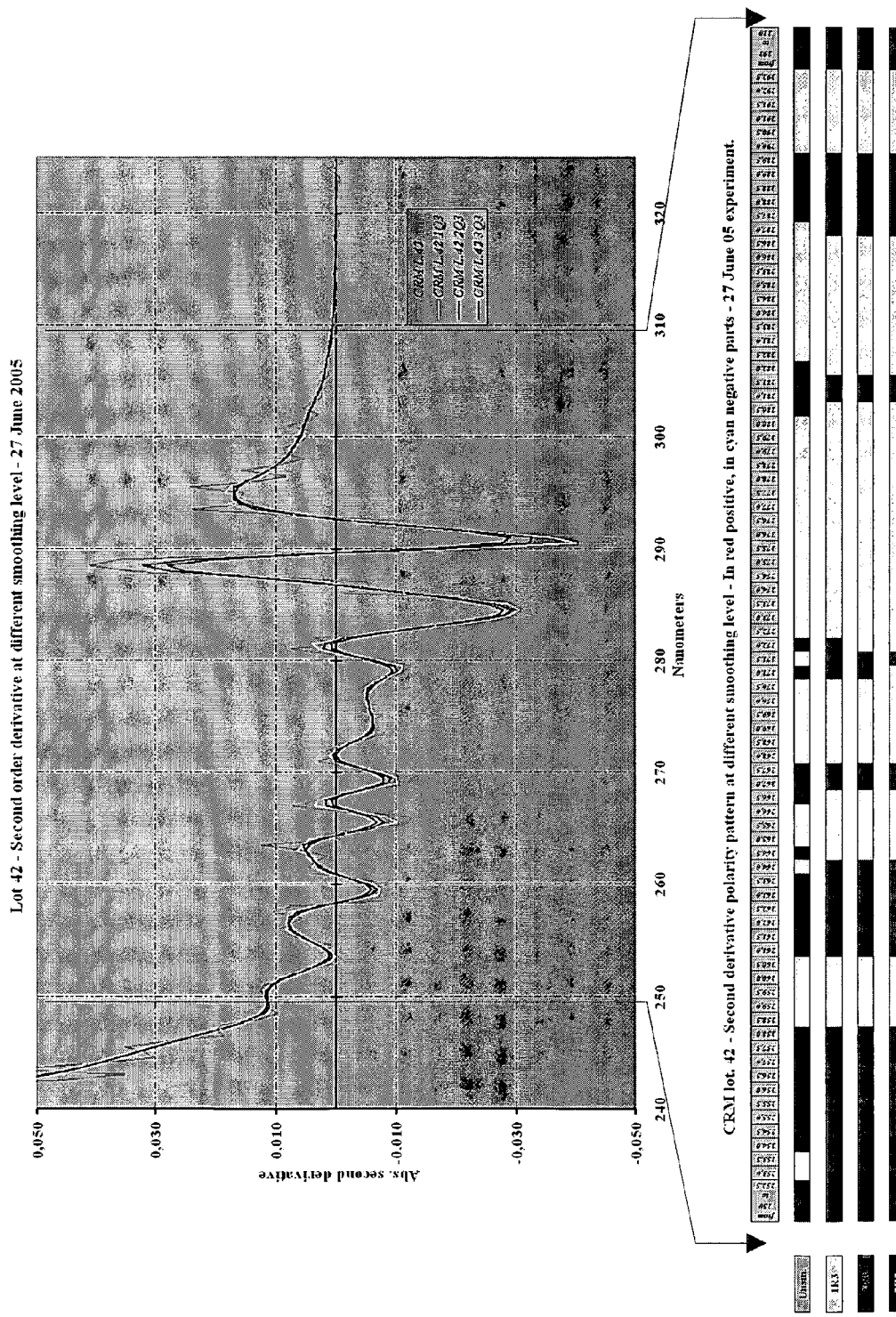

FIG. 28 shows a smoothing progress on second order derivative spectra for CRM lot 42 and its positive (in red) or negative (in cyan) polarity revealing the concavity pattern of the absorbance spectrum.

Figure 29:
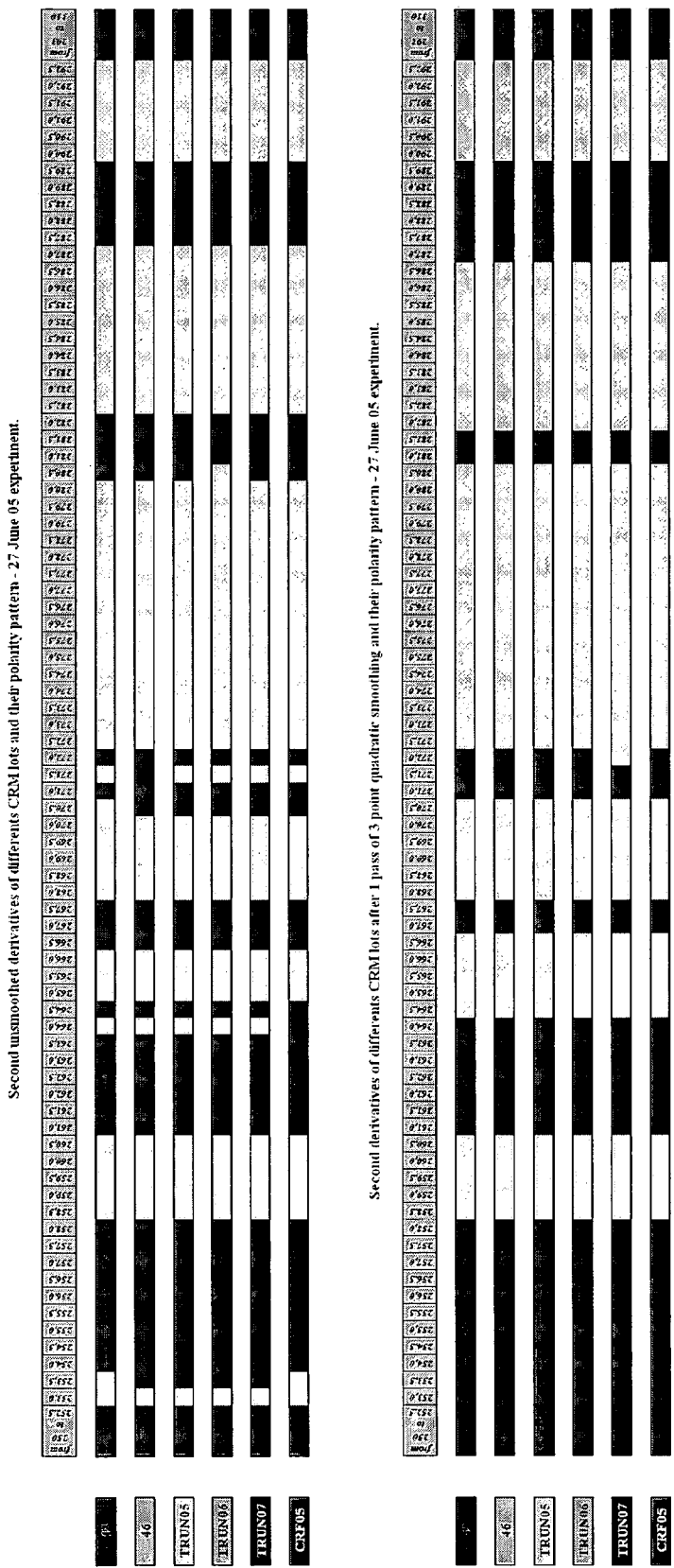
Figure 29:
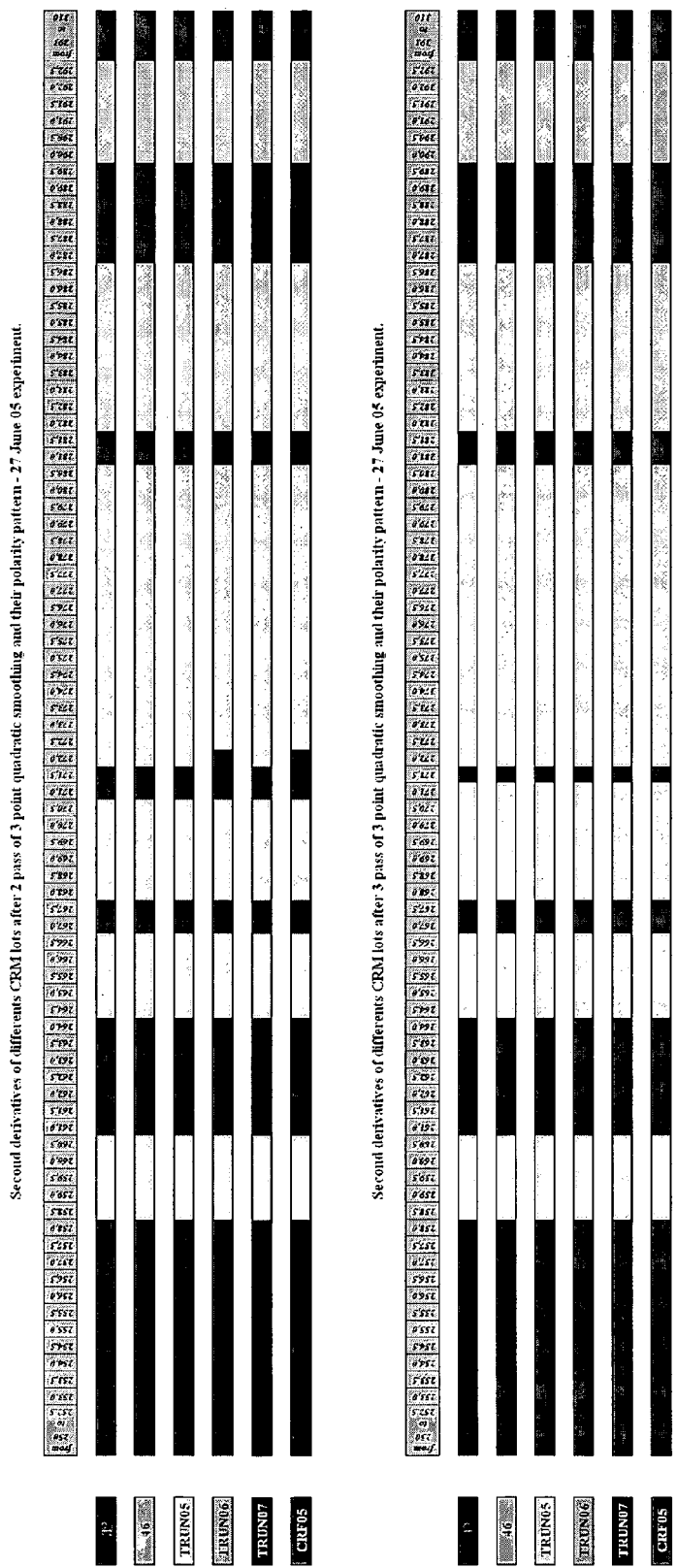

FIG. 29 shows a comparison of the concavity patterns of CRM absorbance spectra via analysis of second derivative polarity at different smoothing levels.

FIG. 30 shows a comparison of a wider (245-310 nm) absorbance concavity pattern (via second derivative analysis) between different samples containing CRM, BSA and other chemical agents after different smoothing levels.

Figure 31:
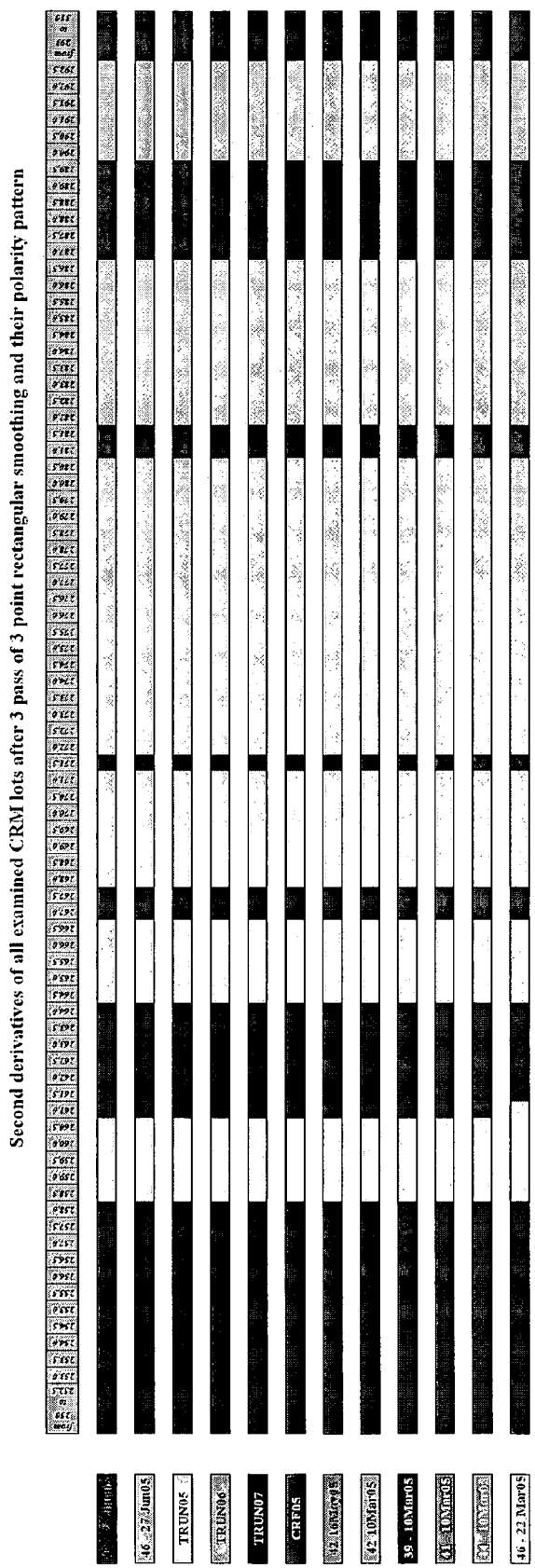

FIG. 31 probes the CRM signature against all the lots of CRM analyzed, merging data from Example 2B (the unoptimized method, with noisy autozero and low day to day reproducibility) and Example 2D (the optimized method).

Figure 32:
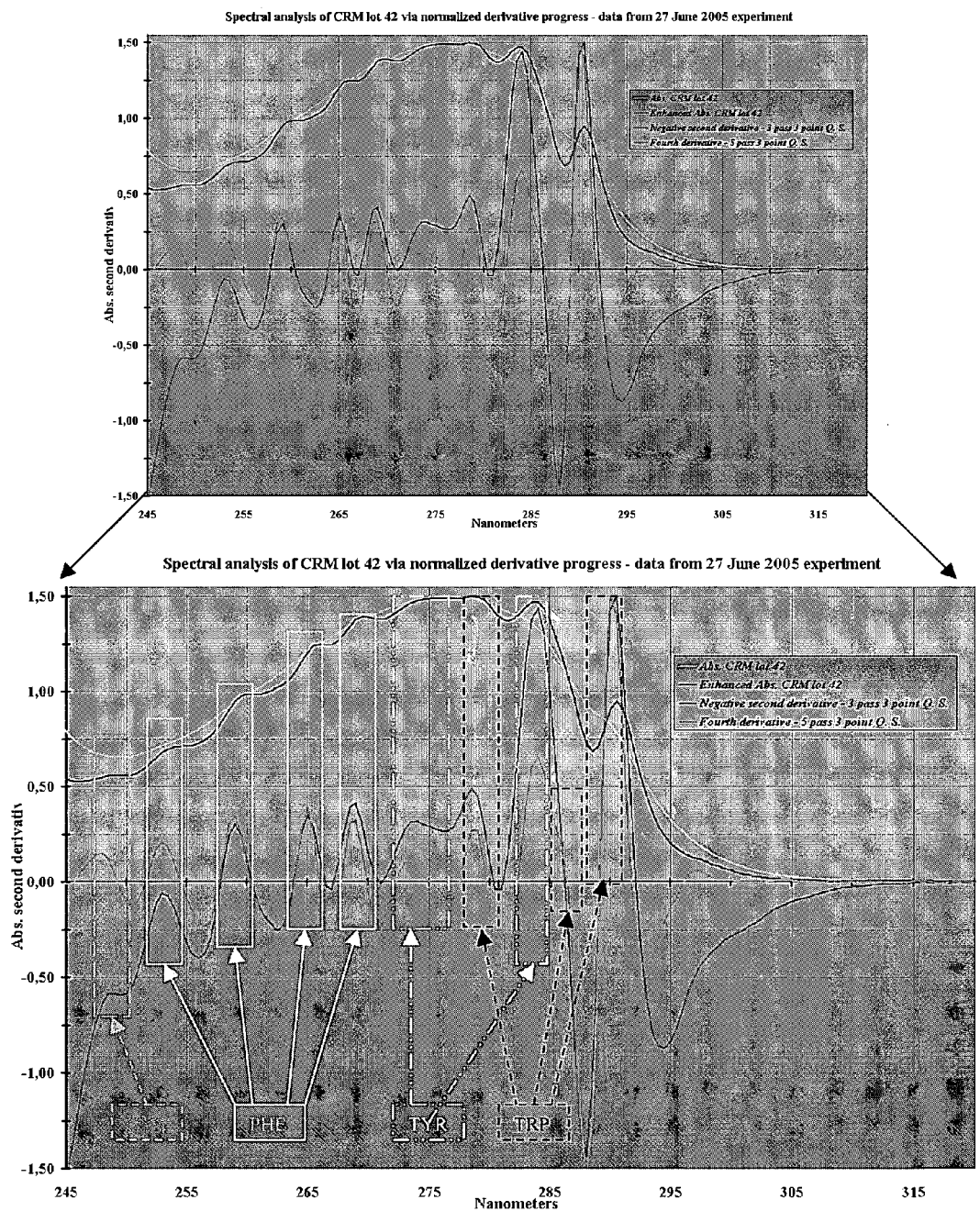

FIG. 32 shows, together in one figure, the original spectrum, the negative of the second derivative spectrum, the enhanced spectrum, and the fourth derivative spectrum for CRM.

Figure 33:
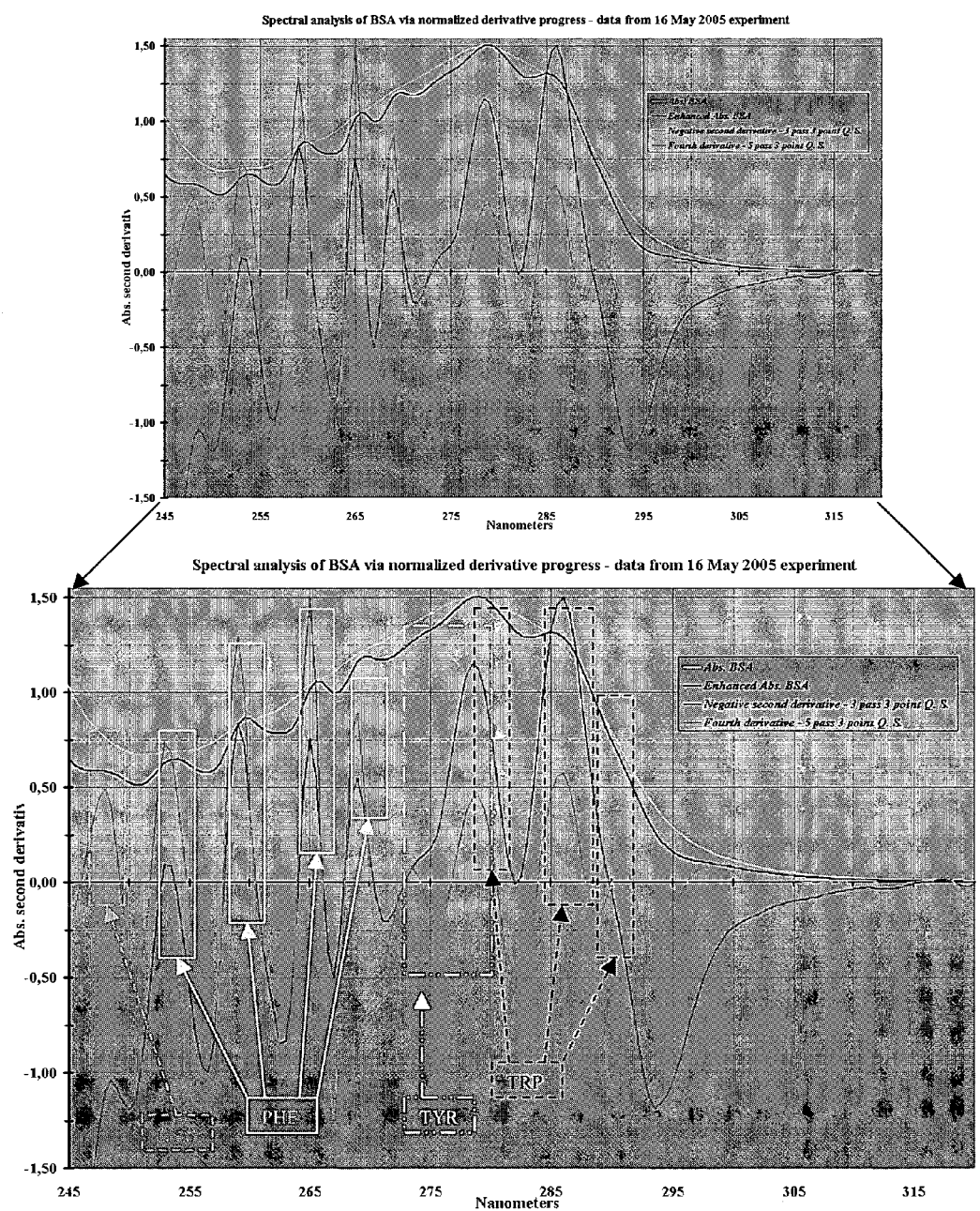

FIG. 33 shows, together in one figure, the original spectrum, the negative of the second derivative spectrum, the enhanced spectrum, and the fourth derivative spectrum for BSA.

Fluorescence Spectroscopy

Figures of Example 4

FIG. 34 shows the 287-953 chimera protein primary sequence.

Figure 35:
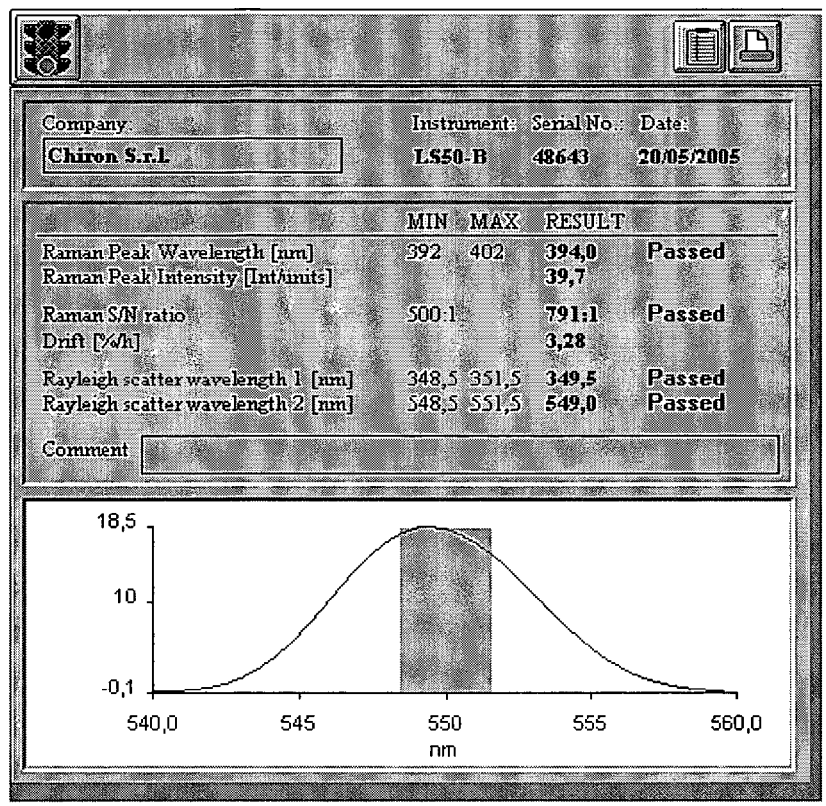

FIG. 35 shows a validation screen from the validation routine of spectrometer software.

Figure 36:
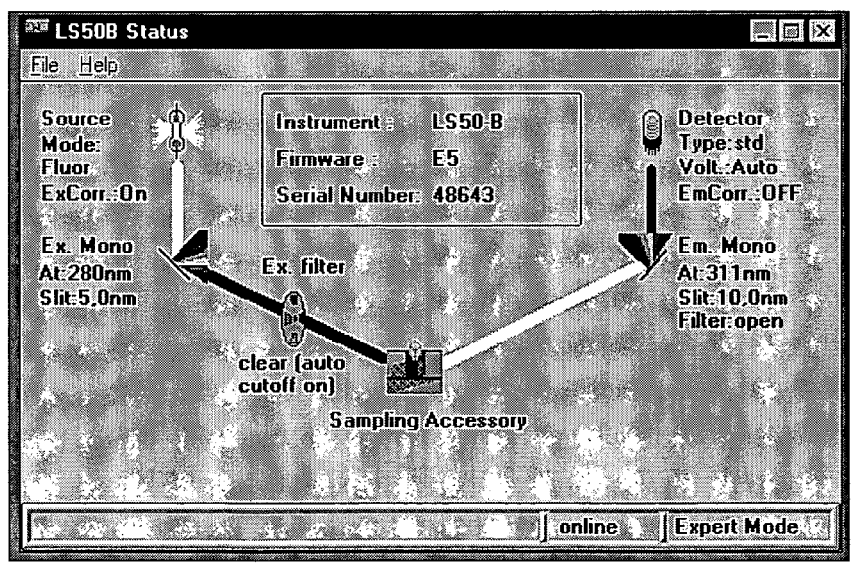
Figure 37:
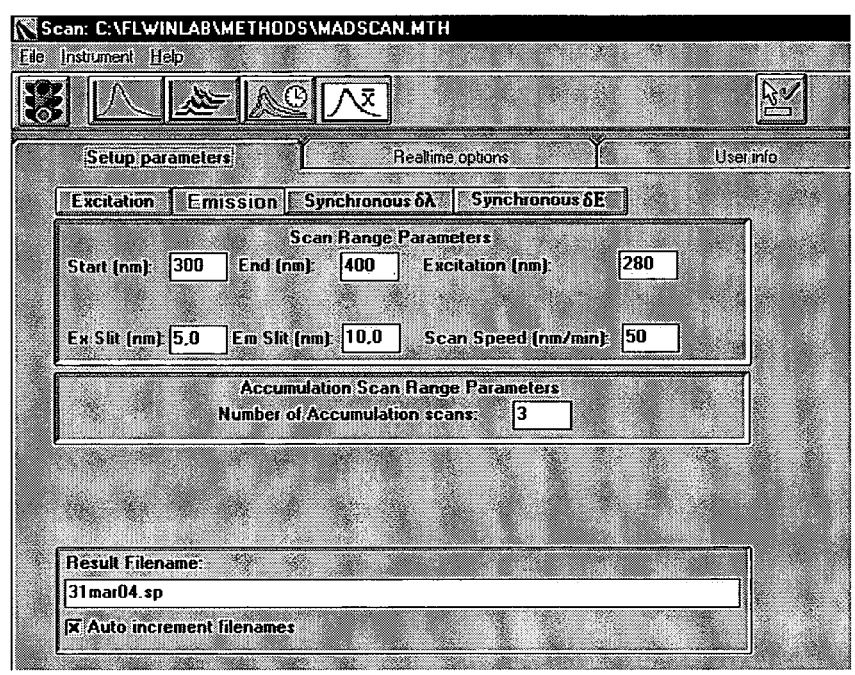

FIG. 36 shows the spectrometer configuration and FIG. 37 shows the method settings for excitation at 280 and 295 nm.

1 Example 4A

Figure 38:
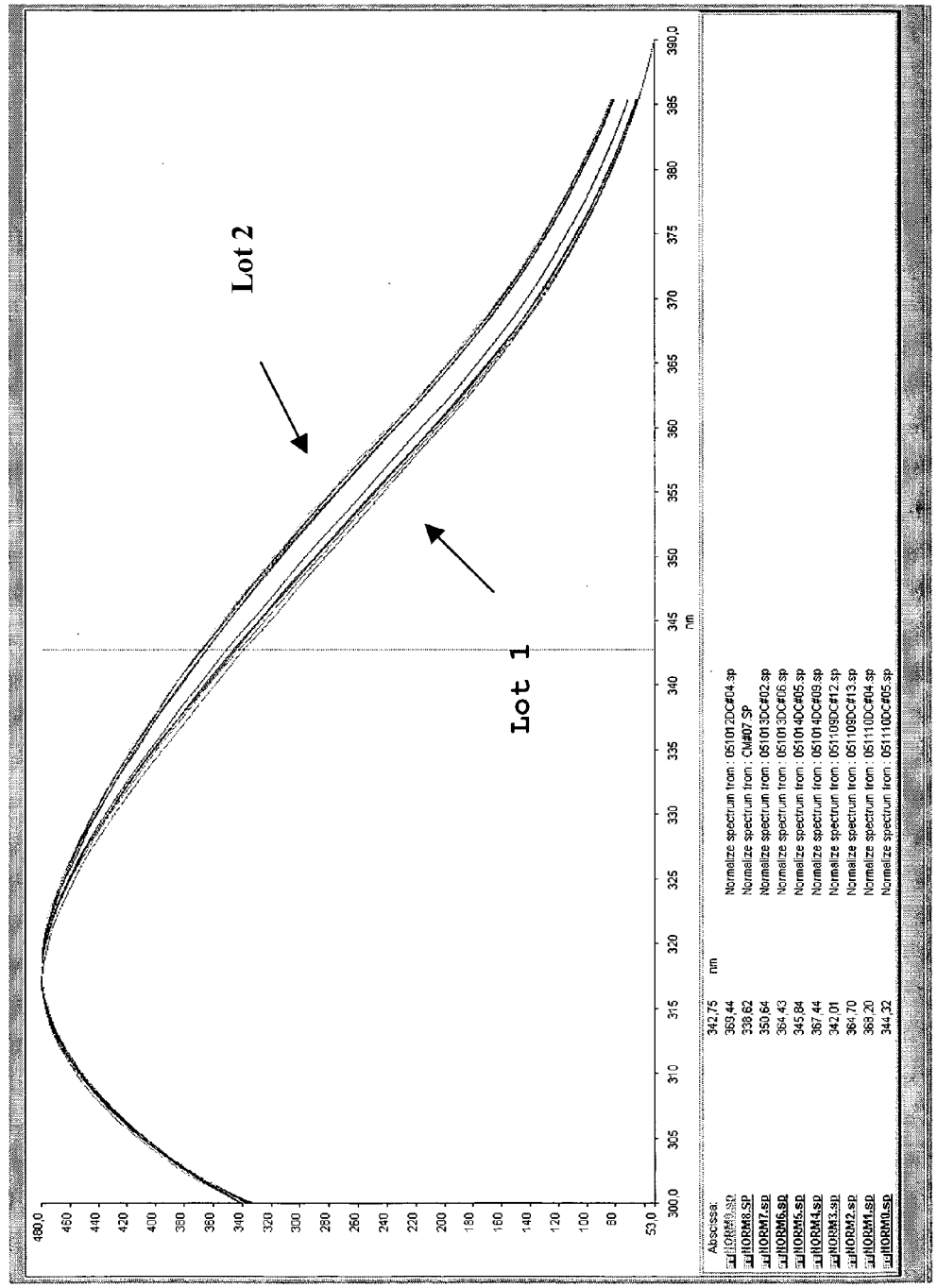

FIG. 38 shows the normalized spectra of 287-953 lots 1 and 2 obtained in all the analytical sessions with excitation at 280 nm.

Figure 39:
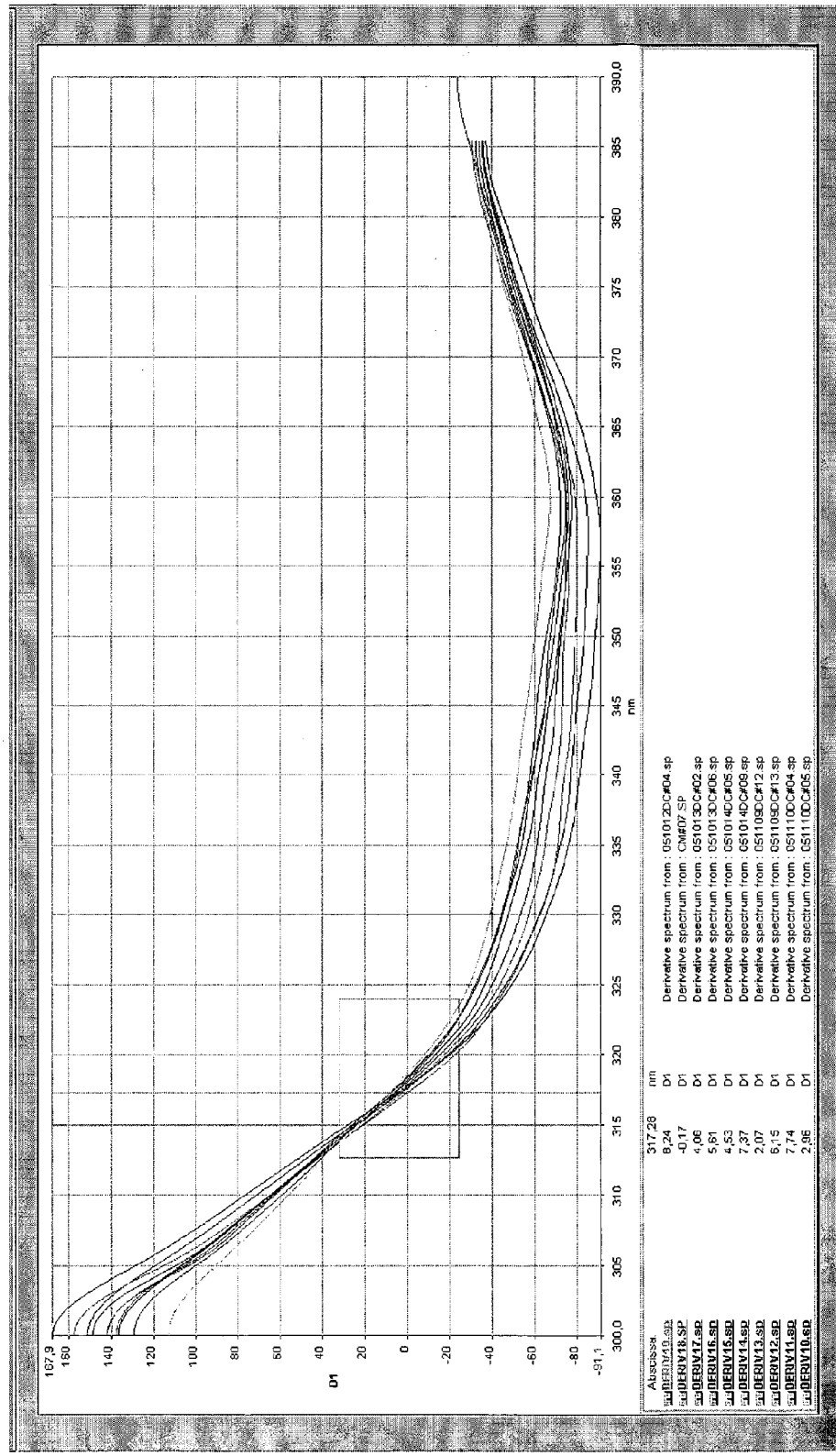
Figure 40:
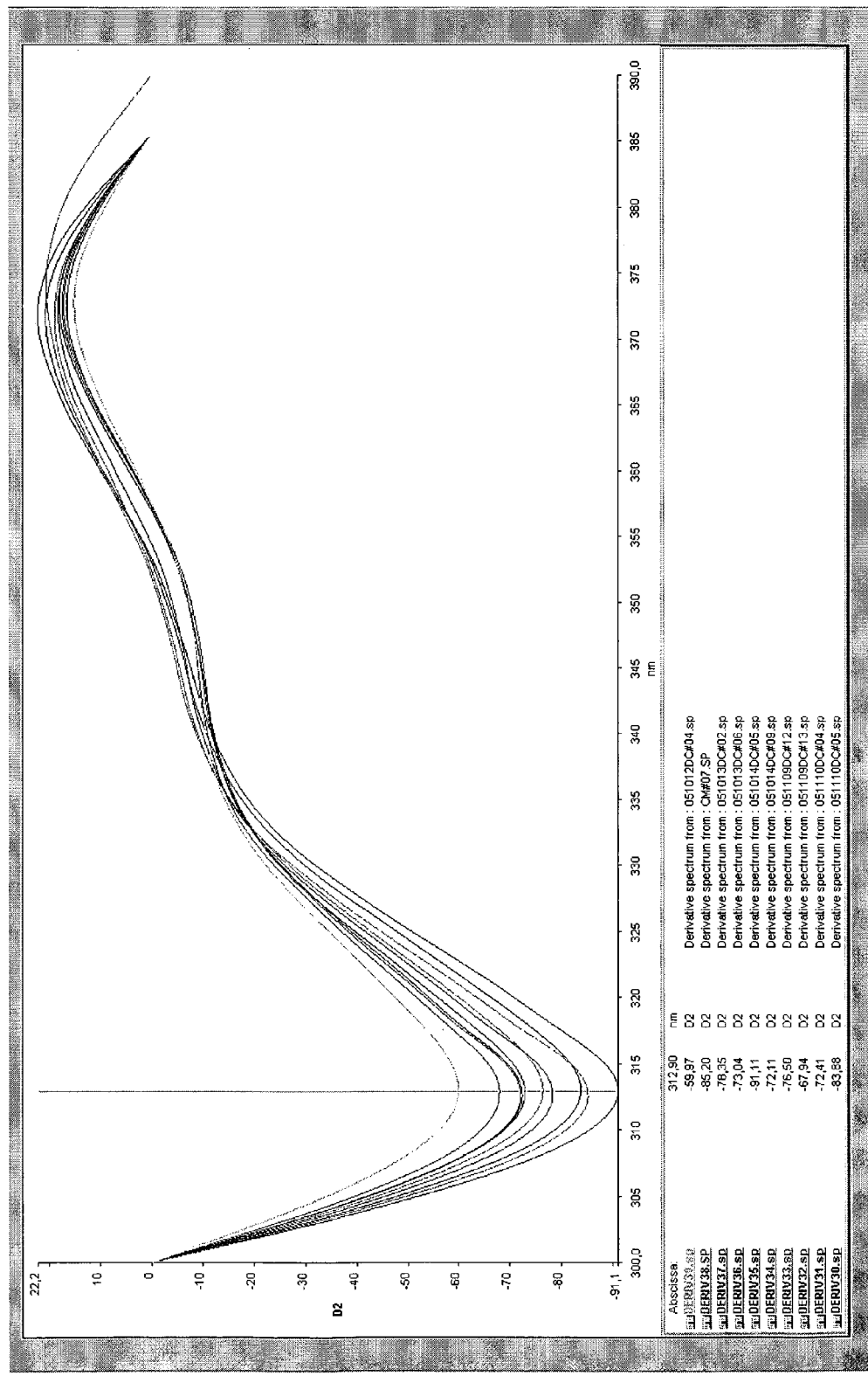

FIGS. 39 and 40 show the first and second order derivatives respectively of the emission spectra described in FIG. 38.

2 Example 4B

Figure 41:
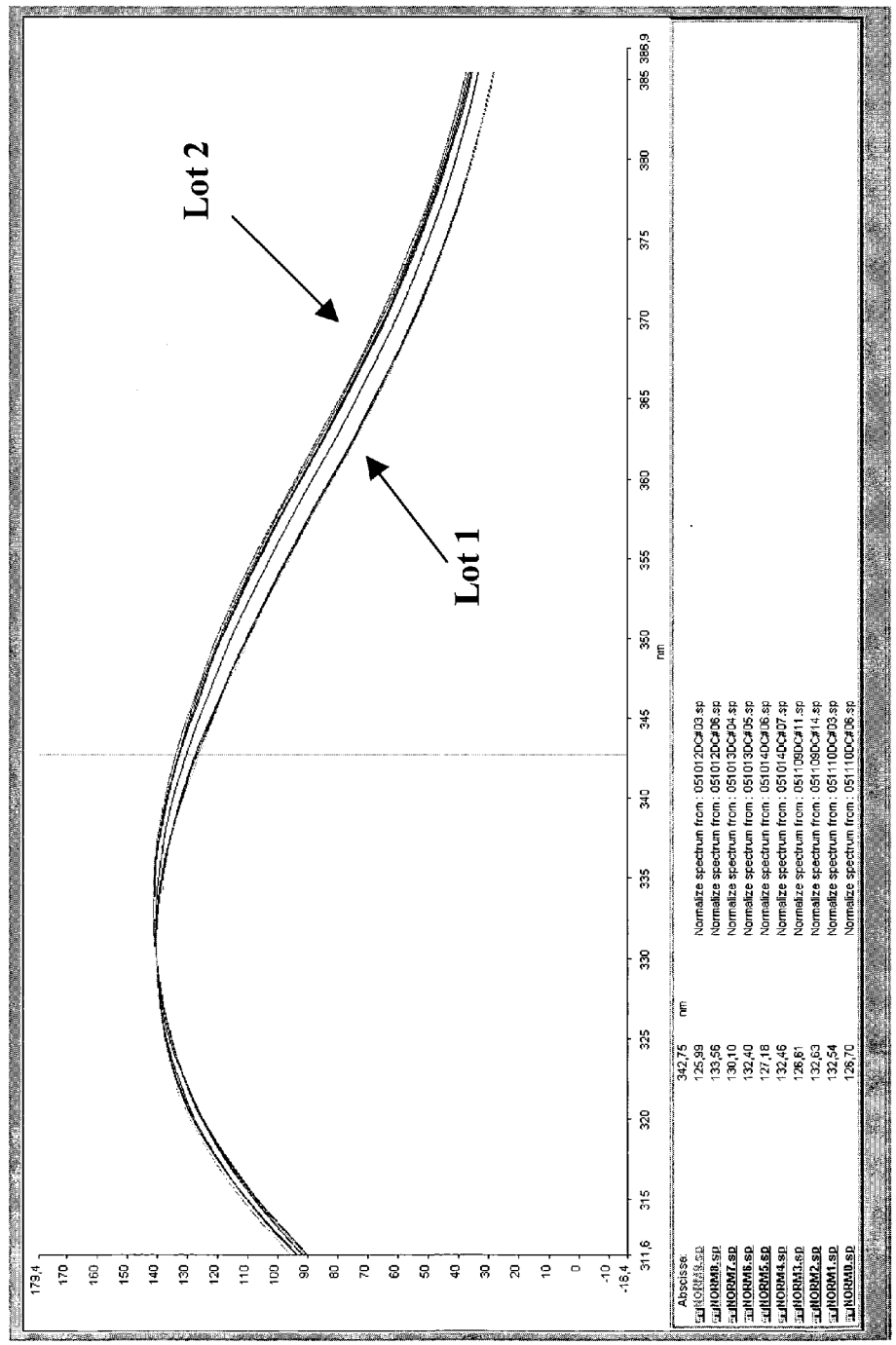

FIG. 41 shows the normalized spectra of 287-953 lots 1 and 2 obtained in all the analytical sessions with excitation at 295 nm.

Figure 42:
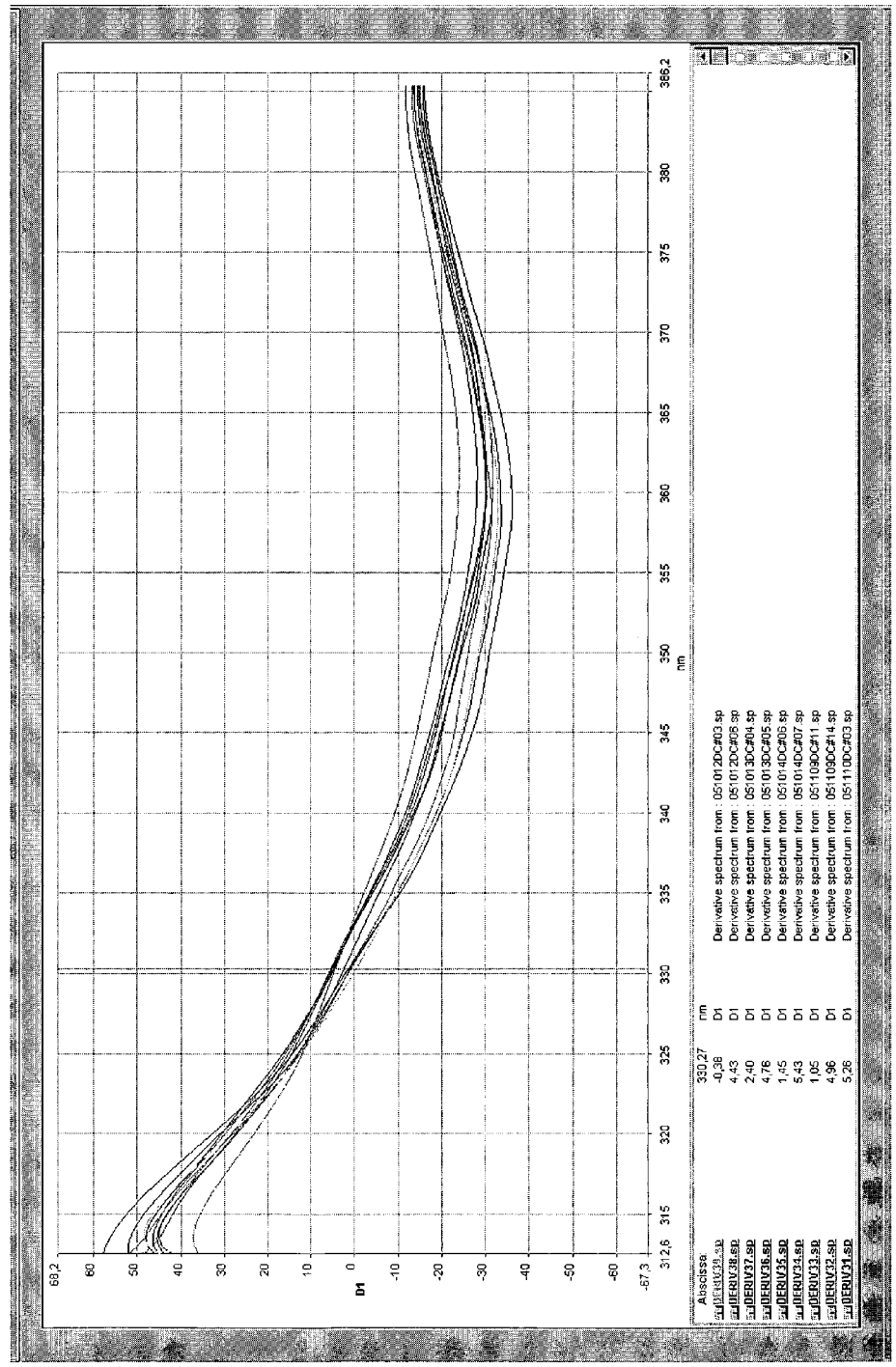
Figure 43:
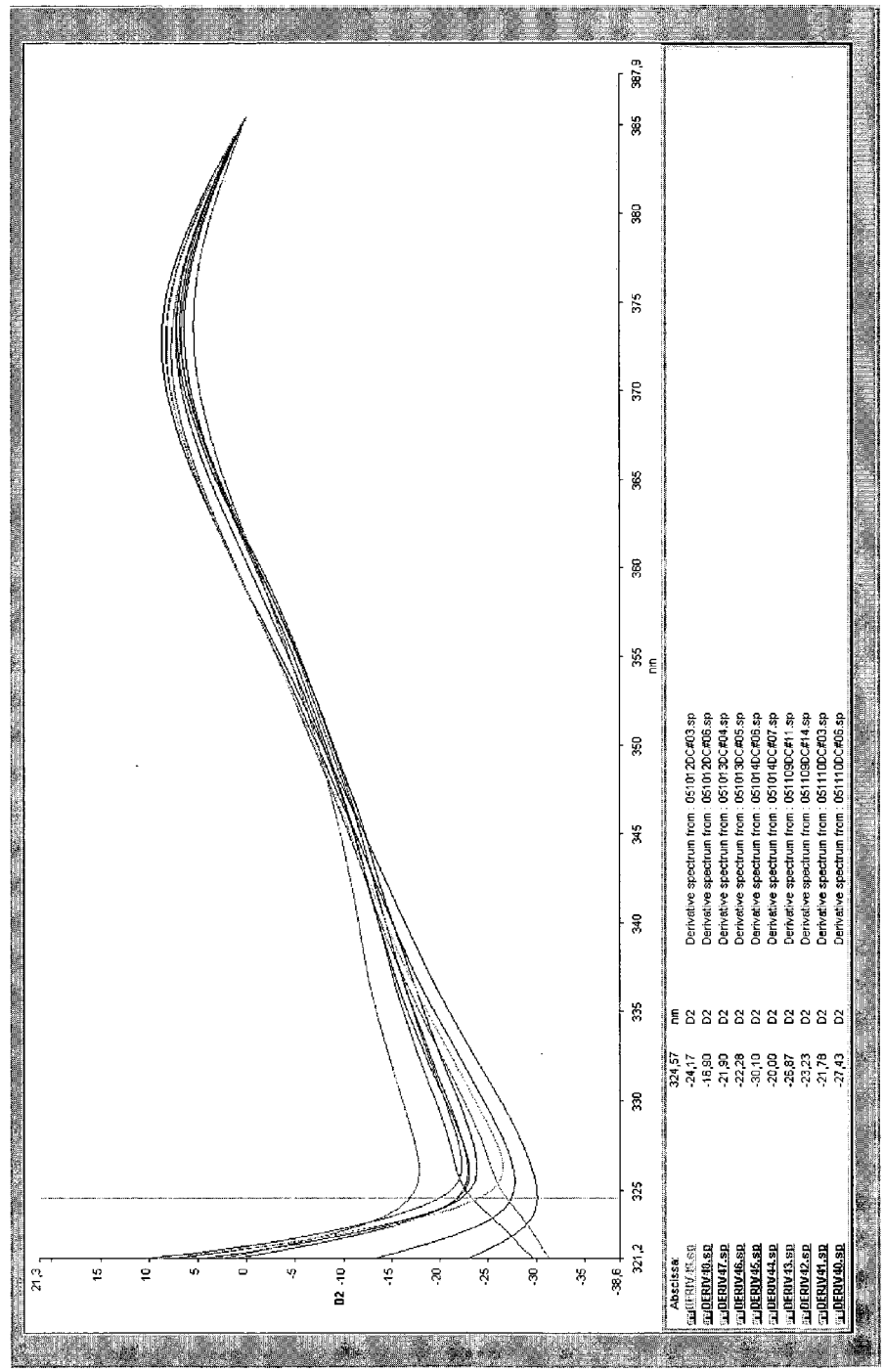

FIGS. 42 and 43 show the first and second order derivatives respectively of the emission spectra described in FIG. 41.

Figures of Example 5

Figure 44:
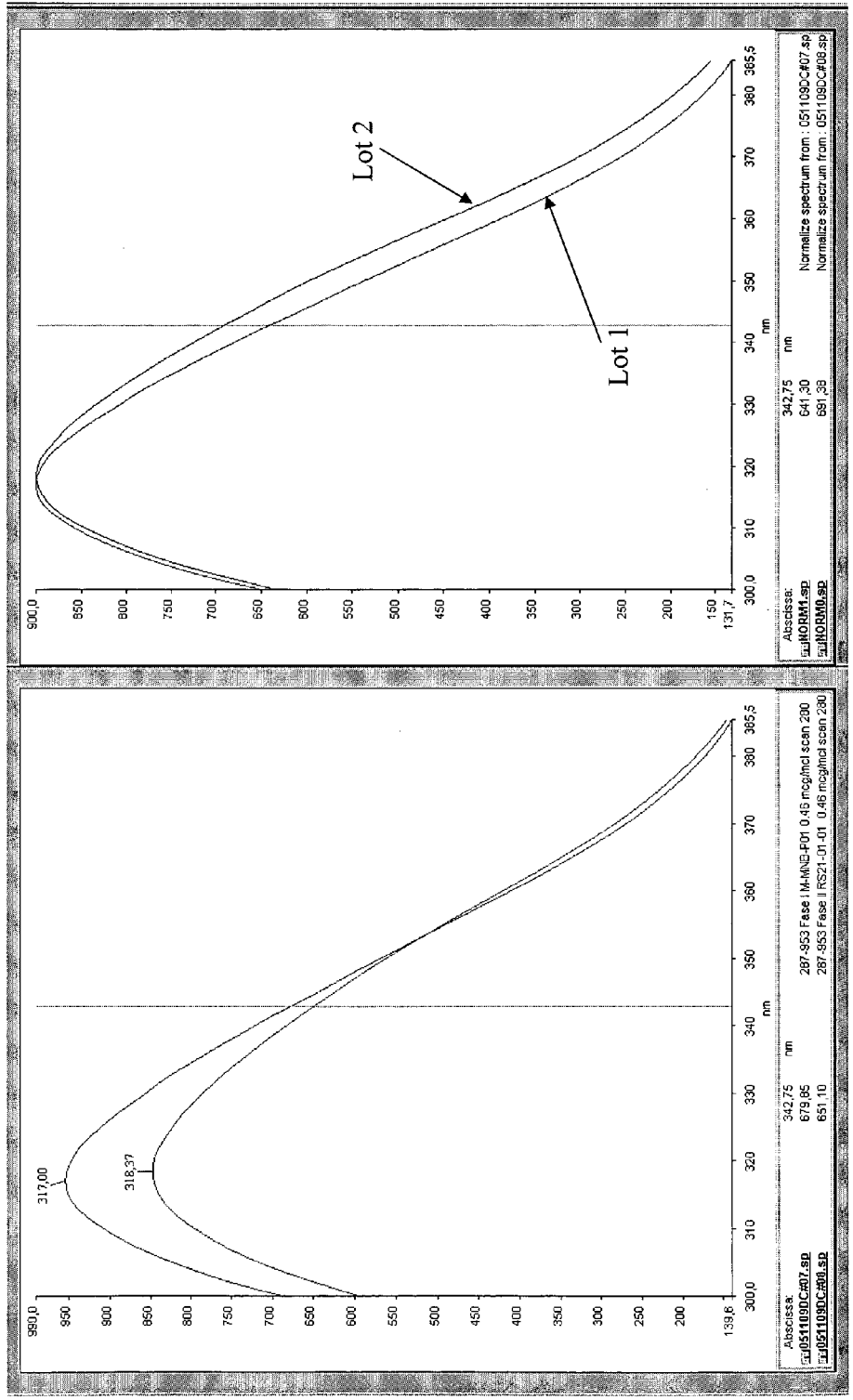

FIG. 44 shows, on the left, the individual spectra of the two lots of Example 5 at 280 nm excitation and, on the right, their normalization.

Figure 45:
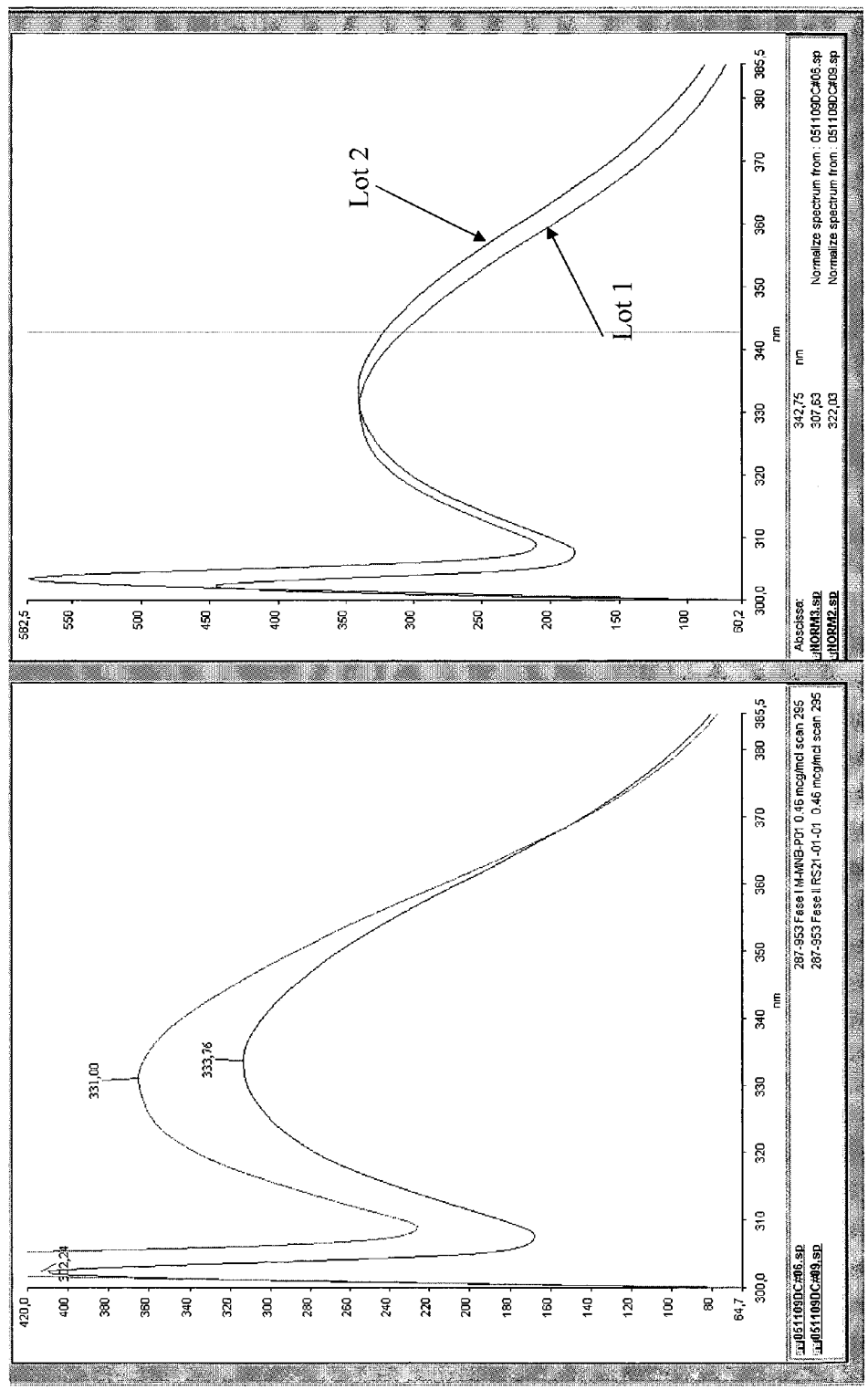

FIG. 45 shows, on the left, the individual spectra of the two lots of Example 5 at 295 nm excitation and, on the right, their normalization.

Figures of Example 6

Figure 46:
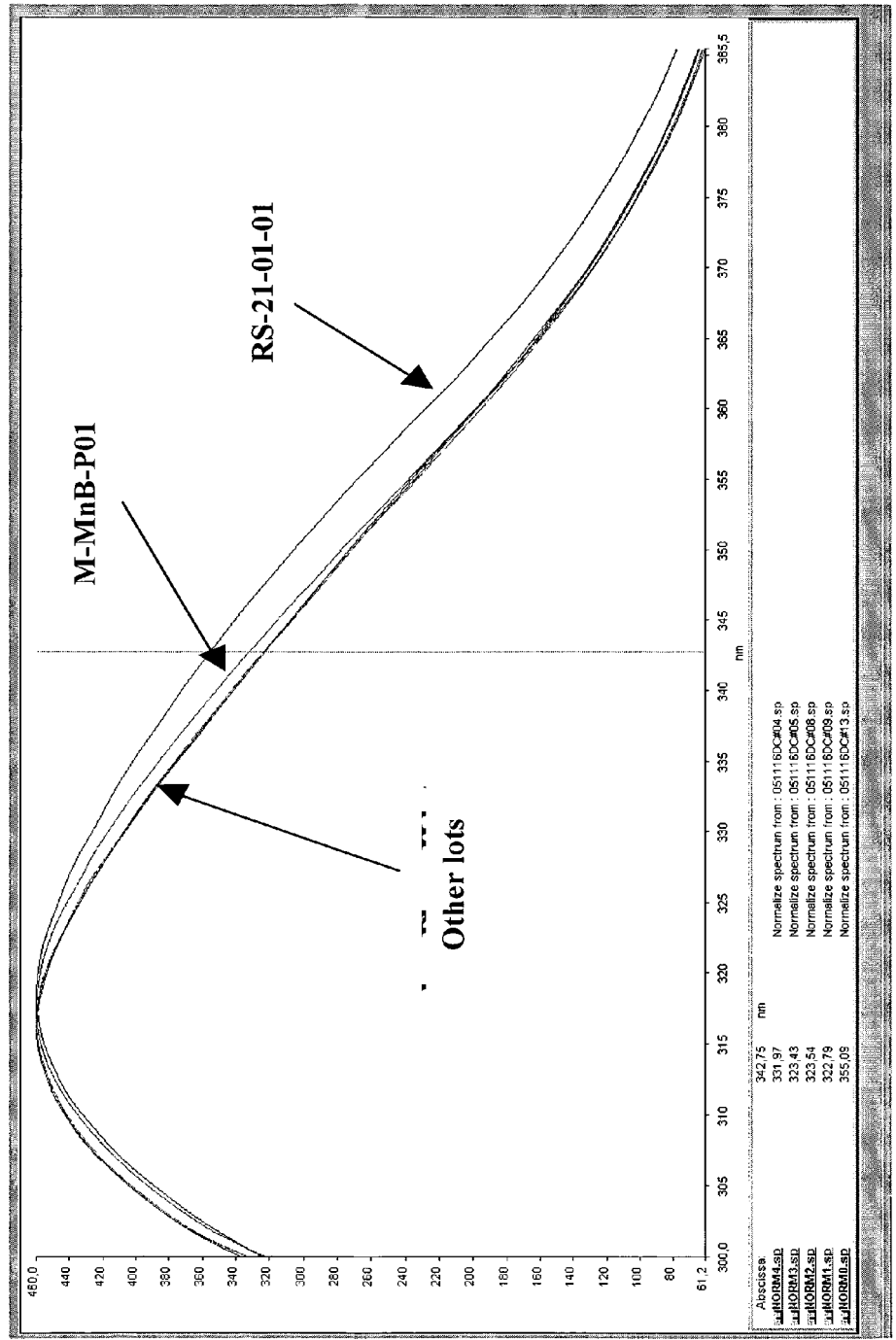

FIG. 46 shows the normalized spectra of the 287-953 lots obtained at 280 nm.

Figure 47:
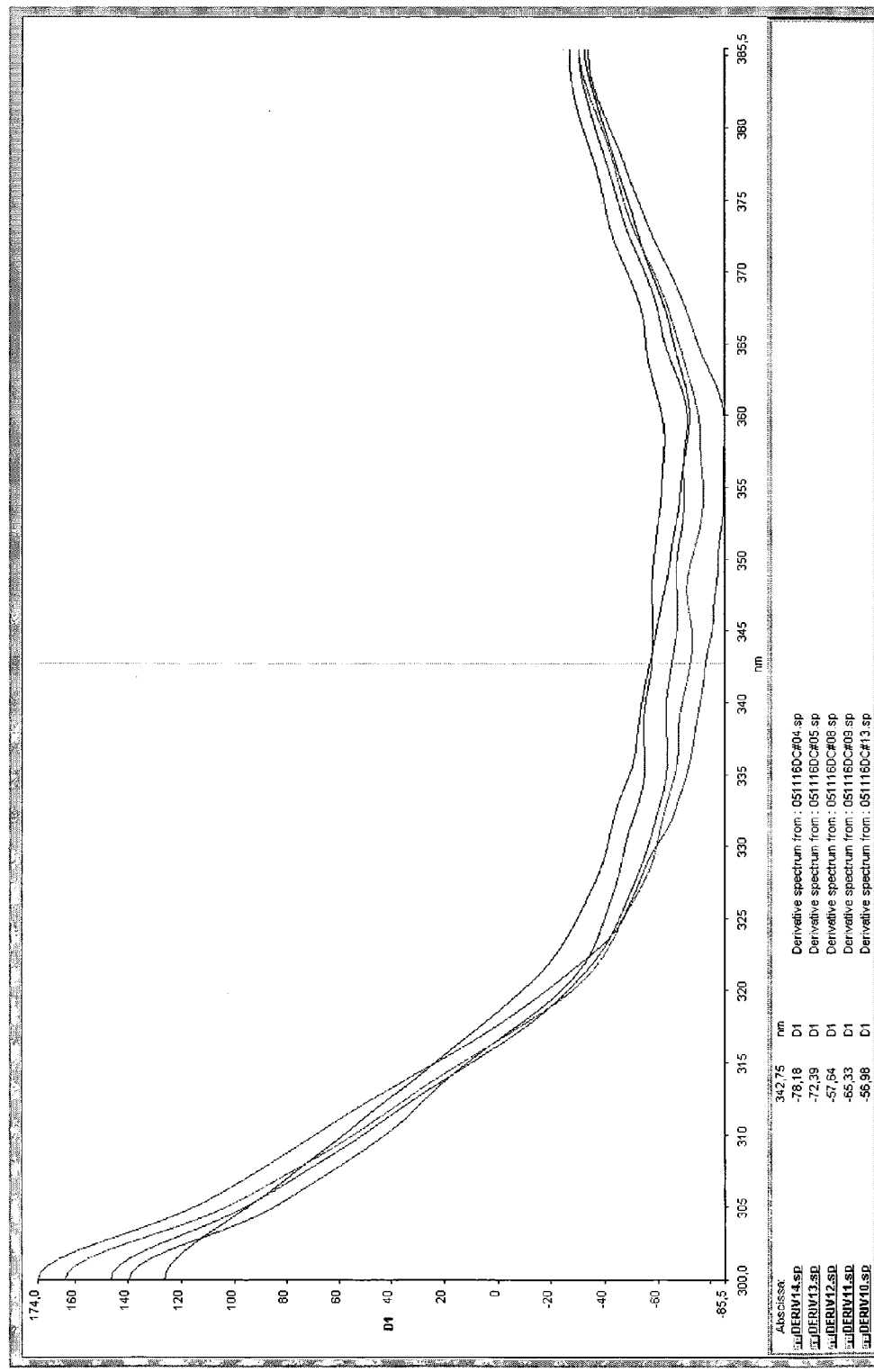
Figure 48:
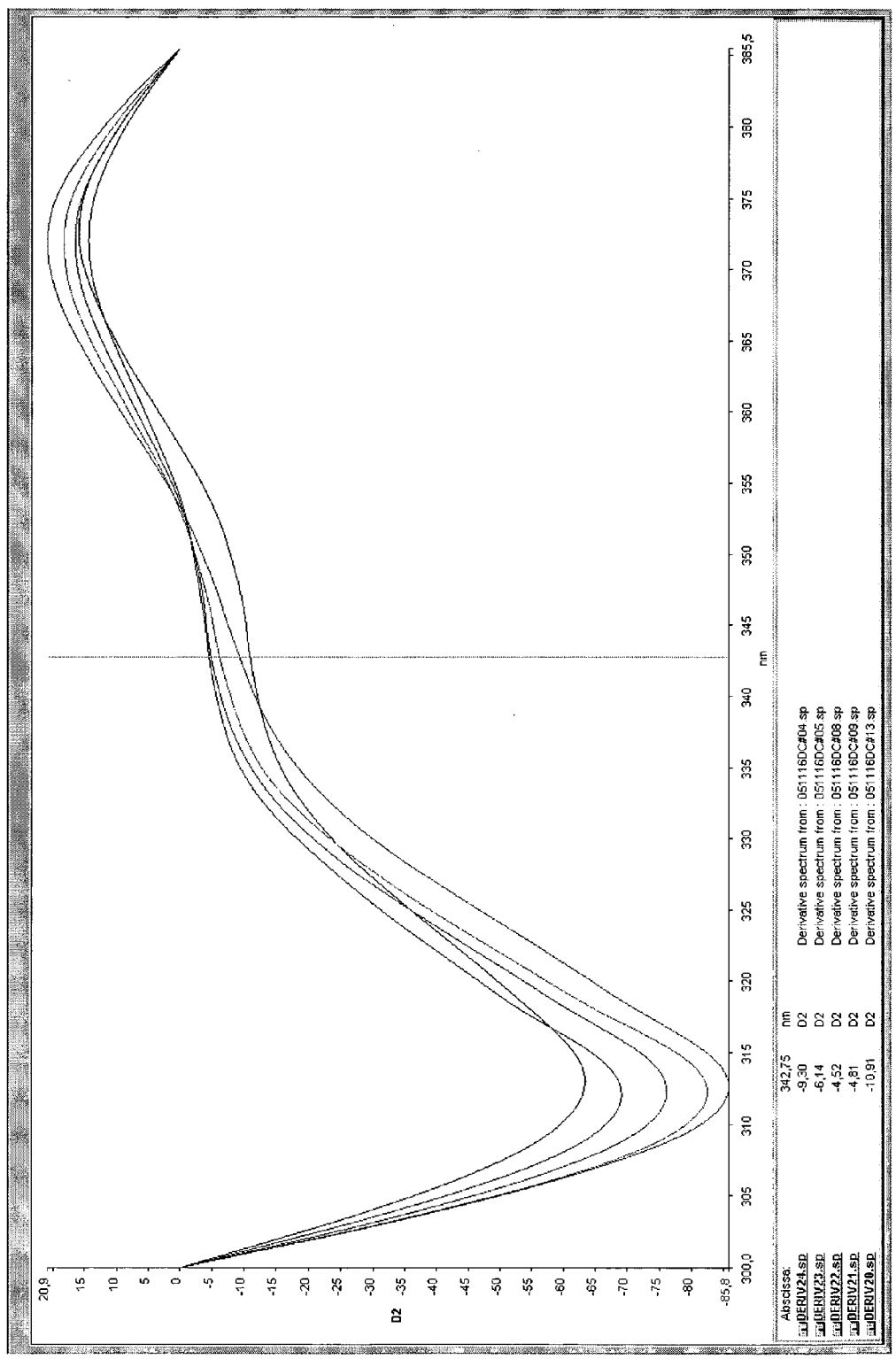

FIGS. 47 and 48 show the first and second order derivatives respectively of the emission spectra described in FIG. 46.

Figure 49:
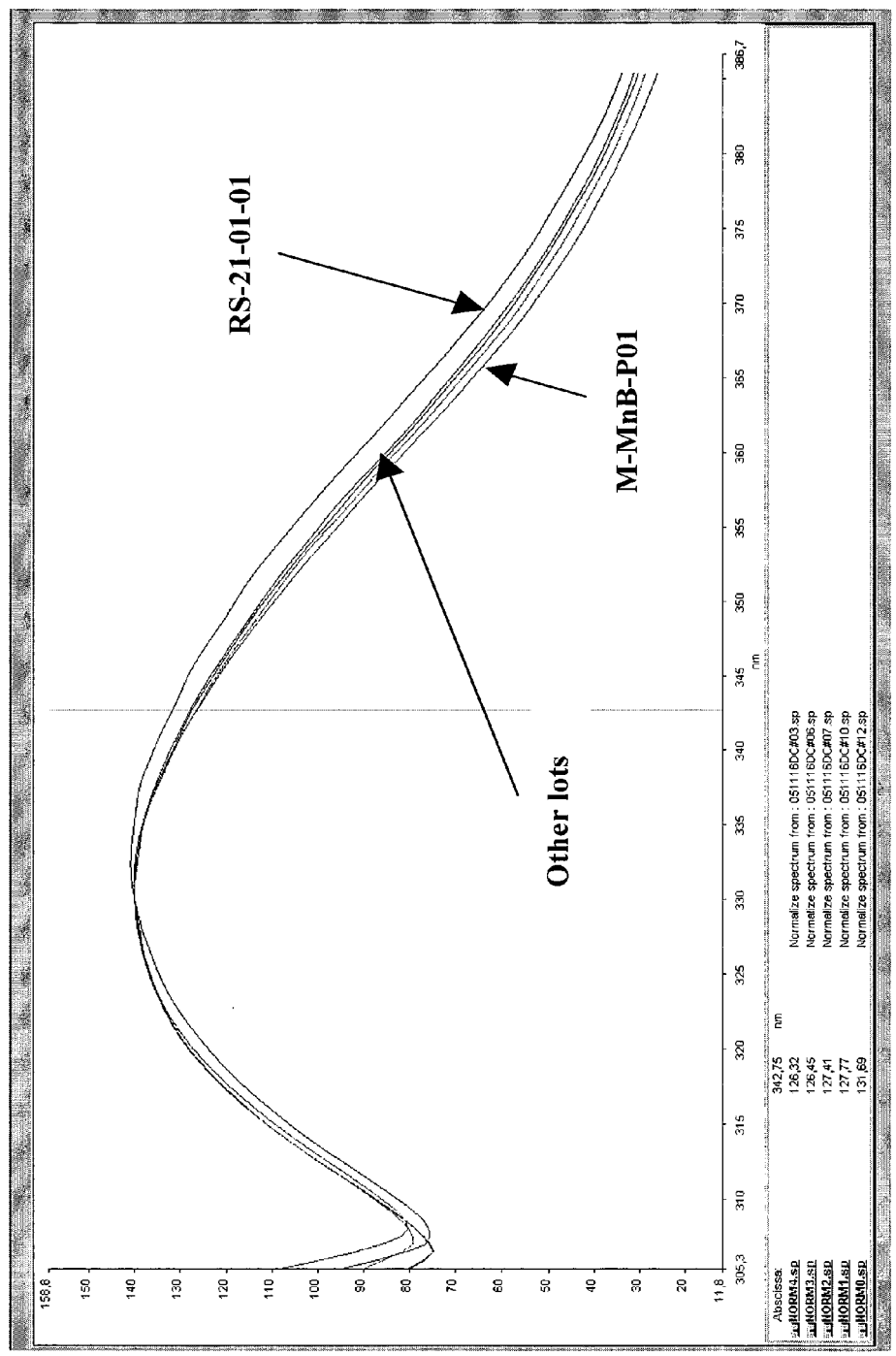

FIG. 49 shows the normalized spectra of the 287-953 lots obtained at 295 nm.

Figure 50:
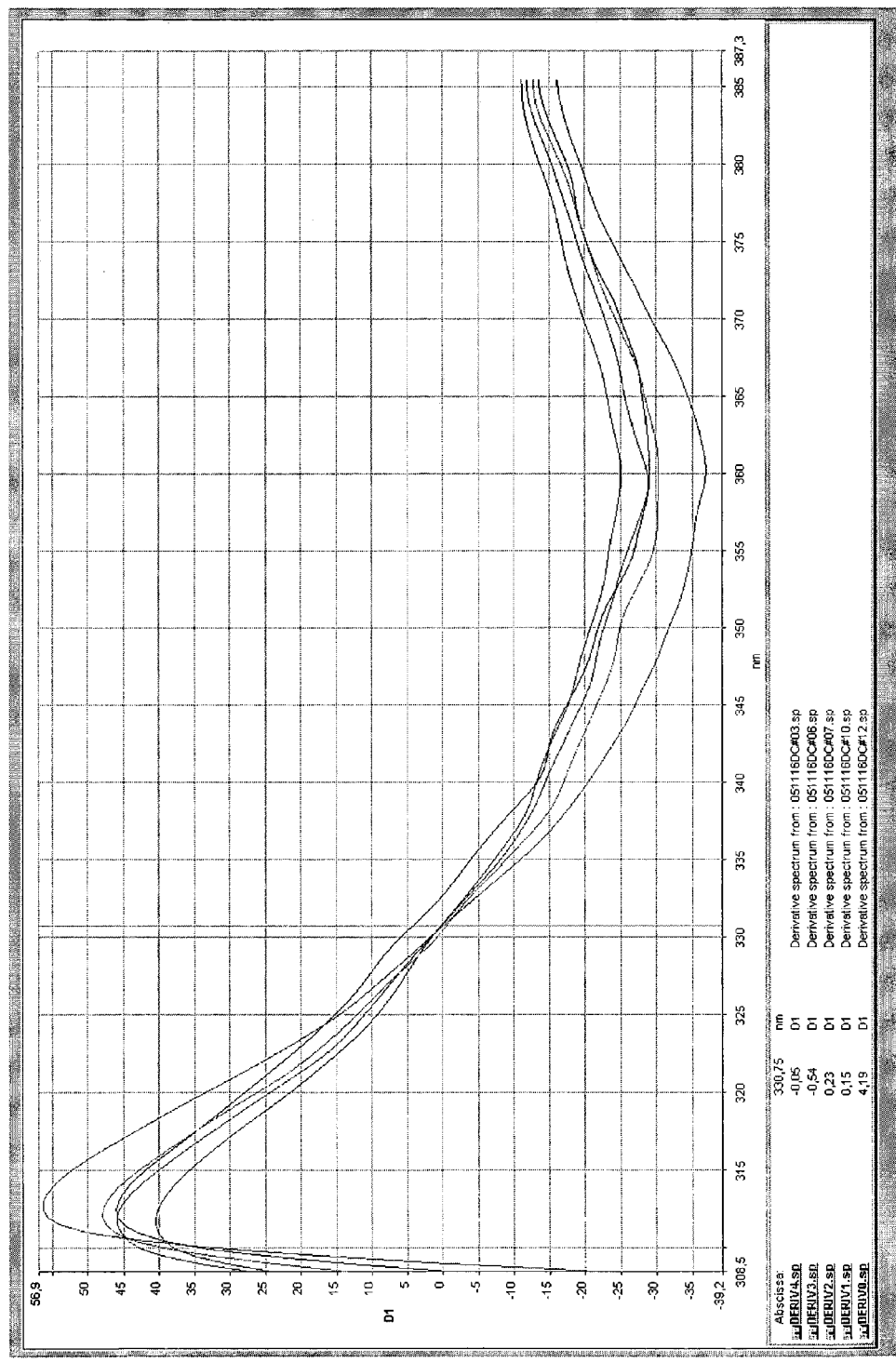
Figure 51:
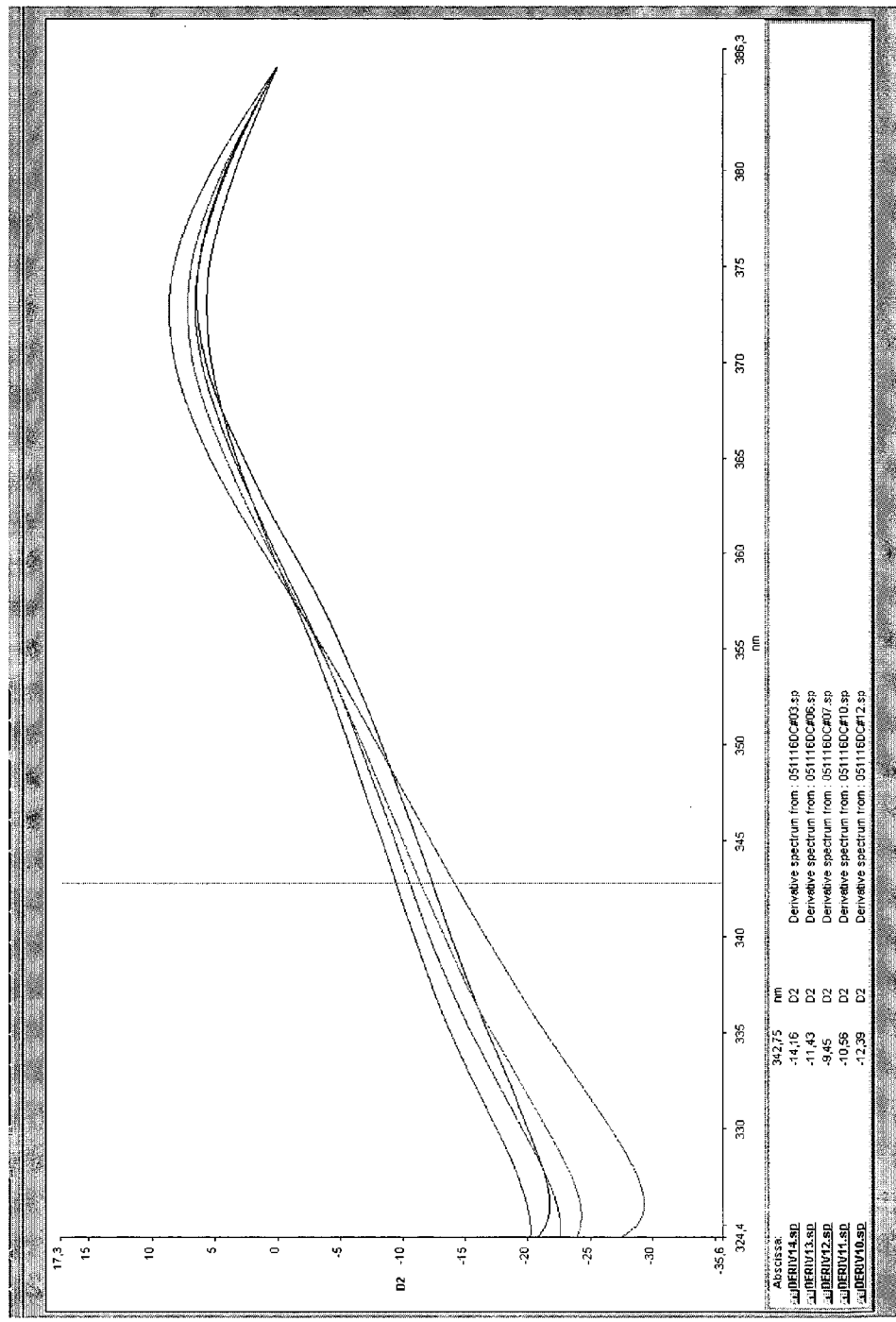

FIGS. 50 and 51 show the first and second order derivatives respectively of the emission spectra described in FIG. 49.

Figures of Example 7

FIG. 52 shows the 936-741 chimera protein primary sequence.

1 Example 7A

Figure 53:
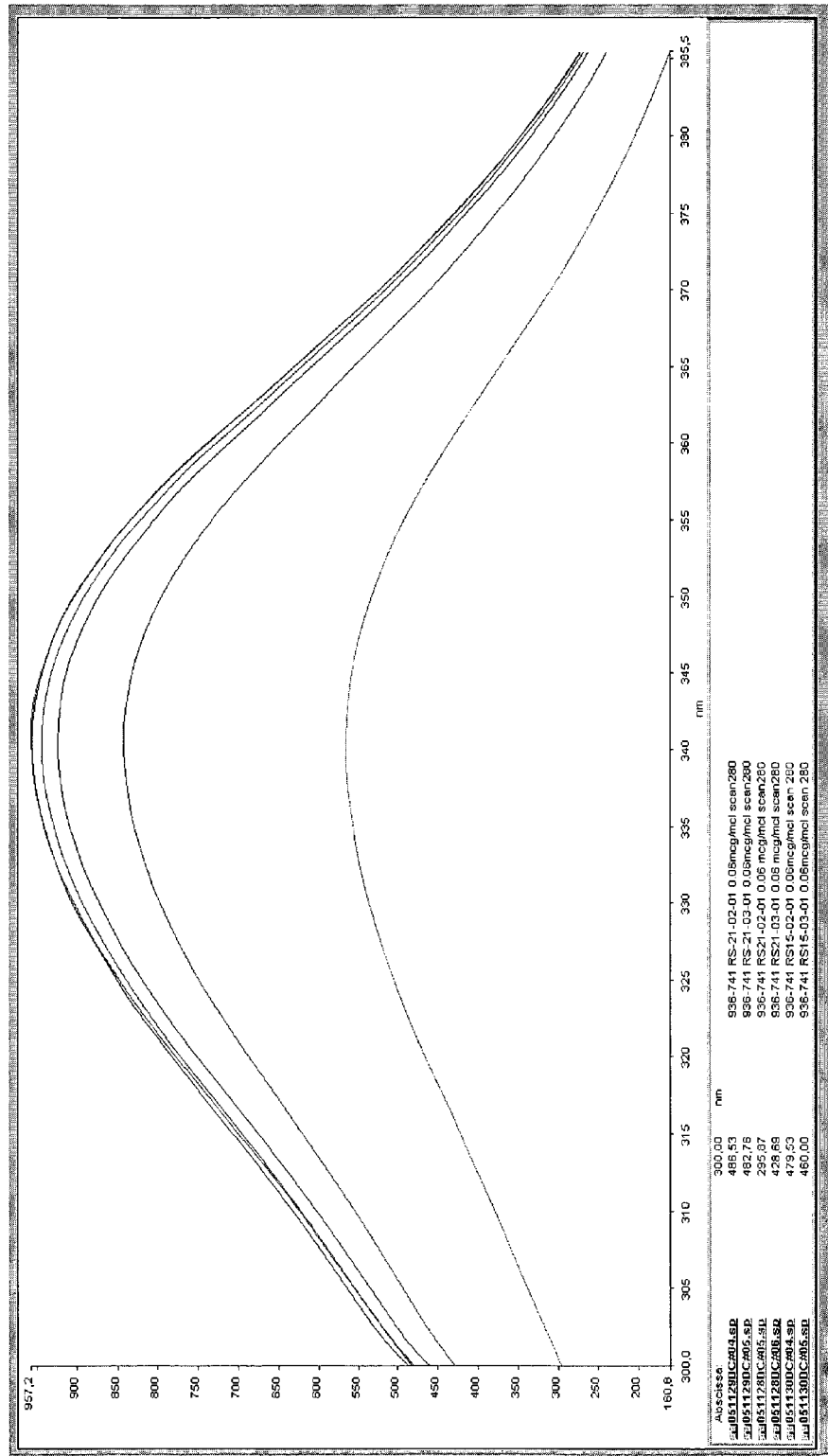

FIG. 53 shows the spectra of 936-741 lots 1 and 2 obtained in all the analytical sessions with excitation at 280 nm. The normalized spectra are shown in FIG. 54.

Figure 54:
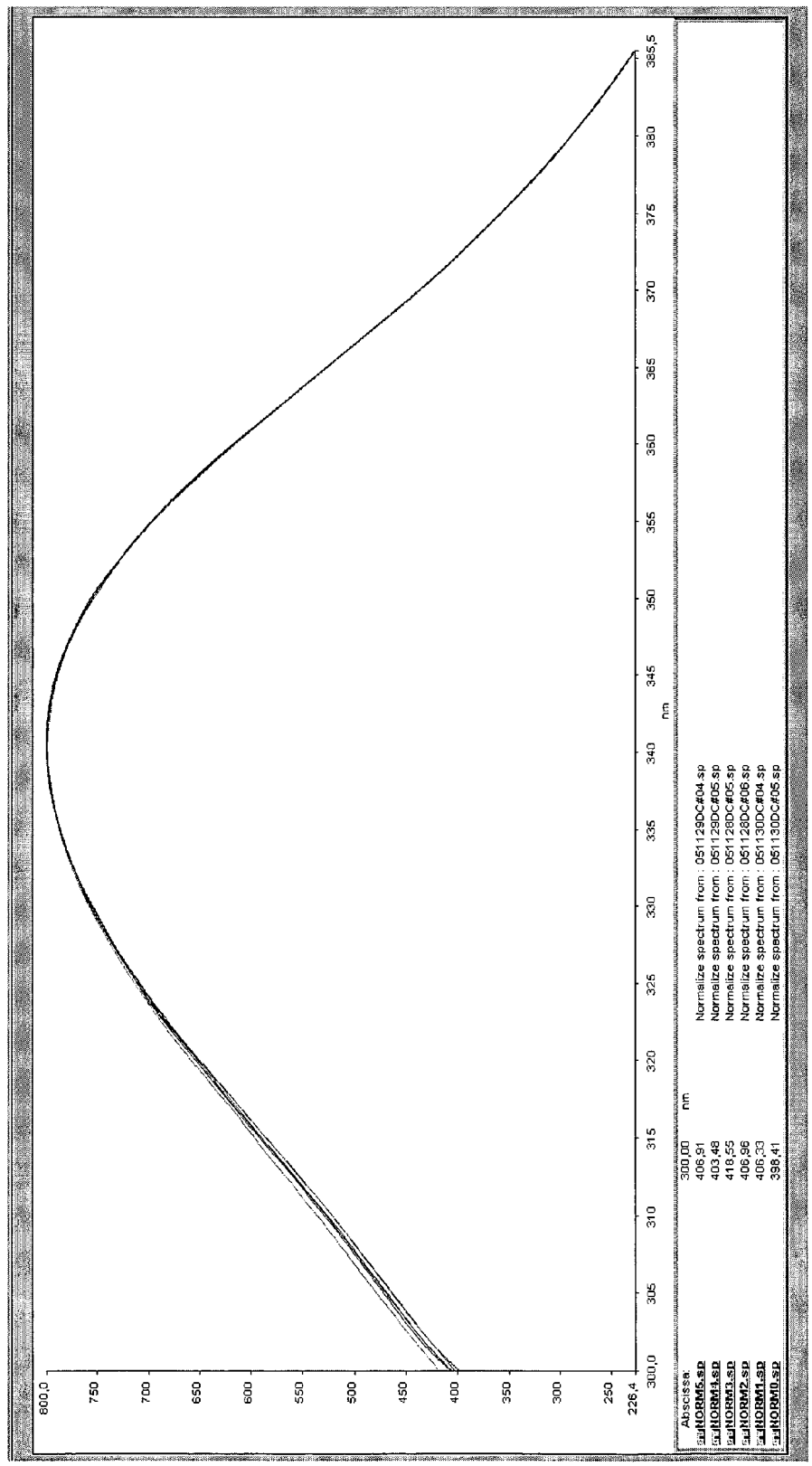
Figure 55:
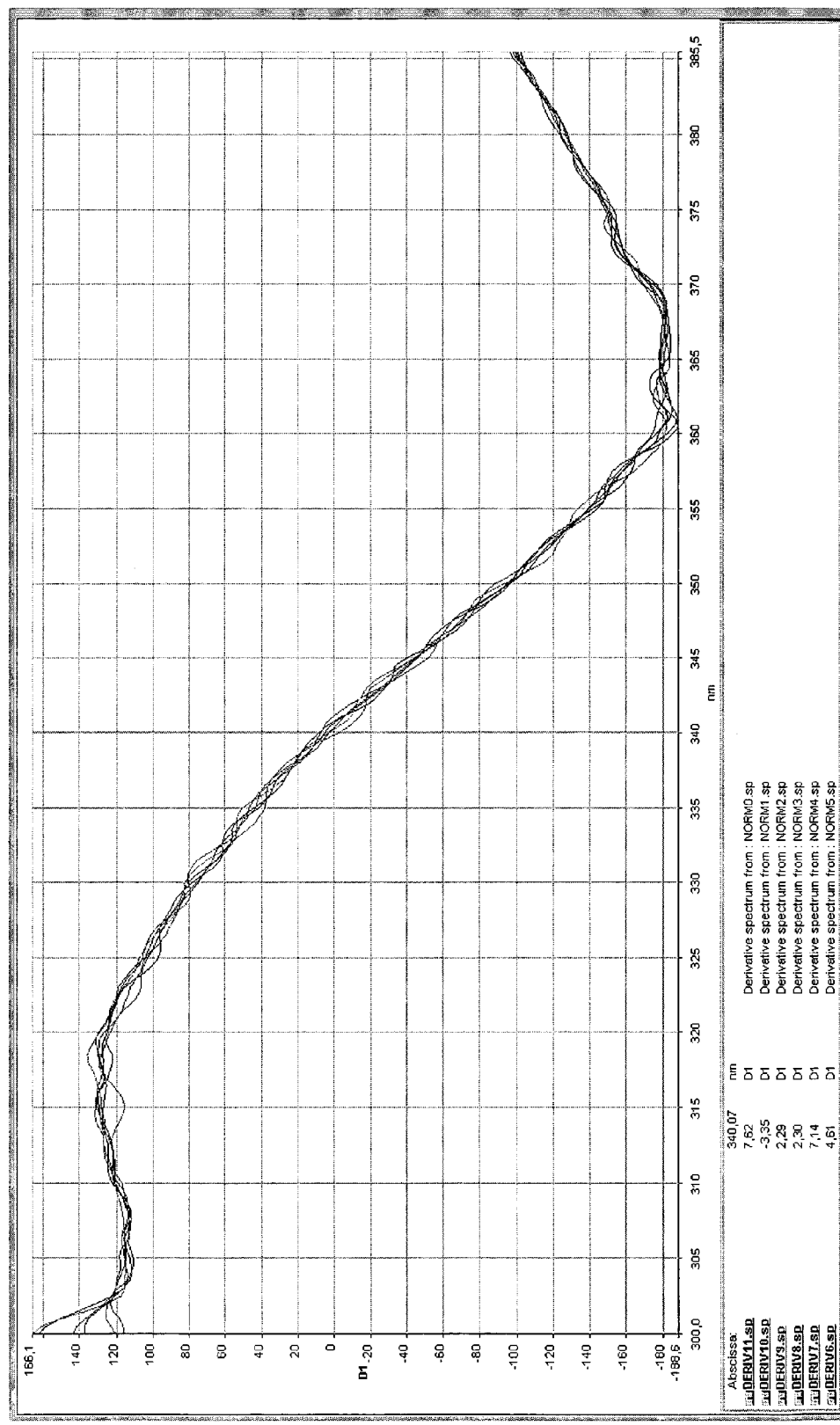
Figure 56:
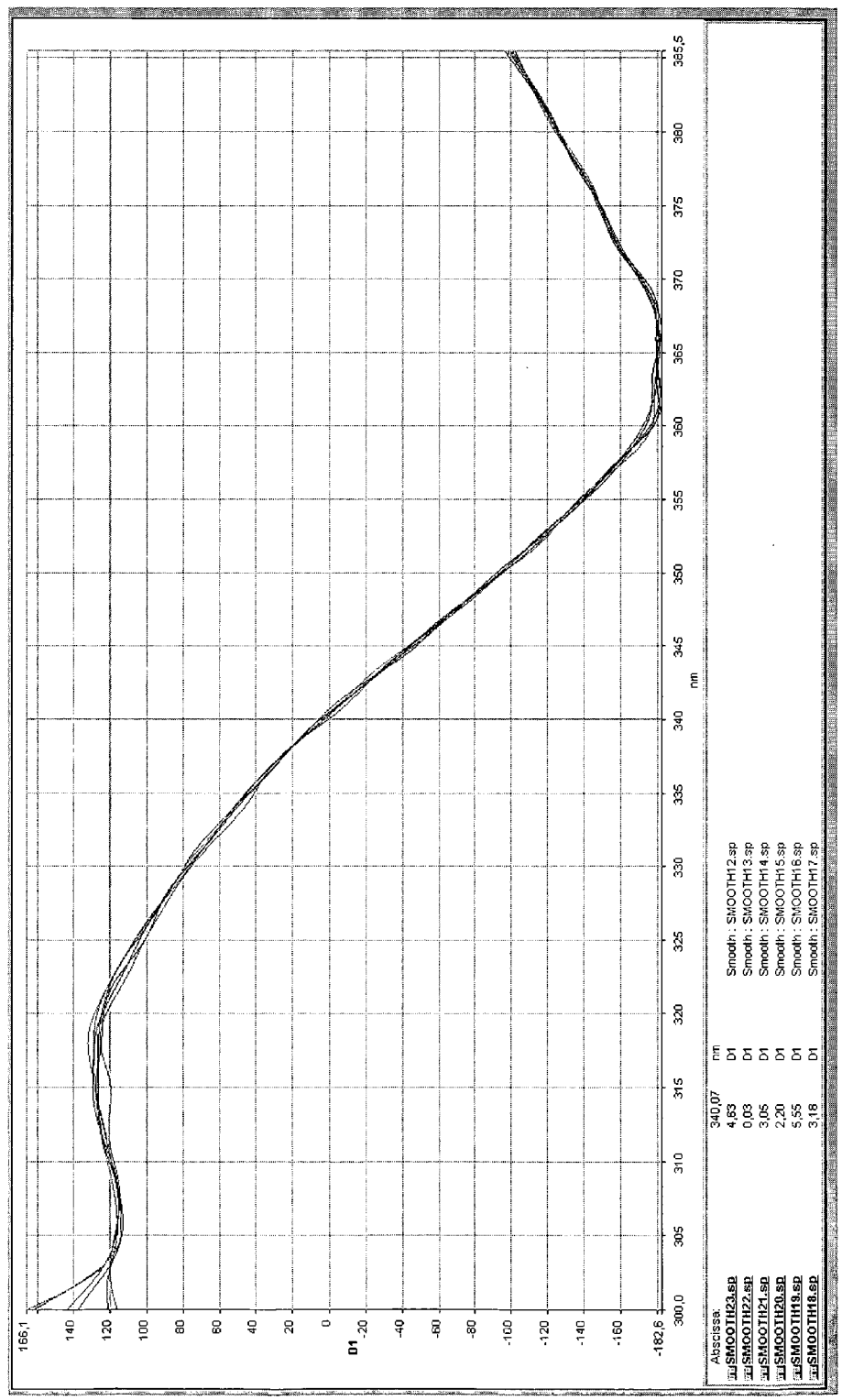

FIGS. 55 and 56 show raw and smoothed first order derivatives respectively of the emission spectra described in FIG. 54.

Figure 57:
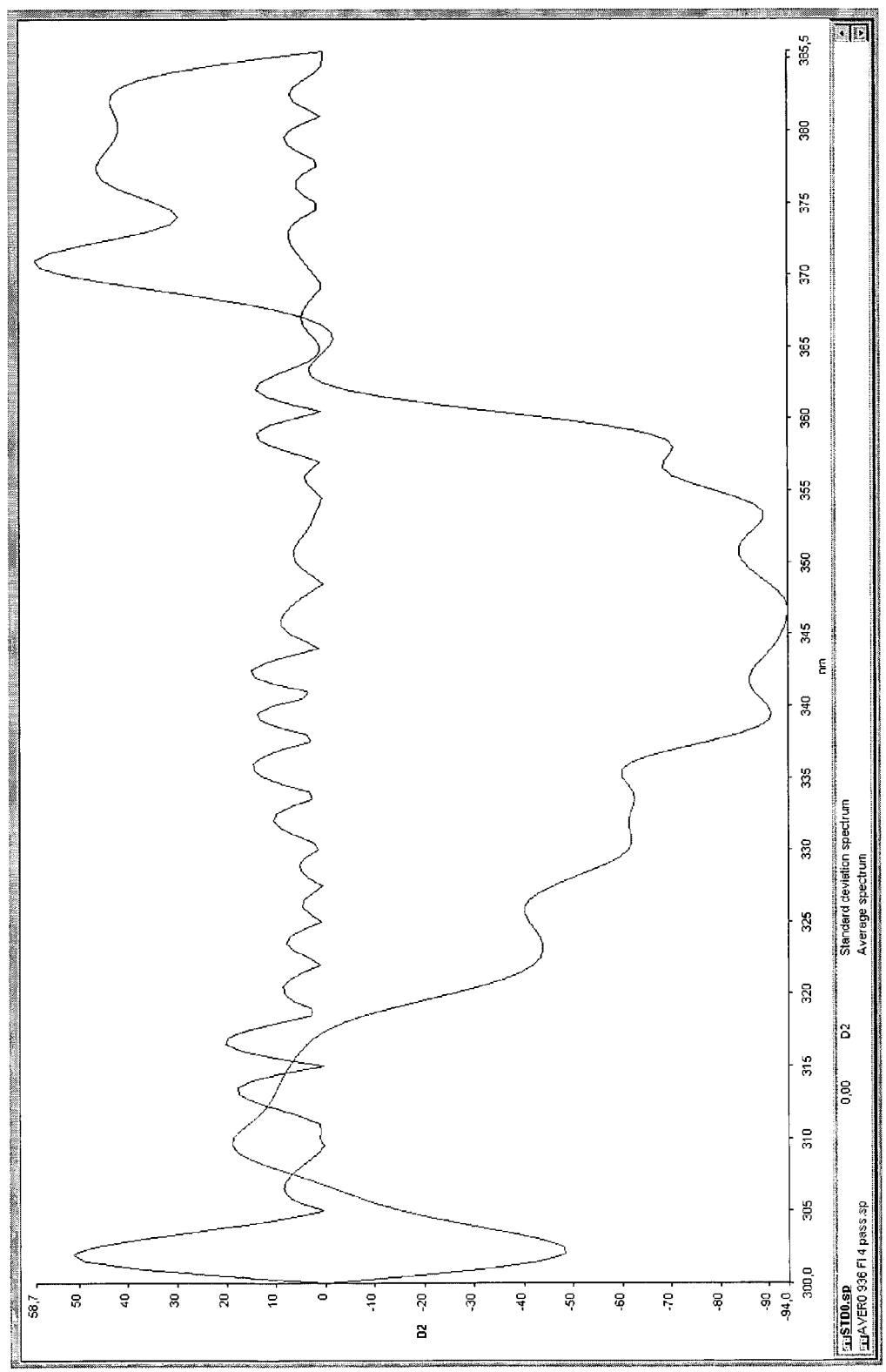
Figure 58:
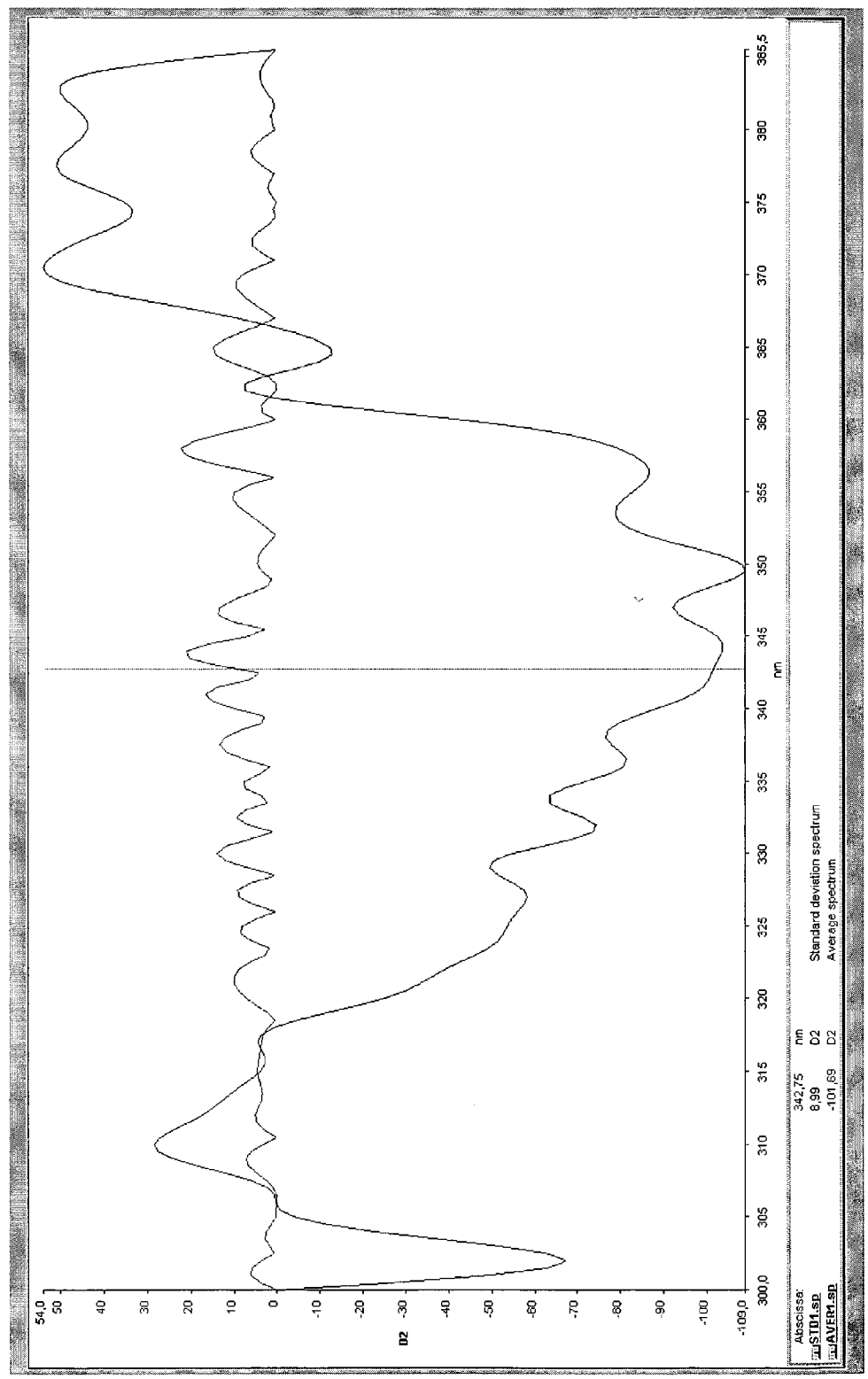

FIGS. 57 (lot 1) and 58 (lot 2) show the average spectrum of single second derivative spectra and their relative standard deviation.

Figure 59:
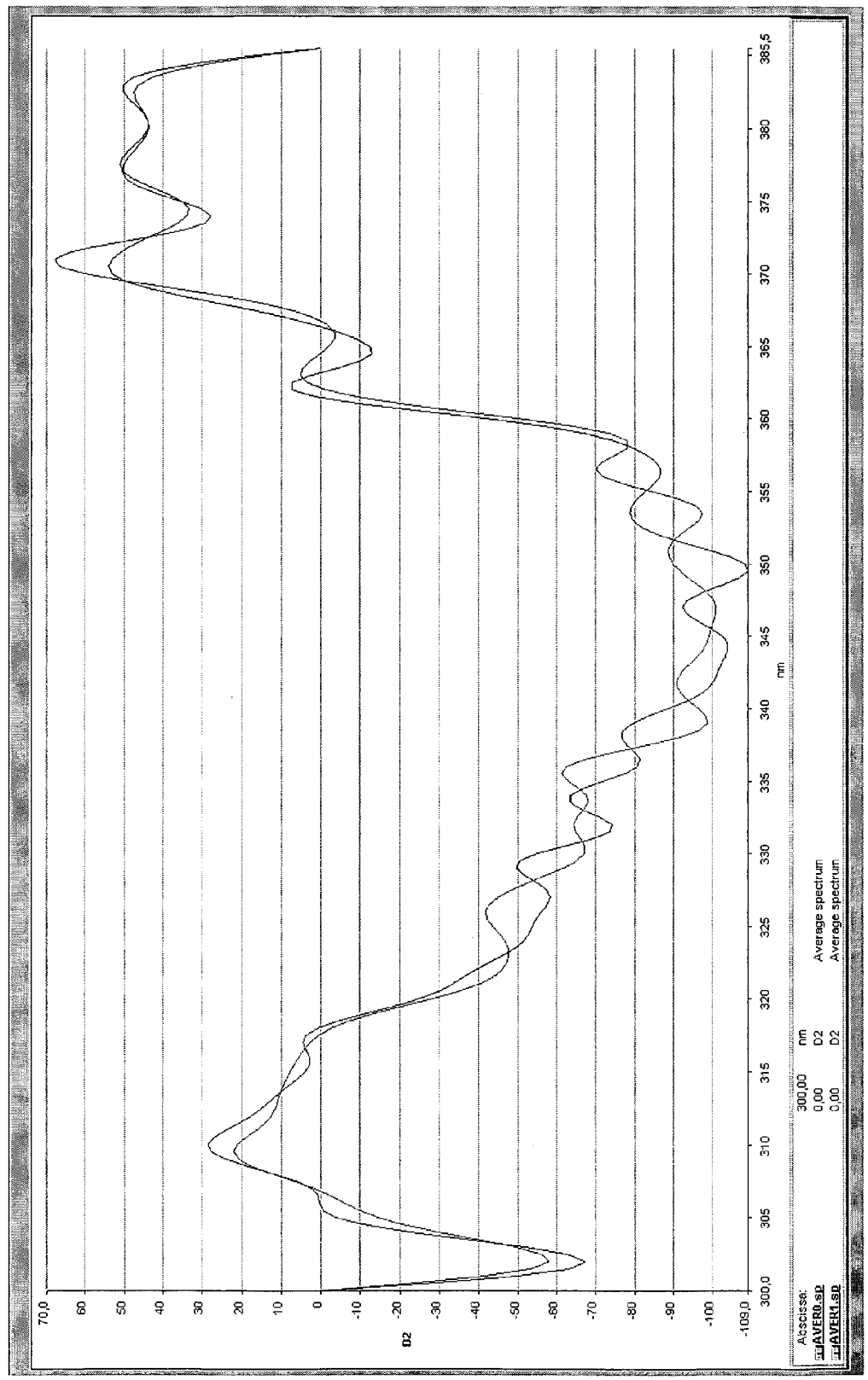

FIG. 59 shows the second derivative average spectra of lot 1 and lot 2 superimposed.

2 Example 7B

Figure 60:
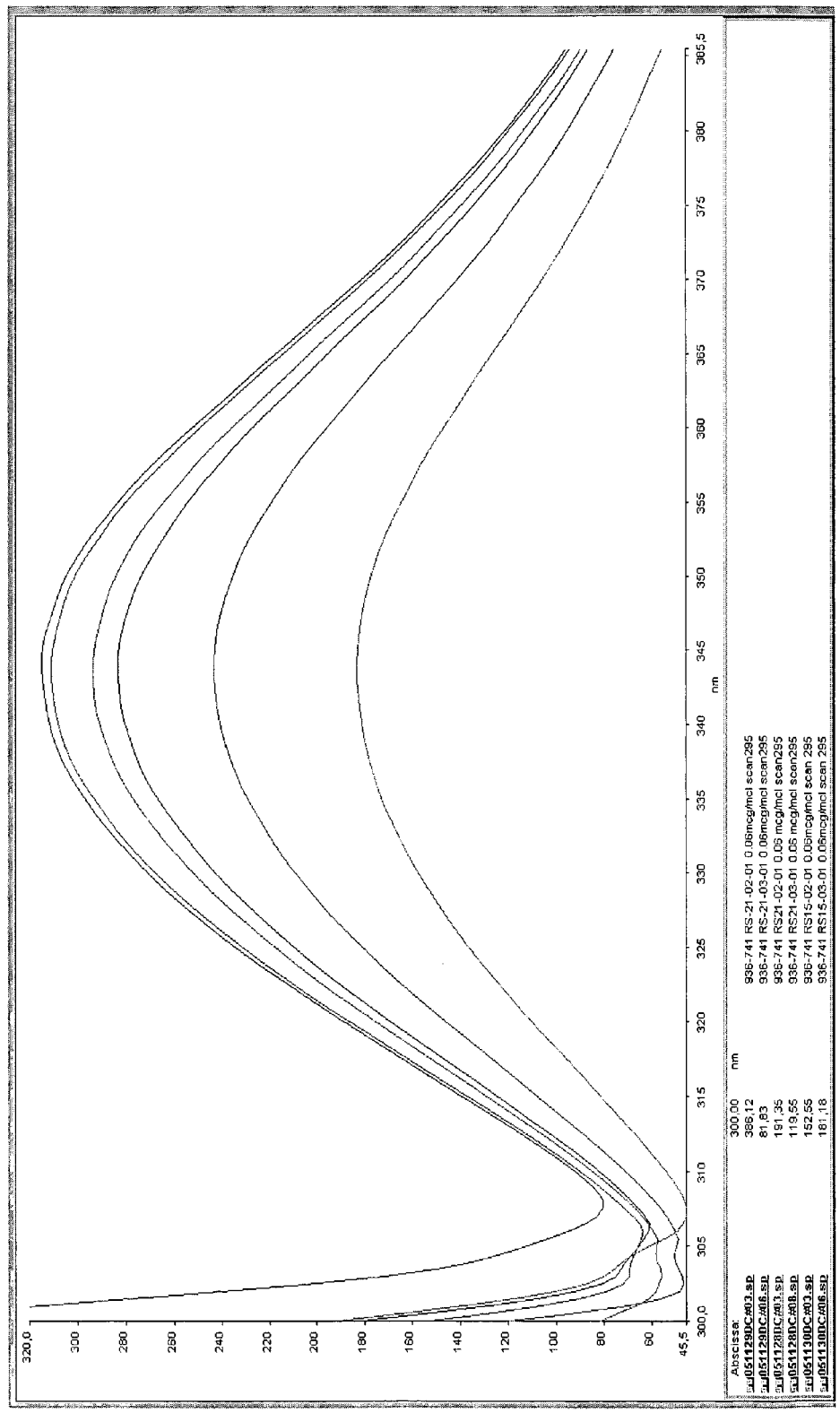

FIG. 60 shows the spectra of 936-741 lots 1 and 2 obtained in all the analytical sessions with excitation at 295 nm. The normalized spectra are shown in FIG. 61.

Figure 61:
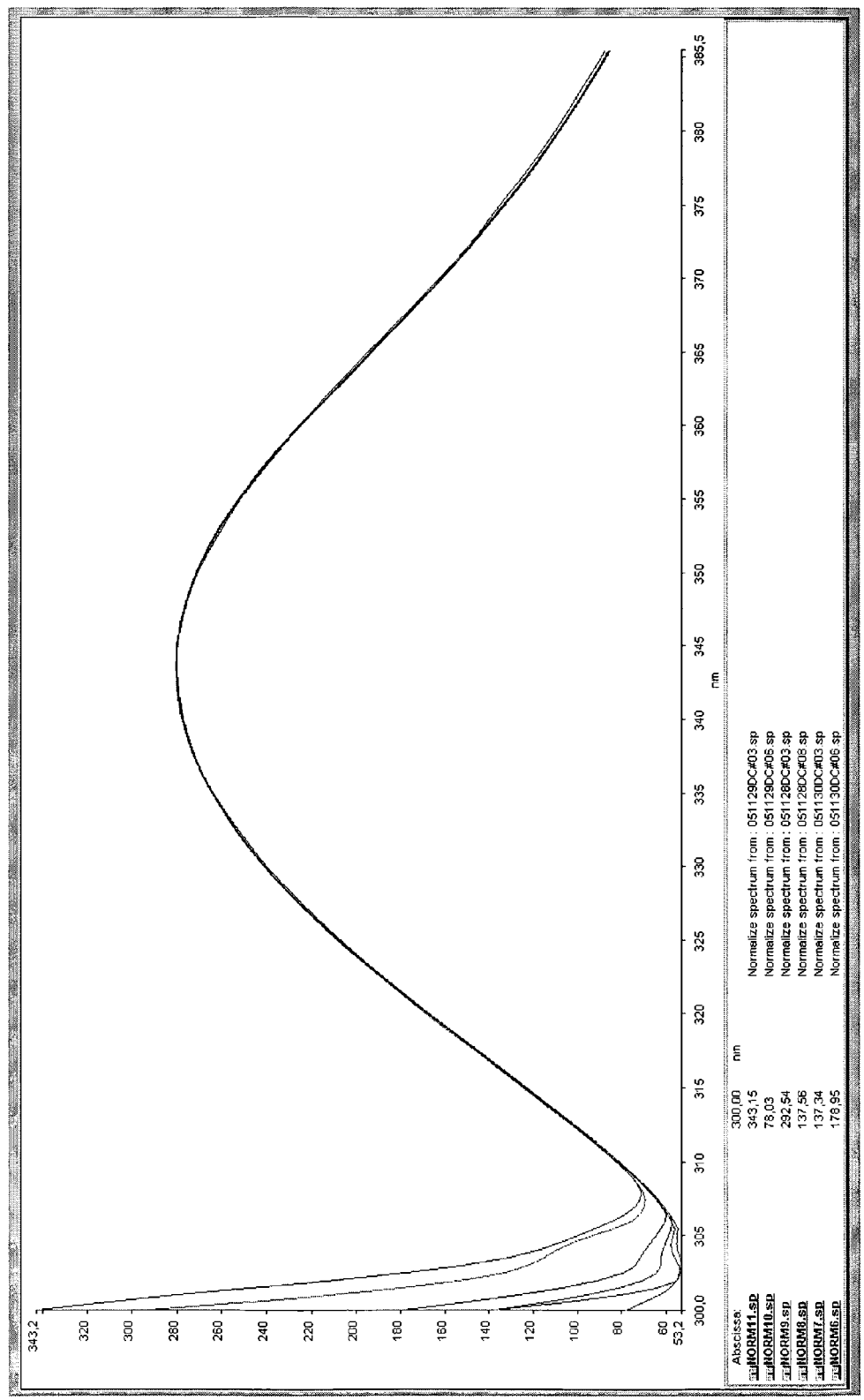
Figure 62:
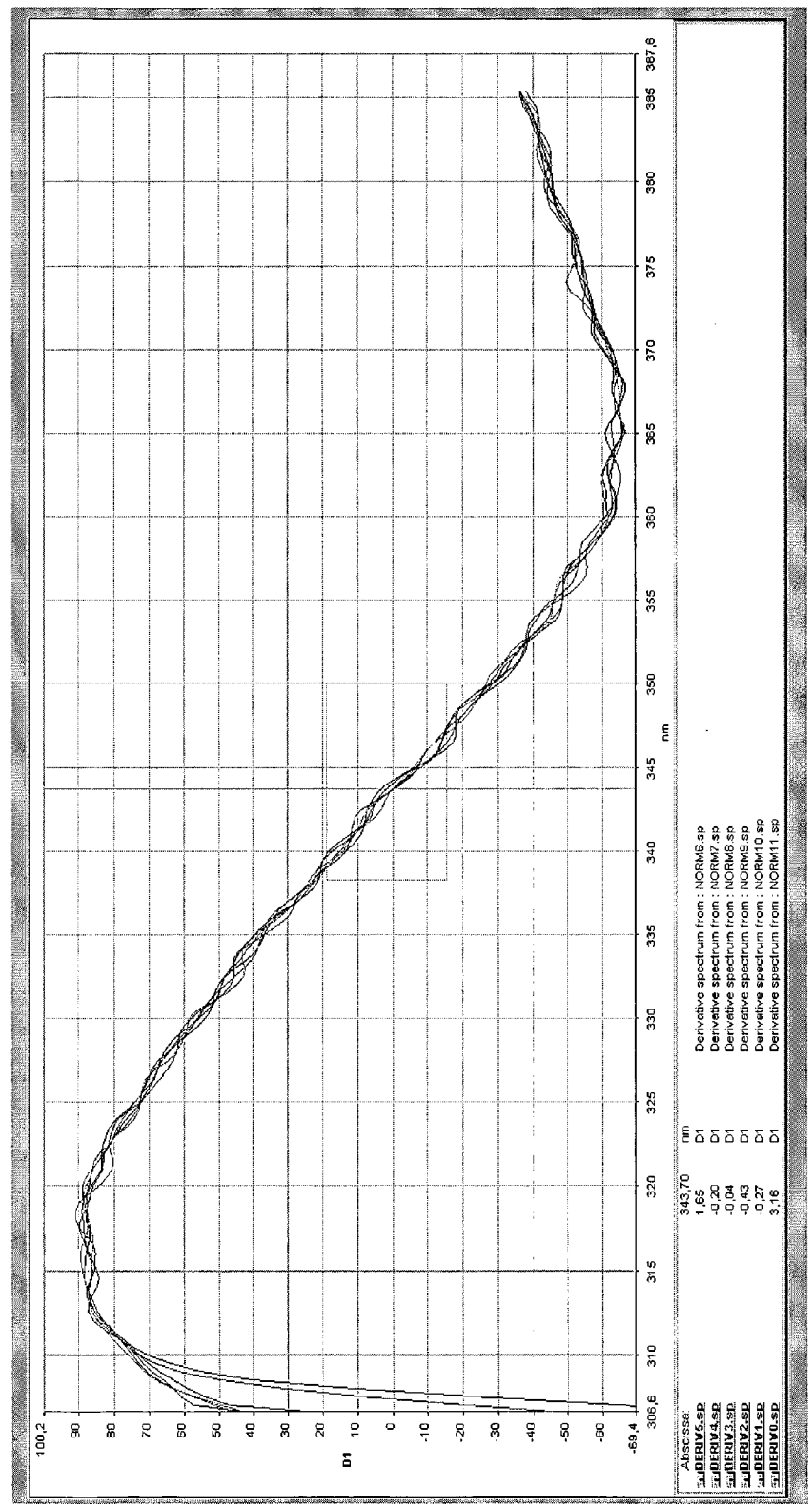
Figure 63:
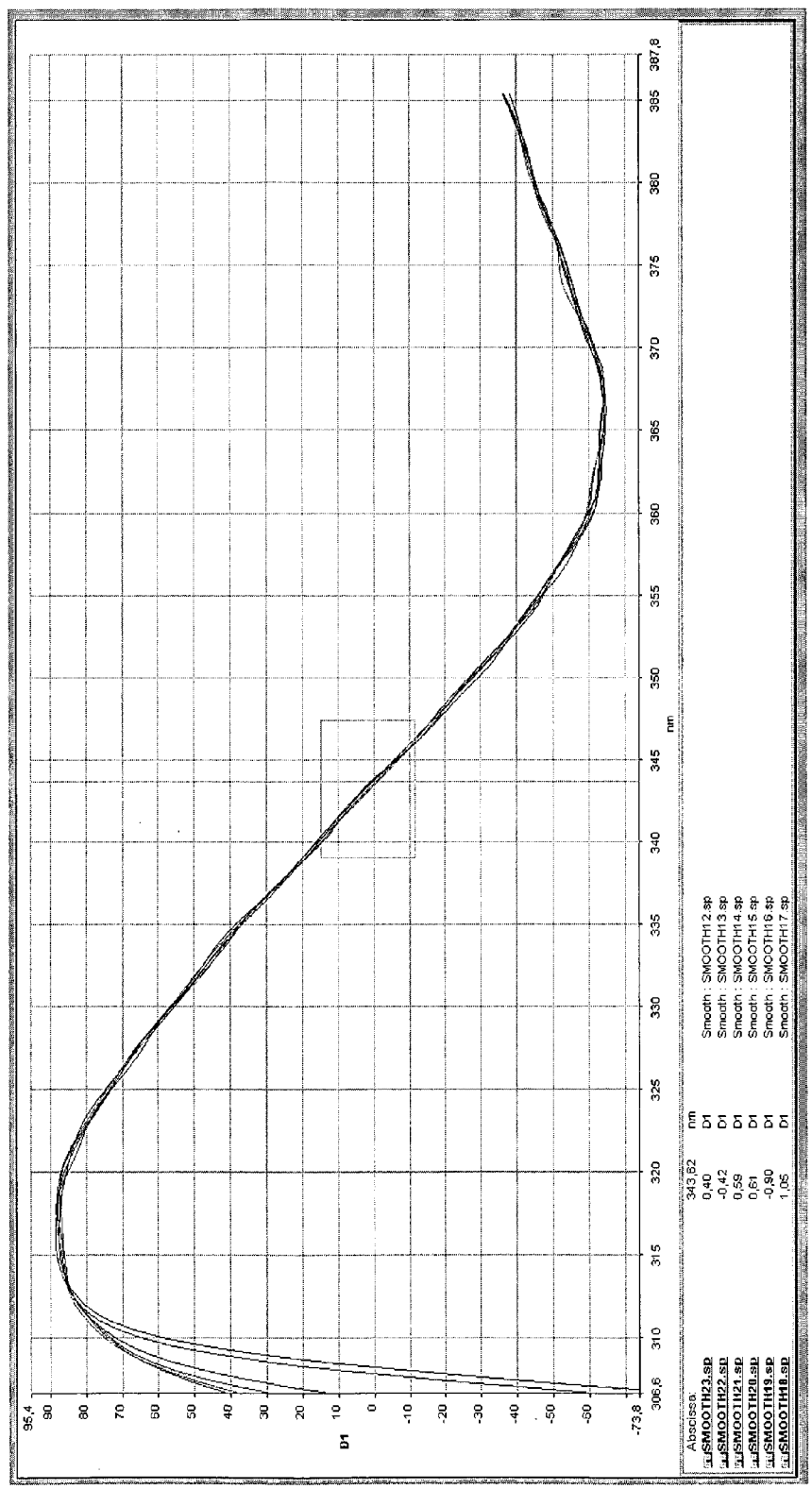

FIGS. 62 and 63 show raw and smoothed first order derivatives respectively of the emission spectra described in FIG. 61.

Figure 64:
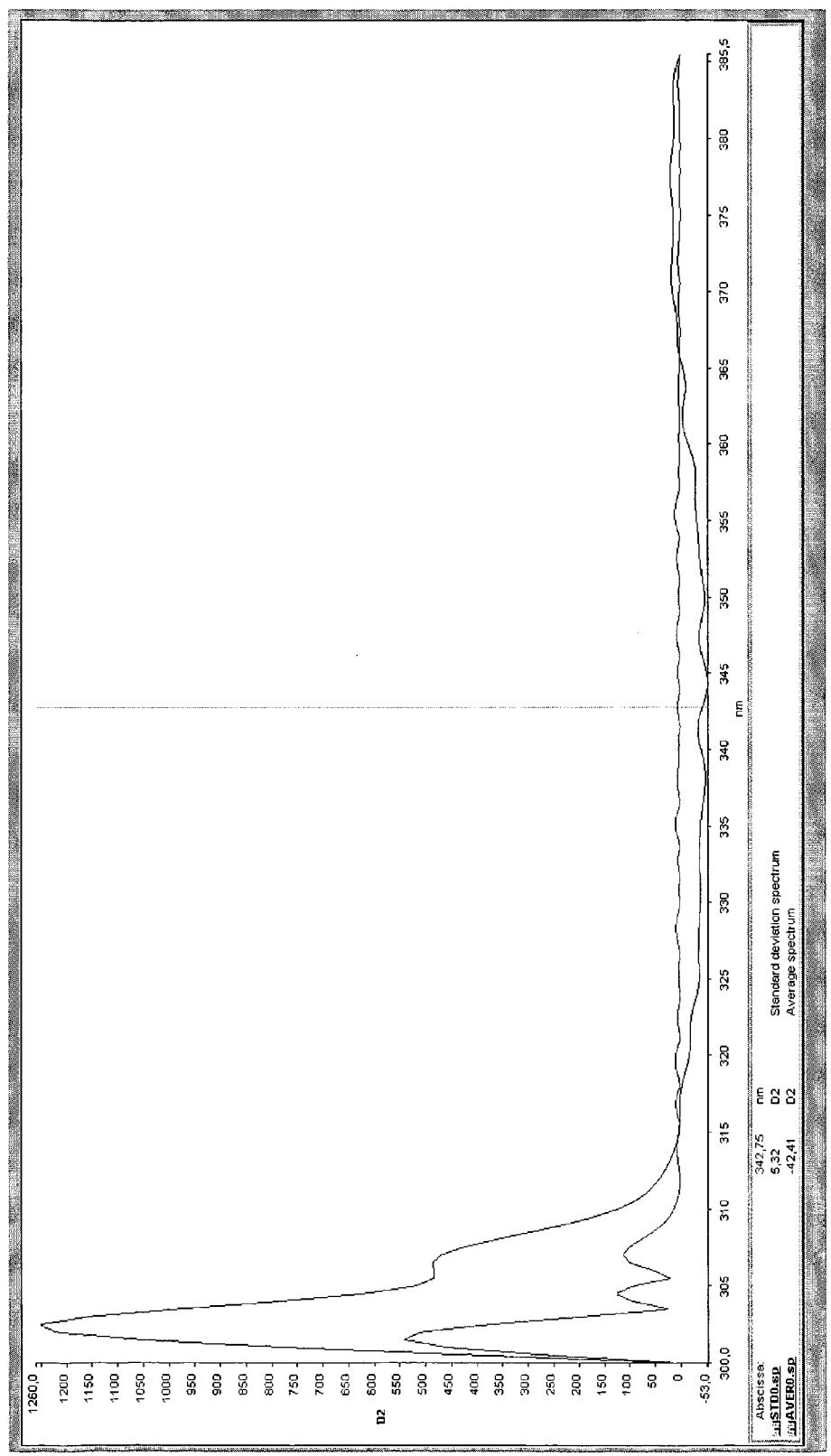

FIGS. 64 (lot 1) and 65 (lot 2) show the average spectrum of single second derivative spectra and their relative standard deviation.

Figure 66:
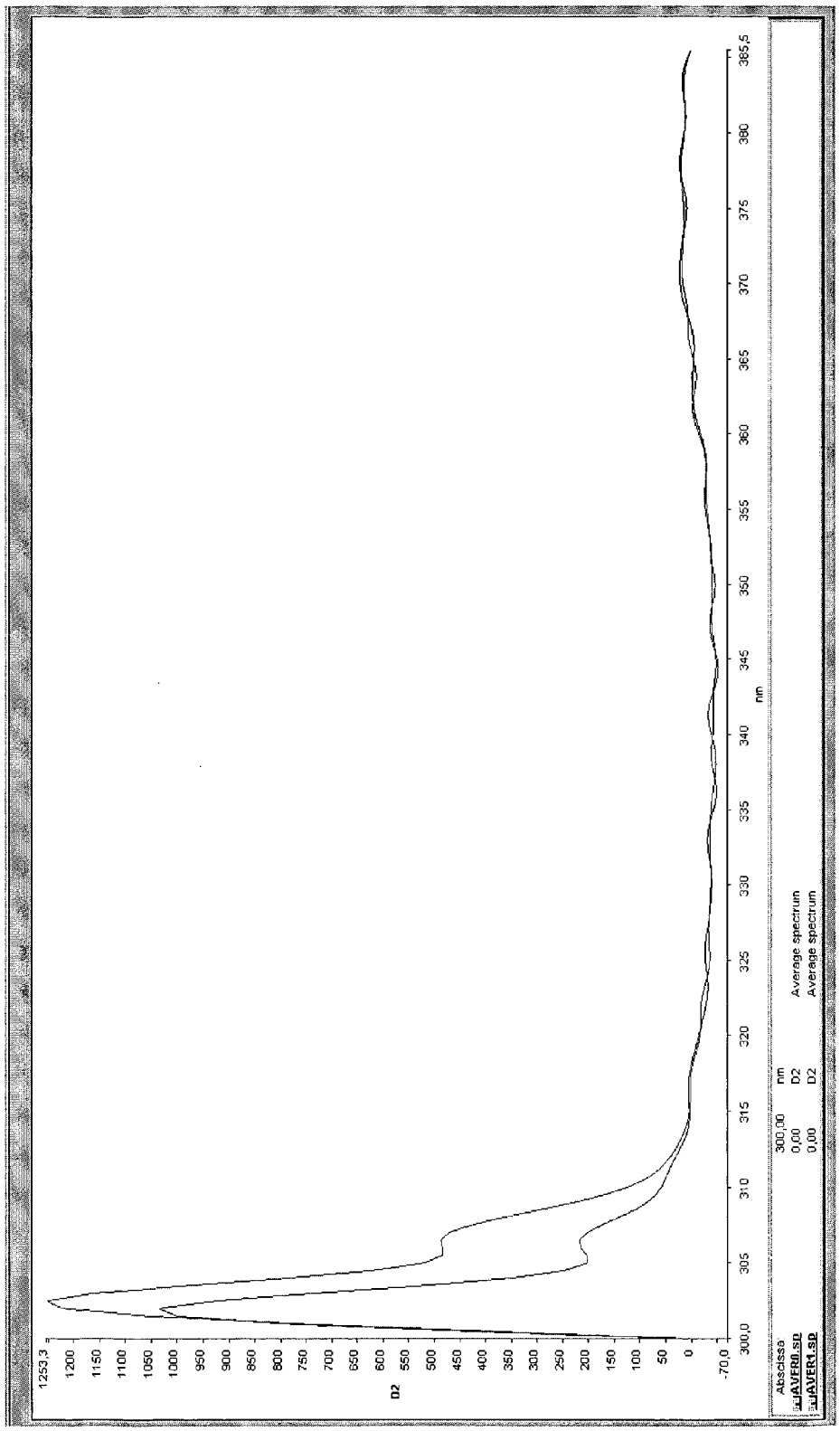

FIG. 66 shows the second derivative average spectra of lot 1 and lot 2 superimposed.

Figures of Example 8

Figure 67:
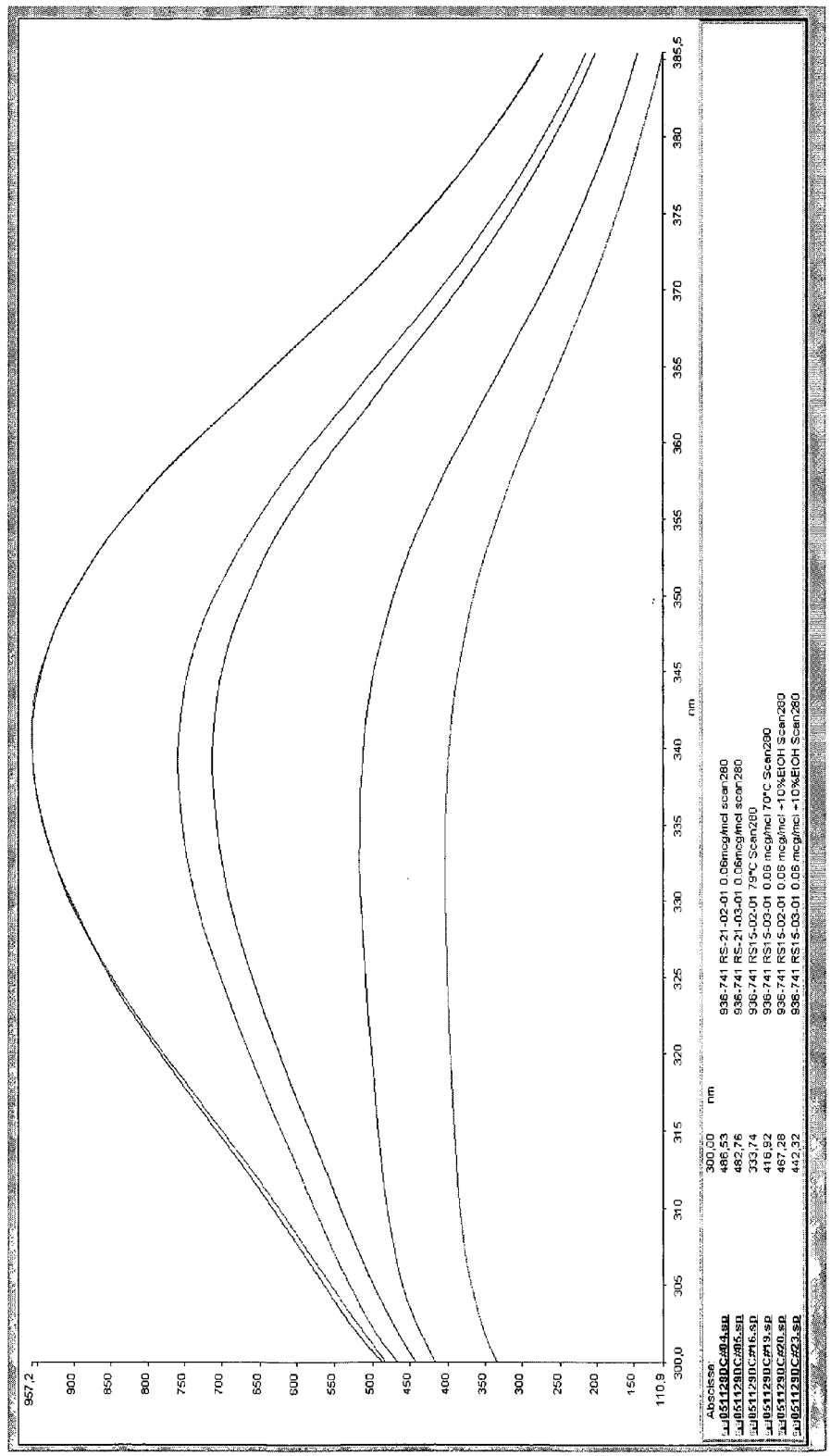
Figure 68:
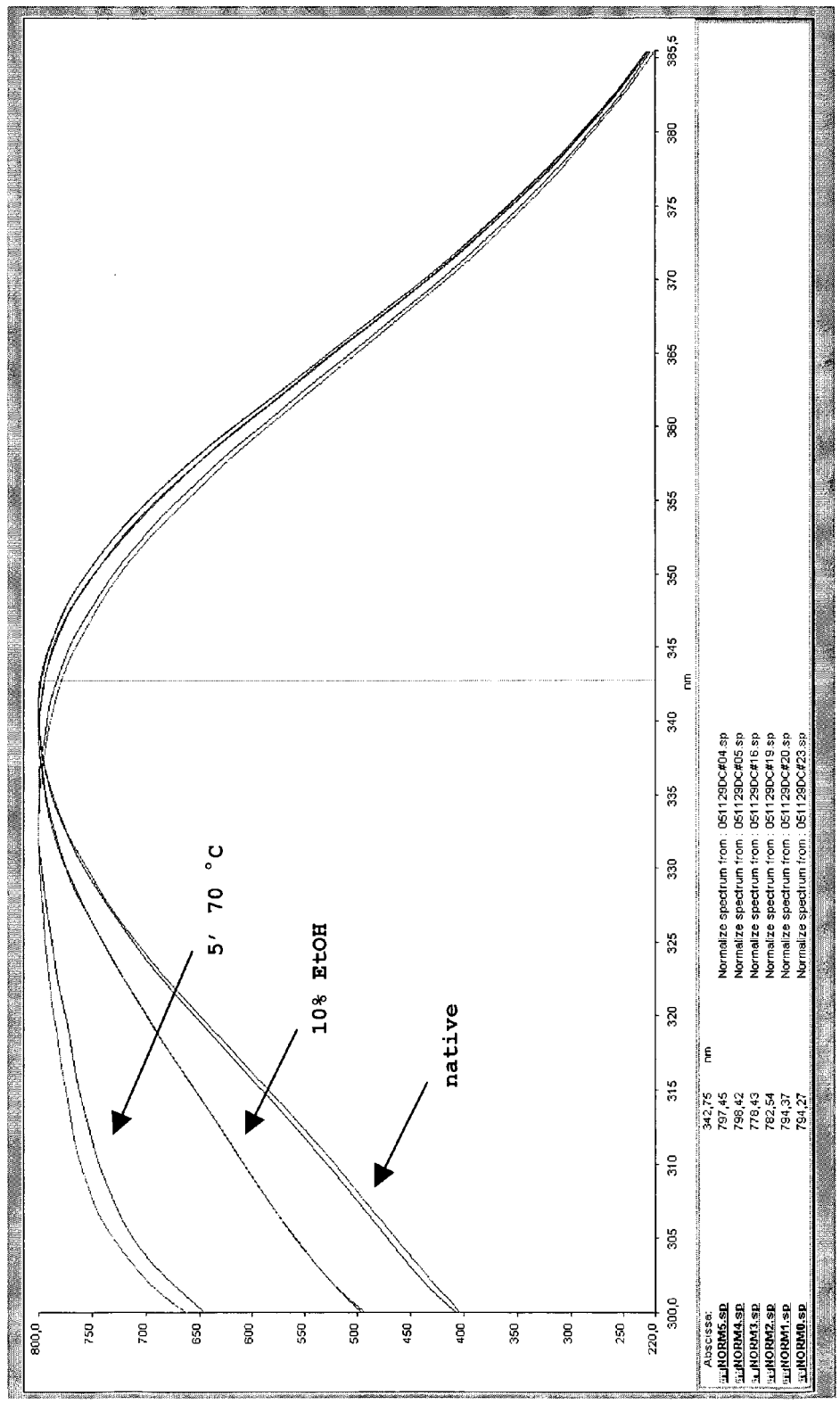

FIG. 67 shows the absorbance spectra of 936-741 lots 1 and 2 modified or unmodified as specified in Table 14 (excitation at 280 nm). FIG. 68 shows the spectra normalized.

Figure 69:
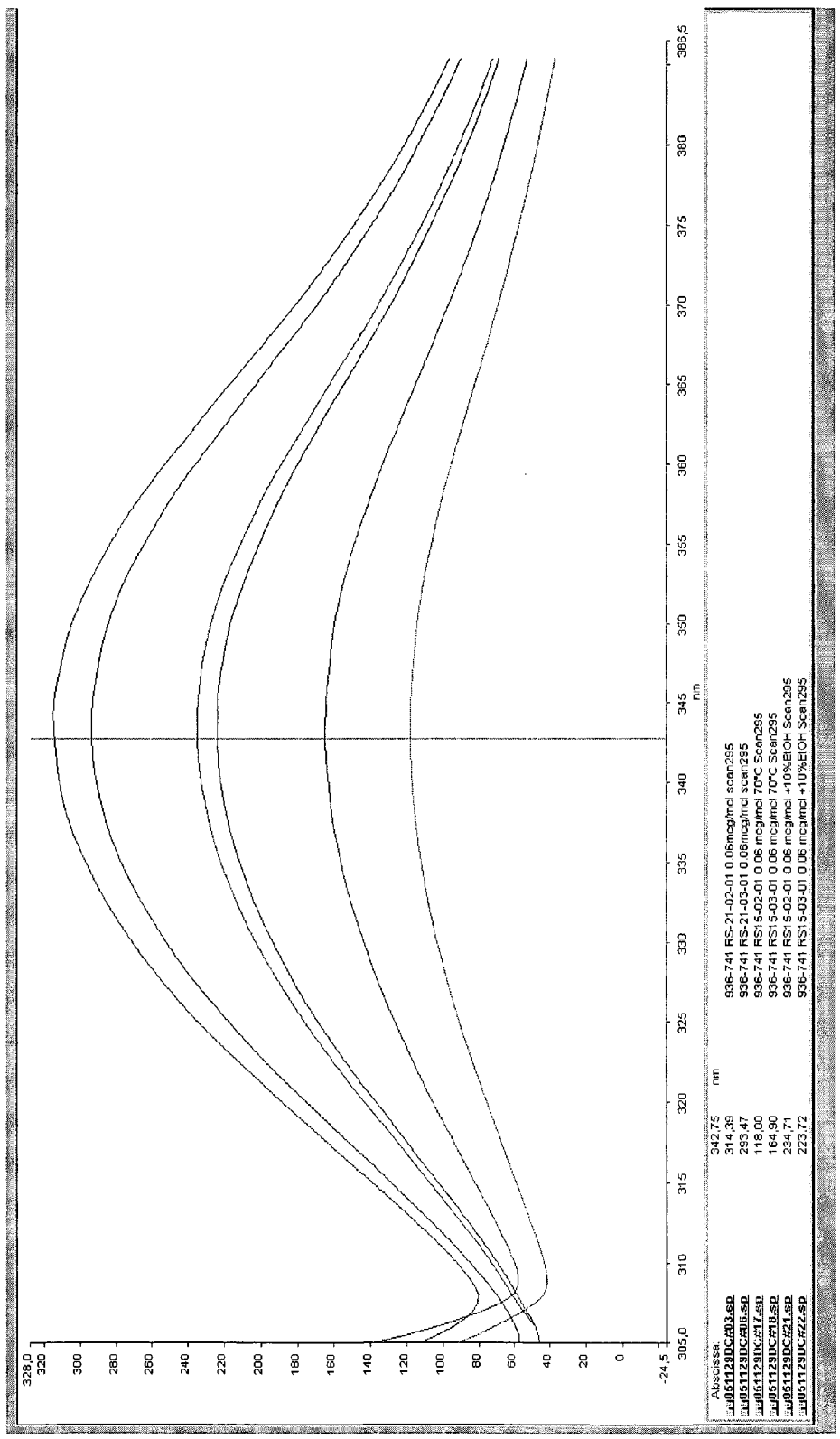
Figure 70:
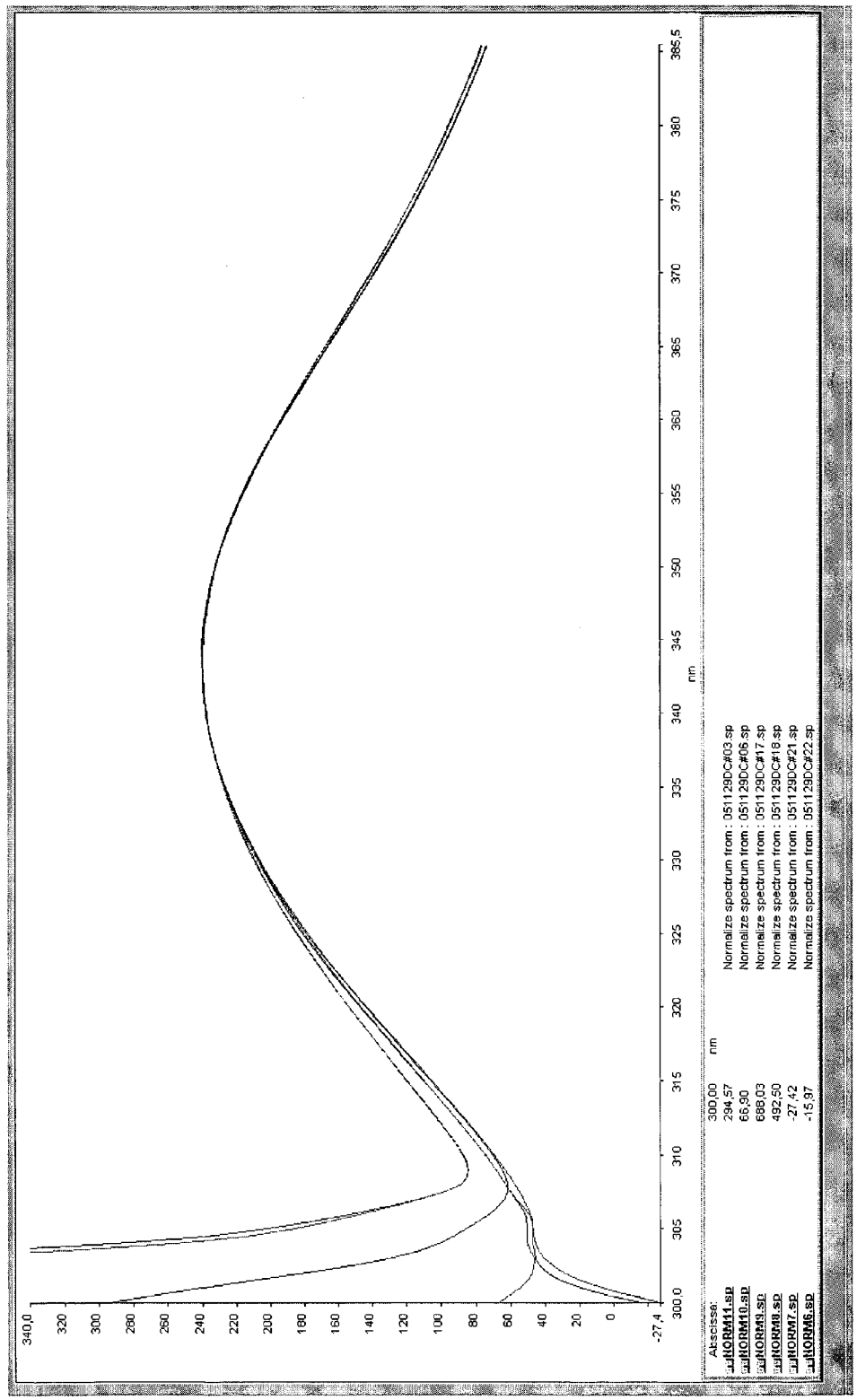

FIG. 69 shows the absorbance spectra of 936-741 lots 1 and 2 modified or unmodified as specified in Table 14 (excitation at 295 nm). FIG. 70 shows the spectra normalized.

Figures of Example 9

1 Example 9A

Figure 71A:
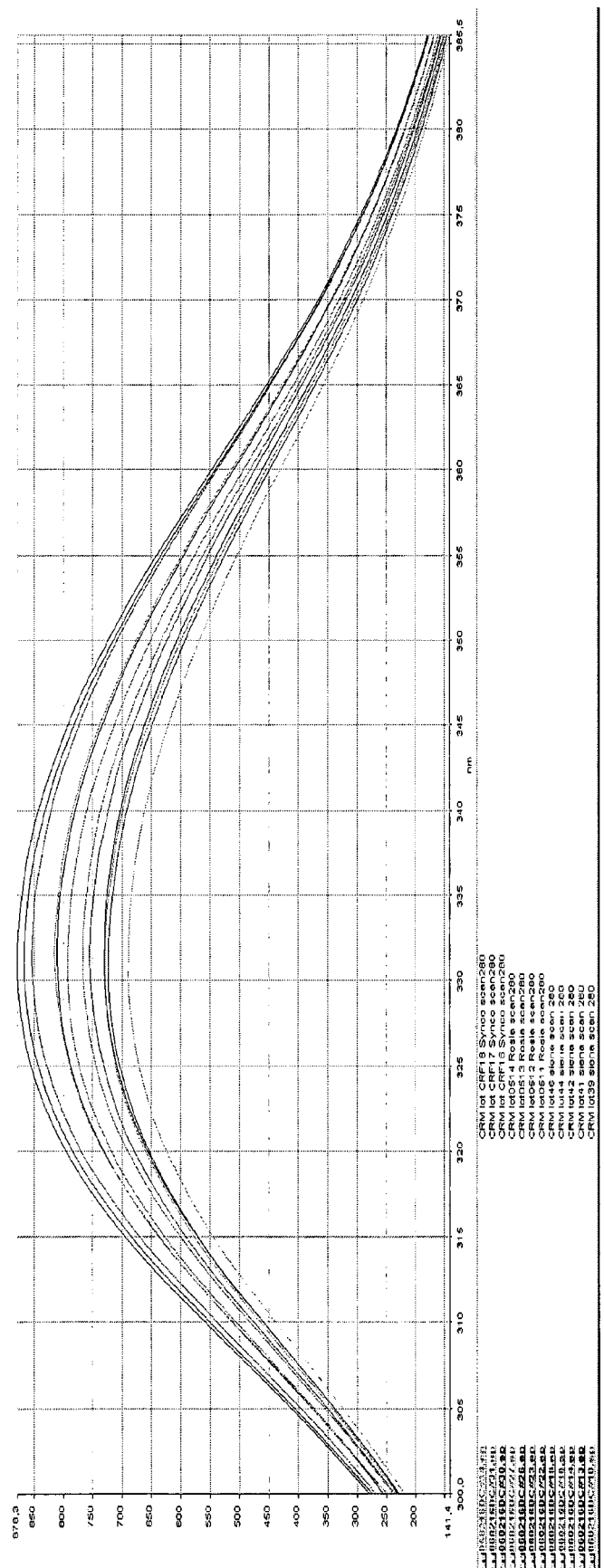
Figure 71B:
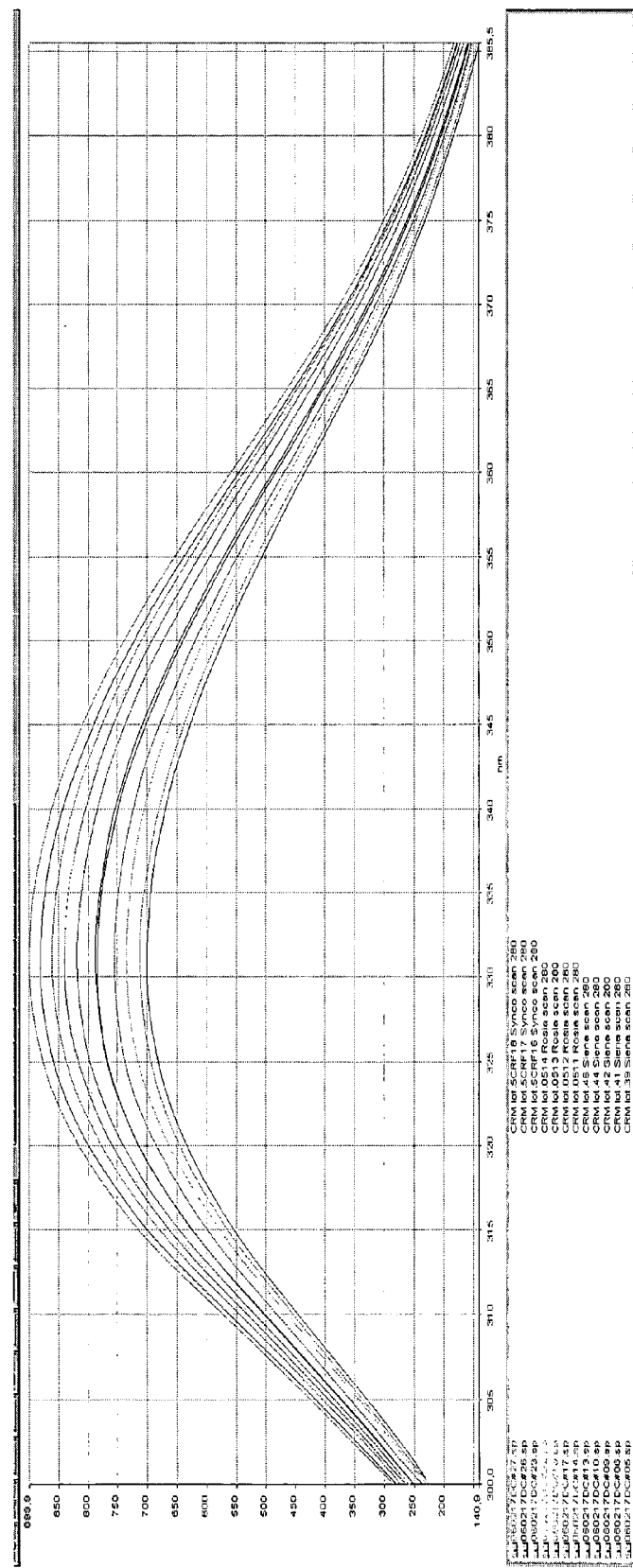
Figure 71C:
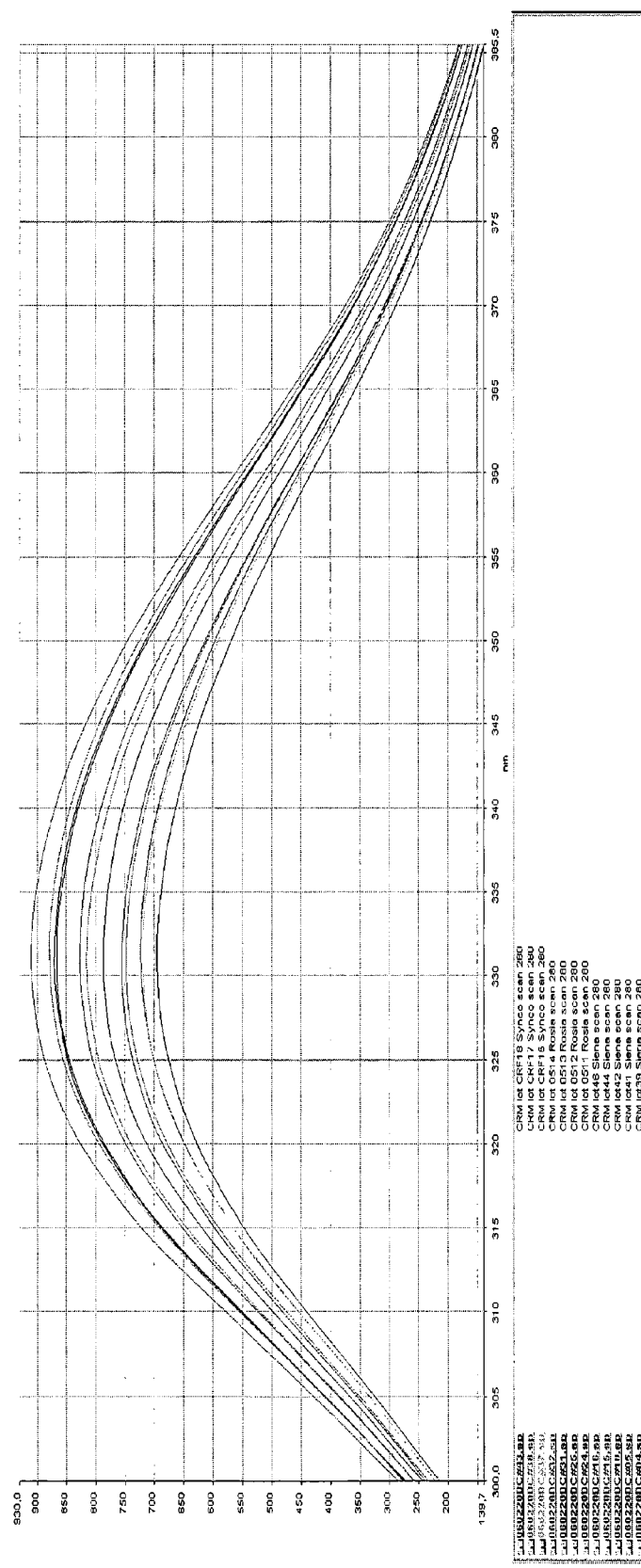
Figure 72:
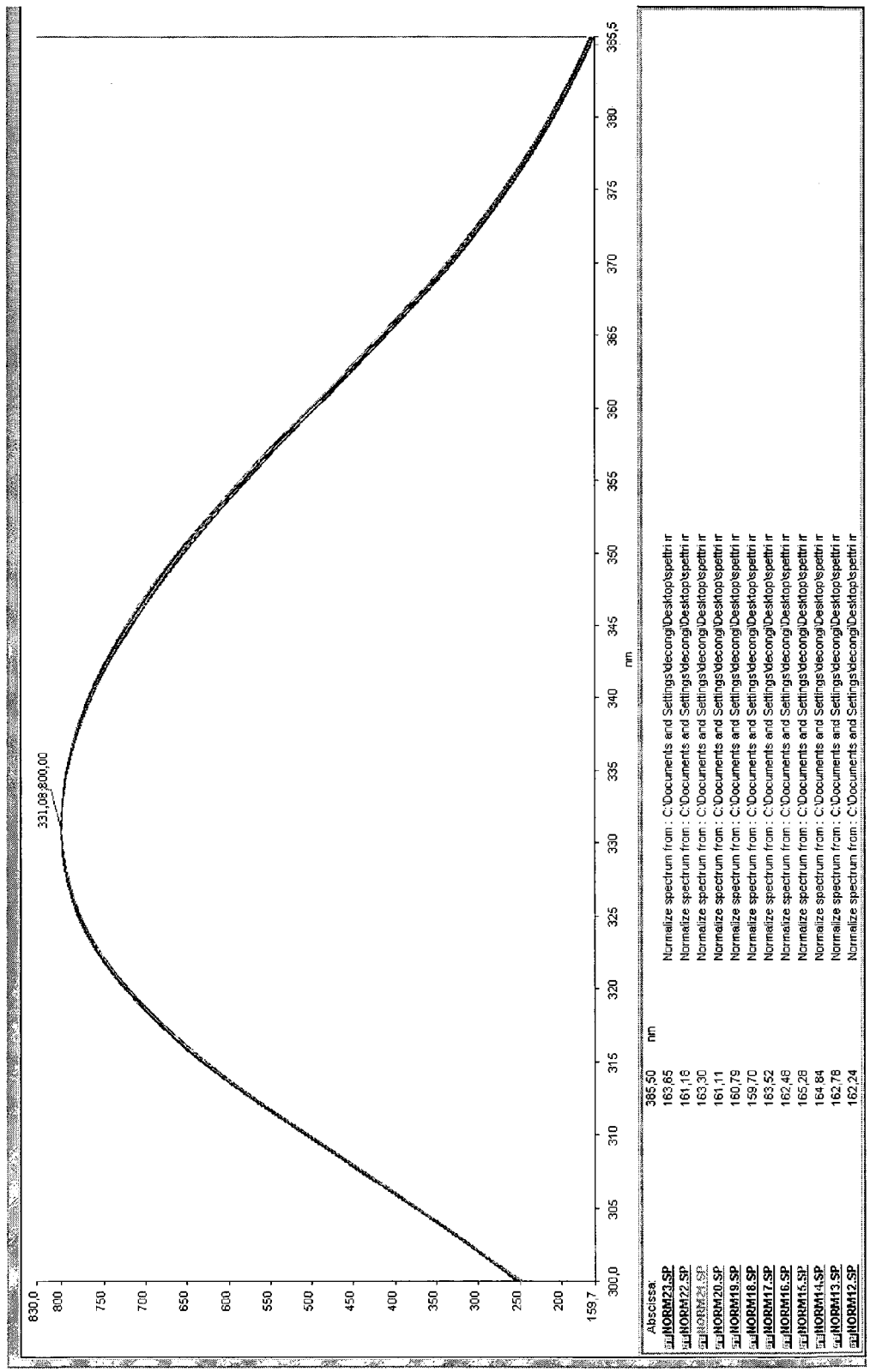

FIGS. 71A-C shown the un-normalized spectra of the 12 $CRM_{197}$ lots made in Site 1, Site 2 and Site 3 analyzed at 280 nm excitation in three analytical sessions over different days. FIG. 72 shows the normalized average spectra (over the three analytical sessions) of each $CRM_{197}$ lot.

Figure 73:
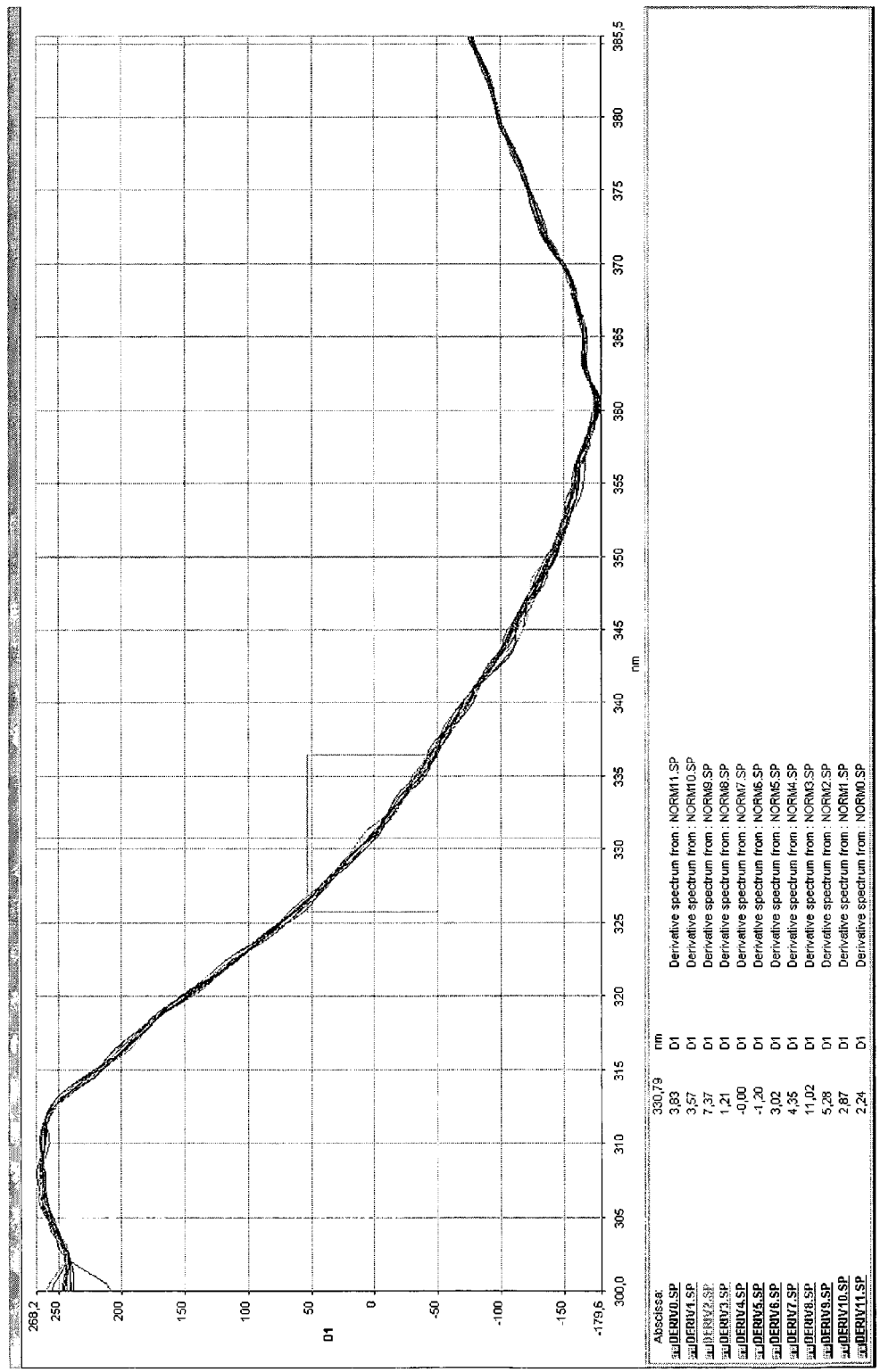

FIG. 73 shows unsmoothed first order derivatives of the emission spectra described in FIG. 72.

Figure 74:
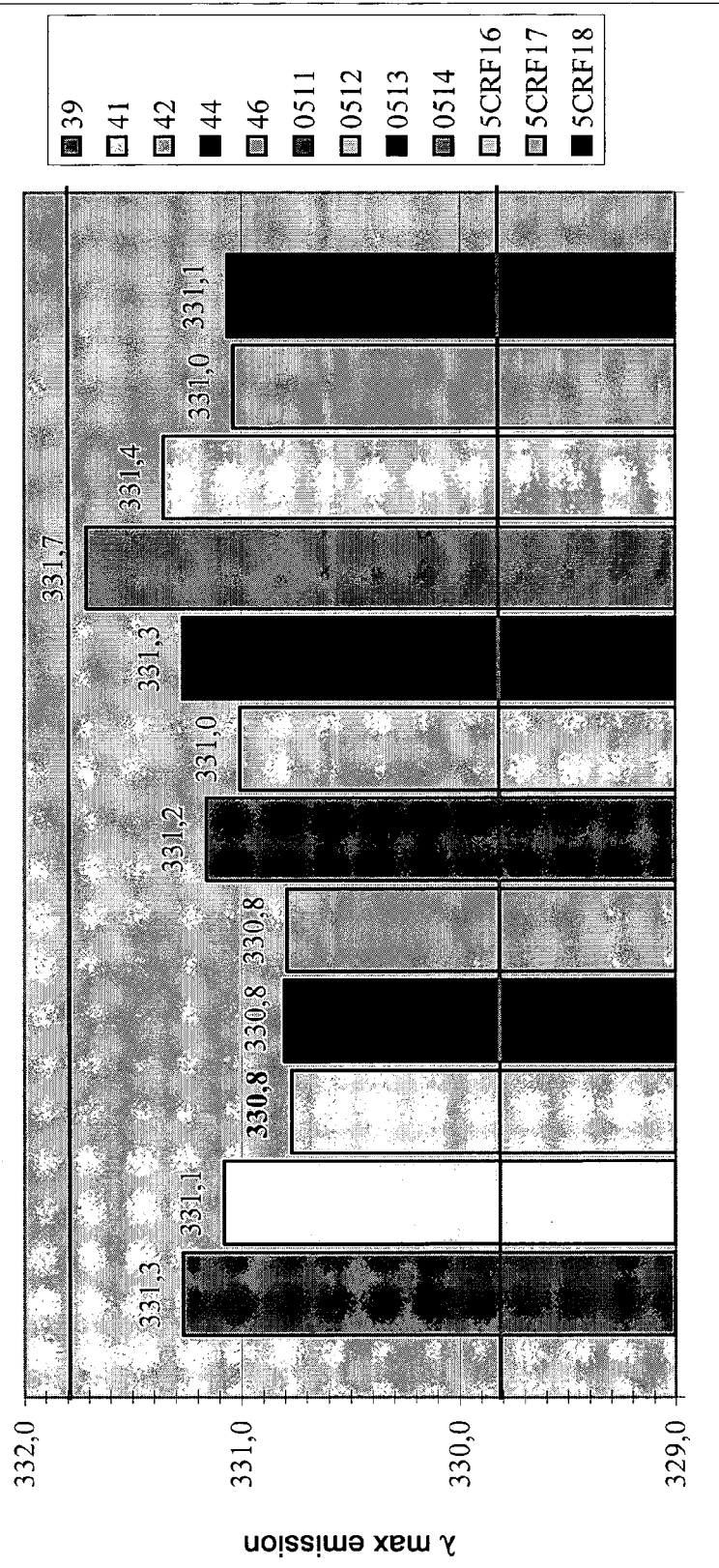

FIG. 74 shows a graphical representation of the $\lambda_{max}$ emission variation of all lots with respect to lot 42 (yellow bar).

Figure 75:
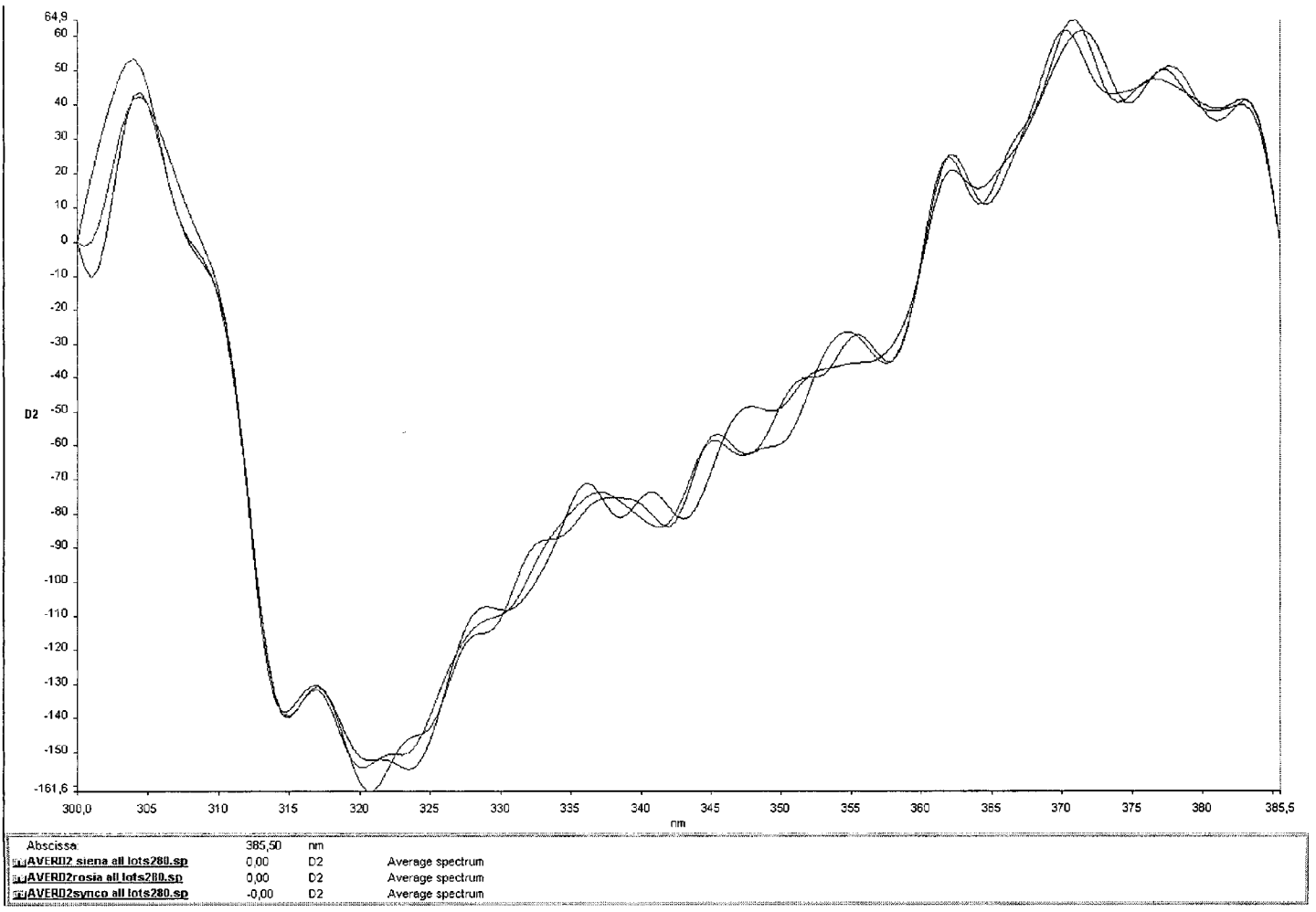

FIG. 75 shows second derivative smoothed average spectra between the lots.

Figure 76:
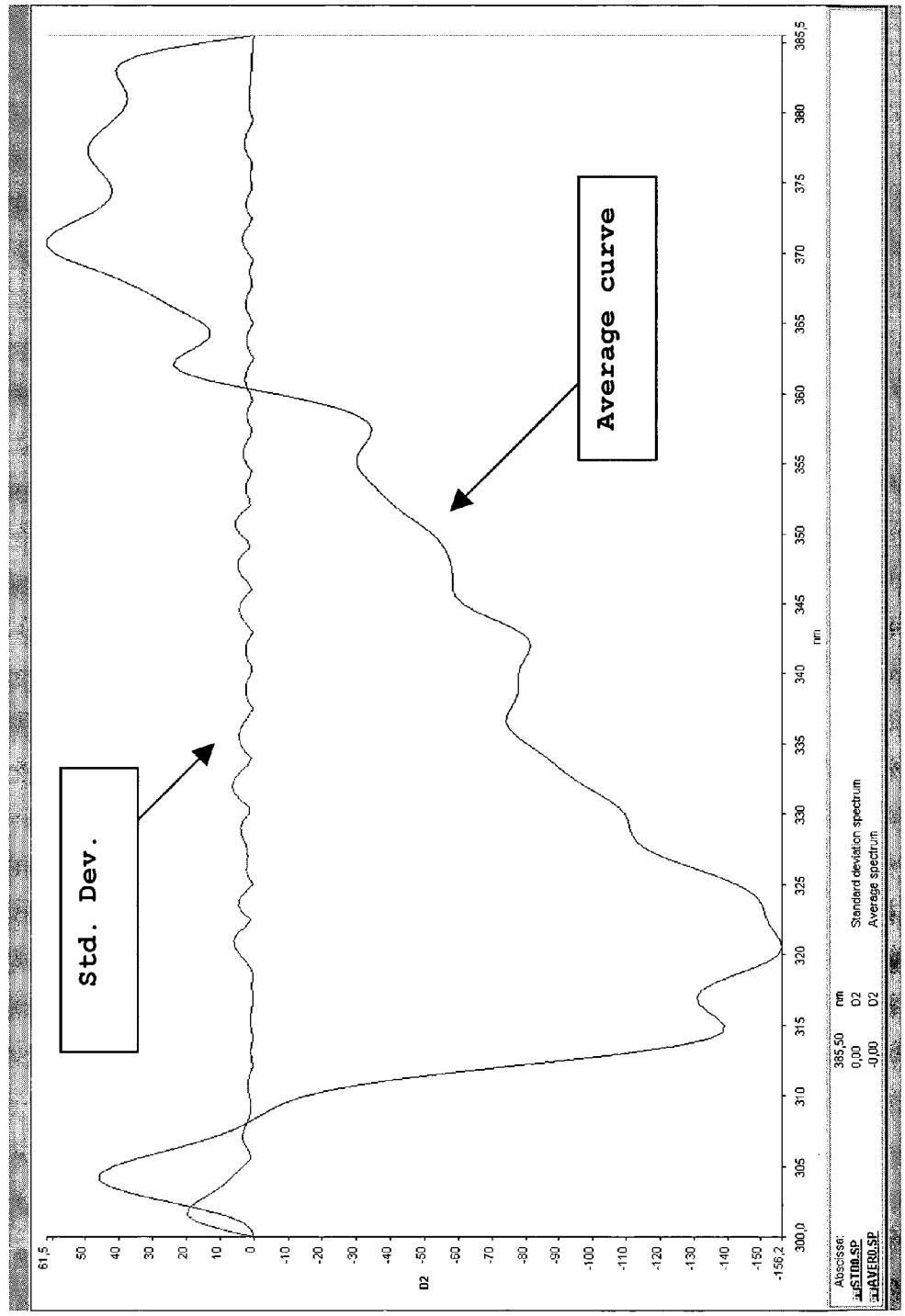

FIG. 76 shows the average curve of the second derivatives of FIG. 75 and their relative standard deviations.

Figure 77:
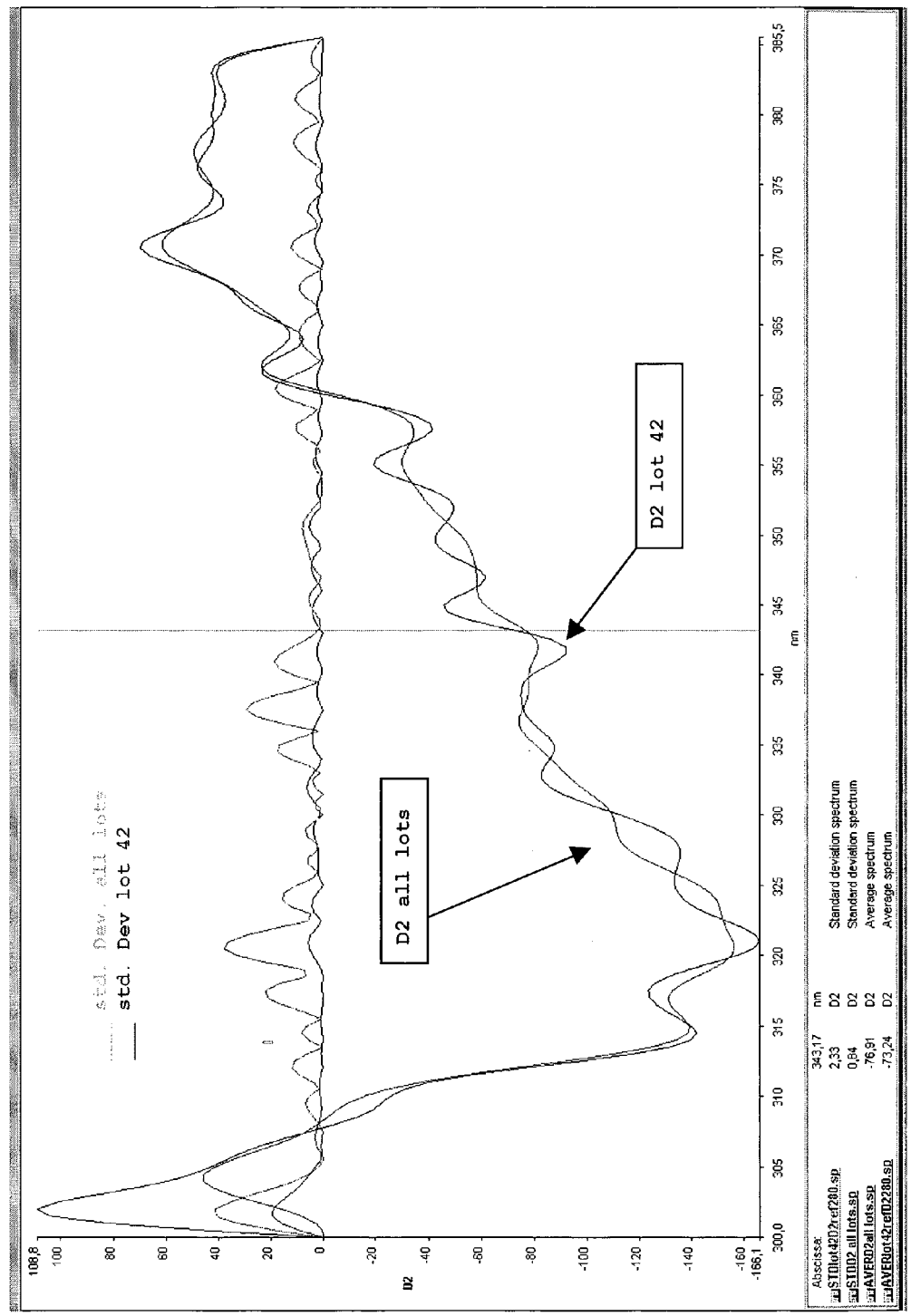

FIG. 77 shows a comparison between second derivative average spectra of the single lot 42 (of three different analyses) and second derivative average spectra of all lots analysed.

2 Example 9B

Figure 78A:
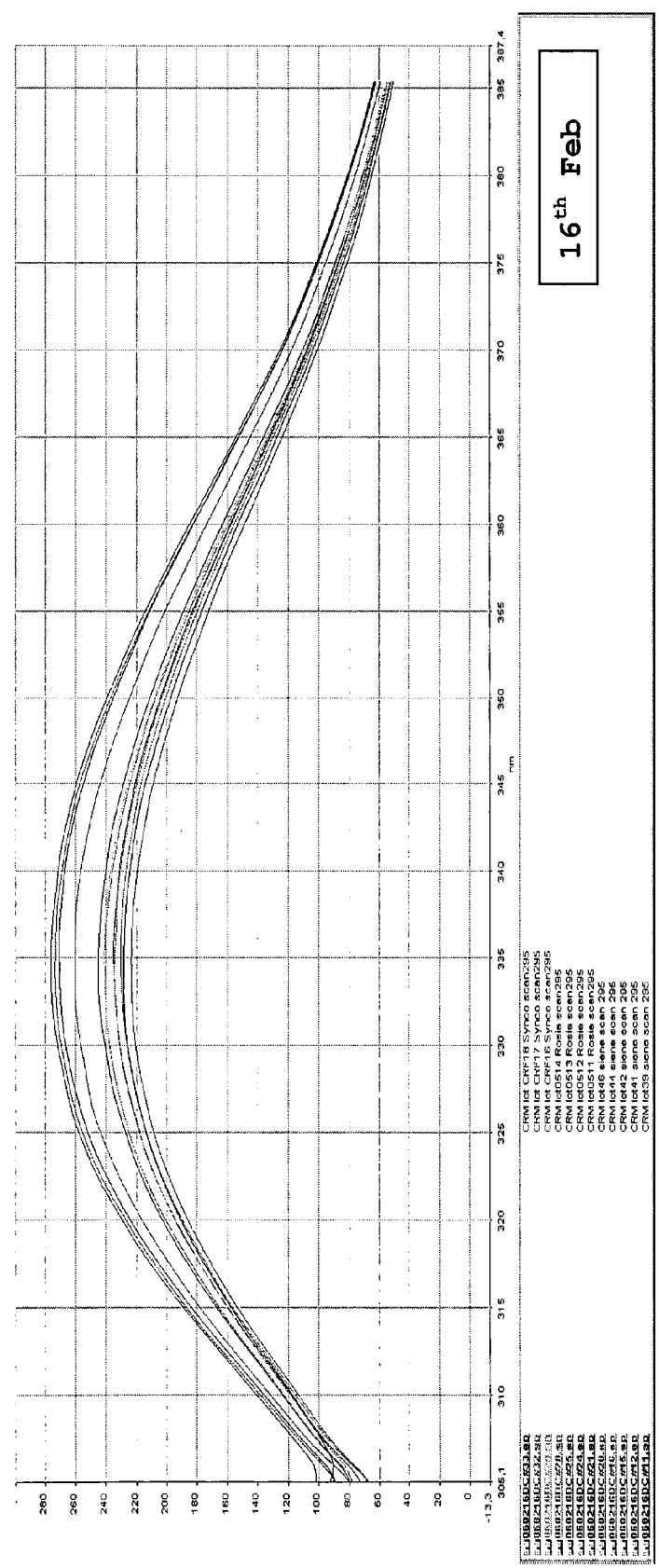
Figure 78B:
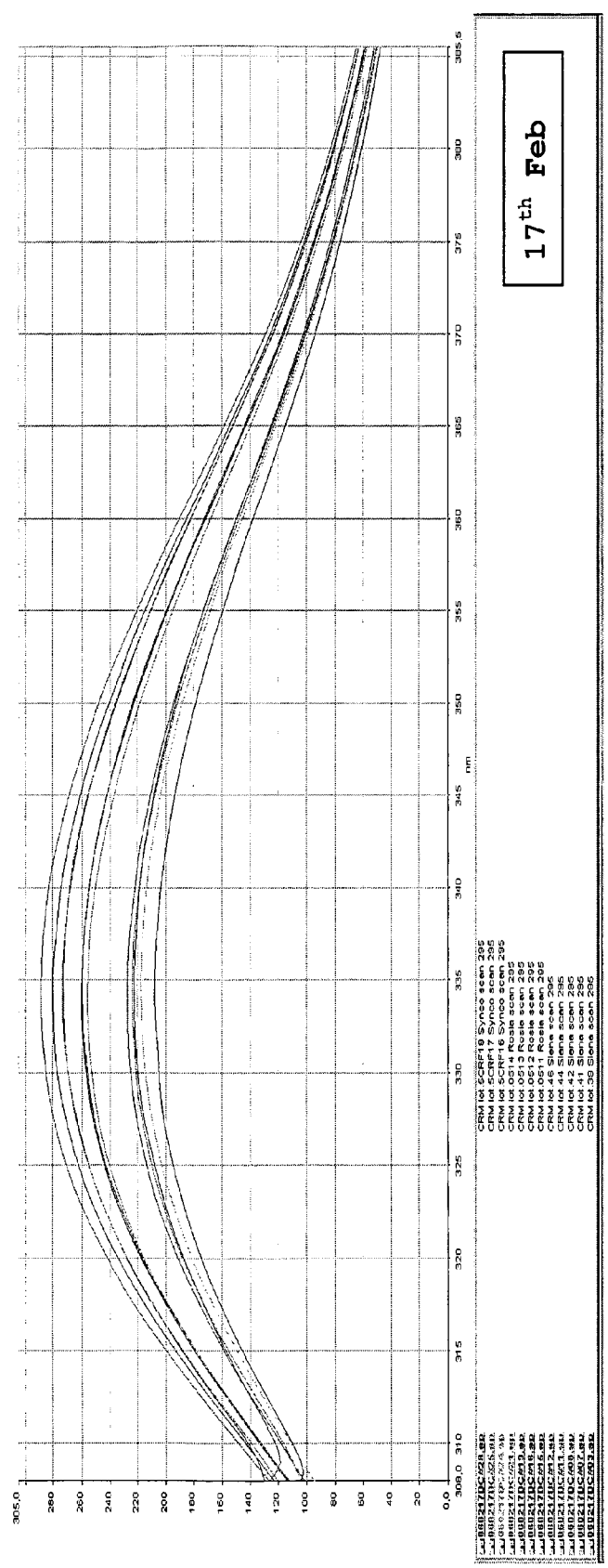
Figure 78C:
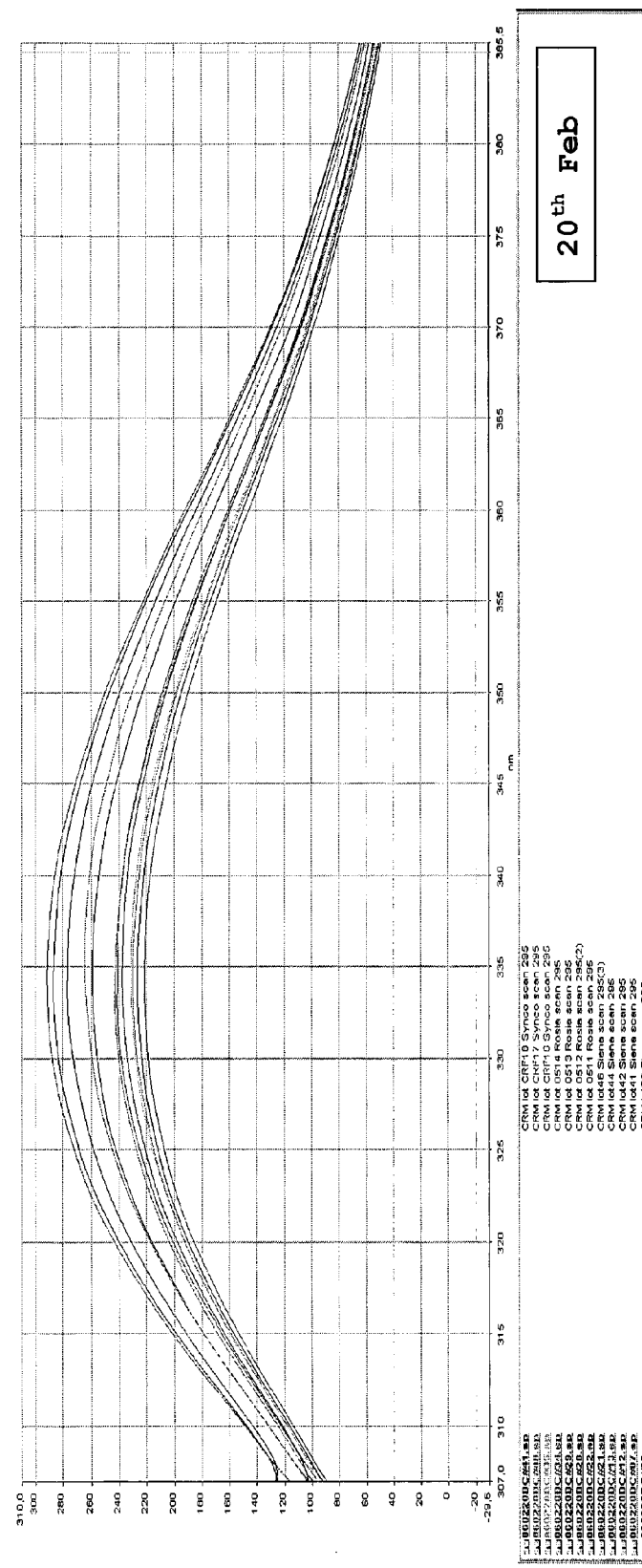
Figure 79:
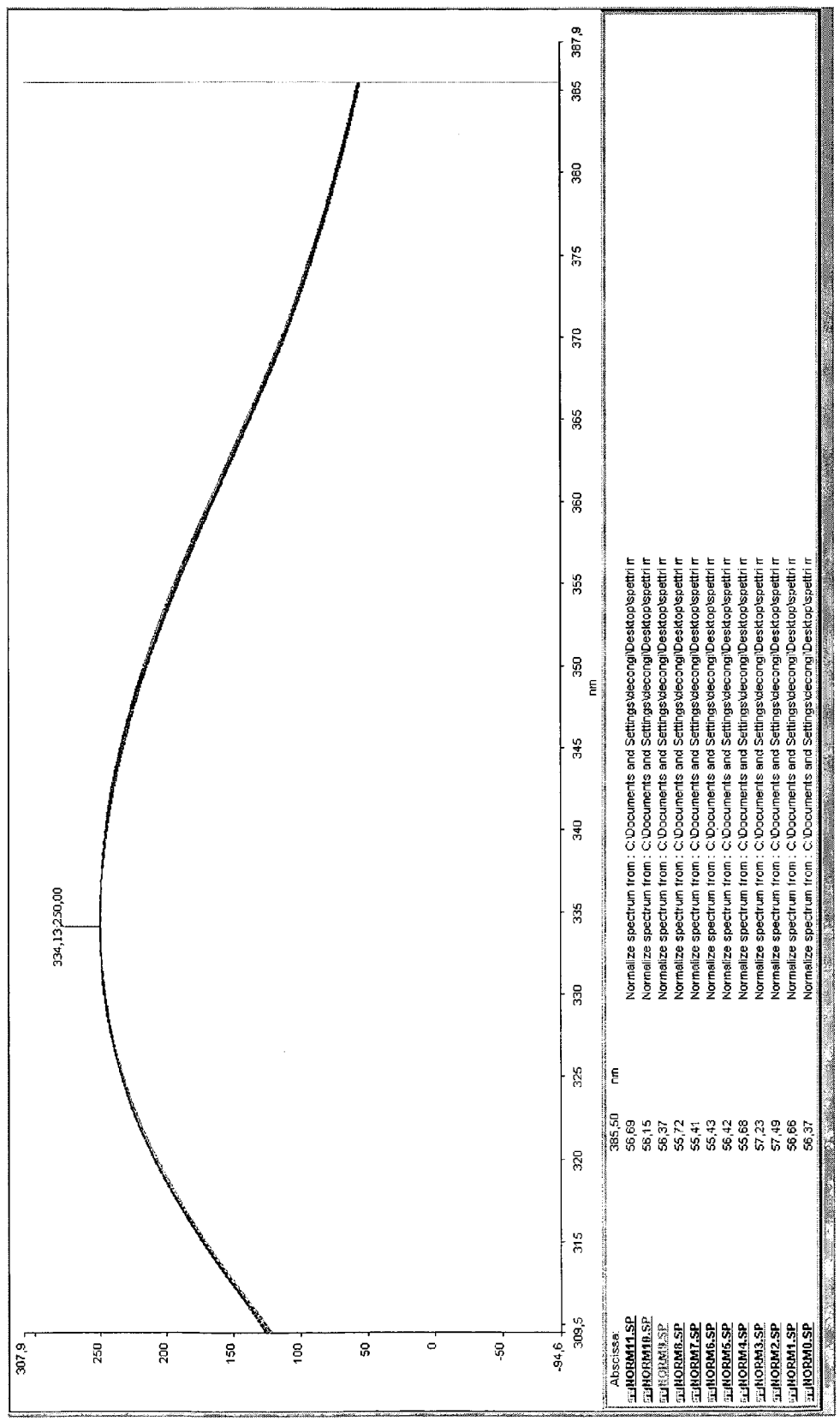

FIGS. 78A-C shown the un-normalized spectra of the 12 $CRM_{197}$ lots made in Site 1, Site 2 and Site 3 analyzed at 295 nm excitation in three analytical sessions over different days. FIG. 79 shows the normalized average spectra (over the three analytical sessions) of each CRM lot.

Figure 80:
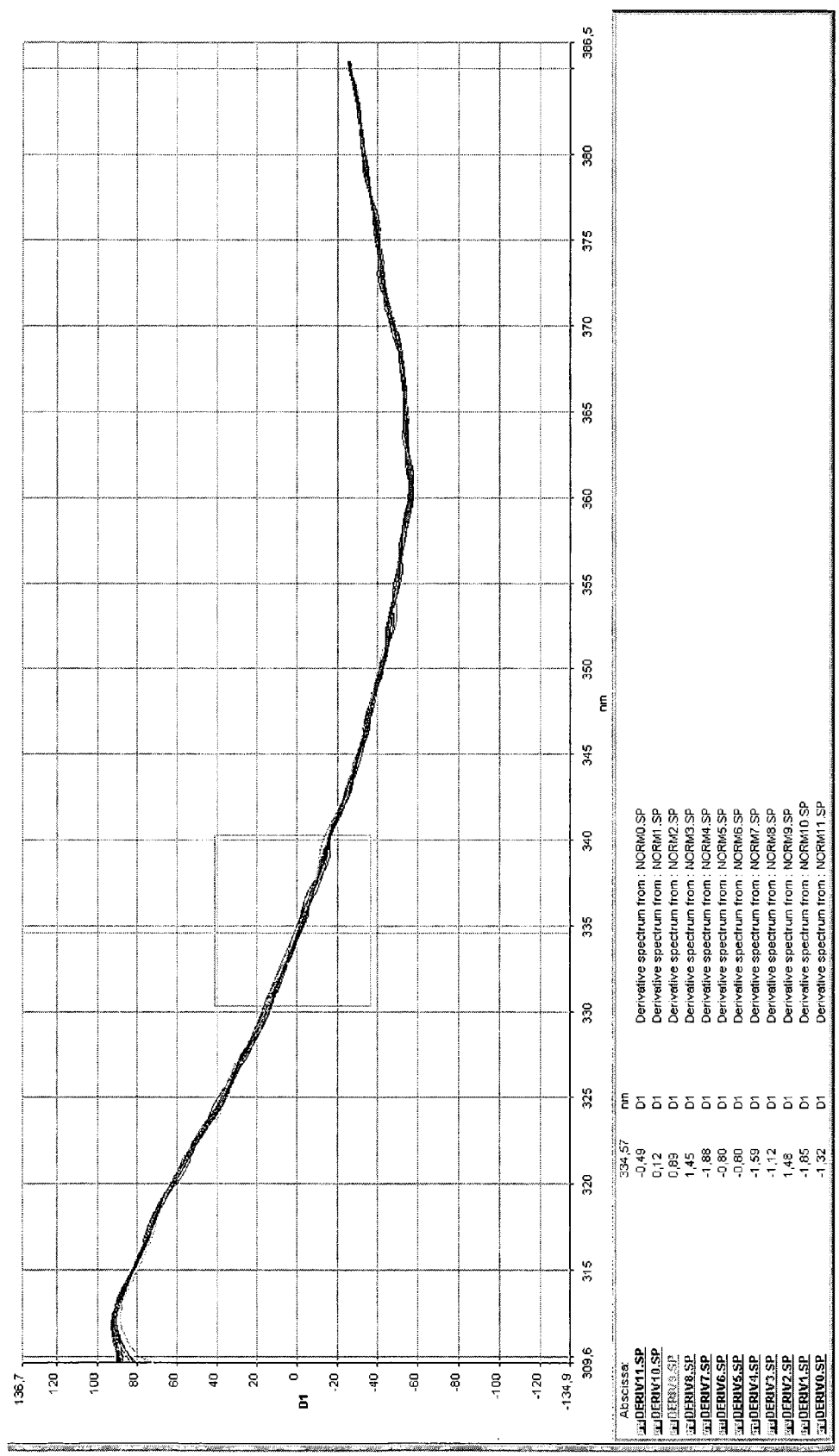

FIG. 80 shows unsmoothed first order derivatives of the emission spectra described in FIG. 79.

Figure 81:
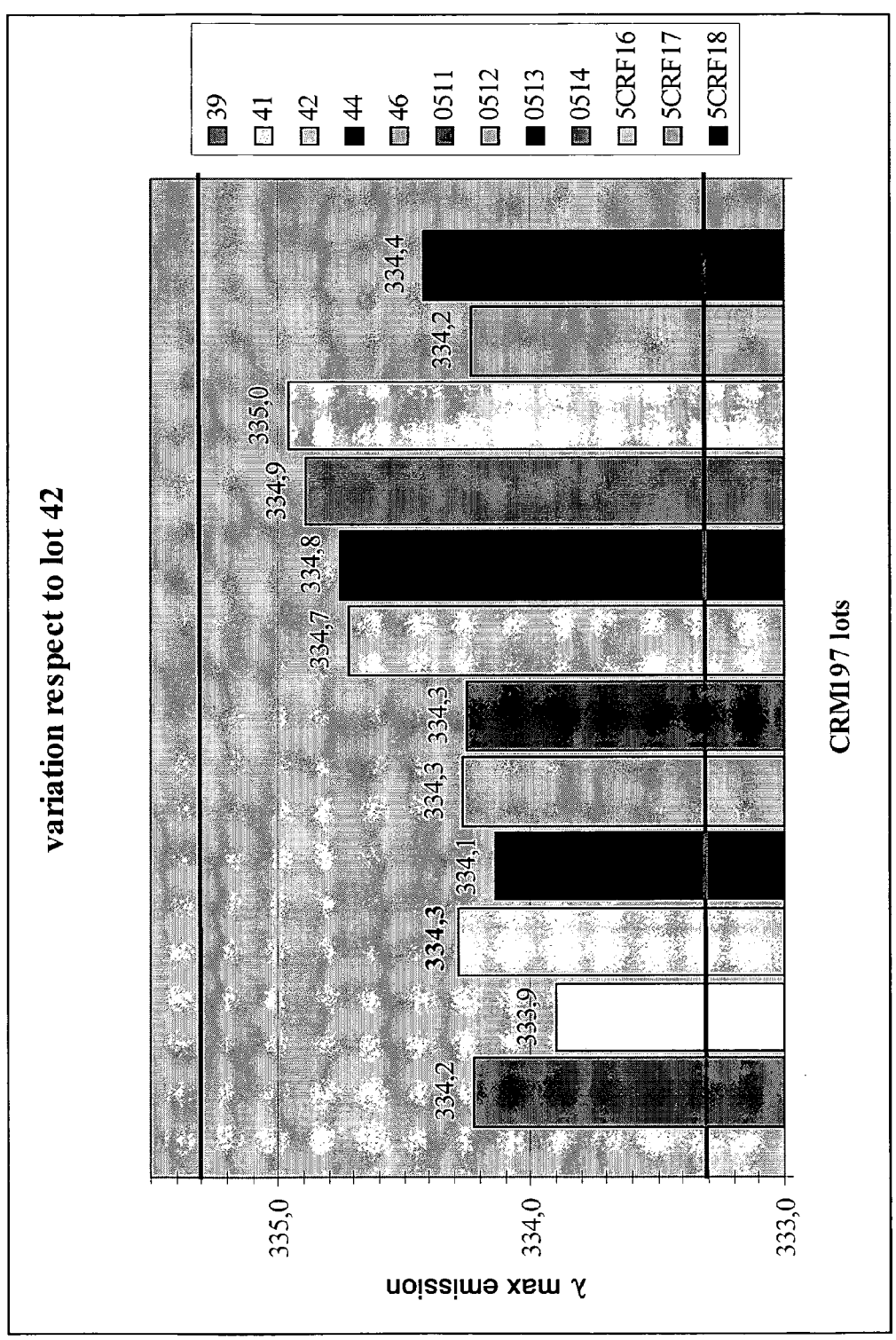

FIG. 81 shows a graphical representation of the $\lambda_{max}$ emission variation of all lots with respect to lot 42 (yellow bar).

Figure 82:
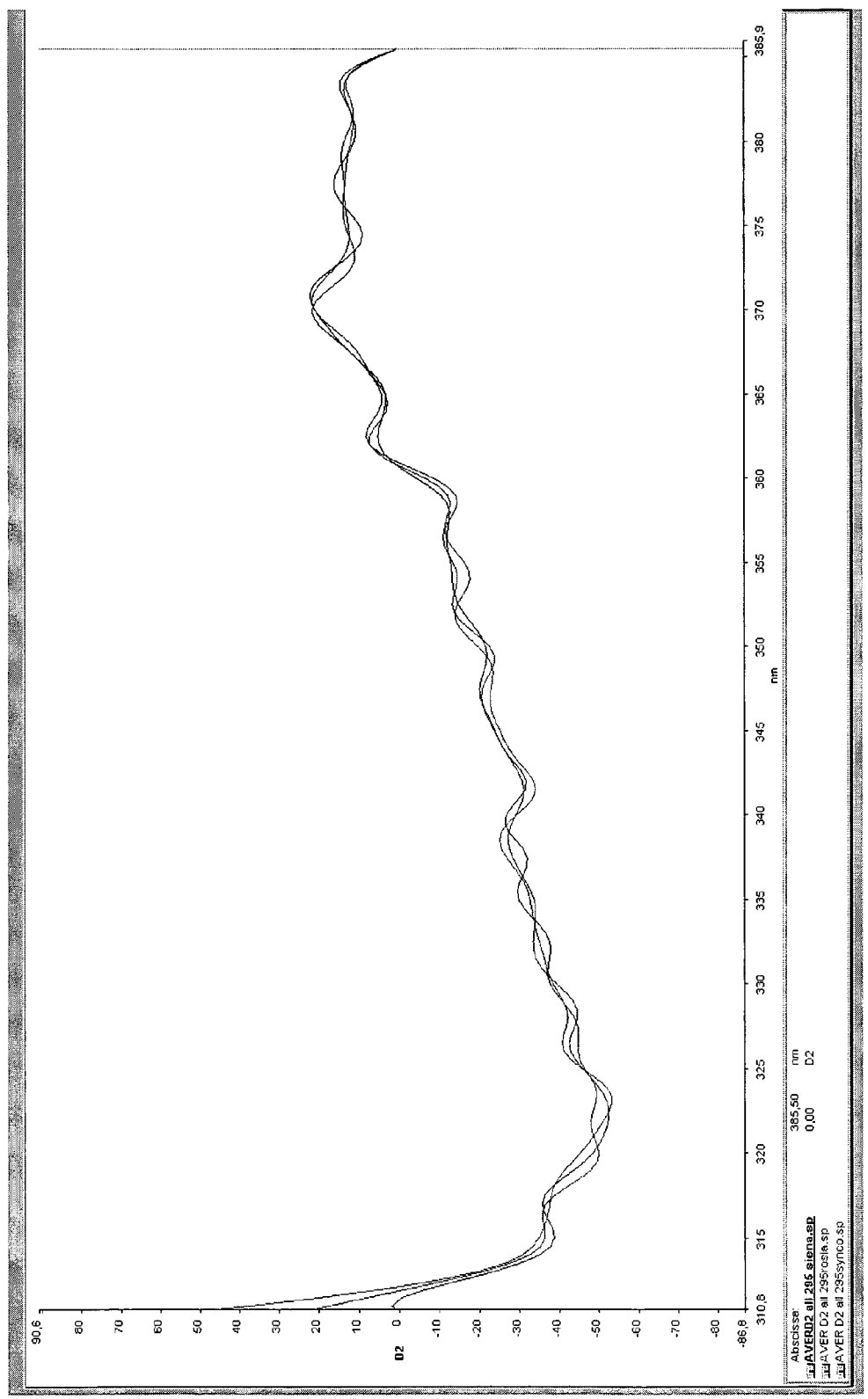

FIG. 82 shows second derivative smoothed average spectra between the lots.

Figure 83:
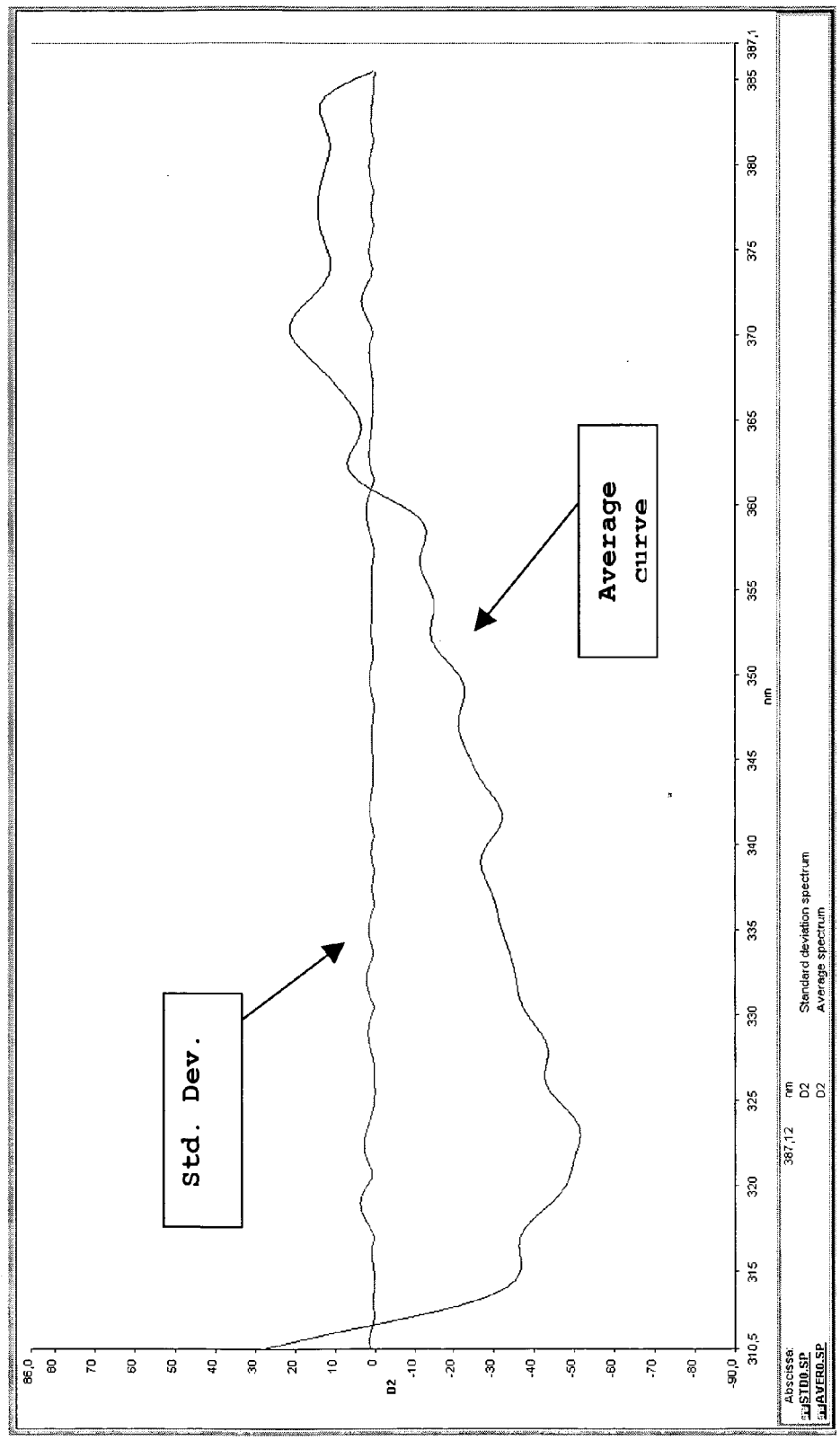

FIG. 83 shows the average curve of the second derivatives of FIG. 82 and their relative standard deviations.

Figure 84:
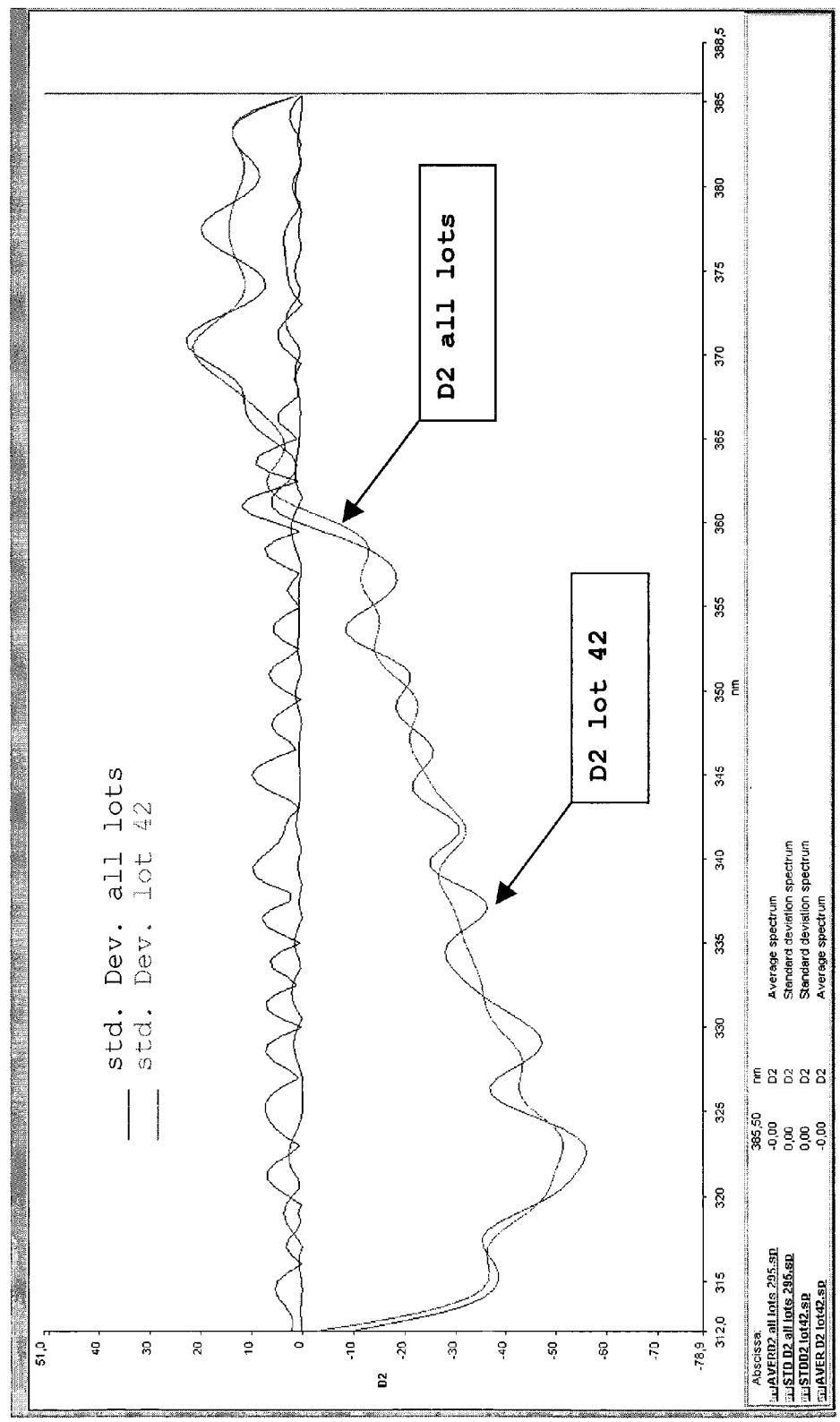

FIG. 84 shows a comparison between second derivative average spectra of the single lot 42 (of three different analyses) and second derivative average spectra of all lots analysed.

Figures of Example 10

3 Example 10B

FIG. 85A shows the $NadA_{A351-405}$ amino acid sequence predicted from the nucleotide sequence of the gene. The nucleotide sequences of the NadA genomic region have been recorded to the Genbank database Genbank/EMBL/DDBJ acc. no AF452-465-88.

FIG. 85B is a schematic representation of $NadA_{A351-405}$, showing the number of amino acids and theoretical MW of C-deleted forms calculated by simulated enzymatic cleavage of the $NadA_{A351-405}$ amino acid sequence.

FIG. 86A shows a representative $NadA_{A351-405}$ spectrum obtained by direct infusion mass spectrometric analysis in an ESI-Q-ToF detector; the spectrum is made complex by multiple signal superimpositions.

FIG. 86B shows the deconvolution of the spectrum in A, revealing the presence of 5 lower mass peptides related to $NadA_{A351-405}$.

FIG. 87A shows a representative denaturing SDS-PAGE of $NadA_{A351-405}$; the entire protein runs in a single band at approximately 37 KDa, while C-deleted forms are visible as 2 lower bands. M, molecular mass markers; DS, Drug Substance $NadA_{A351-405}$ sample.

FIG. 87B shows a representative denaturing blot of $NadA_{A351-405}$; there are bands separated electrophoretically and recognized by polyclonal serum raised against $NadA_{A351-405}$. M, molecular mass markers; DS, Drug Substance $NadA_{A351-405}$ sample.

FIG. 87C shows band attribution by ESI Q-ToF; protein bands were excised and analyzed by mass spectroscopy; the entire $NadA_{A351-405}$ is present in the main band together with the higher MW C-del, other C-deleted forms are separated in the 2 lower gel bands.

Figure 88:
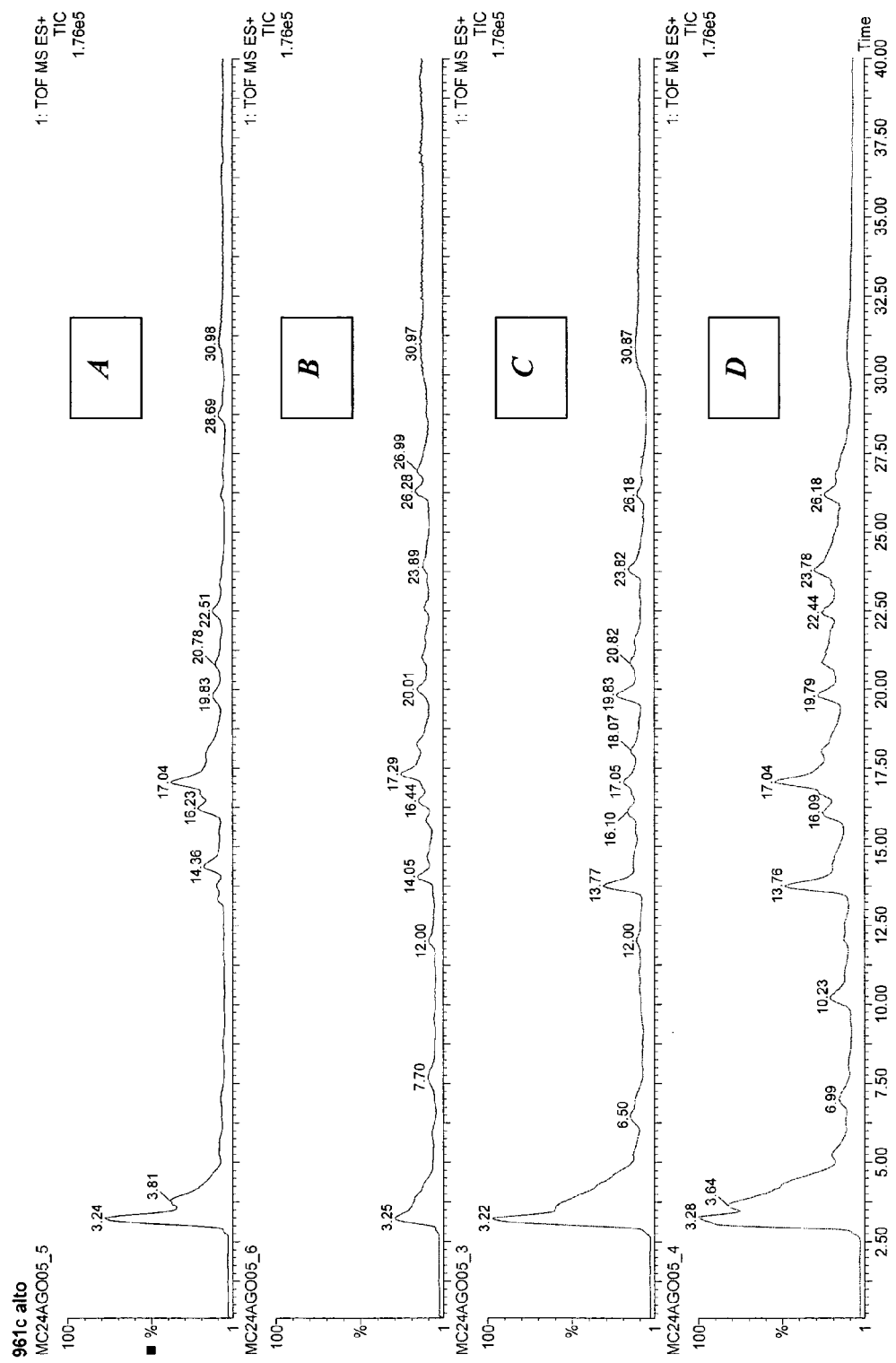

FIG. 88 shows peptide maps of the SDS-PAGE band enzymic digests. After enzymatic digestion, the peptides were extracted from the gel and mass analysed by RP-HPLC coupled with ESI-Q-tOF; Total Ion Current intensity of the different samples is displayed; A, B, C, D correspond to SDS-PAGE bands presented in FIG. 87C; the main one was divided in band A (up) and band B (down) because a double band formation had been observed.

4 Example 10C

Figure 89:
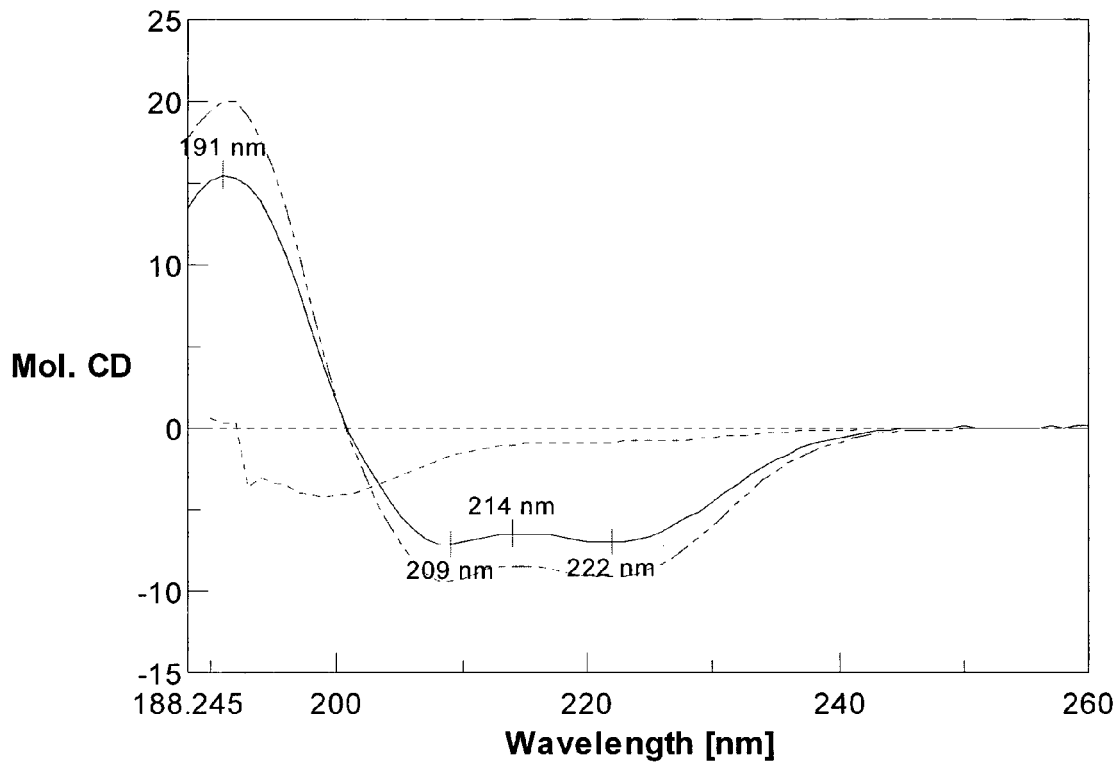

FIG. 89 shows a far UV CD spectra of $NadA_{A351-405}$

FIG. 89A shows the spectra of clinical phase II and III $NadA_{A351-405}$, superimposed to the spectra of a thermally denatured sample. Analyses were carried out between 260-180 nm at RT, approximately 0.1 mg/ml protein solution, with 1 mm optical path length, band-width of 1 nm, and buffer subtraction.

FIG. 89B shows a far UV CD data comparison for different clinical phase lots.

FIG. 89C shows CD spectra deconvolution by Yang algorithm; the fractional percentage of the secondary structure had been calculated by computer fitting to a library of known CD protein spectra.

5 Example 10D

Figure 90:
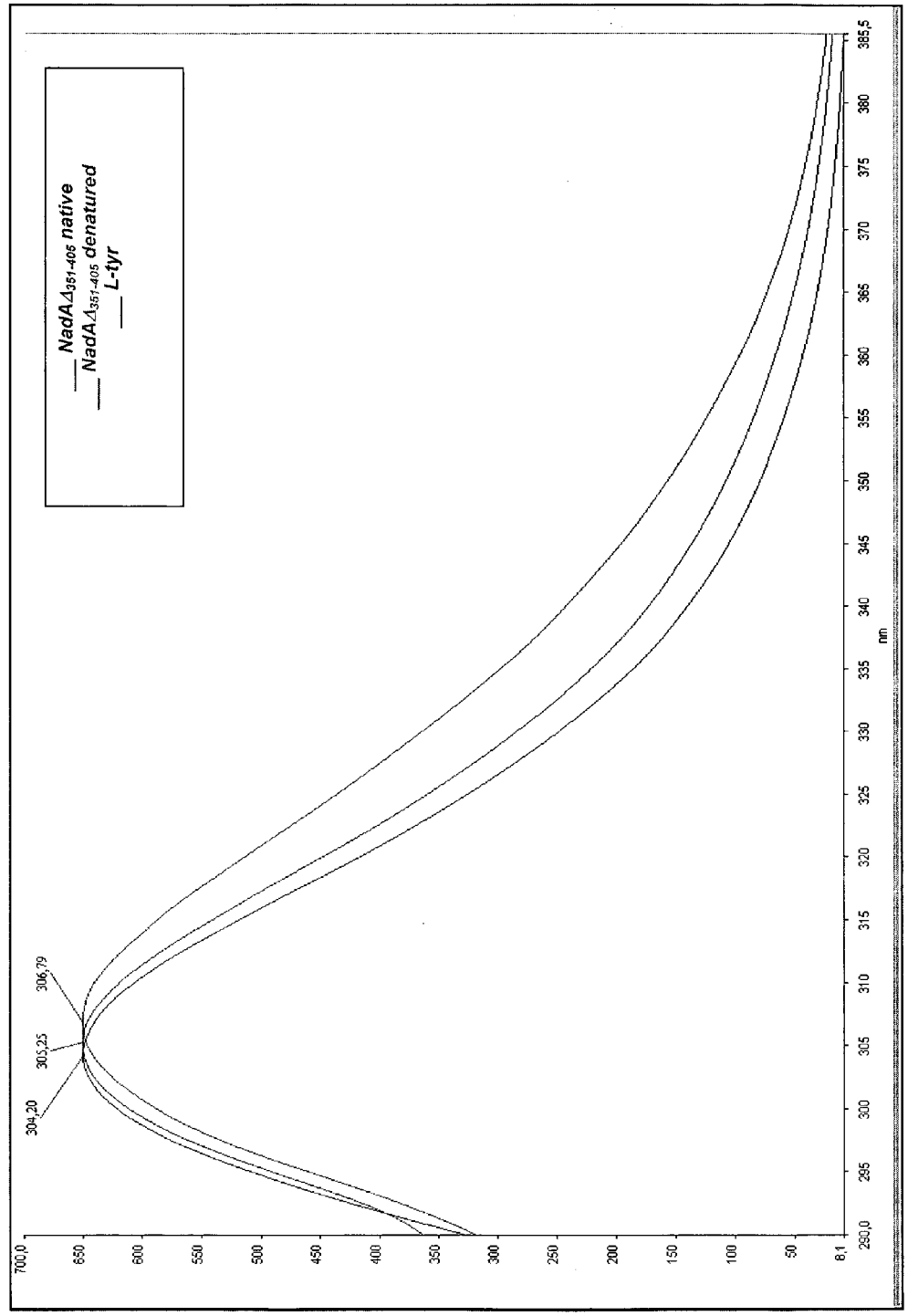

FIG. 90 shows a fluorescence emission spectra of $NadA_{A351-405}$. Normalized emission spectra are shown for native $NadA_{A351-405}$, thermally denatured protein and L-tyrosine in solution. Spectra were recorded at RT, in 1 cm path length quartz cell on solution containing approximately 0.4 mg/ml; excitation wavelength 280 nm. Emission spectra were registered between 290 and 390 nm; each spectrum was averaged on 3 different scanning at 50 nm/min speed.

6 Example 10E

Figure 91:
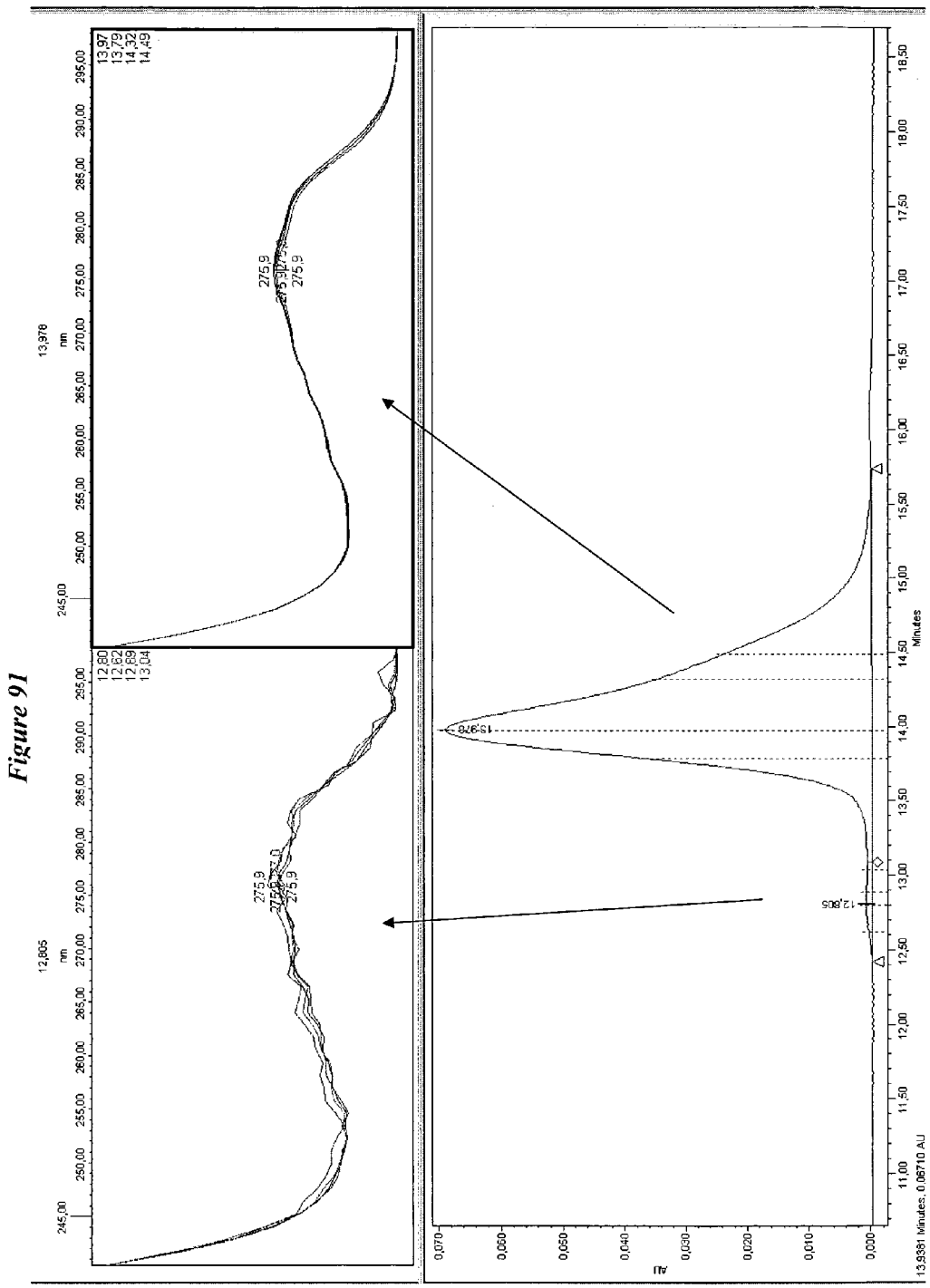

FIG. 91 shows a SEC-HPLC profile of $NadA_{A351-405}$ Dimensional separation was performed on a TSK G3000SW×1 column; the large majority of NadA$_{\Delta 351-405}$ material eluted as a single tailed peak, accompanied by a minor peak at lower retention time. Peak homogeneity is assessed by spectral comparison of all the spectra slices within the single peak. Spectra constituting the NadA$_{\Delta 351-405}$ major peak present a maximum absorption at 275.9 nm and are perfectly superimposed, including the ones of the peak shoulder area, indicating that co-eluting substances are homogeneous from a spectral point of view. Spectra constituting the minor peak show the same trend, although with signal variability due to low protein concentration. Part A: NadA$_{\Delta 351-405}$ peaks spectral analysis between 240-300 nm, part B: NadA$_{\Delta 351-405}$ elution profile at 280 nm.

FIG. 92 shows SEC-HPLC fractioning of NadA$_{\Delta 351-405}$ Part A shows a normalized overlay at 214 nm of un-fractioned NadA$_{\Delta 351-405}$, F1 and F2 peak fractions, part B shows the electrophoretic profiles of un-fractioned NadA$_{\Delta 351-405}$, F1 and F2

Figure 93:
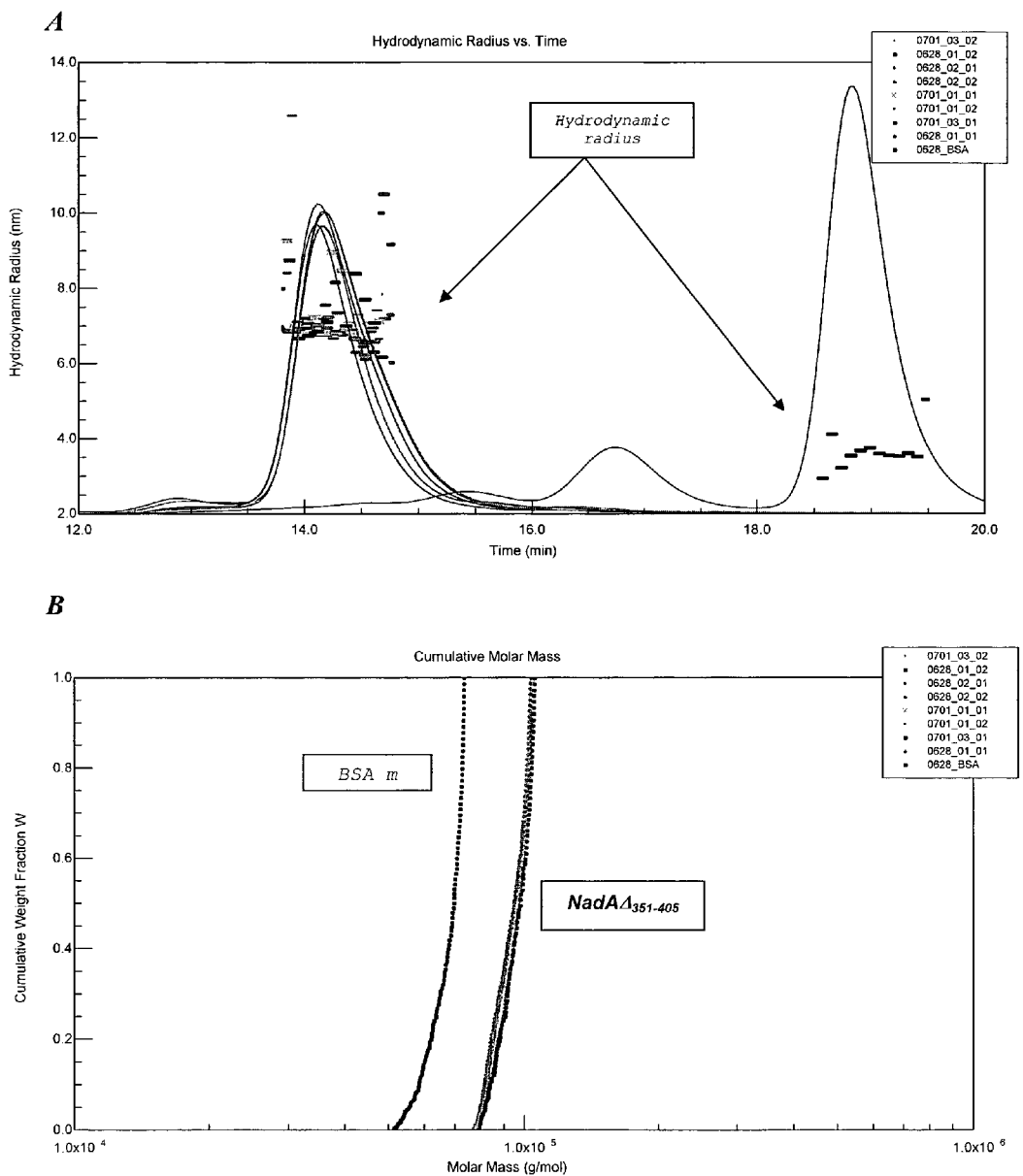

FIG. 93 shows NadA$_{\Delta 351-405}$ absolute dimensions. Part A shows a hydrodynamic radius vs time plot from SEC-MALLS of several NadA$_{\Delta 351-405}$ samples and BSA. Isocratic elution was performed in the same conditions applied for SEC-UV. The continuous line is the refractive index trace; the individual points represent hydrodynamic radius values determined via Q-els detector at each data point. BSAm, monomer of BSA. Part B shows cumulative MW values for NadA$_{\Delta 351-405}$ and BSA monomer samples calculated by Zimm plot on the same SEC-MALLS separations as part A; verticality of the lines indicates peak homogeneity.

Figure 94:
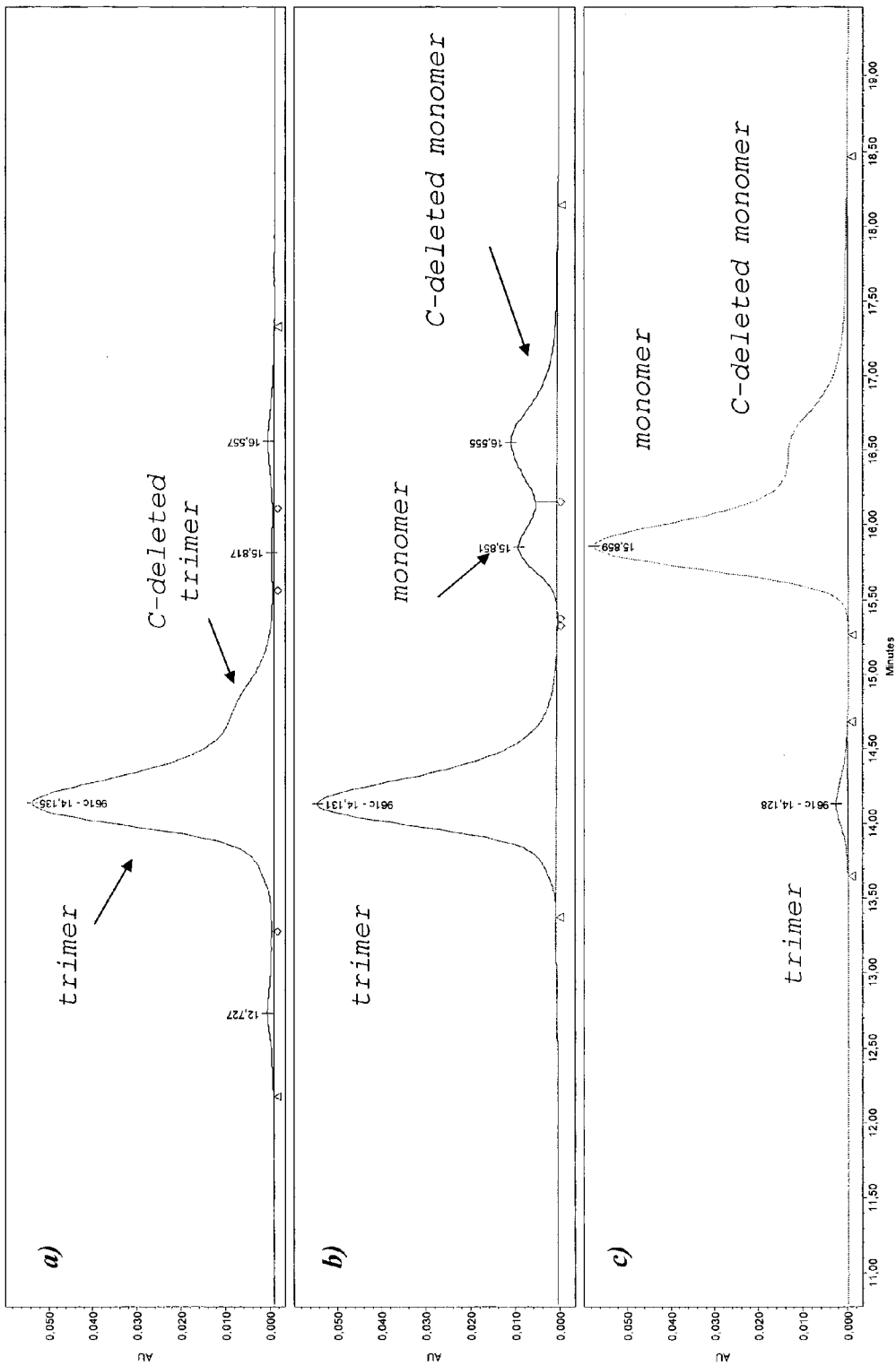

FIG. 94 shows SEC-UV analysis of NadA$_{\Delta 351-405}$ thermal denaturation. Part A shows the chromatographic profile of the native protein, part B shows the chromatographic profile of the protein after 8 minutes at 50° C., and part C shows the chromatographic profile of the protein after 14 minutes at 50° C.

Figure 95:
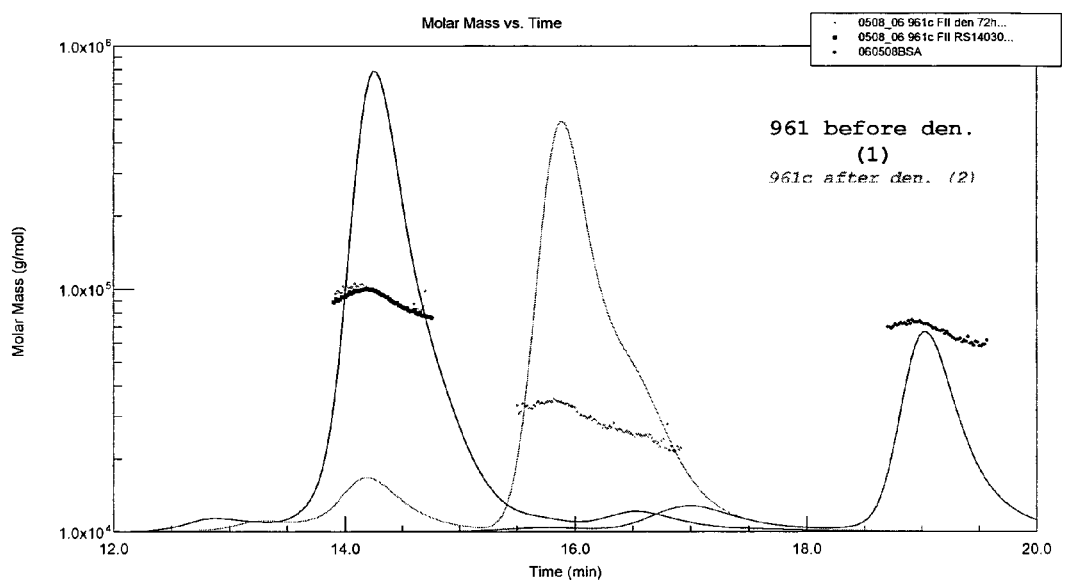

FIG. 95 shows SEC-MALLS analysis of NadA$_{\Delta 351-405}$ thermal denaturation.

Figures of Example 11

7 Example 11B

FIG. 96A-D show four deconvoluted 936-741 spectra obtained by direct infusion mass spectrometric analysis in an ESI-Q-ToF detector; the deconvolution results in the decreased complexity of the spectra by the removal of multiple signal superimpositions. The spectra show that the molecular mass measurements were comparable for different clinical phase lots.

8 Example 11C

Figure 97:
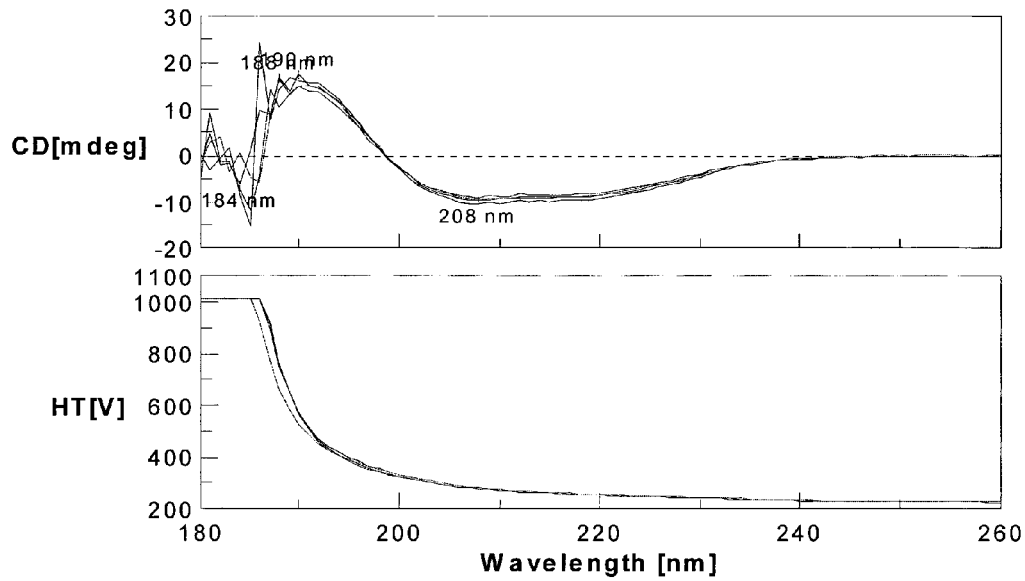

FIG. 97A shows the superimposition of Far UV CD spectra from different clinical phase lots. The similarity between the spectra indicate secondary structural similarity between the clinical phase lots.

FIG. 97B shows the crossover value for each of the clinical phase lots, calculated from the Far UV CD spectra shown in FIG. 97A. The agreement between these values further indicates the secondary structural similarity between clinical phase lots.

9 Example 11D

Figure 98:
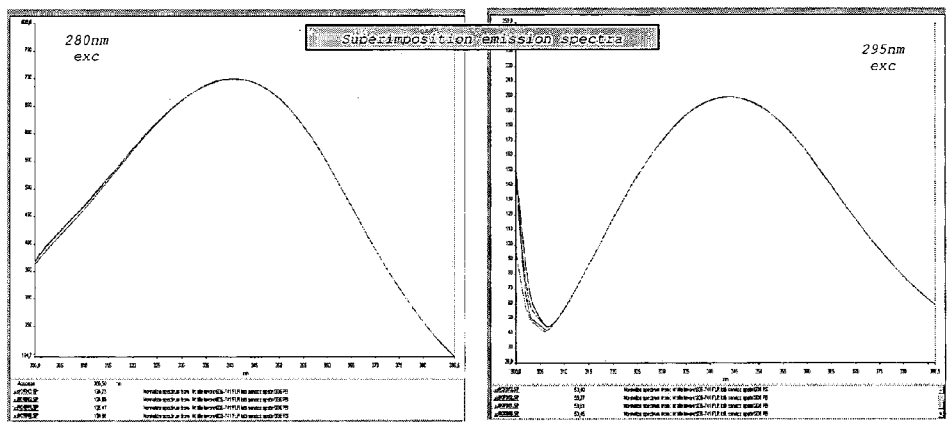

FIG. 98A shows fluorescence emission spectra from different clinical phase lots. These spectra are superimposed and show that the tertiary structure of 936-741 is comparable between the different clinical phase lots.

FIG. 98B shows the crossing points on the fluorescence spectra for different clinical phase lots. The near identical values for each clinical phase lot indicate that the tertiary structure of the antigen in each lot is comparable.

10 Example 11E

FIG. 99A shows superimposed spectra produced by SEC-MALLS to investigate the quaternary structure of 936-741. The superimposed spectra reveal the comparability between different clinical phase lots, and the absence of any additional peaks indicate the absence of protein aggregates.

FIG. 99B shows the Molecular Weight (Mw), polydispersity (Mw/Mn), and hydrodynamic radius (Rh) calculated from the spectra given in FIG. 99A. These values are consistent with the theoretical monomer organisation of 936-741.

FIG. 100A shows the SEC-HPLC spectra from different clinical phase lots. These spectra indicate that all lots contain a single, identical species.

FIG. 100B shows the relative proportion of the clinical lot sample which is found under the curve. The high values indicate the near absence of any further conjugates.

11 Example 11F

Figure 101:
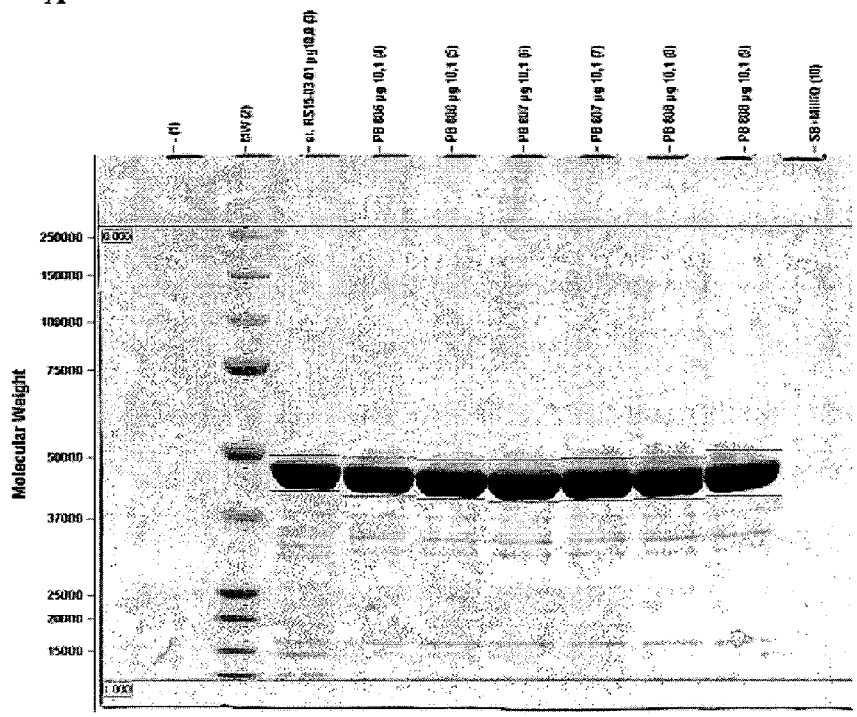

FIG. 101A shows a coomassie SDS-PAGE gel produced to analyse the purity of phase II lots in comparison with phase III lots.

FIG. 101B shows the relative purity values for different clinical phase lots, produced from FIG. 101A. The purity values for the phase III lots are slightly increased with respect to phase II lots.

Figure 102:
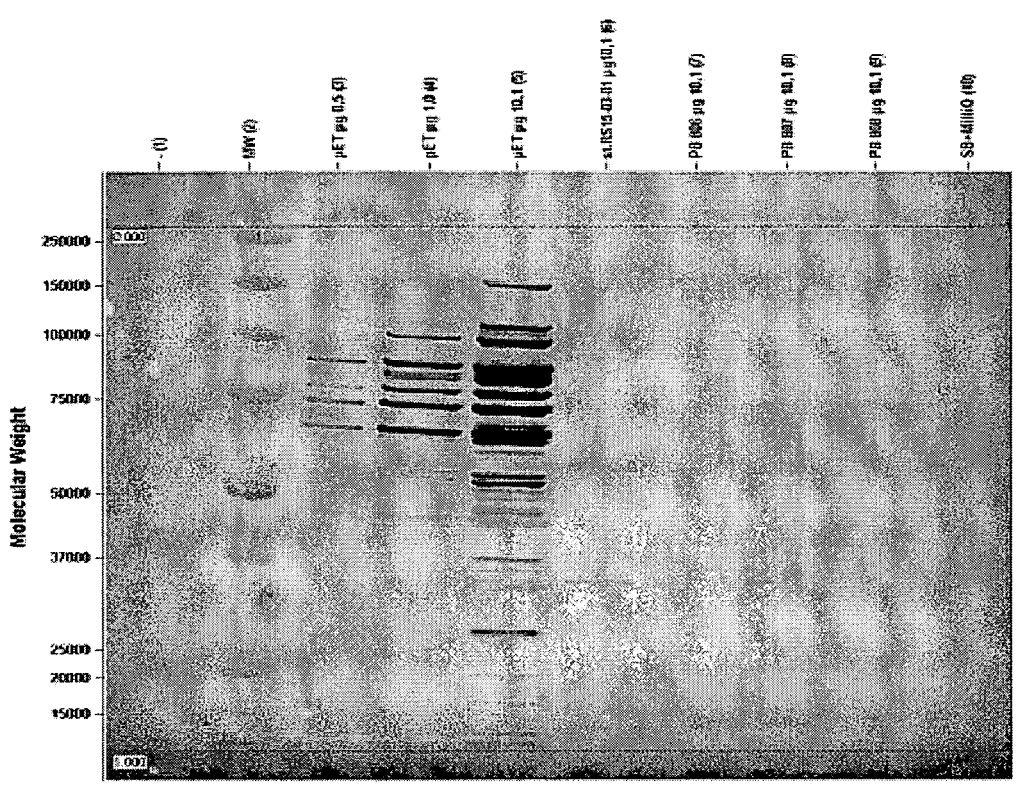

FIG. 102 shows an anti-HCP WB to analyse the purity of different clinical phase lots. The purity of the phase III lot is comparable or better than the purity of the phase II lot.

Figure 103:
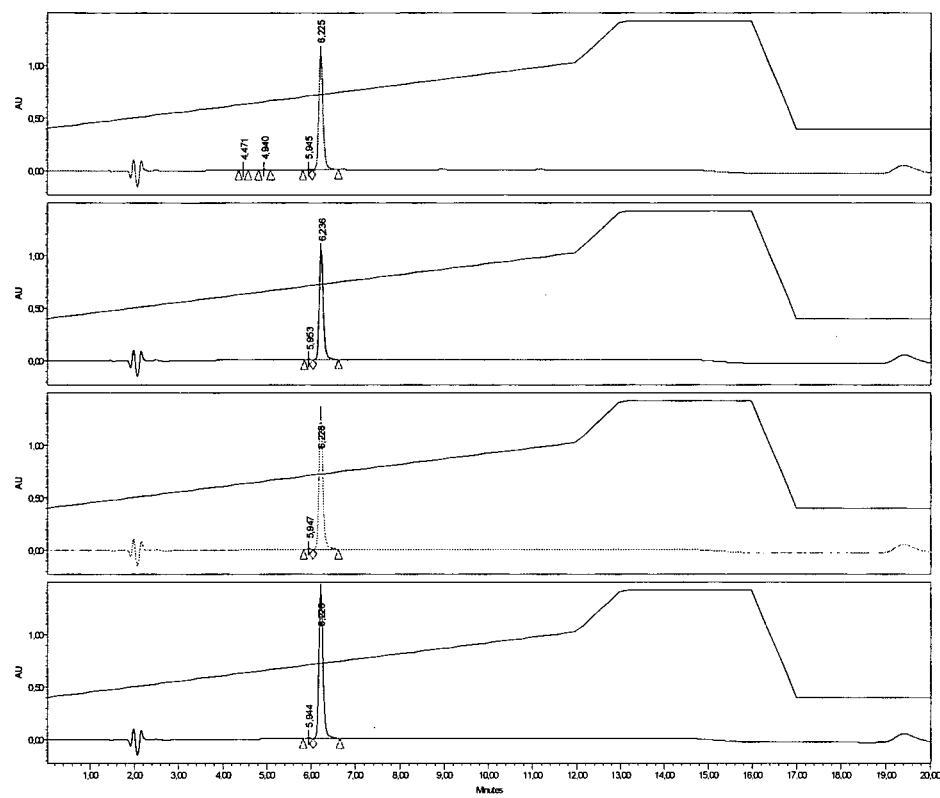

FIG. 103 shows RP-HPLC analysis of different clinical phase lots. The 936-741 profiles are comparable for the phase II and III lots, indicating a similar level of purity. However, the baseline for the phase III lot is slightly cleaner.

MODES FOR CARRY OUT THE INVENTION

UV Absorbance Spectroscopy

Example 1

Spectroscopic Analysis of CRM$_{197}$ Lots

Samples

Table 1 lists the CRM$_{197}$ lots analyzed and the dilution rate applied in the experiments.

TABLE 1

| CRM bulk lot. N. | Protein conc. via microBCA (mcg/mcl) | Sample target concentration (mcg/mcl) | Final sample volume (mcl) | Protein in final volume (mcg) | CRMsample to obtain final volume at taget concentration (mcl) | Nearest CRM sampleable volume (mcl) | Real sample concentration (mcg/mcl) | % of difference from target conc. |
|---|---|---|---|---|---|---|---|---|
| 39 | 47.40 | 0.5 | 1000 | 500 | 10.54852321 | 10.54 | 0.499596 | −0.0808 |
| 41 | 51.70 | 0.5 | 1000 | 500 | 9.671179884 | 9.68 | 0.500456 | 0.0912 |
| 42 | 56.10 | 0.5 | 1000 | 500 | 8.912655971 | 8.92 | 0.500412 | 0.0824 |

TABLE 1-continued

| CRM bulk lot. N. | Protein conc. via microBCA (mcg/mcl) | Sample target concentration (mcg/mcl) | Final sample volume (mcl) | Protein in final volume (mcg) | CRMsample to obtain final volume at taget concentration (mcl) | Nearest CRM sampleable volume (mcl) | Real sample concentration (mcg/mcl) | % of difference from target conc. |
|---|---|---|---|---|---|---|---|---|
| 44 | 54.90 | 0.5 | 1000 | 500 | 9.107468124 | 9.10 | 0.49959 | −0.082 |
| 46 | 48.00 | 0.5 | 1000 | 500 | 10.41666667 | 10.42 | 0.50016 | 0.032 |
| TRUN05 | 43.60 | 0.5 | 1000 | 500 | 11.46788991 | 11.46 | 0.499656 | −0.0688 |
| TRUN06 | 38.20 | 0.5 | 1000 | 500 | 13.08900524 | 13.08 | 0.499656 | −0.0688 |
| TRUN07 | 46.30 | 0.5 | 1000 | 500 | 10.79913607 | 10.80 | 0.50004 | 0.008 |
| 5CRF15 | 43.85 | 0.5 | 1000 | 500 | 11.40250855 | 11.40 | 0.49989 | −0.022 |

The lots were produced on three different manufacturing sites. Lots 39, 41, 42, 44 and 46 were produced on Site 1; lots TRUN05, TRUN 06 and TRUN 07 were produced on Site 2; lot 5CRF15 was produced on Site 3.

Commercial BSA (bovine serum albumin) reference samples (from Sigma, code A8531) were also analyzed to compare with CRM analyses. BSA preparation in dilution buffer was performed daily in order to avoid protein dimerization.

All samples of $CRM_{197}$ and BSA reference were generally diluted to about 0.5 μg/μl with buffer 100 mM KPi+100 mM $Na_2SO_4$ pH 7.2. Some additional dilutions were used for particular experiments (such as buffer containing 20% ethanol or 0.01% formic acid) as specified in the experimental details below.

Instrument Method for Scanning Samples

Common settings for analyses are set out below. Data comparison (see Example 2) between different analyses was obtained through the use of a reference sample of CRM lot 42 in each experiment.

1 Common Instrument Settings

Diluted samples were analyzed with a twin pair of 700 mcl Hellma SUPRASIL Quartz precision 10 mm Spectrophotometry dark cell (code 104.002B-QS, Optical Match 282) on a Perkin Elmer Lambda 20 double beam UV-Vis spectrometer equipped with a Peltier option.

Sample temperature was kept at about 25° C. with the Peltier option integrated in the instrument. A minimum of 15 minutes equilibration was applied to the sample before spectral scanning to ensure reaching of temperature uniformity inside the cuvette.

Wavelengths scan range and data processing applied was between 240 to 325 nm unless differently specified, at the instrument's slit opening of 2.0 nm (Lambda 20 has a fixed slit with). All raw sample spectra were averaged on 3 scans, blanks were removed, and resulting curve normalized to 1,500 Abs at their internal (250-300) $\lambda_{max}$ and to 0 at their $\lambda_{min}$ (325 nm).

2 Specific Instrument Settings 2.1 Example 1A

In this Example, samples from lots 39, 41 and 42 were analysed. Absorption spectra of samples were recorded between 200 and 325 nm at scan speed=7.5 nm/minute at real resolution of 0.1 nm. Autozero was performed with the empty cuvette on the primary beam and the twin cuvette filled with blank (dilution) buffer on the secondary beam of the instrument. Samples were read in the main instrument beam under Peltier control, while a buffer correlation was applied in real time on the secondary beam with the twin cuvette (optical matched) filled with the sample blank matrix. Resulting spectra were blank related but not blank subtracted.

2.2 Example 1B

Samples were from lots 39, 41, 42 and 44 in a first session and from lot 46 in a second session (different autozero between the two sessions). Absorption spectra of samples were recorded at scan speed=7.5 nm/minute at real resolution of 0.1 nm oversampled by the software to 0.5 nm. Daily autozero was performed with the twin cuvette filled with blank (dilution) buffer and inserted in the beams of the instrument, in a way that the following samples raw spectra had already blank absorbance subtracted. Samples were read in the main instrument beam under Peltier control, while a buffer correlation applied in real time on the secondary beam with the twin cuvette (optical matched) filled with the sample blank matrix.

2.3 Example 1C

Samples were all from lot 42 probed during different sessions (different autozero between the sessions) and with different dilution buffers. Absorption spectra of samples were recorded at scan speed=7.5 nm/minute at real resolution of 0.1 nm oversampled by the software to 0.5 nm. Autozero was performed with the cuvette holder of both beams empty (blank against air), so that the raw samples spectra had to be manually blank subtracted. Samples were read in the main instrument beam under Peltier control, with the secondary beam cuvette holder empty. A blank spectrum was obtained by the average of three blank sample scans. After the experiment, net spectra were obtained by mathematical point-to-point subtraction between mean sample scans and mean blank scans. This approach allowed minor day-to-day variability to be minimized (minimizing of the different "blank subtraction" fingerprint), different dilution buffer scans to be carried out in the same analytical session (with different blanks) and a reduction in noise due to environmental influences on the cuvette probed by the secondary beam.

2.4 Example 1D

The optimized settings found in Example 1C were applied on lots 42, 46, TRUN05, TRUN06, TRUN07 and 5CRF15.

Example 2

Mathematical Data Processing of Example 1 Data and Fingerprint Identification

To achieve a full and sharper control on the handling of the data from Example 1, averaging, normalizing, derivative processing and smoothing was performed manually within Microsoft® Excel® on the raw spectral data exported from the instrument's PE UV-Winlab software (as obtained in Example 1).

First to fourth order derivative of the correlated (for Example 1A) or net normalized (for Examples 1B-D) spectra were performed. Derivative data, where necessary, were progressively smoothed in order to obtain a clear (substantially noiseless) and meaningful spectral profile.

The wavelengths of maximum and minimum absorbance were taken from the normalized average unsmoothed spectra obtained. In first derivative spectra, the nearest experimental point to sign changing was considered the zero crossing point. For each of these real (not interpolated) values, a minimum of ±0.5 nm error (equal to instrumental resolution at the best signal to noise ratio point and equal to the λR smoothing range on three points) was considered acceptable.

Raw and processed spectral data were subsequently used as fingerprints for comparison, especially first and second order derivative data. Where possible (spectral data not dominated by noise), even third and fourth derivative spectra were considered for comparison.

When analytical settings or characterization approach were changed between scans, a fixed lot sample (CRM lot 42) was used as bridge sample for data comparison.

Data from Example 1D were also used to characterize a "CRM signature" in a convexity study of the absorbance spectrum.

All the suitable raw and derivative spectra were used to obtain a partial characterization of the CRM protein structure. For this purpose and to help product characterization, resolution enhanced spectra, obtained by combining absorbance (underivatized) data with second derivative data (see "Resolution enhancement") were produced.

Details of single experiments are set out below in Examples 2A-2D. The characterization and the convexity studies are set out in Example 3.

Example 2A

From the analysis in Example 1A, absorbance normalized spectra (FIG. 13) and their first order derivatives between 240 and 325 nm (FIGS. 14-16) were calculated and used as fingerprints between different lots of samples.

The spectra acquired from samples at 0.1 nm resolution appears regular (FIG. 13), but their first order derivatives are dominated by noise (FIG. 14). Blank sample noise shows a similar shape.

As a reference experiment, a 5-point deep triangular smooth was performed on a reference sample from Example 1A (lot 42) to achieve a reasonable derivative signal (FIG. 15). A clear shape appears with just 1 passage of a 5-point deep triangular smooth and an optimum picture appears after 2 passes. However, an increase in the number of smoothing treatments (up to 3 times) does not enhance the signal and still leaves the strong and periodic noise influence seen after the first smoothing.

FIG. 16 shows the first order derivatives obtained from the spectra acquired from the samples of Example 1A using 2 passes of a 5-point triangular smooth.

Noise function in all samples appears to fluctuate with a period of about 0.8-1 nm, meaning that within a half period (0.4-0.5 nm) noise modulation swaps between a maximum and minimum influence and can be successfully averaged.

No differences between low (one passage, 5-point deep), middle (four passages, 5-point deep) and high (four passages, 7-point deep) triangular smoothing appears in first derivative spectra (data not shown), meaning that noise modulation is constant and is probably instrument and resolution-related (hence its periodicity), and that spectral resolution is so high that subsequent level of smoothing does not attenuate resolution or signal amplitude in a detectable way. These data were expected, because the spectrometer is working at the highest resolution possible, where signal/noise ratio is usually the lowest.

These data suggested that another analytical session with a decrease in instrumental resolution and the same scan speed would probably retrieve better results because less noise is expected on a comparable signal. However, even with this limitation, all examined lots of CRM (39, 42, 44) share the same spectral shape and behavior, which is clearly different from the BSA pattern.

Example 2B

From the analysis in Example 1B, absorbance normalized spectra (FIG. 17A) and their first to fourth order derivatives between 240 and 325 nm (FIGS. 17B-21) were calculated and used as fingerprints between different lots of samples within the same analytical session.

Because samples analyzed in different sessions show small differences, probably due to different autozero and daily conditions, a noise reduction approach was performed in order to discover if the revealed differences could be due to real sample differences or due to day to day reproducibility.

The results, shown in FIG. 17B (for first derivative spectra), show that differences were probably not sample related since the differences were almost completely reduced by light noise reduction. However, this aspect was more thoroughly investigated in further experiments, together with a method for evaluation and minimizing day to day variations (see Example 2C).

1 BSA and CRM Lots 39, 41, 42 and 44 (Session 1)

Unsmoothed absorbance and derivatives spectra from samples acquired at 0.5 nm resolution is regular and without any significant influence of noise. A clear difference between CRM and BSA samples is evident, and fingerprint comparison shows that all CRM lots share the same behavior. Small intensity differences appear at the fourth derivative level only, although the peak pattern is fully comparable.

FIG. 18 shows the fingerprint data from the samples of Example 1B. FIG. 18A shows the unsmoothed first order derivatives. FIG. 18B shows the unsmoothed second order derivatives. FIG. 18C shows the unsmoothed third order derivatives. FIG. 18D shows the unsmoothed third order derivatives, without the derivative for BSA. FIG. 18E shows the unsmoothed fourth order derivatives. FIG. 18F shows the unsmoothed fourth order derivatives, without the derivative for BSA.

Figure 19:
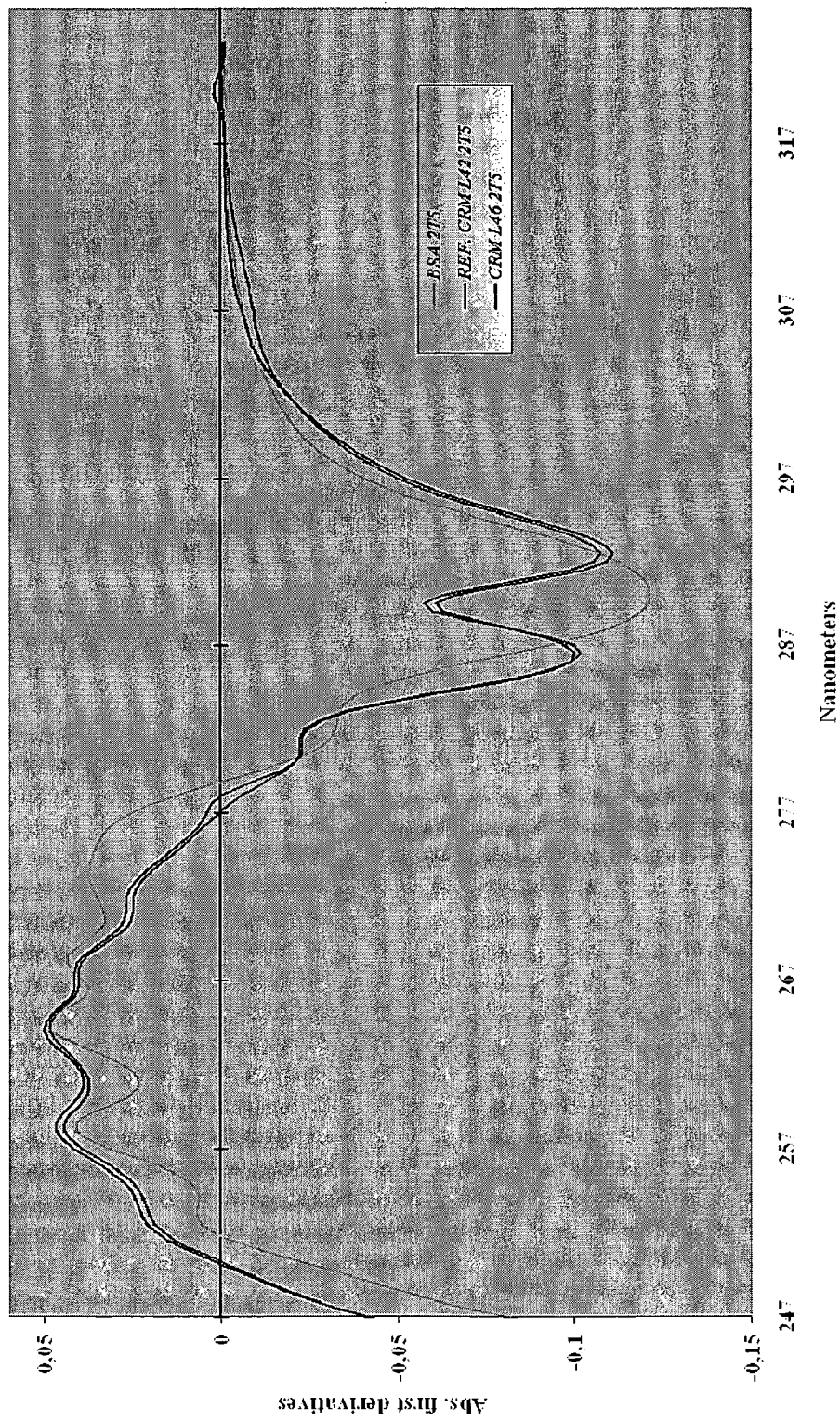

However, after fingerprint recognition, different smoothing approaches were also performed on these same data to achieve a spectral function useful for product characterization. Smoothed data shows complete identity between CRM samples, and there is furthermore no convergence between CRM and BSA spectral data, meaning there is no substantial loss of signal information during the smoothing process (FIGS. 17B and 19). FIG. 19A shows various levels of smoothing of the first order derivative ("2T5" means two 5-point triangular smooths etc). FIG. 19B shows a selected sub-set of the first order derivatives after various levels of smoothing; FIG. 19C shows a further sub-set and specifically compares data from Example 2A with data from Example 2B.

Comparing these data to the data obtained in Example 2A (CRM L42), it can be seen that a decrease in spectral resolution from 0.1 to 0.5 nm removes just the noise without changing the spectral shape or peaks intensity.

2 CRM Lot 46 (Session 2)

FIG. 20 shows the CRM lot 46 absorbance spectrum, which appeared slightly different from the others CRM samples, e.g. measured absorbance is higher than previously observed. Various smoothing levels on the first derivative spectra are shown in FIG. 21. The first derivative spectra show some random fluctuation on the common expected CRM function pattern (FIGS. 21 and 19). Because Lot 46 spectra appears to be dominated by noise, it is not possible to make a direct comparison between this sample and other CRMs in using higher order derivative unsmoothed spectra.

Extra fluctuations were progressively reduced by applying different steps of triangular smoothing (see FIGS. 19 and 21), confirming their possible attribution to noise/different day-to-day instrumental response. With increasing smoothing, a convergence of the lot 46 spectra with other CRM samples examined previously was observed. At the same time this post-processing does not reduce the sample's spectral characteristics, as already seen in the previous session and in Example 2A, so that a strong difference still remains between the CRM and BSA samples. Only one characteristic CRM inflection point at about 282 nm (revealed as a peak in the first derivative) was reduced. However, even under the strongest smoothing treatments this feature nevertheless remains evident.

From all the data examined, spectral differences between sessions can be explained with the day-to-day reproducibility of the analysis: different days means different instrumental autozero/blank subtraction, and this operation is performed by the instrument on a single scan rather than on an average of three spectra.

To improve and evaluate day-to-day reproducibility, a different autozero and blank subtraction technique (average autozero) was used in Example 2C (see Example 1C for settings).

Example 2C

Example 1C and the following Example were focalized on developing and testing a fine-tuning of the methods of Examples 1A/2A and 1B/2B. Specifically, the autozero reading and blank subtraction was refined by briefly separating the two steps and using an average blank for the subtraction. These optimizations should avoid or minimize possible day-to-day variations, and allow the use of a different blank within the same session which is useful for investigating the effects of different dilution buffers and conformational changes on samples.

Raw absorbance spectra were acquired with the spectrometer's software (UV Winlab) and exported to a Microsoft® Excel® datasheet for data processing. Within Excel® net average absorbance spectra (between 240 and 325 nm) were produced by point-to-point subtraction of average blanks as described see ("Instrument method", Example 1C). Normalization between maximum absorbance and 325 nm minimum was performed before first to fourth order derivative were calculated. All these data were used as fingerprints between different scans and samples.

Average blank production and manual buffer subtraction improves day-to-day reproducibility, allowing also lower instrumental noise (better reduction of random fluctuations), since final net spectra become the result of 6 spectra (average of 3 sample scans less average of 3 blank scans) instead of the four as from the previous experiments (only one blank scan that included also autozero normalization). This approach allows also the use of autozero against air instead against cuvette+buffer. In this way each sample has air as reference instead of cuvette+buffer, a reference more reliable when working with different buffers and less dependent on temperature and other environmental factors (only the main beam sample holder is equipped with the Peltier accessory).

In order to test the effectiveness and discriminating power of the new approach, CRM lot 42 was analyzed over several days (tested at day 0, day 3 and day 4) as a model sample to measure reproducibility. Furthermore, during the same analytical session three further samples were analyzed: a) CRM lot 42 mixed with 50% reference BSA; b) CRM lot 42 with dilution buffer containing 20% ethanol; and c) CRM lot 42 after 3 h room temperature treatment with 0.1% formic acid. All these "modified" samples were analyzed within the same session together with a reference unmodified CRM lot 42. These experiments, together with the reproducibility data, provide an indication of whether sample differences can be detected in unknown CRM samples.

BSA mixing allows the evaluation of the effect of strong sample contamination. The denaturing 20% ethanol allows the evaluation of the effect of partial unfolding of the sample. Formic acid treatment mimics an acid chemical attack to the sample.

FIG. 22A shows the normalized absorbance spectra. FIG. 22B shows the unsmoothed first order derivative spectra. FIG. 22C shows the unsmoothed second order derivative spectra. FIG. 22D shows the second order derivative spectra after one pass of 3-point quadratic smooth. FIG. 22E shows the unsmoothed second order derivative spectra for the CRM reproducibility experiment. FIG. 22F shows the second order derivative spectra for the CRM reproducibility experiment after one pass of 3-point quadratic smooth.

FIG. 23A shows the unsmoothed third order derivative spectra. FIG. 23B shows the third order derivative spectra after one pass of 3-point quadratic smooth. FIG. 23C shows the unsmoothed third order derivative spectra. FIG. 23D shows the fourth order derivative spectra after one pass of 3-point quadratic smooth. FIG. 23E shows the unsmoothed fourth order derivative spectra for the CRM reproducibility experiment. FIG. 23F shows the fourth order derivative spectra for the CRM reproducibility experiment after one pass of 3-point quadratic smooth.

The improved autozero/blank subtraction method shows perfect overlapping of the reference sample spectra (absorbance and first to fourth order derivatives) from the three different sessions examined (FIGS. 22 and 23). Only some small fluctuation between same samples emerged before 320 nm, where absorbance level is very low for proteins, and so signal to noise ratio is compromised from second up to higher level derivative.

A 50% BSA contamination of the CRM sample results in an average spectra at halfway between the two separate components, thus showing that large contaminations are easily visible. The presence of a denaturizing agent like ethanol in the dilution buffer shows a strong increase in absorbance together with a significant distortion of the spectra. Treatment with formic acid produced no or little effect on the CRM sample, suggesting that limited acid attacks to the sample do not involve changes in the folding of the protein.

As can be seen from FIGS. 22 and 23, even with the small overall noise level obtained with the improved scanning procedure, smoothing is still preferred for a better understanding of the spectra. Again, smoothing enhances the differences between different samples. The positive contribution from smoothing becomes clearly evident after second derivative spectra, where benefits of noise reduction overcome the slight loss of details due to the small decrease in signal strength, enhancing the signal to noise ratio. Smoothing becomes more important as the derivative level increases because of increase in noise level. In the fourth derivative, the unsmoothed spectra show little differences between different samples, and that as the smoothing increases, characteristics and differences of a single species became more evident. FIG. 24 shows the fingerprint data from 4th derivative spectra at different smoothing levels. FIG. 24A shows the unsmoothed fourth order derivative spectra. FIG. 24B shows the shows the fourth order derivative spectra after one pass of 3-point quadratic smooth. FIG. 24C shows the shows the fourth order derivative spectra after two passes of 3-point quadratic smooth. FIG. 24D shows the fourth order derivative spectra after three passes of 3-point quadratic smooth.

Example 2D

This set of experiments was dedicated to using the method refined in Examples 1C/2C in a comparison between several lots of $CRM_{197}$ from different manufacturing sites (see Example 1D). The examined lots were: 42, 46, TRUN05, TRUN06 and TRUN07 and 5CRF15.

Retest of lot 46 was necessary to evaluate if the slight differences in this CRM lot found during Example 2B were actually due to a day-to-day autozero/blank watermark, as predicted from the analysis of noise reduction progression (see FIGS. 19 and 21), or were due to peculiarities of this lot. This part of the experiment also represented a supplementary test to verify the postulation that noise reduction progress analysis can be used to discriminate real signals from noise components in analyzed spectra in order to identify significant differences between samples. If no difference is found between lots 42 and 46, it can be concluded that no detectable differences were found between lots 39, 41, 42, 44 and 46.

Data from this comparison can show differences between CRM samples produced in different facilities. Data can be compared from a whole panel of 9 CRM lots produced in three different facilities by using CRM lot 42 profile as a bridge sample between the lots tested in Example 1B/2B and further lots.

FIGS. 25 and 26 show the results of this experimental session. FIG. 25 shows the derivative spectra of Nth degree with N−1 passes of a 3-point quadratic smooth. FIG. 25A shows the normalized absorbance spectra of the different CRM lots. FIG. 25B shows the underivatized and second derivative enhanced spectra for lot 42. FIG. 25C shows the unsmoothed first derivative spectra. FIG. 25D shows the second order derivative after 1 pass of a 3-point quadratic smooth. FIG. 25E shows the third order derivative after 2 passes of a 3-point quadratic smooth. FIG. 25F shows the fourth order derivative after 3 passes of a 4-point quadratic smooth. FIG. 26 shows derivative spectra of Nth degree before and after (N−1) passes of a 3-point quadratic smoothing. The highlighted box in red shows the spectral zone where little differences emerged between TRUN06 and other CRM lots. FIG. 26A shows the unsmoothed second order derivative while FIG. 26B shows the second order derivative after 1 pass of a 3-point quadratic smooth. FIG. 26C shows the unsmoothed third order derivative while FIG. 26D shows the third order derivative after 2 passes of a 3-point quadratic smooth. FIG. 26E shows the unsmoothed fourth order derivative while FIG. 26F shows the fourth order derivative after 3 passes of a 3-point quadratic smooth.

No detectable differences appear between lots 42 and 46 up to the fourth derivative level, demonstrating that differences shown in Example 2B were noise related, thereby validating the improved noise reduction approach developed in Example 2C to discriminate real signal versus different kind of noises. Because lot 42 is the reference lot present in each experiment, differences in its revealed spectra from one experiment to another reflects only the changed methods of analysis during optimization.

Comparing unsmoothed lot 42 absorbance and derivative spectra with data from CRM produced from the TRUN and CRF manufacturing sites (FIGS. 25 and 26), it can be seen that all samples share the same general pattern and are almost identical: up to the first derivative degree no detectable difference can be noticed, while a very little fluctuation, localized between 274 and 277 nm, appears in just lot TRUN06 from the second order derivative up to the fourth, with a small increasing strength (as expected) as the derivative order progress increase. This is the only difference found between all the samples analyzed in this session, and considering also data from Example 2B, between all the samples considered.

Using light noise reduction algorithms (quadratic smoothing) on raw functions, even this small fluctuation disappears: 1 pass is sufficient for clear differences in second order derivative, 3 passes for fourth order derivative, widely below the optimal noise reduction progress of 1+(derivative order) passes of quadratic smoothing generally suggested for analysis of this kind of function.

However, because this fluctuation is present only in the sample corresponding to lot TRUN06, and is not due to a single noisy scan (all three components show the same inflections (data not shown)), it is worth exploring the origin of the fluctuation.

In second order derivatives, the first separation between the peak components of the absorbance spectra can be observed, with all components represented as negative peaks. The fluctuations are revealed within the spectral region responsible for the maximum absorbance peak of the protein (maximum absorbance confirmed also by the zero crossing point in the first derivative). Table 2 shows the experimental wavelength data.

TABLE 2A

Data for Example 2B, session 1
(detected λ abs. max. and min., 0.5 nm resolution)

|  | λ Max | λ Min | Zero crossing λ for first derivative | |
|---|---|---|---|---|
| BSA | 278.5 | 251 | 279 | 251.5 |
| 39 | 277.5 | 250 | 277.5 | 250 |
| 41 | 277.5 | 249.5 | 277.5 | 250 |
| 42 | 276.5 | 249.5 | 277 | 250 |
| 44 | 277.5 | 250 | 277 | 250 |
|  | 277 ± 0.5 | 249.5 ± 0.5 | 277.5 ± 0.5 | 250 ± 0.5 |

TABLE 2B

Data for Example 2D (detected λ abs. max. and min., 0.5 nm resolution)

|  | λ Max | λ Min | Zero crossing λ for first derivative | |
|---|---|---|---|---|
| 42 | 276.5 | 249.5 | 277 | 250 |
| 46 | 277 | 249.5 | 277.5 | 250 |
| TRUN05 | 277.5 | 249.5 | 277.5 | 250 |
| TRUN06 | 277.5 | 250 | 277.5 | 250 |
| TRUN07 | 277.5 | 249.5 | 277.5 | 250 |
| SCRF15 | 277.5 | 250 | 278 | 250 |
|  | 277 ± 0.5 | 249.5 ± 0.5 | 277.5 ± 0.5 | 250 ± 0.5 |

Figure 1:
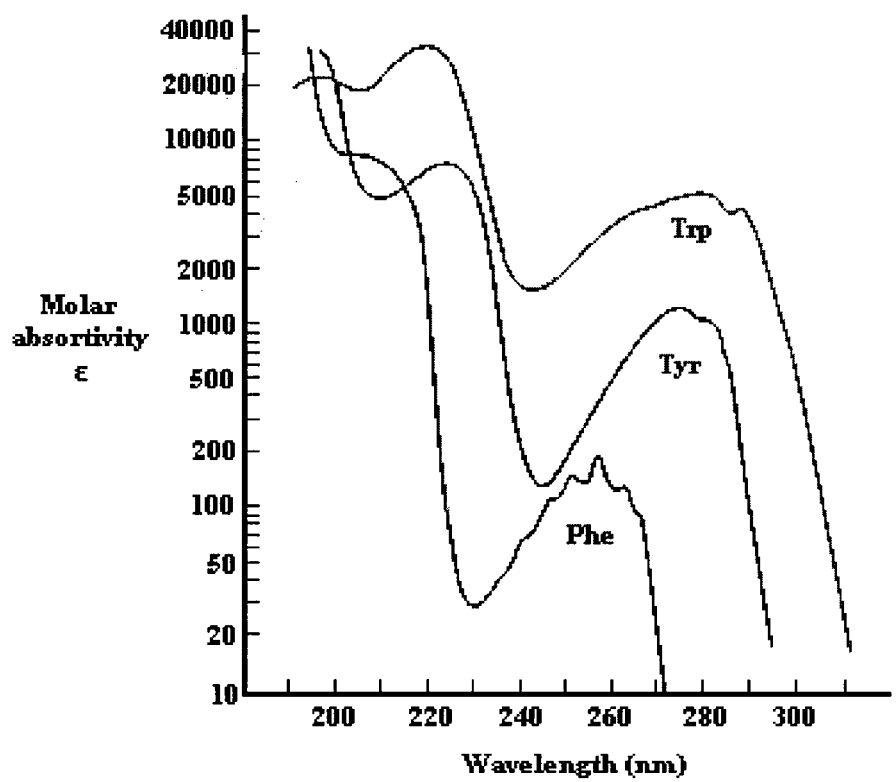
FIG. 1 shows the UV absorbance of amino acids with aromatic rings, and Cysteine.

However, the small fluctuation observed for lot TRUN06 does not affect the minimum and maximum absorbance wavelengths. Therefore, even if there is a difference between lots, it does not alter the main spectral characteristics of the sample. In the detail of the spectra, all the small negative peaks in the region between 274 and 280 nm should represent different spectral components from Tyrosine or Tryptophan groups of the CRM protein (see FIG. 1): each component peak represents one of these groups in a slightly different environment. However, two main species centered around 274 and 280 nm become more evident as the smoothing increases, which correspond to Tyrosine and Tryptophan amino acids.

The small fluctuations revealed in TRUN06 appear related to the Tyrosine groups, as can be seen by fourth derivative analysis of unsmoothed and smoothed spectra, where they are represented clearly as positive peaks. However, even under high level derivative analysis, the slight fluctuations observed remain related to the same amino acid subgroup, meaning that no real differences are present between TRUN06 and the other samples. Even if a difference is present, it is likely due to a slightly different tension in the protein folding near some of these amino acid groups: slightly different tensions can cause small shifts in the position of charged groups in tertiary protein structure, with small influences on the derivative spectra but still without changing folding pattern. This kind of reversible influence is known for preservatives such as Glycerol or Sucrose, even when present at low dilution (see Table 3):

TABLE 3

Substances known as perturbants for tertiary protein structures.

| Perturbant | Mean Diameter (Å) |
|---|---|
| $D_2O$ | 2.2 |
| Dimethylsulphoxide (DMSO) | 4.0 |
| Ethylene glycol | 4.3 |
| Glycerol | 5.2 |
| Arabitol | 6.4 |
| Glucose | 7.2 |
| Sucrose | 9.4 |

In the CRM samples about 10% of sucrose is present, and because each CRM sample has its own protein concentration, by diluting the samples to the same protein concentration slightly different sucrose results. As can be seen from Table 1, TRUN06 bulk has the lowest CRM concentration between the examined lots, and so the analyzed TRUN06 sample, normalized to 0.5 mcg/mcl, has the highest sucrose level between the samples examined, around 0.13% sucrose in final sample against 0.11% of the nearest sample, TRUN05.

These results and considerations are in accord with fluorimetric experiments (see "Example 9—Fluorescence characterization of CRM protein") independently made on the same CRM lots. In that case a normalization of sucrose between samples up to the level present in lot TRUN06 has eliminated the spectral differences previously detected.

However, in these experiments before and during experiment setup residual sucrose levels were not normalized or removed between samples, for two main reasons. First, it was desired to limit perturbing influences on the sample analyzed, to obtain the clearest possible spectral image from the protein, and not from the protein with sucrose. Second, ultrafiltration of samples or similar treatments to remove sucrose also reduces other sample impurities. It was also assumed that such a small amount of sucrose would likely have no impact on the recorded spectra, even if coupled with the derivative technique of the invention. However, as seen from the experiments above in relation to TRUN06, conformational changes are recoded with a very high sensitivity with the invention.

Example 3

CRM Protein Characterization—Deep Analysis of CRM Lot 42

Fingerprint results from Example 2D show that all the CRM lots of Table 1 share the same spectral behavior up to the fourth derivative. Accordingly, one model CRM lot can be used for further experimentation.

$CRM_{197}$ lot 42 was chosen as the reference model for deep characterization because it has been analyzed in each of the Examples above, and so can be directly compared to other samples analyzed. Lot 42 characterization data came mainly from Examples 2C and 2D, where the best signal to noise ratio and inter-session reproducibility was achieved. However, data from Example 2B was also used for other CRM lots.

The fingerprint data were used as obtained from Examples 2C and 2D (FIGS. 18 and 22-26 and Table 2) and reprocessed to achieve optimal smoothing level (FIGS. 27-32, discussed below). In this way, it was possible to both describe the main pattern and trace details from small peaks in crowded spectra.

FIG. 27A shows the first order derivative spectra for lot 42 after 2 passes of a 3 point quadratic smooth. FIG. 27B shows the second order derivative spectra for lot 42 after 3 passes of a 3 point quadratic smooth. FIG. 27C shows the third order derivative spectra for lot 42 after 4 passes of a 3 point quadratic smooth. FIG. 27D shows the fourth order derivative spectra for lot 42 after 5 passes of a 3 point quadratic smooth.

Part of the deep characterization of lot 42 involved a full concavity/convexity study of absorbance spectra performed by using both raw and smoothed second derivative spectra polarity. When a curve is convex, its second derivative becomes negative, while when the curve is concave its second derivative becomes positive. The small shape variations of absorbance spectra which are undetectable in the underivatized spectra can be easily revealed.

FIG. 28 shows a smoothing progress on second order derivative spectra for CRM lot 42 and its positive (in red) or negative (in cyan) polarity revealing the concavity pattern of the absorbance spectrum. FIG. 29 shows a comparison of the concavity patterns of CRM absorbance spectra via analysis of second derivative polarity at different smoothing levels. After 3 passes of a 3-point quadratic smoothing a clear "CRM convexity signature" appears. This signature is much more related to the protein sequence and structure than the wavelength of maximum and minimum absorbance, and is useful for CRM identification and folding integrity tests.

The best concavity/convexity signature is obtained between 250 and 310 nm after 3 passes of 3 points quadratic smoothing. In this way, a curve without noise around zero crossing points but that still retains a good strength at these points is obtained (FIGS. 28 and 29). However, the experimental data shows that the zero crossings of second derivatives from different lots already converge in the unsmoothed derivative spectra, with a maximum crossing difference between spectra equal to the instrumental resolution (see second derivative spectra in FIGS. 22, 25 and 26 and the green curve on FIG. 28 as well as the profiles and data in FIG. 28).

Accordingly, the common signature pattern for CRM can be relied upon because even the raw noisy derivative spectra retain a common shape. By comparing the lot 42 signature with the profile of the others $CRM_{197}$ samples analyzed within the same session (FIG. 29), it can be verified that the fully smoothed fingerprint signature is always the same between samples. However, already after the first smoothing process the spectra are almost identical, with a maximum shift between polarity changing point of just one resolution unit. Interestingly, no changes in the general convexity pattern appears. Small spectral shift discrepancies seem to proceed with a random lot pattern as the smoothing increases. This is the expected behavior for a noise related influence and another indication that the chosen approach is valid.

FIG. 30 shows a comparison of a wider (245-310 nm) absorbance concavity pattern (via second derivative analysis) between different samples containing $CRM_{197}$, BSA and other chemical agents after different smoothing levels. Table 4 shows the adherence to CRM concavity signature (250-310 nm, 0.5 nm steps) of the samples shown in FIG. 30.

TABLE 4

Adherence of samples to CRM concavity signature

| | Steps in CRM signature | Differencies (steps) | Differencies (%) | Identity (%) |
|---|---|---|---|---|
| CRM lot 42 - 27 Jan 05 | 120 | 0 | 0.00 | 100.00 |
| CRM lot 42 - 16 Mar 05 | 120 | 0 | 0.00 | 100.00 |
| CRM lot 42 + Formic Ac. | 120 | 0 | 0.00 | 100.00 |
| CRM lot 42/BSA - 1/1 | 120 | 9 | 7.50 | 92.50 |
| CRM lot 42 + 20% EtOH | 120 | 12 | 10.00 | 90.00 |
| BSA - 16 Mar 05 | 120 | 22 | 18.33 | 81.67 |

Reviewing the spectra represented in FIG. 32 and the related data set out in Table 4 it can be seen that the convexity of different samples is different both in pattern and polarity changing (zero crossing) points. CRM lot 42 samples probed in different days, as well as CRM treated with formic acid, fits perfectly (100%) with the signature, while the CRM/BSA mixture, CRM in 20% Ethanol and BSA shows a progressive difference from the CRM model. As already observed, CRM/BSA mixture shares some features with the model spectra, and has the nearest profile. The next nearest profile is the CRM in 20% ethanol, which has a very noisy and distorted spectra but remains intimately connected to a general shape of the protein spectra. As expected, the BSA sample has the most different profile.

These observations can be seen in all the smoothing steps. As already seen before, smoothing removes only (or mostly) noise and does not generate artifacts, but enhances differences and simplifies the spectral data.

FIG. 31 probes the CRM signature against all the lots of CRM analyzed, merging data from Example 2B (the unoptimized method, with noisy autozero and low day to day reproducibility) and Example 2D (the optimized method). As can be seen, the only little discrepancy (<1%) can be found in the last line, from the first noisy lot 46 scan (Example 2B), made with buffer subtraction integrated with autozero.

While FIG. 31 is a slightly forced comparison (because the methods are not perfectly equal between scans), because it is known that all lots are equal for the technique of the invention, this comparison can help verify the ability of the method of the invention to recognize samples in non-ideal conditions. It can be seen that all the lots fit with the signature, except data from noisy Lot 46 spectra, that has just one resolution point shift difference (less than 1% difference).

Moving from convexity characterization to the spectral analysis of single curves (FIG. 29), as the derivative level increases an enhancement of the small fluctuations against the big peaks is seen. Limits to this approach are represented by the parallel increasing of random noise level, typically recorded by instruments as little fluctuations, and by the resolution of the instrument, two factors usually related.

Figure 2A:
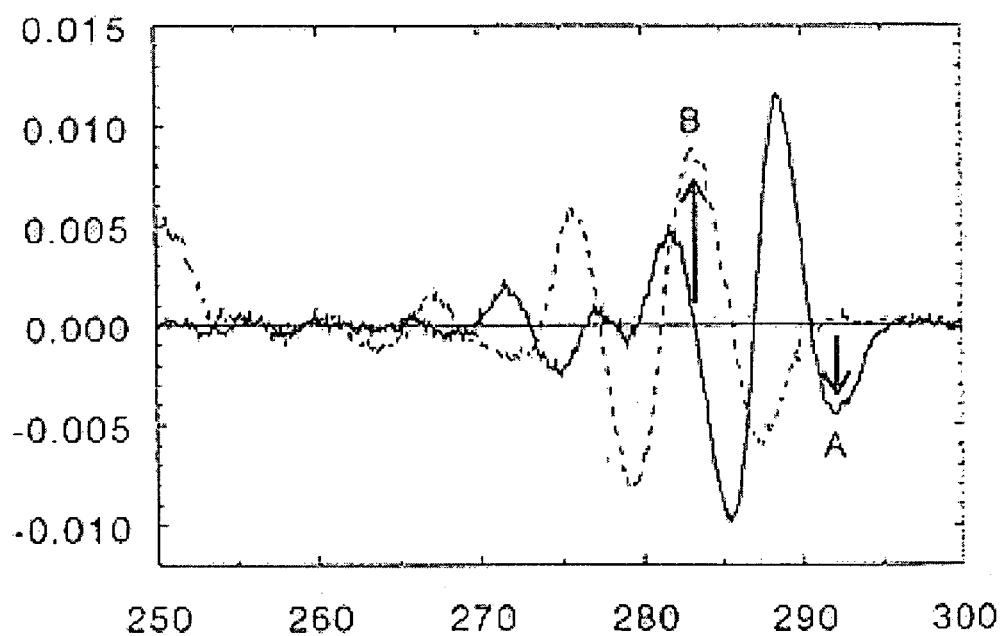
FIG. 2A shows the 4th derivative separation of tryptophan and tyrosine peaks' contribution in model compounds of the two amino acids. The solid line is the spectrum for tryptophan, the dotted line is the spectrum for tyrosine.
Figure 2B:
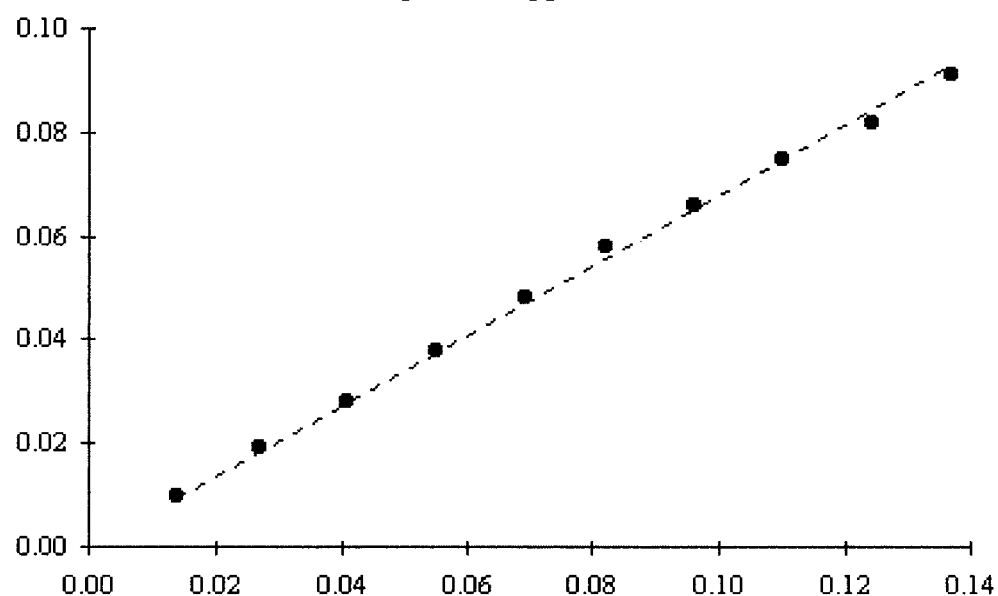
FIG. 2B shows the standard calibration curve of the tryptophan model compounds for 4th derivative spectroscopy.
Figure 3B:
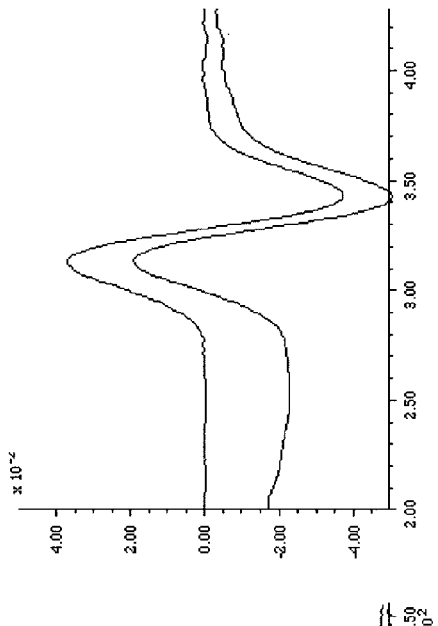
FIG. 3B shows the first order derivative of the spectrum.
Figure 3A:
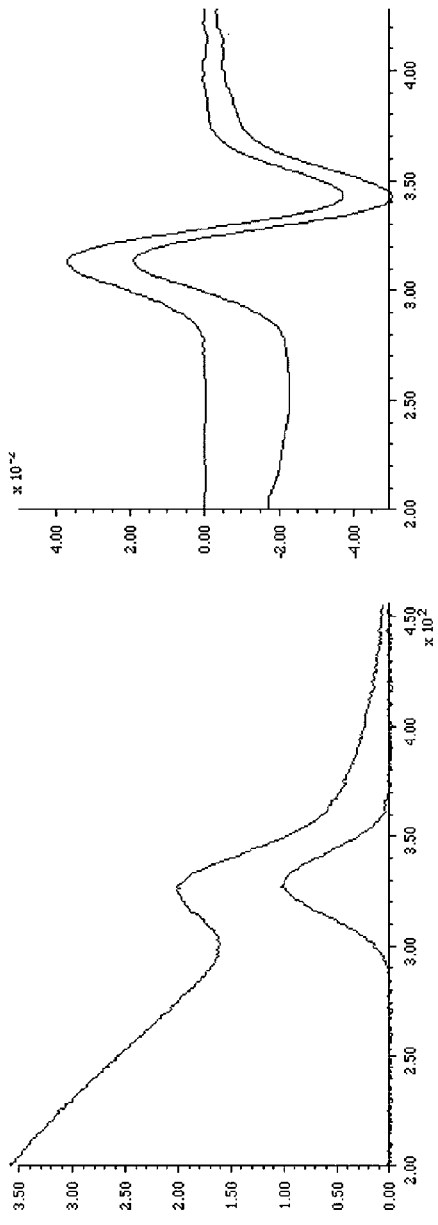
FIG. 3A shows the absorption spectrum of the sample.
Figure 3C:
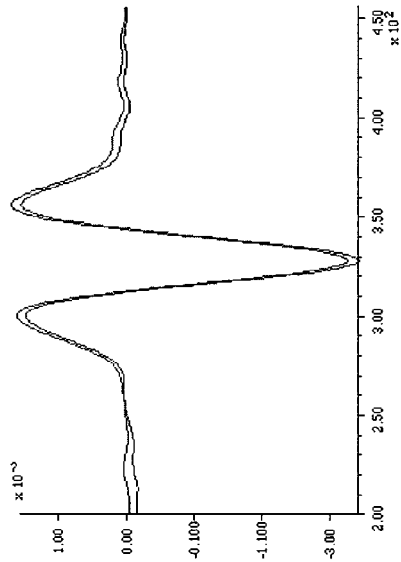
FIG. 3C shows the second order derivative of the spectrum.
Figure 4A:
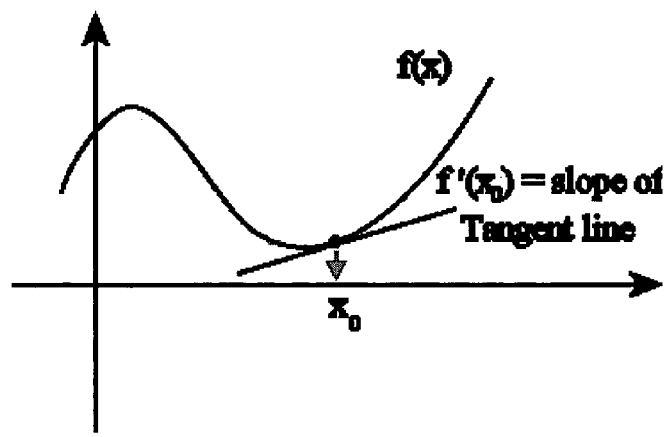
FIG. 4 shows a general technique for derivatization of a curve.
Figure 4B:
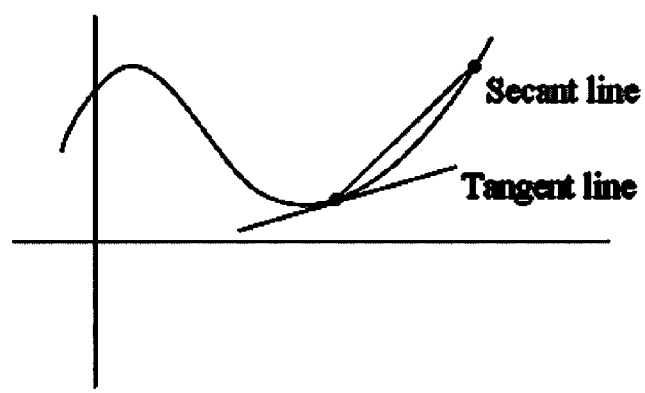
Figure 4C:
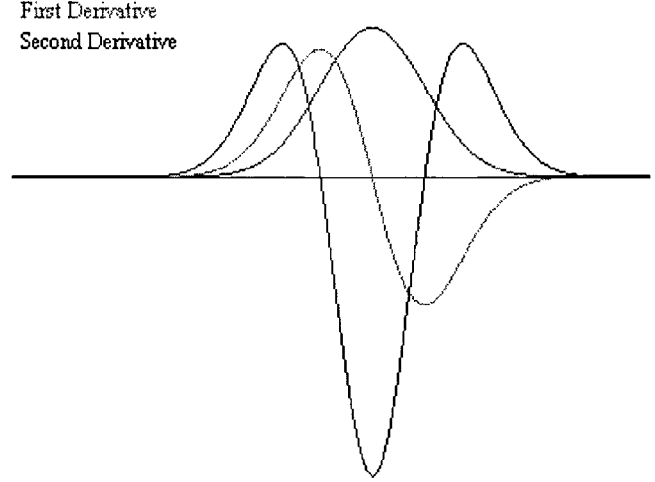
Figure 5:
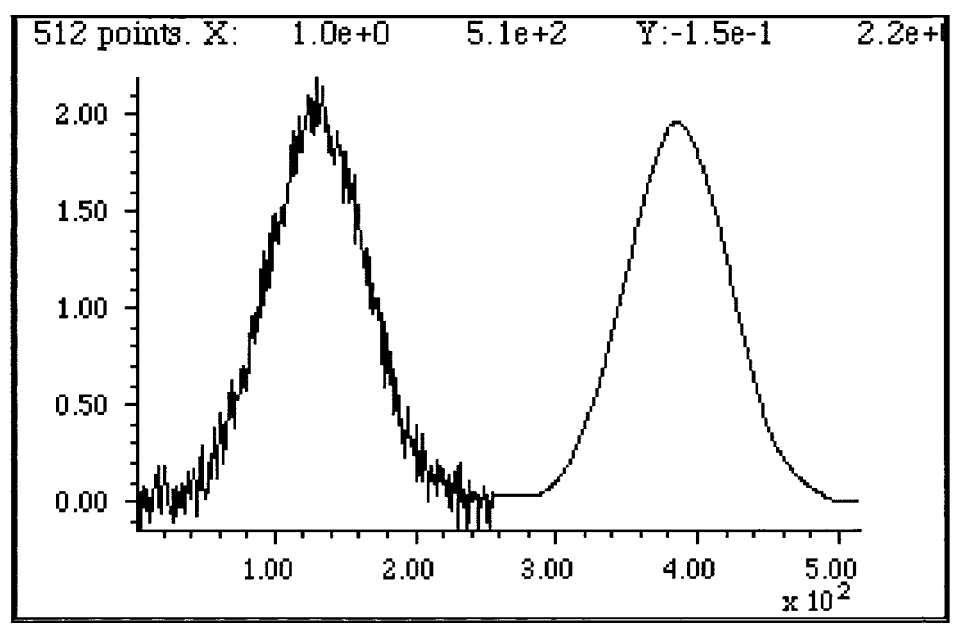
FIG. 5 shows a noisy spectrum before (left) and after smoothing (right).
Figure 6A:
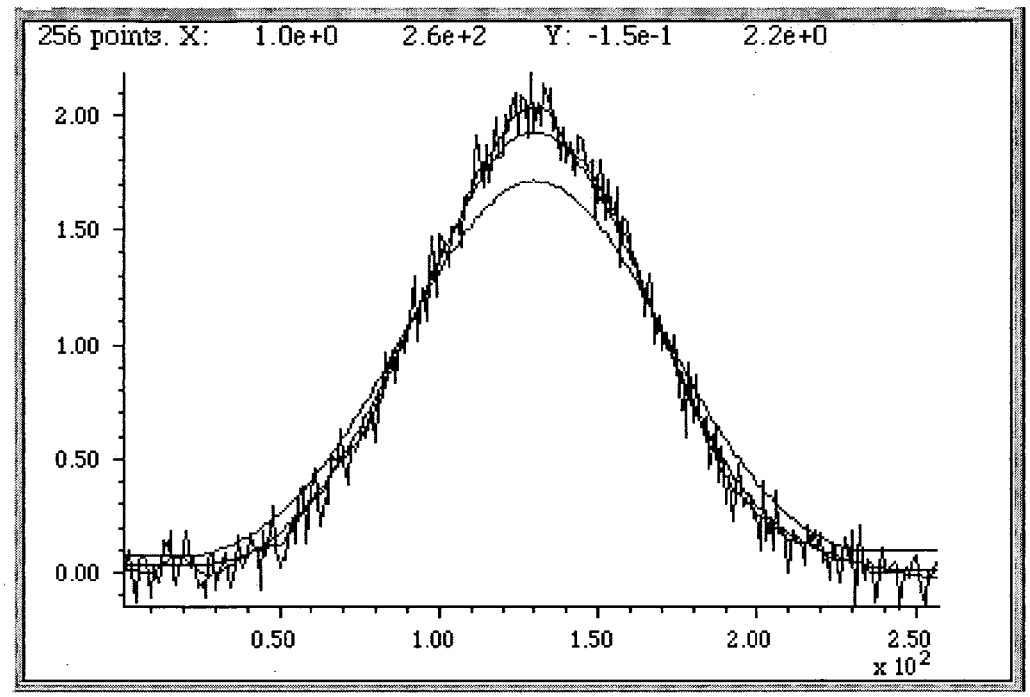
FIG. 6 shows a comparison between different noisy Gaussian peaks (FIGS. 6A and 6B) smoothed with same incremental smooth with. Narrow peaks show an increased sensitivity for height reduction and, in general, peak distortion, since smoothing ratios (smoothing points/points at half with of the peaks) become higher. In red, a) noisy peak with a height of 2.0 (Abs) and a half-with of 80 points b) noisy peak with a height of 1.0 (Abs) and a half-with of 33 points. In green, three curves obtained with increasing levels of triangular smoothing (7.25 and 51 points).
Figure 6B:
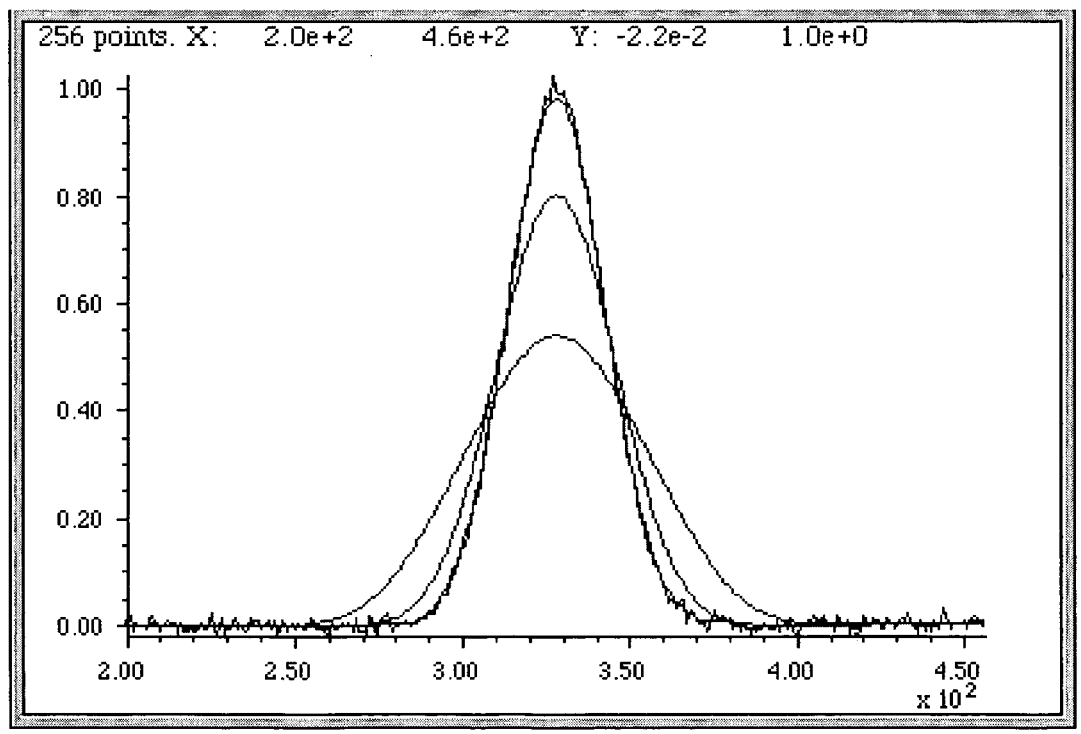

From FIGS. 2C, 5 and 6 it can be seen that the information within derivatives changes with a half period of 2: the first derivative of a spectra enhances the positive flexus points of the original function by representing them as negative peaks, and represents peaks as zero crossing flexus points.

Information about peak components of the original spectra is revealed as negative peaks in second derivatives and as positive peaks in fourth derivatives, while first and third level derivatives simply better characterize numeric information of the preceding pattern.

The supplement of information from derivative functions comes from: a) the sharper identification of original peak edges through the identification of zero crossing points in first and third derivatives; b) reduction of fixed background effects; c) shrinking/separation of peak components during the derivatization process; and d) the enhancing of trace components (narrow small components) as the derivative order increases.

Figures 11A, 11B:

FIG. 11 shows the application of the invention for resolution enhancement.
Figure 12B:
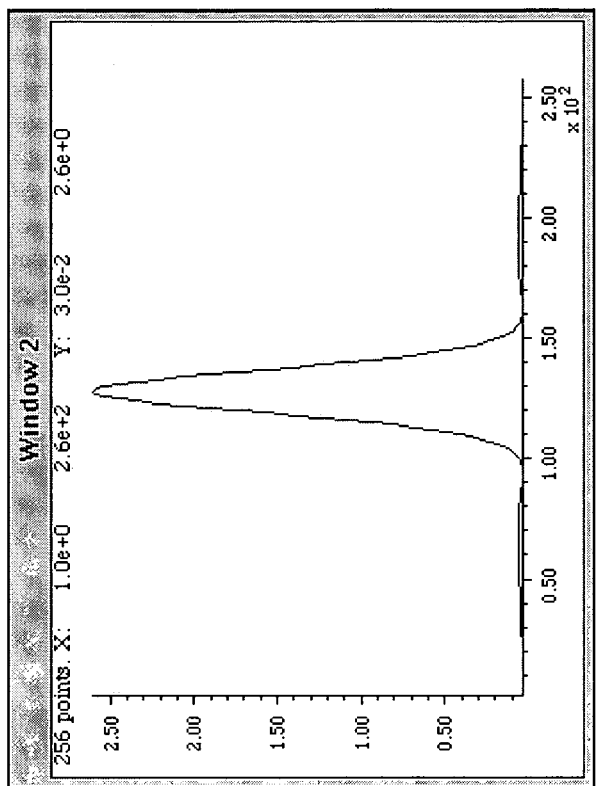
FIG. 12 shows a resolution enhancement algorithm based on the second derivative.
Figure 12A:
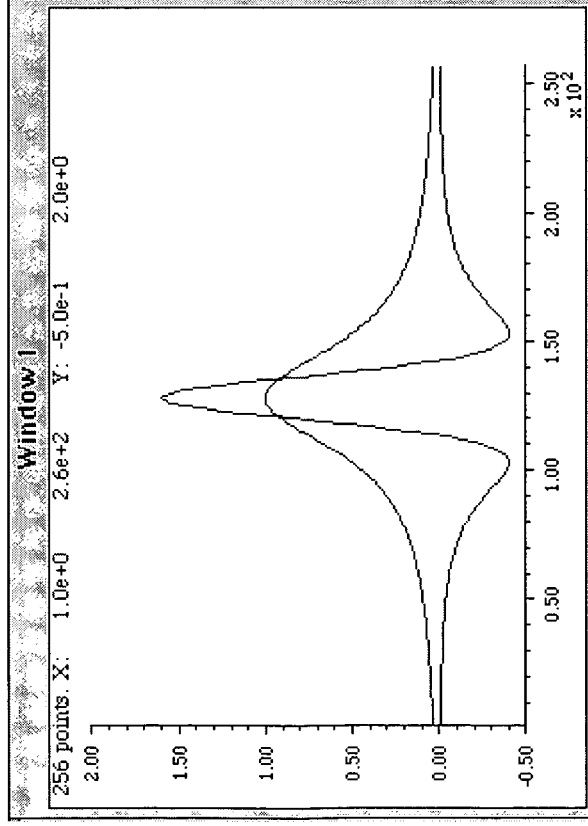
Figure 25A:
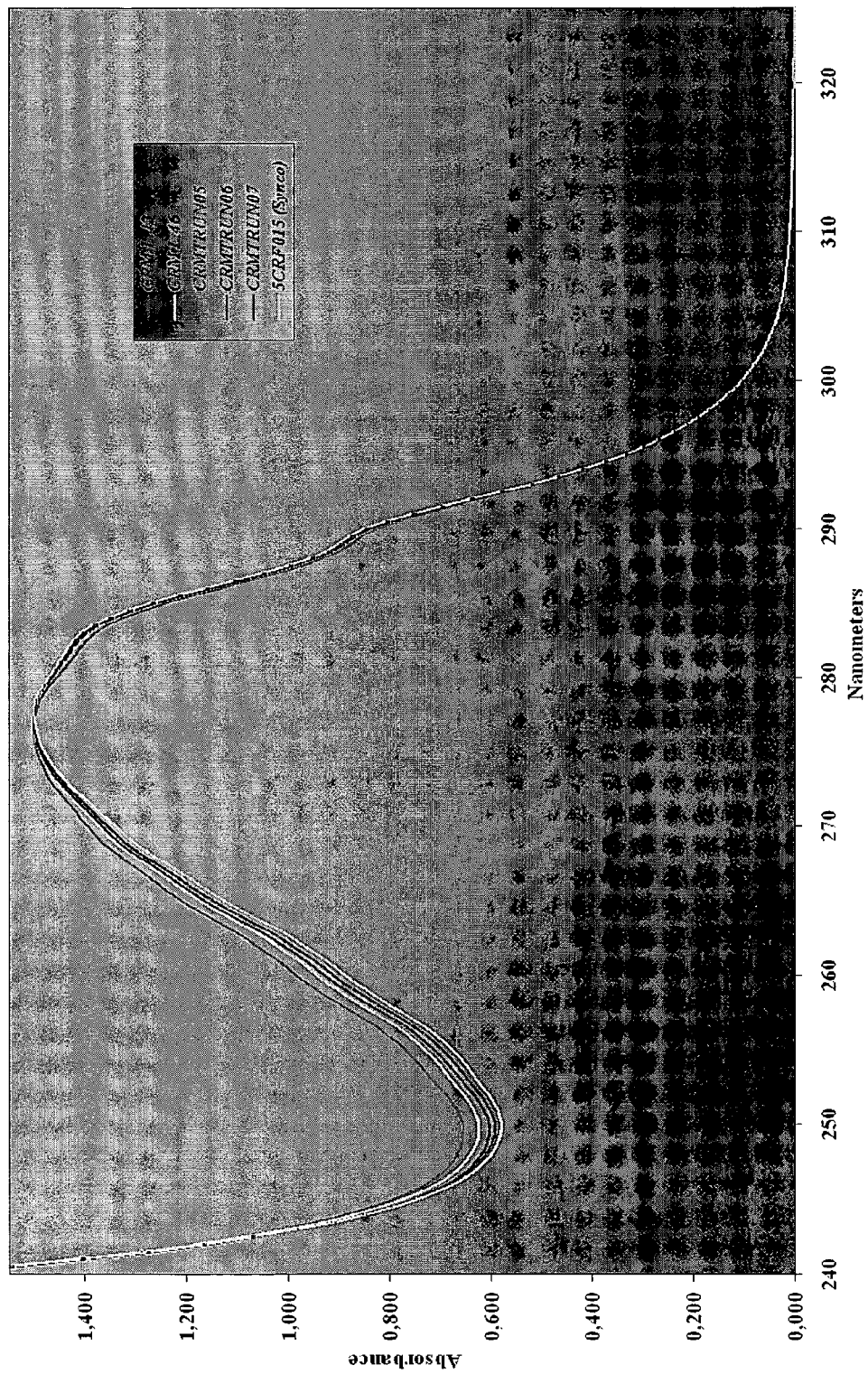
Figure 25B:
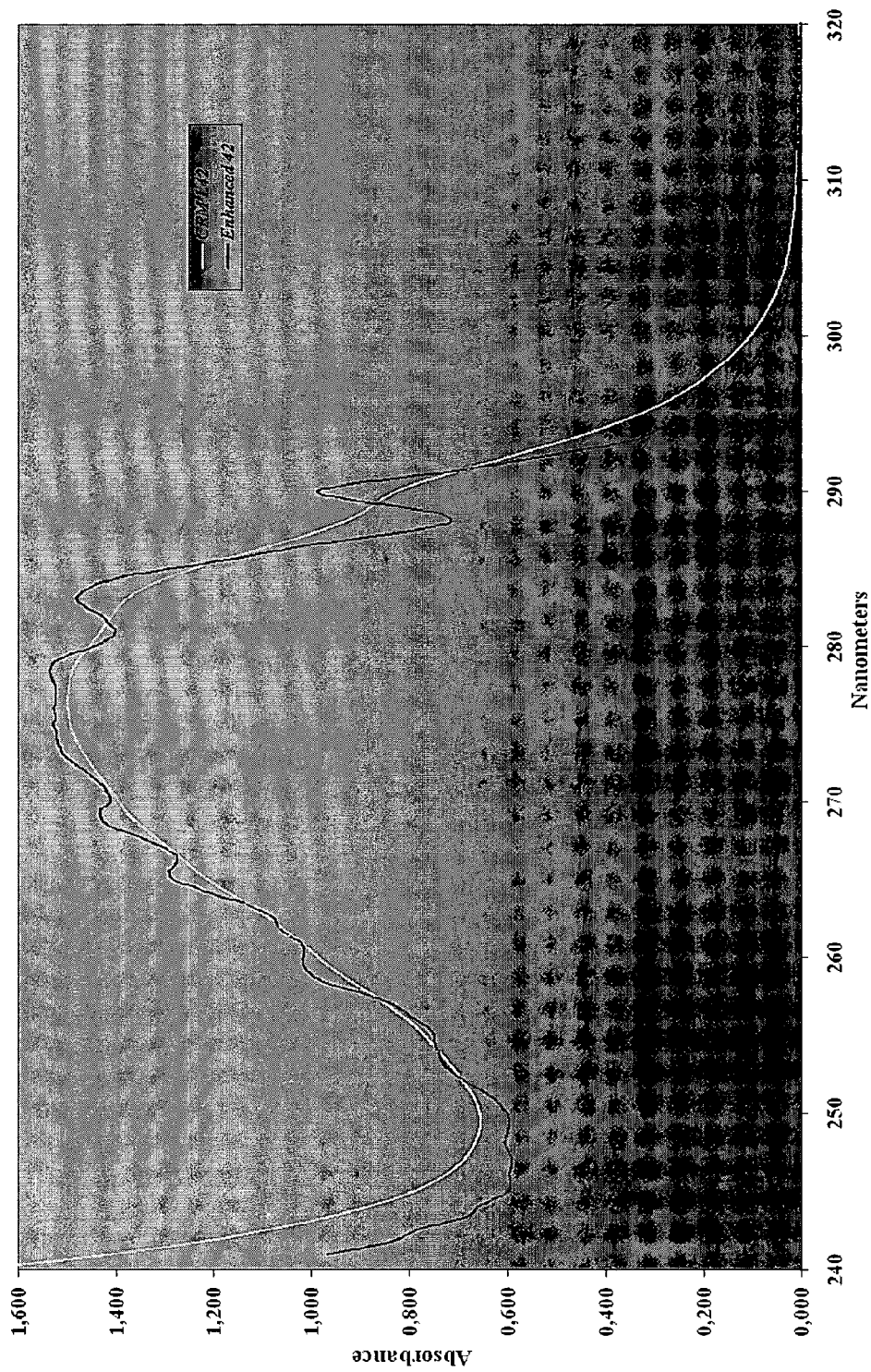
Figure 25C:
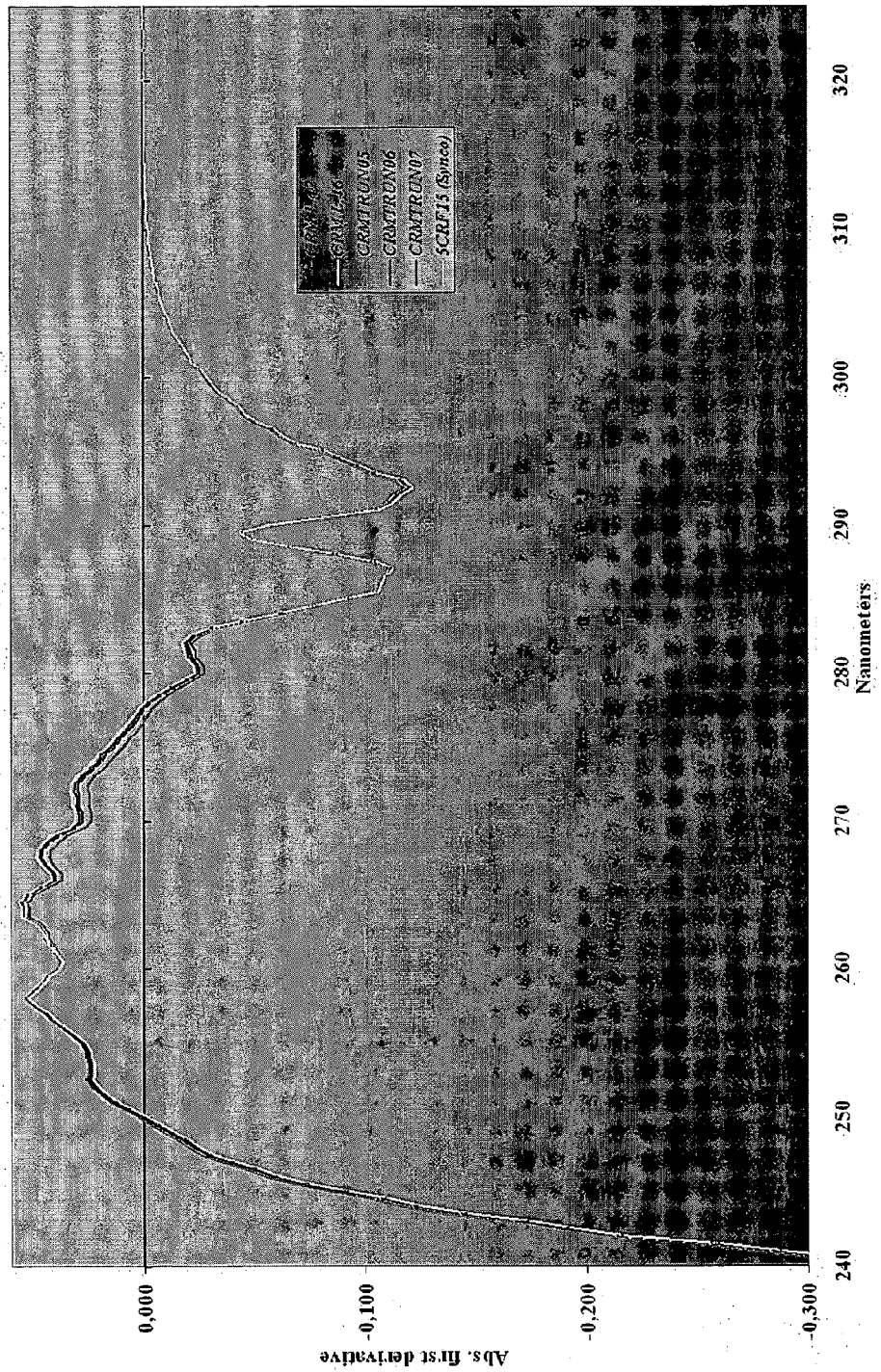
Figure 25D:
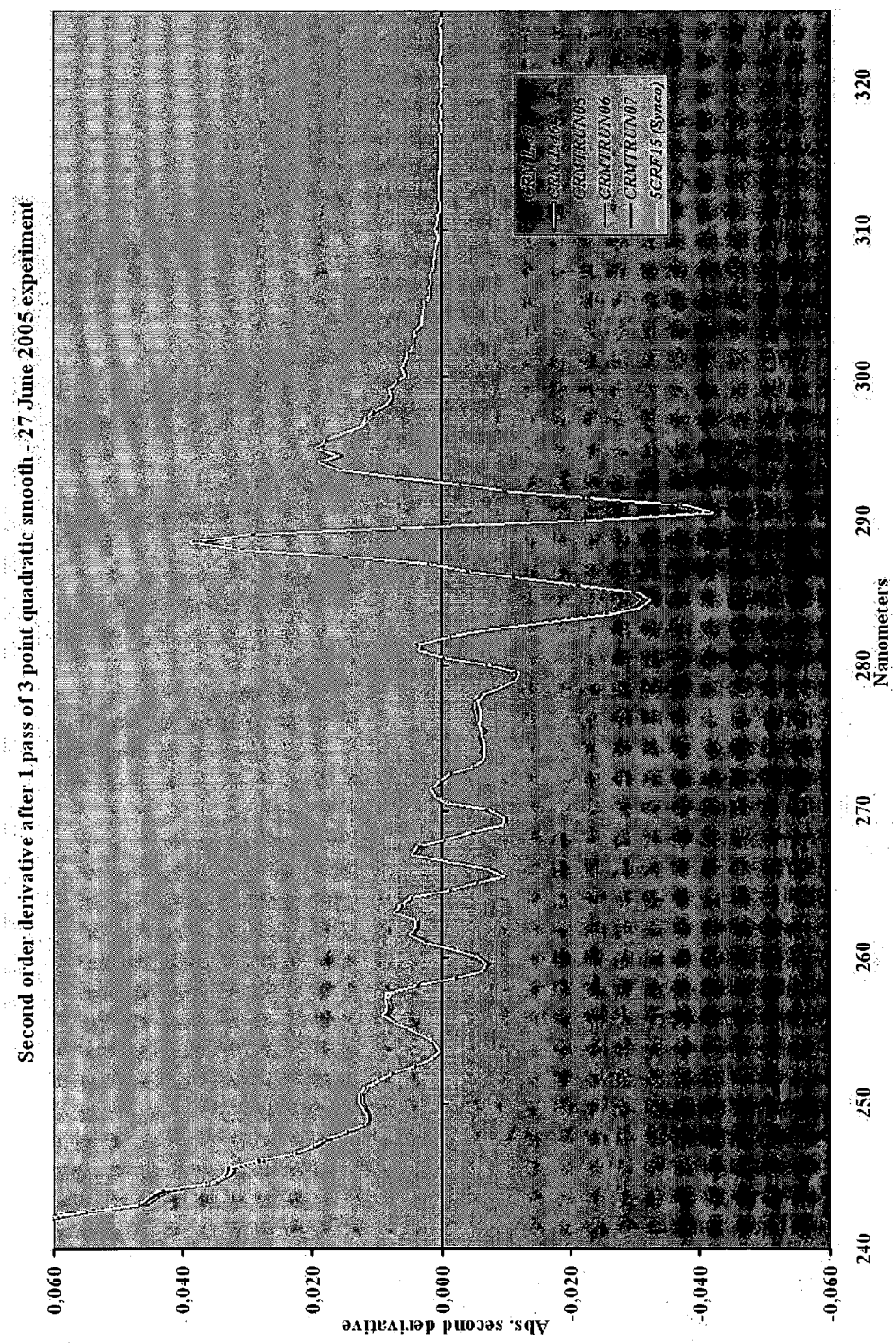
Figure 25E:
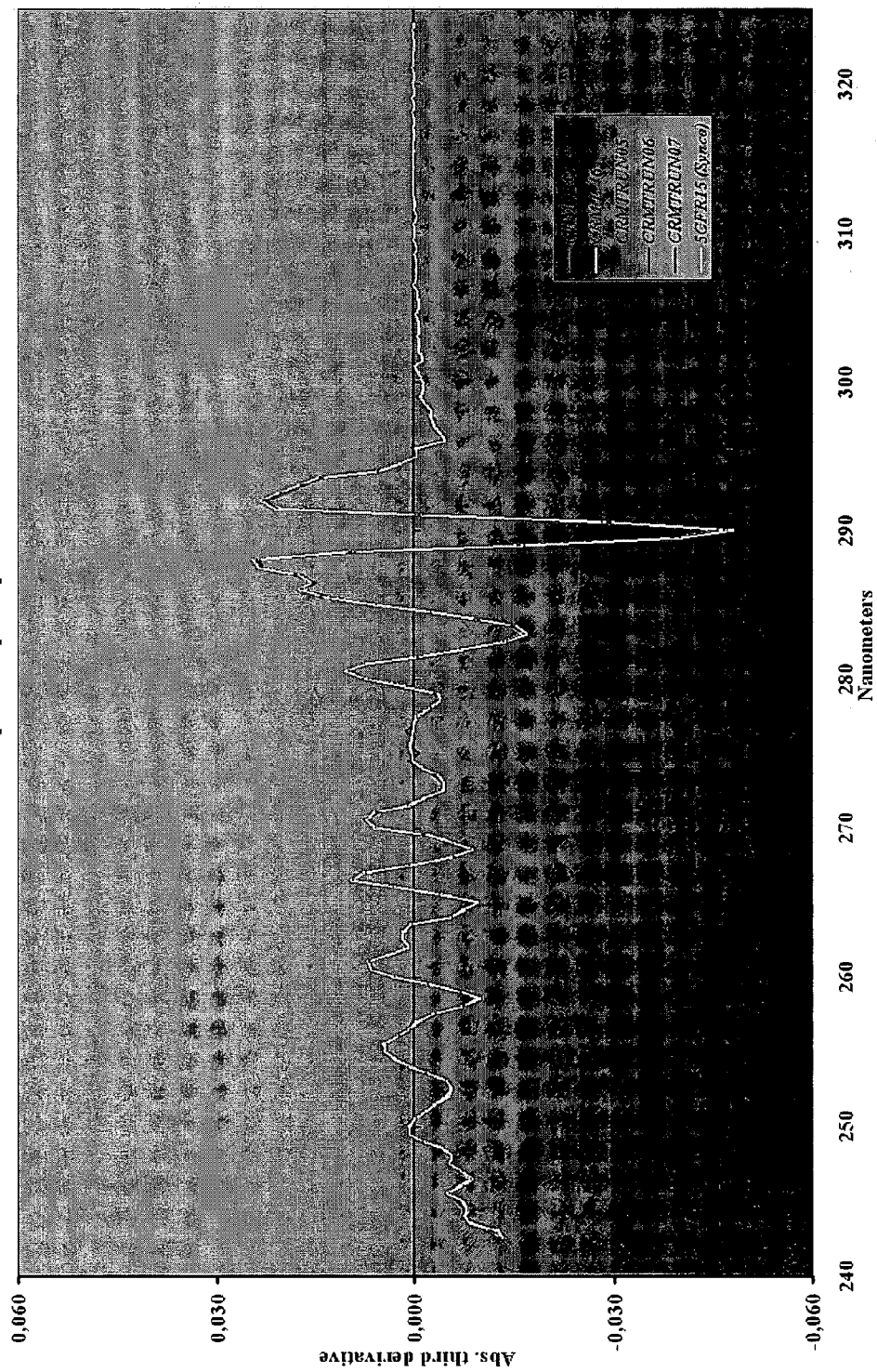
Figure 25F:
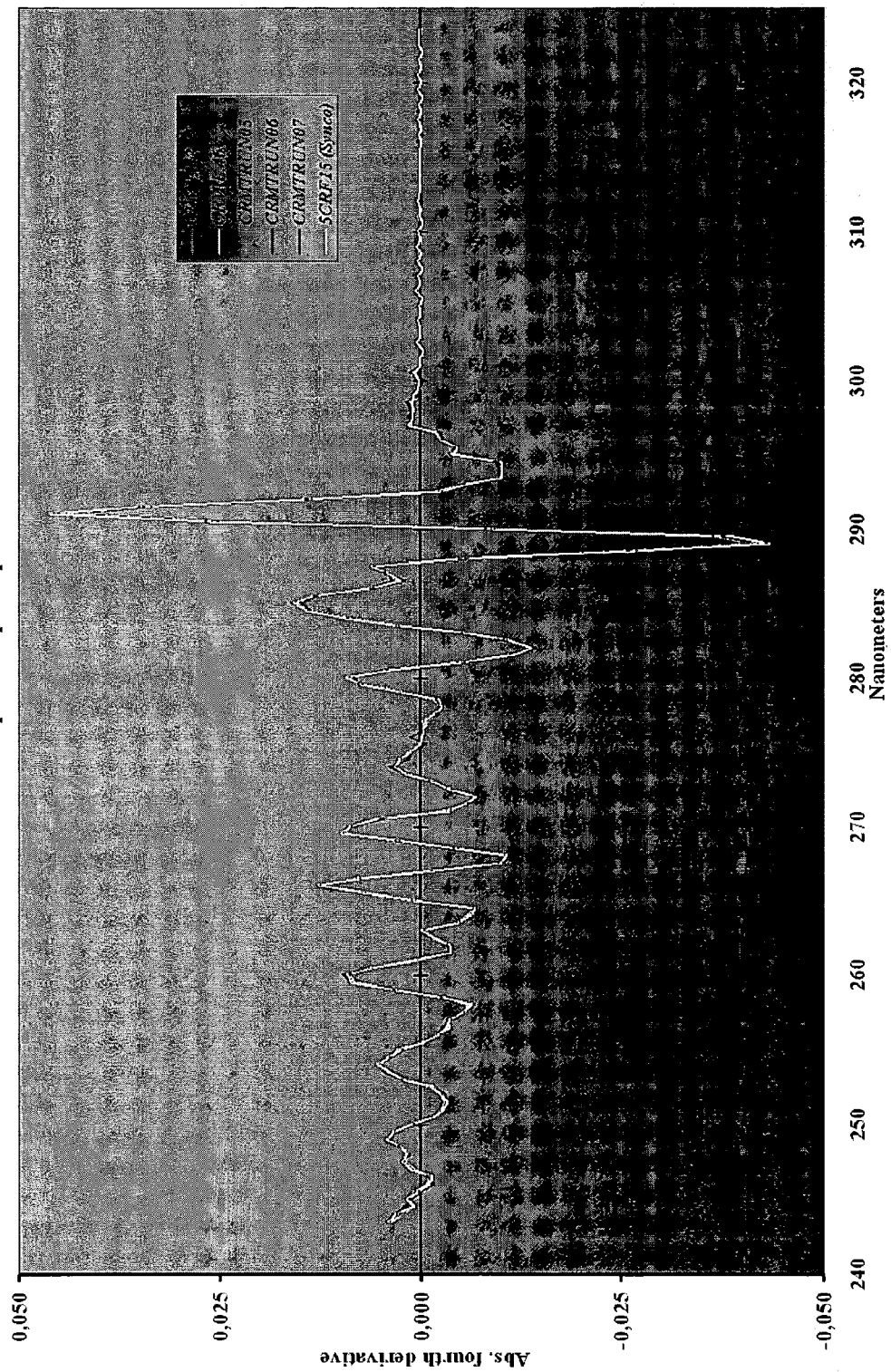
Figure 26A:
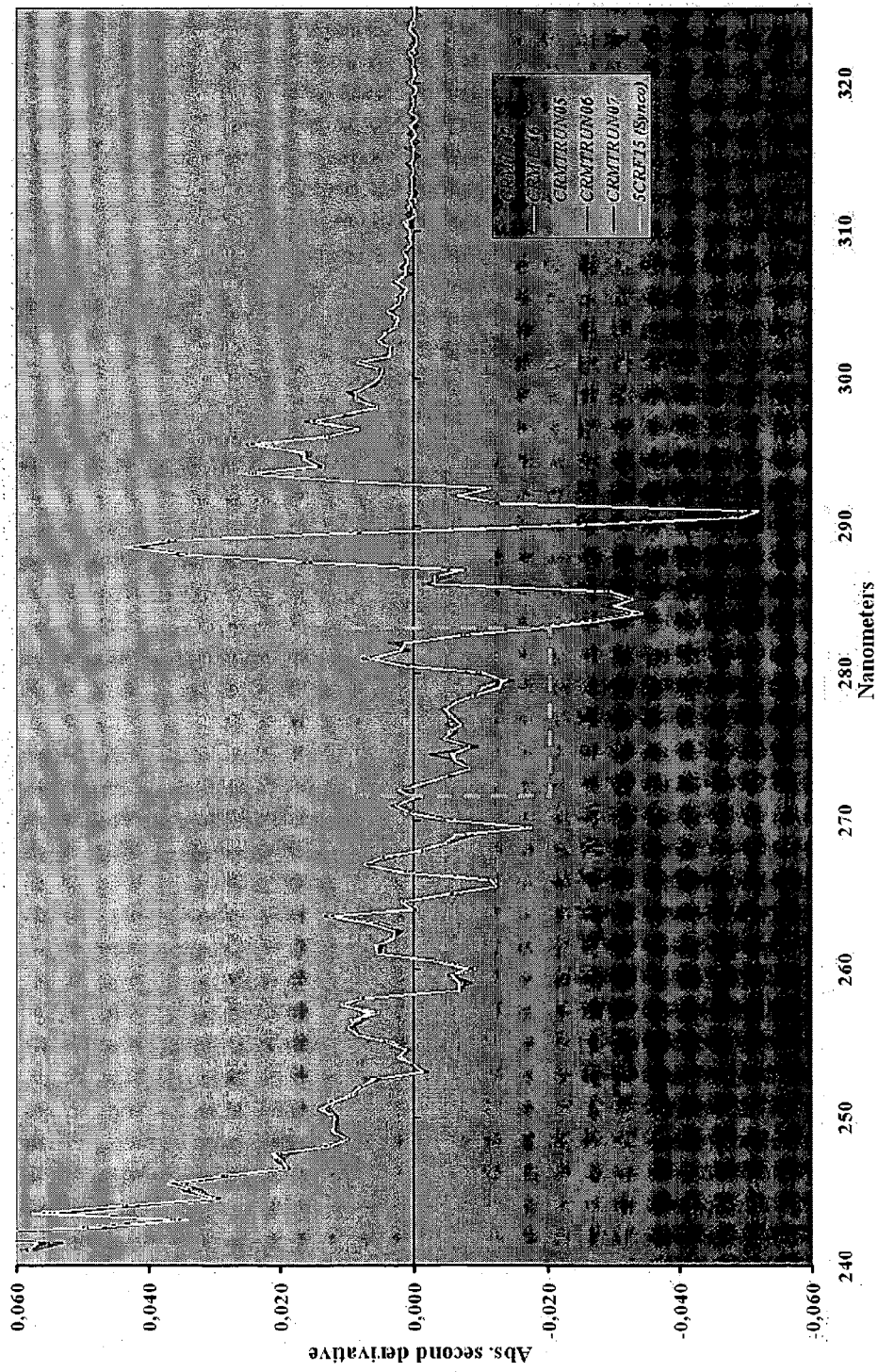
Figure 26B:
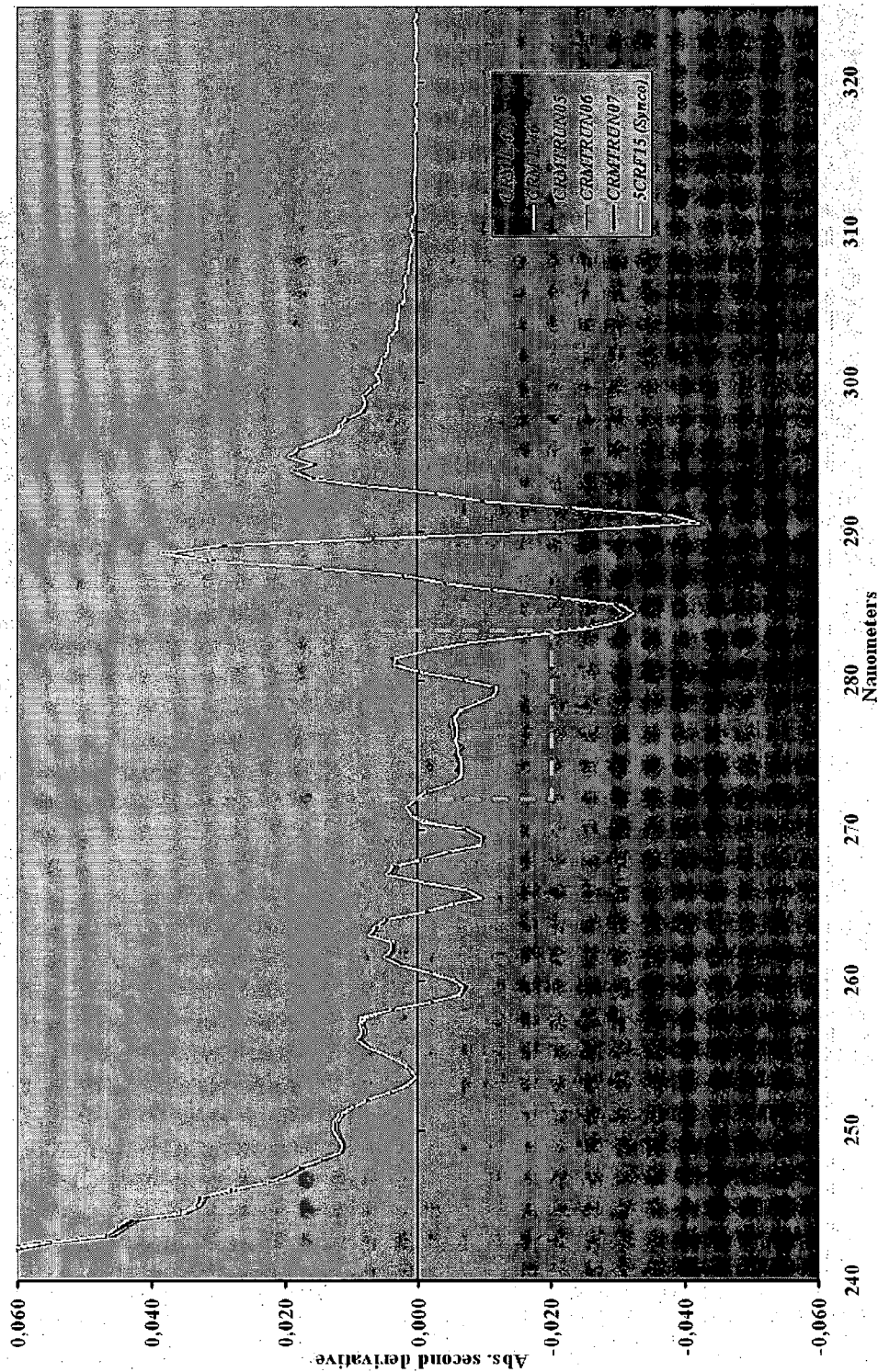
Figure 26C:
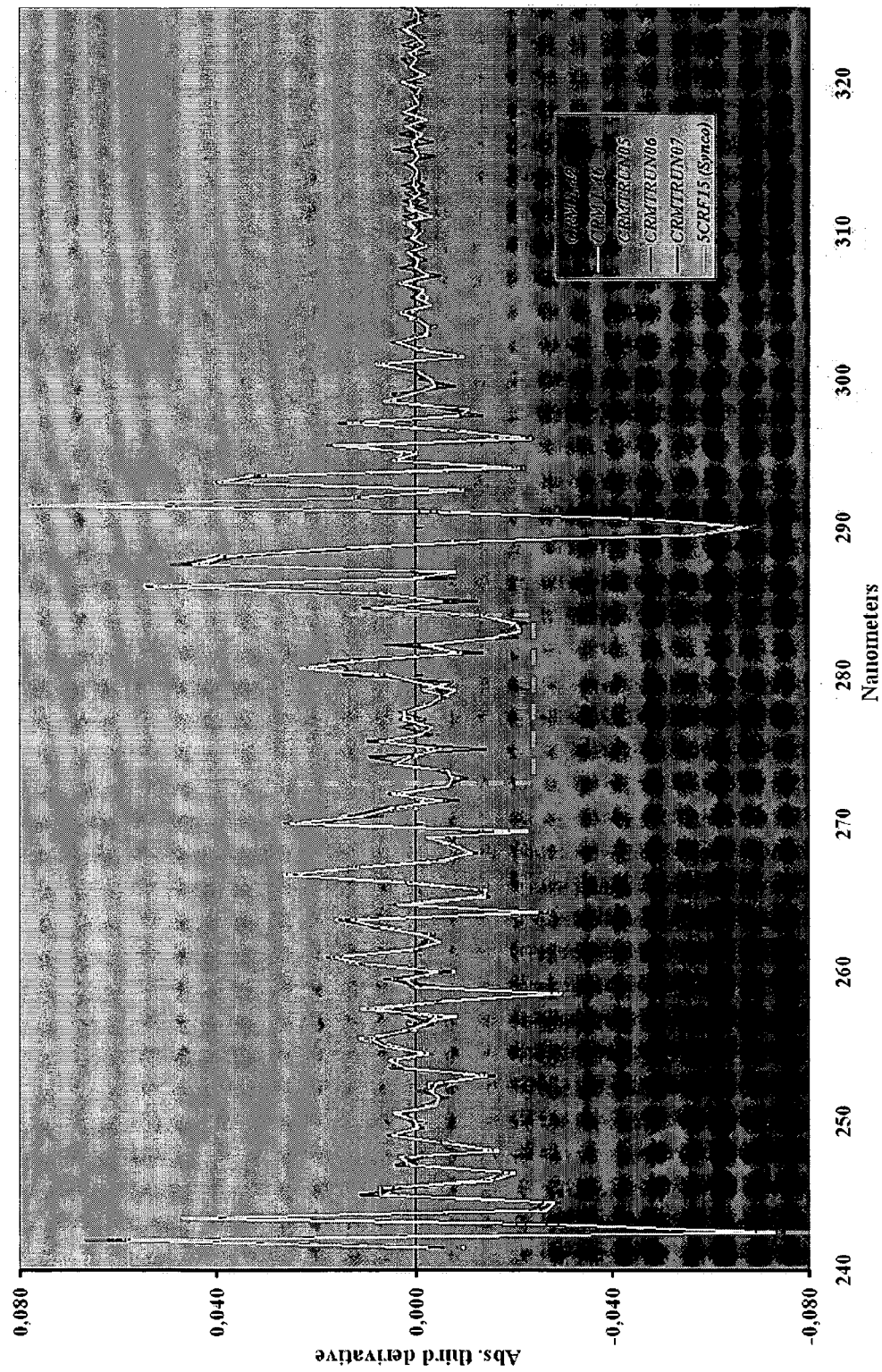
Figure 26D:
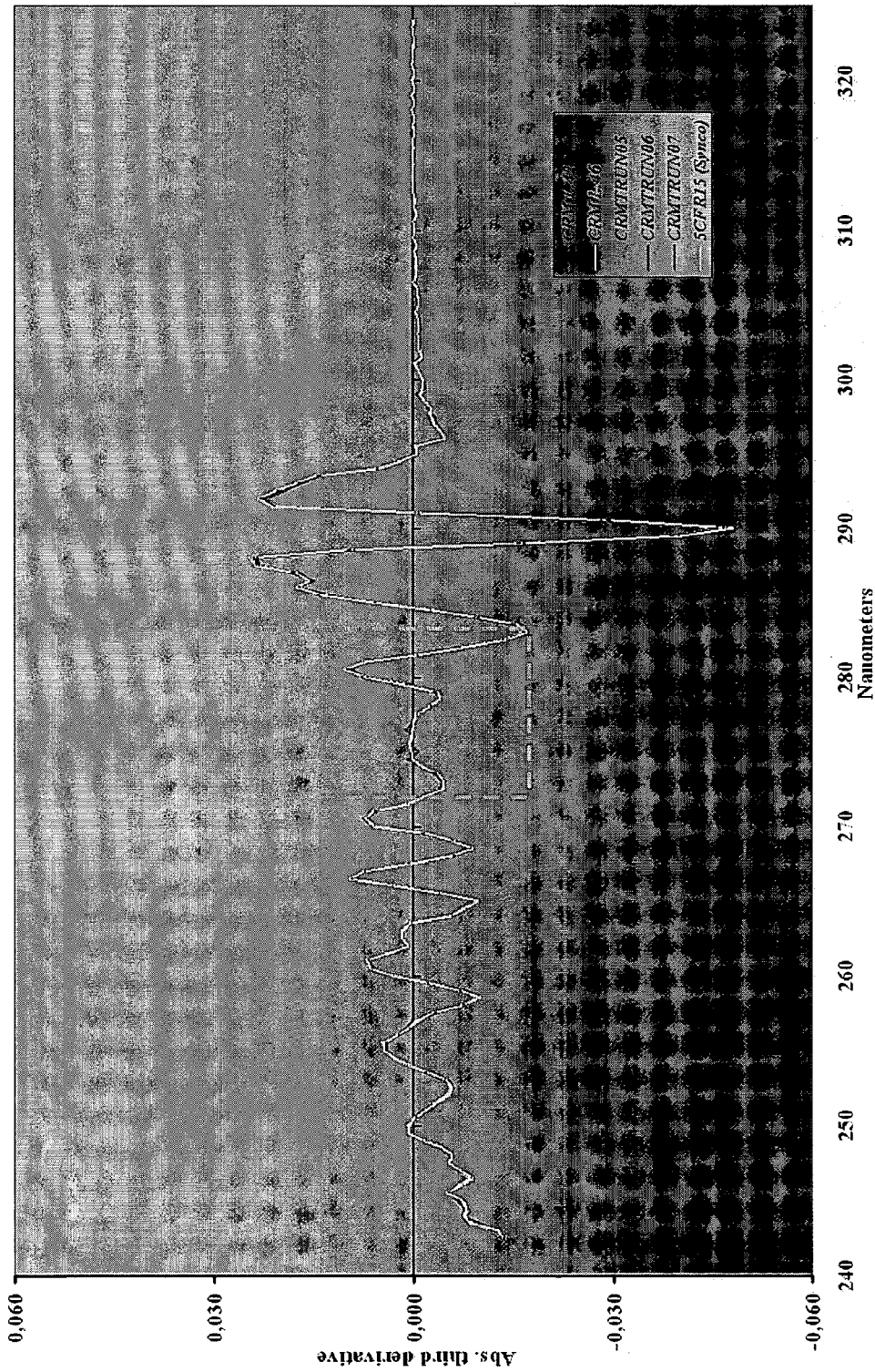
Figure 26E:
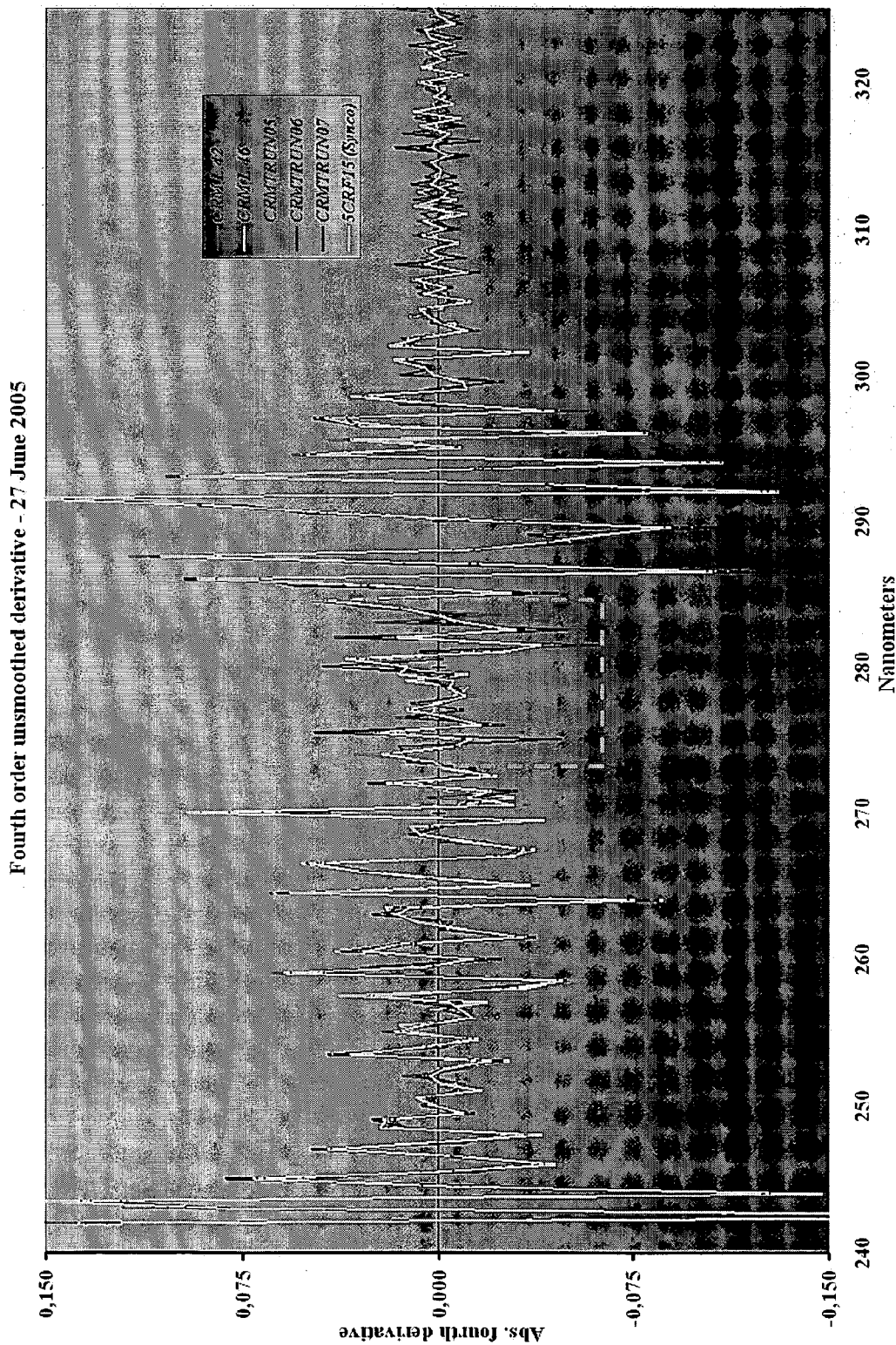
Figure 26F:
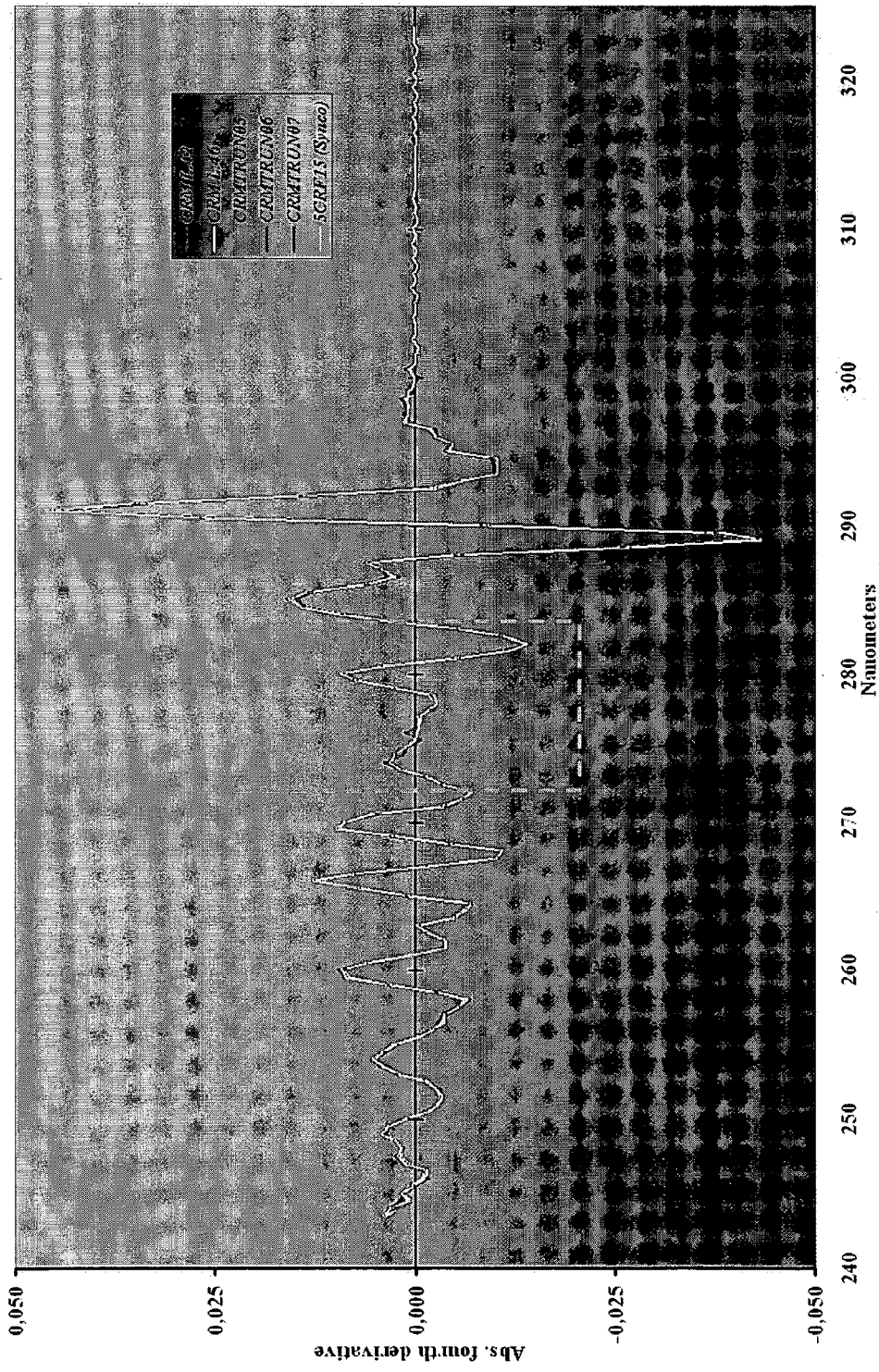

A "resolution enhanced" spectrum is obtained by combining the second smoothed derivative (usually quite noiseless) with the absorbance spectrum (FIG. 25B and FIG. 11). The combined spectra allows the improved characterization of all the main CRM lot 42 sample components revealed within the second derivative in just one picture. The improved characterization is particularly evident if the enhanced spectrum is overlapped with the original absorbance curve.

Together in one figure, the original spectrum, the negative of the second derivative spectrum, the enhanced spectrum, and the fourth derivative spectrum are shown (FIG. 32 for CRM and FIG. 33 for BSA). The four curves make a complete pattern of the spectral components, since peak progression through derivatization progress gives an idea of the relative abundance of components revealed in each pass. Using this kind of analysis, the order that the spectra should be considered is: original, enhanced, second and then fourth order derivative spectra. Looking at the spectral information, enhanced spectra is between the original and the negative of first derivative, but gives all the information in just one picture.

Figure 7:
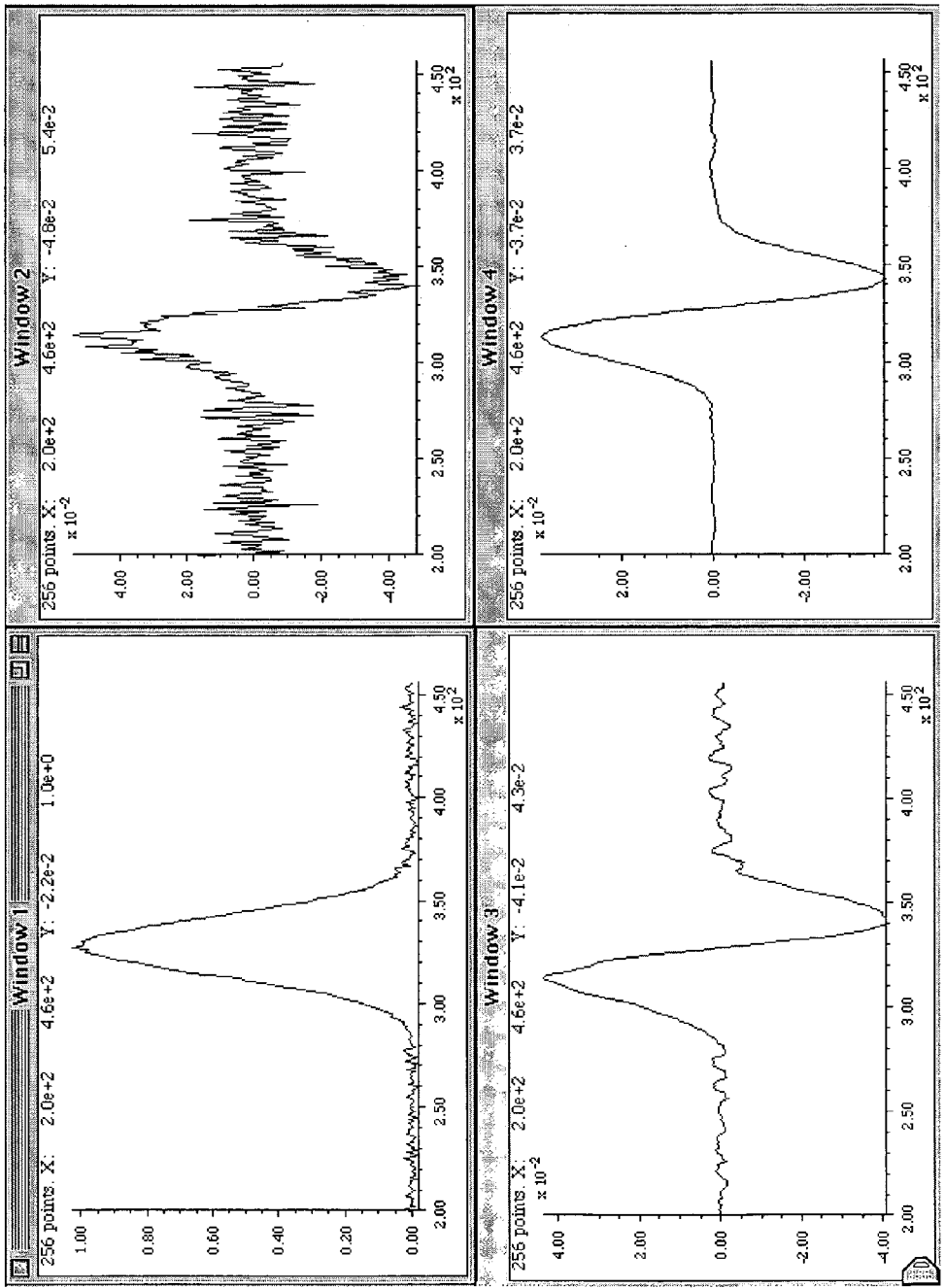
FIG. 7 shows the application of smoothing to the first derivative of a spectrum.
Figure 8:
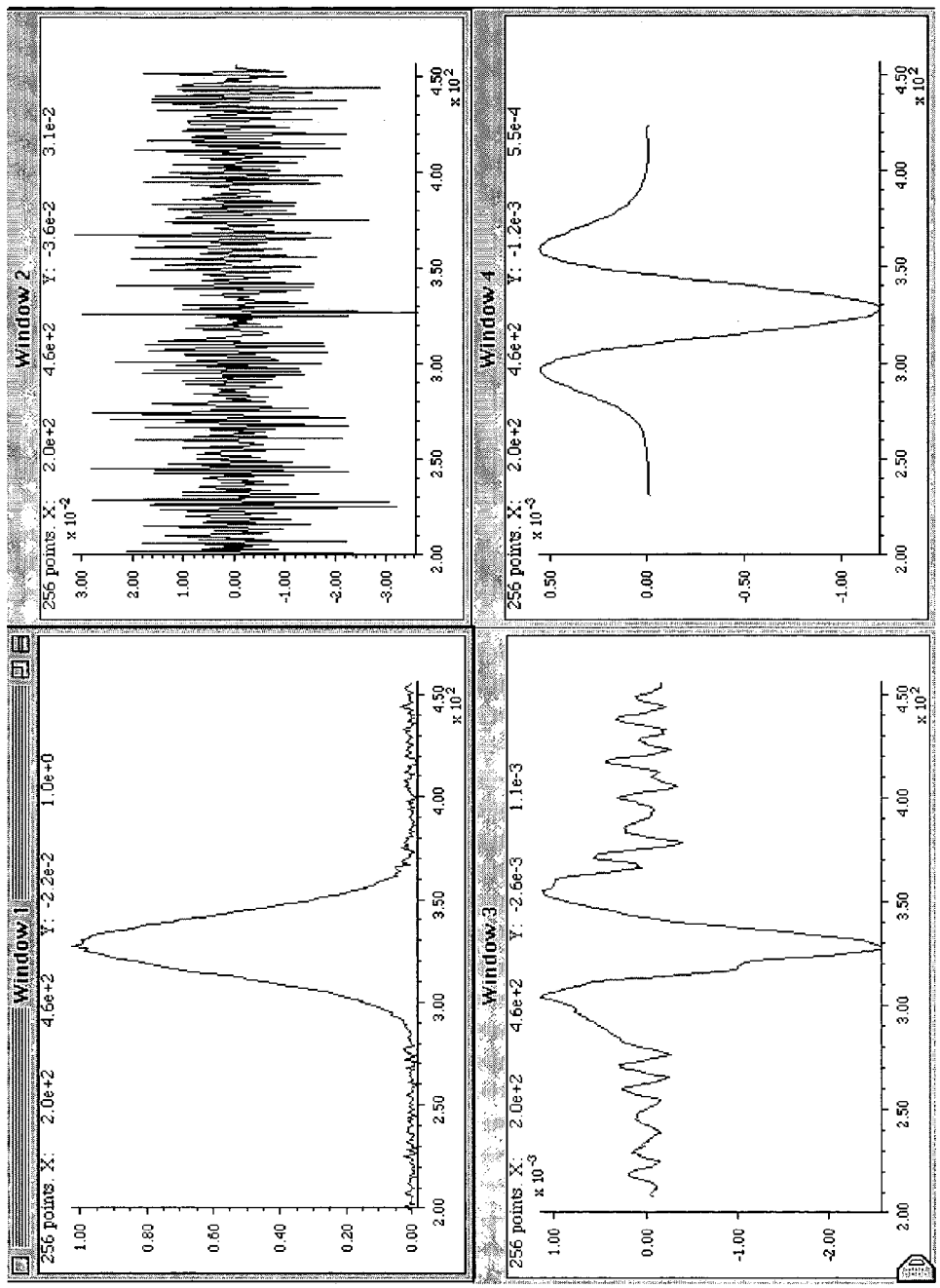
FIG. 8 shows the application of smoothing to the second derivative of a spectrum.
Figure 9A:
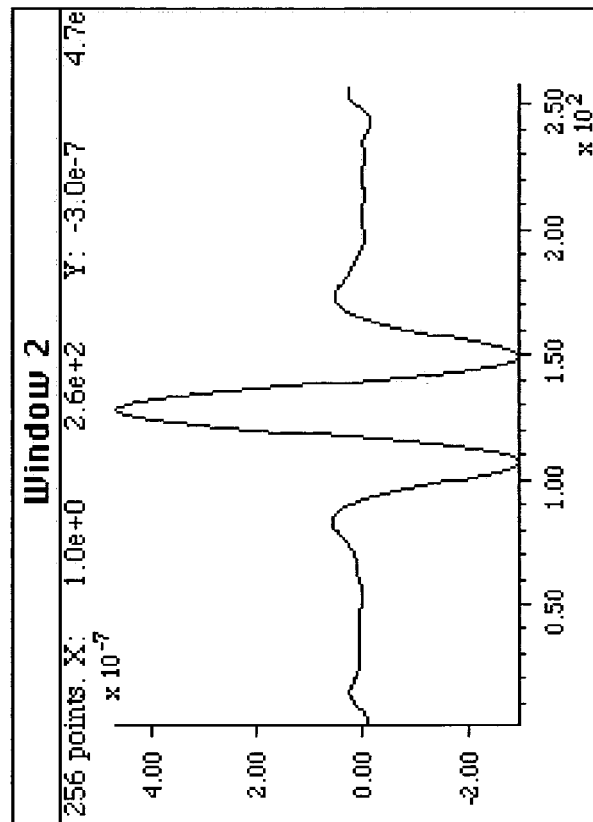
FIG. 9 shows an enhancement of a trace component by fourth derivative analysis.
Figure 9B:
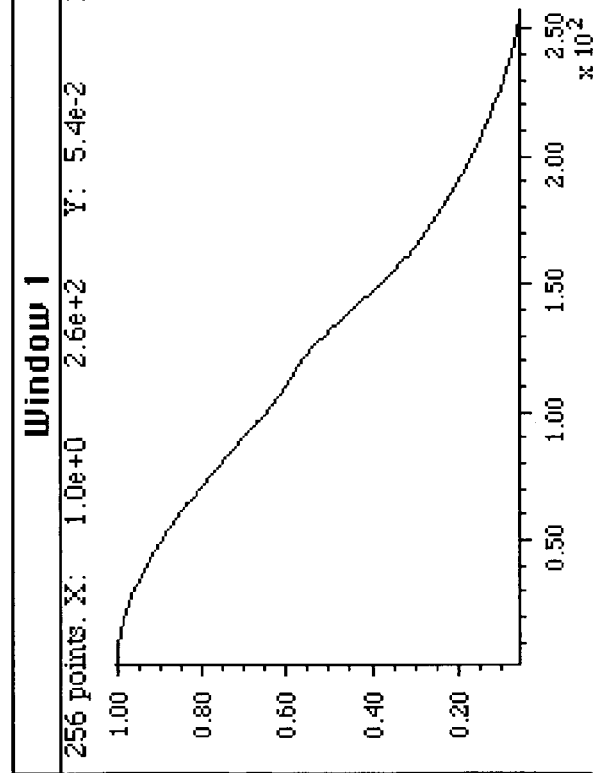
Figures 10A, 10B:
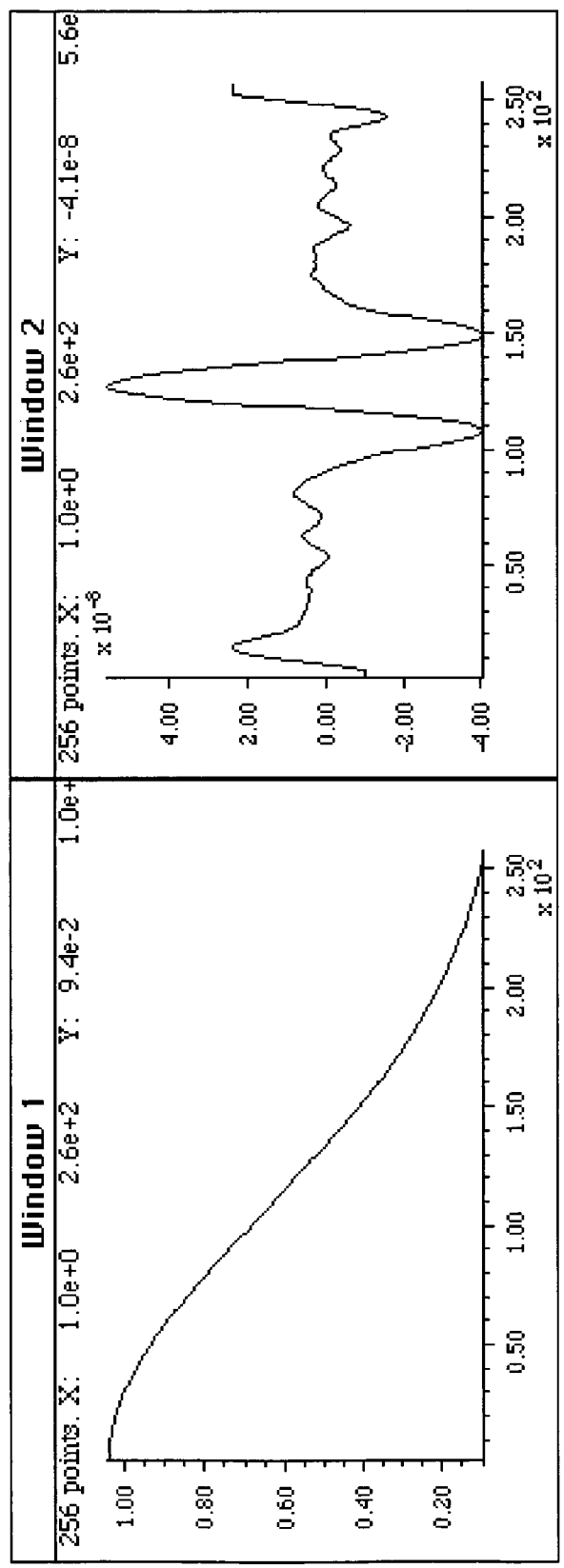
FIG. 10 also shows enhancement of a trace component by fourth derivative analysis with a concentration of analyte lower than FIG. 9.

As can be seen from FIG. 32, in the second derivative the main 277 nm peak of absorbance spectrum (see also FIG. 27) is immediately separated into its two main components at 279 nm and 274 nm, typical (see FIGS. 1 and 7) of tyrosine and tryptophan residues. The two peaks have about the same height, with Trp being a little greater, as expected from their different absorbance and abundance in CRM protein (Trp has exactly four times the absorbance of Tyr, and CRM has 18 Tyr and 5 Trp).

The 5 tryptophan residues probably share the same microenvironment, because together they form a population that gives a very sharp peak. However, as can be seen from fourth derivative and previously examined unsmoothed spectra, tyrosine's large peak means that these residues are in a wider range of microenvironments, even if still recognizable as one single species. This variety is to be expected from residues in a correctly folded protein. Secondary absorbance peaks from these two main absorbent residues can be found at 287 and 290 nm for tryptophan and at around 284 nm for tyrosine.

Moving to the shorter wavelengths, at around 270, 265, 260 and 255 nm signals can be found from the 18 phenylalanine residues contained in the $CRM_{197}$ protein. Since the signal from this residue is 7 times lighter than Tyr and 28 times lighter than Trp, its main signal at around 260 nm is always revealed as a secondary peak on the shoulder of the Tyr and Trp peaks. The 265 and 255 nm signals are secondary peaks, but without looking at the derivative spectra their peaks can appear as the main peaks of an unknown substance.

Finally, at around 250 nm, visible only in derivative spectra, a small signal from the four cysteines can be seen. These residues have only 1.5 times the absorption factor of phenylalanine, but with the help of the fourth derivative spectrum the signal can be clearly seen.

Looking at the similar spectra described in FIG. 33 for BSA, the same theme can be seen, shifted for a stronger presence of Phe, Cys and Tyr, and a lighter signal for Trp.

The main 278.5 nm peak of absorbance spectrum is not separated into its two main components at 279 nm and 274 nm until fourth derivative, as expected for a protein with many Tyr residues (20) and few Trp residues (2). The two peaks have a stronger height than in CRM, and the main contributor is due to Tyr and not Trp, as can be seen due to the lack of a typical Trp peak around 290 nm.

Moving to the shorter wavelengths, around 270, 265, 260 and 255 nm the very strong signals from the 27 phenylalanine residues contained in the protein can be seen.

Finally, at around 250 nm, visible already in second derivative spectra, the small signal from the 35 Cysteines can be found.

Fluorescence Spectroscopy

Example 4

Fluorescence Characterization of Chimera Protein 297-953

The chimera protein 287-953 can be used as a component of a Meningococcus type B vaccine. The protein is a monomer, composed of 644 amino acids, with a theoretical molecular weight of 67,859 Da and a pI of 5.10. It is produced under GMP conditions and purified to homogeneity.

The 287-953 primary sequence (from 2996 strain, *N. meningitidis* Group B) and amino acid composition are shown in FIG. 34 and Table 5 [62, 63]. The linker peptide between 287 and 953 is indicated in bold in FIG. 34.

TABLE 5

| Amino acid composition of 287-953 | | |
|---|---|---|
| Ala (A) 66 | 10.2% | |
| Arg (R) 18 | 2.8% | |
| Asn (N) 44 | 6.8% | |
| Asp (D) 48 | 7.5% | |
| Cys (C) 4 | 0.6% | |
| Gln (Q) 30 | 4.7% | |
| Glu (E) 35 | 5.4% | |
| Gly (G) 79 | 12.3% | |
| His (H) 11 | 1.7% | |
| Ile (I) 22 | 3.4% | |
| Leu (L) 24 | 3.7% | |
| Lys (K) 45 | 7.0% | |
| Met (M) 14 | 2.2% | |
| Phe (F) 27 | 4.2% | |
| Pro (P) 33 | 5.1% | |
| Ser (S) 50 | 7.8% | |
| Thr (T) 40 | 6.2% | |
| Trp (W) 2 | 0.3% | |
| Tyr (Y) 17 | 2.6% | |
| Val (V) 35 | 5.4% | |
| Asx (B) 0 | 0.0% | |

TABLE 5-continued

| Amino acid composition of 287-953 | |
|---|---|
| Glx (Z) 0 | 0.0% |
| Xaa (X) 0 | 0.0% |

Total number of negatively charged residues (Asp + Glu): 83
Total number of positively charged residues (Arg + Lys): 63

A comparison of different 287-953 concentrated bulk lots was carried out to assess any physico-chemical modification occurring in the proteins produced for the different lots.

Samples

The samples for analysis were 287-953 protein antigen (purified concentrated bulk) of two lots:
1. lot M-MnB-P01 (lot 1), concentration 460 mcg/ml (BCA),
2. lot RS-21-01-01 (lot 2), concentration 750 mcg/ml (BCA)
both in KPi 10 mM+NaCl 150 mM pH 7.0+10% sucrose Before the analysis, samples of each lot were diluted to 200 mcg/ml in buffer KPi 10 mM+NaCl 150 mM pH 7.0, or in KPi 10 mM+NaCl 150 mM pH 7.0+10% sucrose.

Instrument Method

Diluted samples were analyzed in a Perkin Elmer luminescence spectroscopy cell (cod. B0631124) on a Perkin Elmer LS 50B luminescence spectrometer, at 2 different excitation wavelengths, 280 and 295 nm.

Emission spectra were registered between 300 and 390 nm, with subtraction of the buffer blank; each spectrum was the average of 3 different scans at 50 nm/min speed.

Every experimental day, before analyses, performance of the system is checked with the validation method provided in the FL WinLab 4.00.02 (Perkin Elmer) package (shown in FIG. 35), on a MQ water sample in a 1 ml quartz cuvette.

Configuration of the instrument is shown in FIG. 36. Method settings for the excitation at 280 and 295 nm are shown in FIG. 37.

Results

1 Example 4A

λ Excitation 280 nm

Table 6 shows the results obtained in 5 different analytical sessions by the excitation of the 287-953 purified lots 1 and 2 with $\lambda_{max}$ excitation at 280 nm. The table shows the indicated lots, $\lambda_{max}$ of emission spectrum, λ of zero crossing for the first derivative (D1 $\lambda_{x=0}$), and $\lambda_{min}$ of the second derivative (D2 $\lambda_{min}$). For each lot the averaged value, standard deviation and % relative standard deviation (% RSD) are presented.

TABLE 6

| | excitation at 280 nm | | |
|---|---|---|---|
| 287-953 lot | $\lambda_{max}$ em. (nm) | D1 $\lambda_{x=0}$ (nm) | D2 $\lambda_{min}$ (nm) |
| M-MnB-P01 | 317.0 | 317.0 | 315.8 |
| (Lot 1) | 318.1 | 318.1 | 312.5 |
| | 317.9 | 317.8 | 316.5 |
| | 317.8 | 317.6 | 313.1 |
| | 317.7 | 317.7 | 314.3 |
| average | 317.7 | 317.6 | 314.4 |
| Std. deviation | 0.37 | 0.35 | 1.53 |
| % RSD | 0.12 | 0.11 | 0.49 |
| RS-21-01-01 | 318.6 | 318.6 | 313.7 |
| (Lot 2) | 318.0 | 318.0 | 314.7 |
| | 318.5 | 318.4 | 314.7 |
| | 317.9 | 317.9 | 316.1 |
| | 318.0 | 318.1 | 316.1 |

TABLE 6-continued

| | excitation at 280 nm 280 nm excitation | | |
|---|---|---|---|
| 287-953 lot | $\lambda_{max}$ em. (nm) | D1 $\lambda_{x=0}$ (nm) | D2 $\lambda_{min}$ (nm) |
| average | 318.2 | 318.2 | 315.1 |
| Std. deviation | 0.30 | 0.27 | 0.91 |
| % RSD | 0.09 | 0.09 | 0.29 |

In FIG. 38, the normalized spectra of 287-953 lots 1 and 2 obtained in all the analytical sessions with excitation at 280 nm are presented. As can be seen, while the maximums of emission are similar in all the spectra, the curve slope presents a different trend in spectra belonging to lot 1 or lot 2 287-953.

FIGS. 39 and 40 show the first and second order derivatives respectively of the emission spectra described in FIG. 38.

Table 6 shows similarity of $\lambda_{max}$ of emission between the lots, similarity of the corresponding 0 crossing $\lambda$ of the first derivative curve and of the $\lambda_{min}$ of the second derivative.

As expected, $\lambda_{min}$ of the second derivative does not correspond exactly to the maximum of the original spectrum: this can be explained by the necessity to interpolate the data on a large interval (70 points) in order to obtain a good compromise between curve distortion and signal-to-noise ratio.

However, a careful examination of spectra presented in FIG. 38 and second derivative curves in FIG. 40 can reveal a different trend in the curve slope between lots 1 and 2, conserved in all the different experimental sessions.

2 Example 4B $\lambda$ Excitation 295 nm

Table 7 shows results obtained in 5 different analytical sessions by the excitation of the 287-953 purified lots (lots 1 and 2) with $\lambda_{max}$ excitation at 295 nm. The table shows the indicated lots, $\lambda_{max}$ of emission spectrum, $\lambda$ of zero crossing for the first derivative (D1 $\lambda_{x=0}$), and $\lambda_{min}$ of the second derivative (D2 $\lambda_{min}$). For each lot the averaged value, standard deviation and % relative standard deviation (% RSD) are presented.

TABLE 7

| | excitation at 295 nm 295 nm excitation | | |
|---|---|---|---|
| 287-953 lot | $\lambda_{max}$ em. (nm) | D1 $\lambda_{x=0}$ (nm) | D2 $\lambda_{min}$ (nm) |
| M-MnB-P01 | 329.5 | 329.6 | 320.0 |
| (Lot 1) | 331.9 | 332.0 | 317.5 |
| | 331.2 | 331.4 | 319.5 |
| | 330.3 | 330.5 | 317.2 |
| | 330.5 | 330.5 | 321.0 |
| average | 330.7 | 330.8 | 319.0 |
| Std. deviation | 0.80 | 0.80 | 1.45 |
| % RSD | 0.24 | 0.24 | 0.45 |
| RS-21-01-01 | 333.8 | 333.7 | 320.0 |
| (Lot 2) | 332.5 | 332.6 | 317.5 |
| | 333.7 | 333.6 | 318.8 |
| | 332.6 | 332.8 | 318.1 |
| | 333.6 | 333.5 | 320.9 |
| average | 333.2 | 333.2 | 319.1 |
| Std. deviation | 0.57 | 0.47 | 1.23 |
| % RSD | 0.17 | 0.14 | 0.39 |

From Table 7 some differences are observable in the maximum of emission: that for lot 2 is consistently shifted to higher $\lambda_{max}$ with respect to lot 1.

As in Table 6, $\lambda_{min}$ of the second derivative does not correspond exactly to the maximum of the original spectrum: this can be explained with the necessity to interpolate the data on a large interval (70 points) in order to obtain a good compromise between curve distortion and signal-to-noise ratio.

In FIG. 41 the normalized spectra of 287-953 lots 1 and 2 obtained in all the analytical sessions with excitation at 295 nm are presented. A different trend in the spectra belonging to lots 1 and 2 can be seen.

FIGS. 42 and 43 show the first and second order derivatives respectively of the emission spectra described in FIG. 41.

FIG. 42 shows how the 0 crossing $\lambda$ of lots 1 and 2 form two distinct clusters, with a shift of lot 2 to higher $\lambda$ with respect to lot 1. The difference seen on the slope at 280 nm excitation is evidenced more clearly at 295 nm, probably due to the greater sensitivity of Tryptophan emission to environmental conditions relative to Tyrosine.

Example 5

Further Characterization of Chimera Protein 297-953

Additional tests were performed to ensure that the differences observed between the lots in Example 4 were related to the protein differences and not due to experimental conditions. Therefore, the residual concentration of sucrose in the diluted samples was checked, and also the fluorescence analyses were repeated with higher protein concentrations.

To ensure that the different residual concentrations of sucrose in the two lots after dilution was not responsible for the observed differences, Example 4 was repeated diluting samples in buffer KPi 10 mM+NaCl 150 mM pH 7.0+10% sucrose and the same results were obtained (not shown).

To investigate linearity of response, the two lots were analysed at a concentration of 460 mcg/ml, in the same experimental conditions as Example 4. Both samples were diluted in buffer in KPi 10 mM+NaCl 150 mM pH 7.0+10% sucrose. The results are shown in FIGS. 44 and 45 and confirm and enhance the differences observed in Example 4.

FIG. 44 shows, on the left, the individual spectra of the two lots at 280 nm excitation and, on the right, their normalization.

FIG. 45 shows, on the left, the individual spectra of the two lots at 295 nm excitation and, on the right, their normalization.

Example 6

Analysis of Differences Seen in the Characterization of Protein 297-953

Additional experiments were conducted to explain the causes of the differences in fluorescence observed for lots 1 and 2 of protein 297-953.

From mass spectrometry analysis it is known that lot 1 and lot 2 have different degrees of carbamylation, due to purification processes involving permanence in urea buffers.

Furthermore, the two lots have different traces of a residual purification impurity from *E. coli* organism used to produce 287-953, identified by anti-lysate Western blot and confirmed using specific antibodies.

Table 8 summarizes presence of carbamylation and *E. coli* impurity in lots 1 and 2 and other 3 additional lots produced. For each lot, concentration, relative carbamylation degree and *E. coli* impurity presence are shown.

TABLE 8

Relative carbamylation and *E. coli* impurity presence in lots 1-5

| 287-953 lot | conc. mcg/ml | carbam. | *E. coli* impurity |
|---|---|---|---|
| M-MnB-P01 (lot 1) | 460 | + | +/− |
| RS-21-01-01 (lot 2) | 750 | + | ++ |
| TRfaseII02 | 657 | − | − |
| RS-21-03-01 | 659 | +/− | − |
| RS-21-03-02 | 708 | + | − |

Additional fluorescence analyses were conducted including the additional lots.

Diluted samples were analyzed at 2 different excitation wavelengths, 280 and 295 nm. Emission spectra were registered between 300 and 390 nm, with subtraction of the buffer blank; each spectrum was the resulting media of 3 different scans. Before the analysis, samples of each lot were diluted to 200 mcg/ml in buffer KPi 10 mM+NaCl 150 mM pH 7.0+10% sucrose. Results are listed in Tables 9 and 10, and plotted in FIGS. 46-51.

TABLE 9

Results at 280 nm excitation

| 287-953 lot | $\lambda_{max}$ em. (nm) | D1 $\lambda_{x=0}$ (nm) | D2 $\lambda_{min}$ (nm) |
|---|---|---|---|
| M-MnB-P01 (lot 1) | 317.44 | 317.62 | 312.62 |
| TRfaseII02 | 316.44 | 316.56 | 312.25 |
| RS-21-03-01 | 316.38 | 316.6 | 312.09 |
| RS-21-03-02 | 315.96 | 316.19 | 312.27 |
| RS-21-01-01 (lot 2) | 318.44 | 318.55 | 313.01 |
| average | 318.01 | 317.1 | 312.45 |
| Std. deviation | 1.00 | 0.87 | 0.33 |
| % RSD | 0.32 | 0.27 | 0.11 |

TABLE 10

Results at 295 nm excitation

| 287-953 lot | $\lambda_{max}$ em. (nm) | D1 $\lambda_{x=0}$ (nm) | D2 $\lambda_{min}$ (nm) |
|---|---|---|---|
| M-MnB-P01 (lot 1) | 330.49 | 330.73 | 326.08 |
| TRfaseII02 | 330.51 | 330.44 | 325.49 |
| RS-21-03-01 | 330.89 | 330.88 | 324.75 |
| RS-21-03-02 | 331.27 | 330.83 | 324.77 |
| RS-21-01-01 (lot 2) | 332.28 | 332.71 | 326.07 |
| average | 331.09 | 331.12 | 325.43 |
| Std. deviation | 0.66 | 0.81 | 0.59 |
| % RSD | 0.20 | 0.24 | 0.18 |

In FIG. 46, the normalized spectra of the 287-953 lots obtained in this additional analytical session with excitation at 280 nm are presented. It can be seen that the maximum of emission of lot 2 is shifted compared with all the others spectra, and its curve slope presents a different trend compared with all others spectra. The lot 1 results are more similar to the additional lots examined, but its slope does show some differences.

FIGS. 47 and 48 show the first and second order derivatives respectively of the emission spectra described in FIG. 46. These Figures confirm the observations described above. In FIG. 47 the 0 crossing λ of the 3 additional lots are similar, and the crossing of lot 1 is intermediate between these crossings and that of lot 2. In FIG. 48, the second derivative of lot 2 has a different shape with respect to the others.

FIG. 49 shows the normalized spectra of the 287-953 lots obtained in additional analytical sessions with excitation at 295 nm. As for results at 280 nm excitation, it can be seen that the maximum of emission of lot 2 is shifted, and its curve slope presents a different trend compared with all others spectra. Lot 1 results are more similar to the additional lots examined than to lot 2.

FIGS. 50 and 51 show the first and second order derivatives respectively of the emission spectra described in FIG. 49. These figures confirm that lot 1 results are more similar to the additional lots examined than to lot 2. In FIG. 51, the second derivative of lot 2 has a different shape with respect to the others.

From the data obtained, a correspondence of fluorimetric behavior among the additional lots, and the closer similarity of these 3 lots to lot 1 than to lot 2, can be seen. These results correlate with the traces of *E. coli* impurities that are more represented in lot 2, less in lot 1 and absent in the remaining lots (see Table 8).

Example 7

Fluorescence Characterization of Chimera Protein 936-741

The chimera protein 936-741 can be used as a component of a Meningococcus type B vaccine. The protein is a monomer, composed of 434 amino acids, with a theoretical molecular weight of 46,252 Da and a pI of 9.10. It is produced under GMP conditions and purified to homogeneity.

The 936-741 primary sequence (from 2996 strain, *N. meningitidis* Group B), and amino acid composition are shown in FIG. 52 and Table 11 [62, 63]. The linker peptide between 936 and 741 is indicated in bold.

TABLE 11

Amino acid composition of 936-741

| Ala (A) 47 | 10.8% |
|---|---|
| Arg (R) 20 | 4.6% |
| Asn (N) 16 | 3.7% |
| Asp (D) 23 | 5.3% |
| Cys (C) 0 | 0.0% |
| Gln (Q) 30 | 6.9% |
| Glu (E) 21 | 4.8% |
| Gly (G) 49 | 11.3% |
| His (H) 8 | 1.8% |
| Ile (I) 25 | 5.8% |
| Leu (L) 32 | 7.4% |
| Lys (K) 30 | 6.9% |
| Met (M) 4 | 0.9% |
| Phe (F) 10 | 2.3% |
| Pro (P) 8 | 1.8% |
| Ser (S) 28 | 6.5% |
| Thr (T) 34 | 7.8% |
| Trp (W) 1 | 0.2% |
| Tyr (Y) 15 | 3.5% |
| Val (V) 33 | 7.6% |
| Asx (B) 0 | 0.0% |
| Glx (Z) 0 | 0.0% |
| Xaa (X) 0 | 0.0% |

Total number of negatively charged residues (Asp + Glu): 44
Total number of positively charged residues (Arg + Lys): 50

A comparison of different 936-741 concentrated bulk lots was carried out to assess any physico-chemical modification occurring in the proteins produced for the different lots.

Samples

The samples for analysis were 936-741 protein antigen (purified concentrated bulk) of two lots:
1. lot RS-15-02-01 (lot 1), concentration 1374.1 mcg/ml (BCA), in NaPi 10 mM pH 7.2
2. lot RS-15-03-01 (lot 2), concentration 1193.9 mcg/ml (BCA) in NaPi 10 mM pH 7.2

Before the analysis, samples of each lot were diluted to 60 mcg/ml in buffer KPi 10 mM+NaCl 150 mM pH 7.0.

Instrument Method

The same instrument method was used as in Example 4.

Data Processing

All data were obtained by calculation with FL Win Lab Software. Original spectra obtained in the analytical sessions were processed as follows:

1. Original spectra obtained in three different analytical sessions were normalized.
2. On the normalized data, derivative spectra with 3-point interval were calculated.
3. Passes of 5-point wide triangular smoothing were applied on first derivative spectra (usually a total of 3-4 passes) to increase signal-to-noise ratio.
4. Passes of 5-point wide triangular smoothing were applied on second derivative spectra (usually a total of 3-4 passes) to achieve good noise reduction.
5. From point 4, all-days second derivative average spectra and the corresponding standard deviation were calculated for each lot.

Results

1 Example 7A

λ Excitation 280 nm

Table 12 shows results obtained in 3 different analytical sessions by the excitation of the 936-741 purified lots 1 and 2 at 280 nm. The table shows the indicated lots, $\lambda_{max}$ of emission spectrum, λ of zero crossing for the first derivative (D1 $\lambda_{x=0}$), and emission intensity of spectrum at $\lambda_{max}$. For each lot the averaged value, standard deviation and % relative standard deviation (% RSD) are presented.

TABLE 12

| 936-741 lot | excitation at 280 nm 280 nm excitation | | |
|---|---|---|---|
| | $\lambda_{max}$ em. (nm) | D1 $\lambda_{x=0}$ (nm) | emission intensity |
| RS-15-02-01 | 339.8 | 339.9 | 565.5 |
| (Lot 1) | 340.7 | 340.7 | 956.5 |
| | 340.4 | 340.4 | 944.1 |
| average | 340.3 | 340.3 | 822.1 |
| Std. deviation | 0.37 | 0.33 | 181.47 |
| % RSD | 0.11 | 0.10 | 22.07 |
| RS-15-03-01 | 340.9 | 340.8 | 842.7 |
| (Lot 2) | 341.2 | 341.1 | 957.2 |
| | 340.3 | 340.3 | 923.7 |
| average | 340.8 | 340.7 | 907.9 |
| Std. deviation | 0.37 | 0.36 | 48.06 |
| % RSD | 0.11 | 0.11 | 5.29 |

From Table 12 the similarity of $\lambda_{max}$ of emission among the lots can be seen and the corresponding 0 crossing λ of the first derivative. Emission intensity among the analytical sessions shows reproducibility, with exception of the first lot 1 scan showing a lower value with respect to the others, probably due to a mistaken different dilution.

In FIG. 53, the spectra of 936-741 lots 1 and 2 obtained in all the analytical sessions with excitation at 280 nm are shown, while the same spectra are presented normalized in FIG. 54. FIGS. 55 and 56 show raw and smoothed first order derivatives respectively of the emission spectra described in FIG. 54.

Second derivative spectra were obtained from normalized spectra presented in FIG. 54 by three passes of triangular smoothing (interpolation interval=5 point, see "Data processing"). Successively, the average spectrum of single second derivatives and their relative standard deviation were obtained for each of the two lots, and are presented in FIGS. 57 (lot 1) and 58 (lot 2).

Repeated smoothing passes applying a small interpolation interval (5 points) were used instead of a single smoothing pass on a large interpolation interval in order to obtain an increased signal-to-noise ratio with minimized loss of spectral information. Second derivative smoothed average spectra were calculated to show more easily comparable data of the two lots, and to minimize day to day variability.

Second derivative average spectra of lot 1 and lot 2 are superimposed in FIG. 59. The overall similarity of the curves suggests that the proteins in the two lots have the same tertiary conformation. In the range of 320-360 nm, even without a perfect overlapping (which is probably caused by noise related fluctuations), the curves show the same trend.

2 Example 7B

λ Excitation 295 nm

Table 13 shows the results obtained in 3 different analytical sessions by the excitation of the 936-741 purified lots (lots 1 and 2) at 295 nm. The table shows the indicated lots, $\lambda_{max}$ of emission spectrum, λ of zero crossing for the first derivative (D1 $\lambda_{x=0}$), and emission intensity of spectra at 295 nm. For each lot the averaged value, standard deviation and % relative standard deviation (% RSD) are presented.

TABLE 13

| 936-741 lot | excitation at 295 nm 295 nm excitation | | |
|---|---|---|---|
| | $\lambda_{max}$ (nm) | D1 $\lambda_{x=0}$ (nm) | emission intensity |
| RS-15-02-01 | 343.6 | 343.6 | 183.2 |
| (Lot 1) | 344.3 | 344.2 | 315.1 |
| | 343.6 | 343.7 | 311.0 |
| average | 343.8 | 343.8 | 269.8 |
| Std. deviation | 0.30 | 0.26 | 61.25 |
| % RSD | 0.09 | 0.08 | 22.71 |
| RS-15-03-01 | 343.7 | 343.7 | 243.4 |
| (Lot 2) | 343.7 | 343.6 | 293.6 |
| | 344.0 | 344.0 | 283.5 |
| average | 343.8 | 343.8 | 273.5 |
| Std. deviation | 0.17 | 0.17 | 21.71 |
| % RSD | 0.05 | 0.05 | 7.94 |

From Table 13 the similarity of $\lambda_{max}$ of emission among the lots and of the corresponding 0 crossing λ of the first derivative can be seen. Emission intensity among the analytical sessions shows reproducibility, with exception of the first lot 1 scan showing a lower value with respect to the others, probably due to a mistaken different dilution.

In FIG. 60 spectra of 936-741 (lots 1 and 2) obtained in all the analytical sessions with excitation at 295 nm are shown, while the same spectra are presented normalized in FIG. 61. FIGS. 62 and 63 show raw and smoothed first order derivatives respectively of the emission spectra described in FIG. 61.

Figure 65:
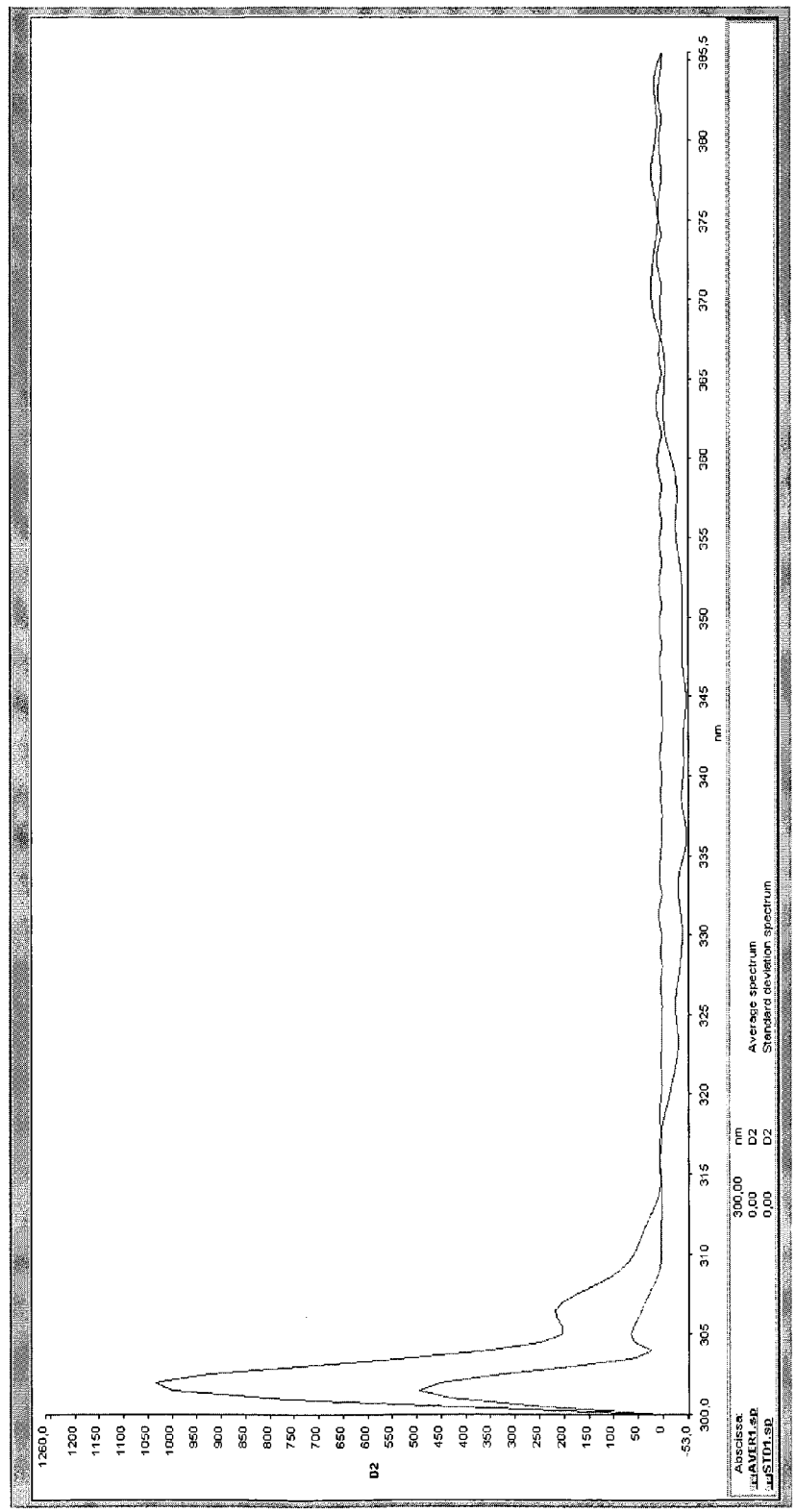

FIGS. 64 and 65 show average of second derivatives spectra and relative standard deviation at 295 nm excitation same way as of lot 1 and 2 respectively. The spectra showed in these figures were obtained by three passes of smoothing (interpolation interval=5 point), with the same theoretical considerations mentioned in Example 7A.

In FIG. 66, the second derivative averaged spectra of lots 1 and 2 are shown superimposed. The curve trends show a good similarity in the overall spectral interval (300-390 nm), indicating equivalency of the protein material in the two lots.

Example 8

Native v. Denatured Analysis of Protein 936-741

Additional fluorescence analyses on 936-741 lots 1 and 2 were performed to investigate the influence of sample denaturation on spectra and derivatives.

Lots 1 and 2 were used native, or denatured at +70° C. or with 10% of ethanol (EtOH) for comparison of the protein native conformation with its condition in presence of a physical or chemical denaturant.

Sample preparation, instrument methods and settings were the same as described in Example 7.

Table 14 shows the results obtained in one analytical session by the excitation of the 936-741 purified lots 1 and 2 at 280 nm. The table shows the indicated lots, $\lambda_{max}$ of emission spectrum, $\lambda$ of zero crossing for the first derivative (D1 $\lambda_{x=0}$), emission intensity of spectrum at $\lambda_{max}$, and the denaturant. For each lot the averaged value, standard deviation and % relative standard deviation (% RSD) are presented.

TABLE 14 excitation at 280 nm with and without denaturants
280 nm excitation

| 936-741 lot | $\lambda_{max}$ em. (nm) | D1 $\lambda_{x=0}$ (nm) | emission intensity | Denaturant |
|---|---|---|---|---|
| RS-15-02-01 | 340.7 | 340.7 | 956.5 | No |
| (Lot 1) | 332.0 | 332.2 | 403.5 | 5 min at +70° C. |
|  | 339.3 | 339.2 | 758.8 | 10% EtOH |
| average | 337.4 | 337.3 | 706.3 |  |
| Std. deviation | 3.81 | 3.72 | 228.82 |  |
| % RSD | 1.13 | 1.10 | 32.40 |  |
| RS-15-03-01 | 341.2 | 341.1 | 957.2 | No |
| (Lot 2) | 332.5 | 332.5 | 517.1 | 5 min at +70° C. |
|  | 339.3 | 339.2 | 713.1 | 10% EtOH |
| average | 337.7 | 337.6 | 729.1 |  |
| Std. deviation | 3.71 | 3.68 | 180.03 |  |
| % RSD | 1.10 | 1.09 | 24.69 |  |

In FIG. 67, absorbance spectra of 936-741 (lots 1 and 2) described in Table 14 are shown, while in FIG. 68 the same spectra are presented normalized.

From Table 14 and FIGS. 67 and 68, the difference of $\lambda_{max}$ of emission among native and treated samples can be seen, likely indicating conformational changes caused in the protein by the presence of denaturant. Samples analyzed by fluorescence before and after treatment at +70° C. for 5 minutes show major differences: maximum of emission of 936-741 is shifted and the curve slope presents a different trend. Samples analyzed by fluorescence after treatment with 10% of EtOH present minor differences of $\lambda_{max}$ of emission, slightly shifted compared with normal spectra, while the curve trend is intermediate between native and thermally denatured samples.

It can therefore be hypothesized that treatment with 10% EtOH induces only a partial denaturation of the protein, while heating at +70° C. has a more dramatic effect.

The behavior of lots 1 and 2 exposed to denaturants is the same, which is another indication of their equivalence.

Table 15 shows the results obtained in one analytical session by the excitation of the 936-741 purified lots 1 and 2 at 295 nm. The table shows the indicated lots, of emission spectrum, $\lambda$ of zero crossing for the first derivative (D1 $\lambda_{x=0}$), emission intensity of spectra at 295 nm, and the denaturant. For each lot the averaged value, standard deviation and % relative standard deviation (% RSD) are presented.

TABLE 15 excitation at 295 nm with and without denaturants
295 nm excitation

| 936-741 lot | $\lambda_{max}$ em. (nm) | D1 $\lambda_{x=0}$ (nm) | emission intensity | Denaturant |
|---|---|---|---|---|
| RS-15-02-01 | 344.3 | 344.2 | 315.1 | No |
| (Lot 1) | 343.5 | 343.5 | 118.1 | 5 min at +70° C. |
|  | 343.8 | 343.6 | 234.8 | 10% EtOH |
| average | 343.8 | 343.8 | 222.7 |  |
| Std. deviation | 0.33 | 0.29 | 80.87 |  |
| % RSD | 0.10 | 0.08 | 36.32 |  |
| RS-15-03-01 | 343.7 | 343.6 | 293.6 | No |
| (Lot 2) | 343.0 | 343.0 | 164.95 | 5 min at +70° C. |
|  | 344.4 | 344.3 | 224.0 | 10% EtOH |
| average | 343.7 | 343.6 | 227.5 |  |
| Std. deviation | 0.57 | 0.55 | 52.61 |  |
| % RSD | 0.17 | 0.16 | 23.12 |  |

In FIG. 69, the absorbance spectra of 936-741 (lots 1 and 2) described in Table 15 are shown, while in FIG. 70 the same spectra are presented normalized.

These data obtained by excitation at 295 nm show less variation of fluorimetric behavior among the normal and denaturant treated 936-741 with respect to the data obtained by excitation at 280 nm. This result may be justified, however, by the presence of only one Tryptophan residue in the protein, whose environment can either represent only part of the denaturation, or whose emission is not so effective in showing conformational differences.

Example 9

Fluorescence Characterization of CRM Protein

Samples

The following $CRM_{197}$ protein samples were tested. $CRM_{197}$ lots 39, 41, 42, 44, 46 produced on manufacturing Site 1; 0511, 0512, 0513, 0514 produced on manufacturing Site 2; and CRF16, CRF17, CRF18, produced on manufacturing Site 3.

The analyzed lots and their concentrations obtained with microBCA and/or Lowry methods are shown in Table 16. For all, the purification phase corresponds to purified concentrated bulk, and the solution buffer is NaPi 10 mM pH 7.2+ 10% sucrose:

TABLE 16 lots and concentrations

| Lot | Purification phase | protein conc. Lowry mg/ml | protein conc. MicroBCA mg/ml |
|---|---|---|---|
| 39 | 13.090 | 56 | 47.4 |
| 41 | 13.090 | 49 | 51.7 |
| 42 | 13.090 | 60 | 56.1 |
| 44 | 13.090 | 55 | 54.9 |
| 46 | 13.090 | 58 | 48.0 |
| 0511 | CRM 290 | 47 | 42.7 |
| 0512 | CRM 290 | 51 | 43.1 |
| 0513 | CRM 290 | on going | 47.5 |
| 0514 | CRM 290 | on going | on going |
| 5CRF16 | BPR-CRM-3020 | 59 | no |
| 5CRF17 | BPR-CRM-3020 | 62 | no |
| 5CRF18 | BPR-CRM-3020 | 57 | no |

Before analysis, samples of each lot were diluted to around 40 mcg/ml in buffer NaPi 10 mM pH 7.2+10% sucrose with a two dilution steps illustrated in Table 17.

TABLE 17 dilution steps of samples

| Lot | protein conc. Lowry mg/ml | protein conc. MicroBCA mg/ml | concentration 1 from micro BCA mcg/ml | Dilution 1 (folds) | volume of conc sol in mcl to 1 ml | concentration 2 from micro BCA mcg/ml | Dilution 2 | volume of sol 1 in mcl a 6055 mcl |
|---|---|---|---|---|---|---|---|---|
| Site 1 | | | | DILUTION 1 | | | DILUTION 2 | |
| 39 | 56 | 47.4 | 3.0 | 15.8 | 63.3 | 37.2 | 80.6 | 75 |
| 41 | 49 | 51.7 | 3.0 | 17.2 | 58.0 | 37.2 | 80.6 | 75 |
| 42 | 60 | 56.1 | 3.0 | 18.7 | 53.5 | 37.2 | 80.6 | 75 |
| 44 | 55 | 54.9 | 3.0 | 18.3 | 54.6 | 37.2 | 80.6 | 75 |
| 46 | 58 | 48.0 | 3.0 | 16.0 | 62.5 | 37.2 | 80.6 | 75 |
| Site 2 | | | | DILUTION 1 | | | DILUTION 2 | |
| 0511 | 47 | 42.7 | 3.0 | 14.2 | 70.3 | 37.2 | 80.6 | 75 |
| 0512 | 51 | 43.1 | 3.0 | 14.4 | 69.6 | 37.2 | 80.6 | 75 |
| 0513 | on going | 47.5 | 3.0 | 15.8 | 63.2 | 37.2 | 80.6 | 75 |
| 0514 | on going | on going (44.4)* | 3.0 | 14.8 | 67.6 | 37.2 | 80.6 | 75 |
| Site 3 | | | | DILUTION 1 | | | DILUTION 2 | |
| 5CRF16 | 59 | no | 3.0 | 19.7 | 50.8 | 37.2 | 80.6 | 75 |
| 5CRF17 | 62 | no | 3.0 | 20.7 | 48.4 | 37.2 | 80.6 | 75 |
| 5CRF18 | 57 | no | 3.0 | 19.0 | 52.6 | 37.2 | 80.6 | 75 |

*considered the media value of the 3 preceding Site 2 lots

To calculate dilutions, the microBCA concentrations were used for Site 1 and Site 2 lots, the Lowry concentrations for the Site 3 lots. Diluted samples were stored at +4° C. and analyzed in 3 different analytical daily sessions.
Instrument Method
The same instrument method was used as in Example 4.
Data Processing
All data were obtained by calculation with FL Win Lab Software. Original spectra obtained in the analytical sessions were processed as follows:
1. Original spectra obtained in three different analytical sessions were normalized.
2. First and second order derivative spectra with 3-point interval were calculated on the normalized spectra.
3. A total of 3 passes of 5-point wide triangular smoothing were applied on second order derivative spectra to achieve good noise reduction.
4. From point 1, all-days average spectra and the corresponding standard deviation were calculated for each lot.
5. From point 4, all-days second derivative average spectra and the corresponding standard deviations were calculated for each lot.
6. From point 4, groups of $CRM_{197}$ (Site 1; Site 2; Site 3) second derivative average spectra and the corresponding standard deviations were calculated.
Results
1 Example 9A λ Excitation 280 nm In FIGS. 71A-C un-normalized spectra of the 12 $CRM_{197}$ lots made in Site 1, Site 2 and Site 3 analyzed with 280 nm excitation in three analytical sessions over different days are shown. The similarity of curve trend and the small variation of emission intensity among lots and different days can be seen.

In FIG. 72 normalized average (over the three analytical sessions) spectra of each $CRM_{197}$ lot with excitation at 280 nm are shown. A perfect superimposition of all spectra, and good similarity of maximum of emission, can be seen.

FIG. 73 shows unsmoothed first order derivatives of the emission spectra described in FIG. 72, calculated on the smaller interpolation interval allowed by the software. All curves present a similar trend and a good superimposition, with no need of smoothing to increase signal to noise ratio.

Table 18 presents the results obtained in all analytical sessions at 280 nm excitation, listed as 2 of zero crossing for the first derivative (D1 $\lambda_{x=0}$). The first derivative of any curve goes through zero at the curve's maxima and minima, allowing a more precise measurement of $\lambda_{max}$ for a certain spectrum. For each lot (far right) or each analytical session (bottom) the averaged value, standard deviation and % relative standard deviation (% RSD) are presented.

TABLE 18 first derivative data

| | 280 D1 zero crossing (nm) | | | | | |
|---|---|---|---|---|---|---|
| Lot | 16 Feb. 2006 | 17 Feb. 2006 | 20 Feb. 2006 | media | std. dev. | RSD % |
| SIENA | | | | | | |
| 39 | 331.6 | 331.3 | 330.9 | 331.3 | 0.30 | 0.09 |
| 41 | 331.6 | 330.7 | 331.0 | 331.1 | 0.38 | 0.12 |

TABLE 18-continued first derivative data

280 D1 zero crossing (nm)

| Lot | 16 Feb. 2006 | 17 Feb. 2006 | 20 Feb. 2006 | media | std. dev. | RSD % |
|---|---|---|---|---|---|---|
| 42 | 331.0 | 330.7 | 330.6 | 330.8 | 0.18 | 0.05 |
| 44 | 330.9 | 330.5 | 331.1 | 330.8 | 0.23 | 0.07 |
| 46 | 330.9 | 330.7 | 331,.8 | 330.8 | 0.10 | 0.03 |
| ROSIA | | | | | | |
| 0511 | 331.30 | 330.74 | 331.44 | 331.2 | 0.30 | 0.09 |
| 0512 | 331.07 | 331.16 | 330.79 | 331.0 | 0.16 | 0.05 |
| 0513 | 330.96 | 331.39 | 331.46 | 331.3 | 0.22 | 0.07 |
| 0514 | 331.68 | 331.65 | 331.81 | 331.7 | 0.07 | 0.02 |
| SYNCO | | | | | | |
| 5CRF16 | 331.39 | 331.26 | 331.42 | 331.4 | 0.07 | 0.02 |
| 5CRF17 | 330.87 | 331.34 | 330.90 | 331.0 | 0.21 | 0.06 |
| 5CRF18 | 330.46 | 331.41 | 331.32 | 331.1 | 0.43 | 0.13 |
| media | 331.1 | 331.1 | 331.2 | | | |
| std. dev | 0.32 | 0.37 | 0.37 | | | |
| RSD % | 0.10 | 0.11 | 0.11 | | | |

The resolution limit of the instrument is 0.5 nm and the reported results are automatically calculated by interpolation between two consequent points. The resulting average values for lots and analytical sessions range between 330.8 and 331.7 nm (0.9 nm discrepancy), in good agreement with previous studies and literature data, demonstrating lot equivalency with respect to fluorimetric behavior.

Furthermore, considering $CRM_{197}$ lot 42 produced in Site 1 as a reference protein for lot to lot equivalence evaluation, the average values for $\lambda_{max}$ emission of all the $CRM_{197}$ lots analyzed lie within ±1 nm of the lot 42 average value of 330.8 nm.

FIG. 74 shows a graphical representation of the $\lambda_{max}$ emission (average of data obtained in three analytical sessions) variation of all lots with respect to lot 42 (yellow bar). Horizontal red lines mark the ±1 nm range considered.

Second derivative spectra were calculated from normalized average spectra of each group of $CRM_{197}$ (Site 1; Site 2; Site 3) obtained in all analytical sessions by three passes of triangular smoothing (interpolation interval=5 point) with the procedure described in the paragraph "Data processing". Repeated smoothing passes applying a small interpolation interval (5 points) were used instead of a single smoothing pass on a large interpolation interval in order to obtain an increased signal-to-noise ratio with minimized loss of spectral information.

Second derivative smoothed average spectra were calculated to show more easily comparable data between the lots, and are shown in FIG. 75. Second derivative smoothed average spectra of each group of $CRM_{197}$ (Site 1; Site 2; Site 3) present a similar curve trend and a good superimposition, indicating consistency of the protein produced at different sites.

Successively, the average curve of second derivatives of FIG. 75 and their relative standard deviations were calculated and are presented in FIG. 76.

In FIG. 77 a comparison between second derivative average spectra of the single lot 42 (of three different analyses) and second derivative average spectra of all lots analyzed (same as FIG. 76), is shown to demonstrate that the small fluctuations among second derivative presented in FIG. 75 produce a relative standard deviation smaller than the one produced for 3 analyses of the same lot.

The results confirm a good similarity of $CRM_{197}$ lots analyzed and furthermore the validity of the spectral comparison method.

2 Example 9B

λ Excitation 295 nm

In FIG. 78A-C un-normalized spectra of the $CRM_{197}$ lots made in Site 1, Site 2 and Site 3 analyzed with 295 nm excitation in three analytical session over different days are shown. The similarity of curve trend and the small variation of emission intensity among lots and different days can be seen.

In FIG. 79 normalized average (over three analytical sessions) spectra of each $CRM_{197}$ lot with excitation at 295 nm is shown. As already seen for 280 nm excitation data, there is a perfect superimposition of the spectral curves and comparability of emission maxima.

FIG. 80 shows unsmoothed first order derivatives of the emission spectra described in FIG. 79, calculated on a three-point interval, i.e. the smaller interpolation interval allowed by the software. All curves present a similar trend and a good superimposition, with no need of smoothing to increase signal to noise ratio.

Table 19 shows the results obtained in all analytical sessions at 295 nm excitation, listed as λ of zero crossing for the first derivative (D1 $\lambda_{x=0}$). For each lot (far right) or each analytical session (bottom) the averaged value, standard deviation and % relative standard deviation (% RSD) are presented.

TABLE 19 first derivative data

295 D1 zero crossing (nm)

| Lot | 16 Feb. 2006 | 17 Feb. 2006 | 20 Feb. 2006 | media | std. dev. | RSD % |
|---|---|---|---|---|---|---|
| SIENA | | | | | | |
| 39 | 334.2 | 333.8 | 334.7 | 334.2 | 0.36 | 0.11 |
| 41 | 333.9 | 334.6 | 333.1 | 333.9 | 0.62 | 0.19 |
| 42 | 334.8 | 333.9 | 334.1 | 334.3 | 0.37 | 0.11 |
| 44 | 335.0 | 334.0 | 333.5 | 334.1 | 0.65 | 0.19 |
| 46 | 334.3 | 334.0 | 334.4 | 334.3 | 0.18 | 0.05 |
| ROSIA | | | | | | |
| 0511 | 334.4 | 334.5 | 333.9 | 334.3 | 0.24 | 0.07 |
| 0512 | 335.8 | 334.6 | 333.8 | 334.7 | 0.86 | 0.26 |
| 0513 | 335.3 | 334.6 | 334.4 | 334.8 | 0.42 | 0.13 |
| 0514 | 335.2 | 334.2 | 335.4 | 334.9 | 0.52 | 0.15 |
| SYNCO | | | | | | |
| 5CRF16 | 335.5 | 334.7 | 334.7 | 335.0 | 0.35 | 0.10 |
| 5CRF17 | 334.3 | 333.9 | 334.5 | 334.2 | 0.24 | 0.07 |
| 5CRF18 | 334.0 | 334.5 | 334.8 | 334.4 | 0.32 | 0.09 |
| media | 334.7 | 334.3 | 334.3 | | | |
| std. dev | 0.60 | 0.32 | 0.60 | | | |
| RSD % | 0.18 | 0.09 | 0.18 | | | |

The resolution limit of the instrument is 0.5 nm and the reported results are automatically calculated by interpolation between two consequent points. The resulting average values for lots and analytical sessions range between 333.9 and 335.0 nm (1.1 nm discrepancy), in good agreement with previous studies and literature data, demonstrating lot equivalency with respect to fluorimetric behavior.

Furthermore, considering CRM$_{197}$ lot 42 produced in Site 1 as a reference protein for lot to lot equivalence evaluation, the average values for $\lambda_{max}$ emission of all the CRM$_{197}$ lots analyzed lie within ±1 nm of the lot 42 average value of 334.3 nm.

FIG. 81 shows a graphical representation of the $\lambda_{max}$ emission (average of data obtained in three analytical sessions) variation of all lots with respect to lot 42 (yellow bar). Horizontal red lines mark the ±1 nm range considered.

Second derivative spectra were calculated from normalized average spectra of each group of CRM$_{197}$ (Site 1; Site 2; Site 3) obtained in all analytical sessions by three passes of triangular smoothing (interpolation interval=5 point) with the procedure described in the paragraph "Data processing". Repeated smoothing passes applying a small interpolation interval (5 points) were used instead of a single smoothing pass on a large interpolation interval in order to obtain an increased signal-to-noise ratio with minimized loss of spectral information.

Second derivative smoothed average spectra were calculated to show more easily comparable data between the lots, and are shown in FIG. 82. Second derivative smoothed average spectra of each group of CRM$_{197}$ (Site 1; Site 2; Site 3) present a similar curve trend and a good superimposition, indicating consistency of the protein produced at different sites.

Successively, the average curve of second derivatives of FIG. 82 and their relative standard deviations were calculated and are presented in FIG. 83.

In FIG. 84 a comparison between second derivative average spectra of the single lot 42 (of three different analyses) and second derivative average spectra of all lots analyzed (same as FIG. 83), is shown to demonstrate that the small fluctuations among second derivatives presented in FIG. 82 produce a relative standard deviation smaller than the one produced for 3 analyses of the same lot.

The results confirm a good similarity of CRM$_{197}$ lots analyzed and furthermore the validity of spectral comparison method utilized.

Example 10

*Neisseria meningitidis* Serogroup B NadA$_{\Delta 351-405}$ Antigen Characterisation Samples & Results 1 Example 10A Protein Production of a Candidate Compound for Recombinant MenB Vaccine The DNA sequence of NadA allele 3, cloned from the hypervirulent *N. meningitidis* B strain 2996, encoding the deletion mutant NadA$_{\Delta 351-405}$, with no outer membrane anchor, was cloned into a pET21b vector (Novagen). The protein secreted into the extracellular medium was then purified by standard methods, using Q Sepharose XL, Phenyl Sepharose 6 Fast Flow (Pharmacia) and Hydroxyl apatite ceramic column (HA Macro-Prep BioRad) chromatographies.

2 Example 10B

Primary Structure Analysis

As shown in FIG. 85A, the amino acid sequence predicted from the known nucleotide sequence of the gene provided a polypeptide chain of 327 amino acids with a theoretical molecular weight of 34,557,9 Da.

2.1 Direct Infusion Mass Spectrometric Analysis

Experimental mass measurements of NadA$_{\Delta 351-405}$ were obtained by direct infusion on an ESI Q-ToF detector (Micromass) for different clinical phase lots. Analysis was carried out by MassLynx software 4.0 (Micromass).

Prior to analysis, purified samples stored at −20° C. were thawed and ultra filtered on PES membrane with a cut-off of 5000 Da, to remove buffers and stabilizers, using 5 mM ammonium acetate as washing buffer, the filtered samples were then were diluted with aqueous acetonitrile and formic acid to a final concentration of 5% AcCN and 0.05% formic acid (protein conc. about 1 mg/ml).

Samples were injected into the Q-ToF spectrometer at a flow rate of 5 µl/min, with typical instrument parameters including capillary voltage=3000 V, cone voltage=30 V, extraction cone=1 V, source temperature=100° C., in positive mode. FIG. 86 shows a representative NadA$_{\Delta 351-405}$ spectrum and its deconvolution, while mass measurements for clinical phase I-III lots are listed in Table 20.

TABLE 20

|  | Molar mass (Da) | | | |
| --- | --- | --- | --- | --- |
|  | theoretical | exp phase I | exp phase II | exp phase III |
| NadA$\Delta_{351-405}$ | 34,557.9 | 34,544 | 34,564 | 34,568 |
| C-del 1 | 33,581.8 | 33,568 | 33,587 | 33,597 |
| C-del 2 | 33,310.4 | 33,298 | 33,316 | 33,321 |
| C-del 3 | 27,605.1 | 27,595 | 27,610 | 27,616 |
| C-del 4 | 25,448.8 | 25,439 | 25,453 | 25,457 |
| C-del 5 | 24,692.0 | 24,682 | 24,696 | 24,700 |

FIG. 86B shows that the spectrum deconvolution revealed 5 related forms of lower MW than the expected 34.5 KDa molecule. These may be attributed to C-deletion forms of the full length NadA$_{\Delta 351-405}$ sequence.

Reducing SDS-PAGE was performed using NuPAGE® pre-cast 4-12% Bis-Tris Gels, loaded with proteins diluted to a final concentration of between 8 and 12 µg (total proteins, Micro BCA determination) in phosphate buffer, NuPAGE® LDS Sample Buffer and NuPAGE® Sample Reducing Agent. Samples were heated up to 70° C. for ten minutes, and then 20 µl were added to the gel and proteins separated using the INVITROGEN Xcell SureLock™ Mini-Cell system, in reducing conditions. Molecular weight standards (Broad Range Biorad) were loaded onto each gel for reference and calibration.

After the electrophoretic run, gels were stained with Coomassie Brilliant Blue R 250 Biorad and de-stained with 40% (v/v) Methyl Alcohol and 10% (v/v) glacial acetic acid before immersion in 7% (v/v) acetic acid preservative.

Gel images were then digitalized on Acer Scan Prisa 620 UT Scanner and the resulting data processed through computer-assisted densitometry with Image Master® 1D Elite version 3.0 Software. The protein electrophoretic pattern shown in FIG. 87A confirmed the presence of the C-deleted forms of NadA$_{\Delta 351-405}$.

Following the electrophoretic separation described above, the protein samples were subjected to immunoblotting. For this, the proteins (sample loading amount in this case 1.6±0.5 µg) were transferred onto an immobiliser matrix, Nitrocellulose Amersham Hybond-c 0.45 micron and identified by immuno-complex formation with specific rabbit polyclonal antibodies anti-NadA$_{\Delta351\text{-}405}$ These complexes were revealed by anti-rabbit secondary antibody conjugated with peroxidase (Cappel), in the presence of the specific chromogenic substrate. The results of the ImmunoBlot are shown in FIG. 87B.

C-deletion is dependent on the time of contact of NadA$_{\Delta351\text{-}405}$ with the fermentation broth. Rapid processing of the bacterial paste resulted in higher integrity of the purified NadA$_{\Delta351\text{-}405}$ protein, while slower processing resulted in increased degradation. Following purification, the proportion of C-del forms remained constant. NadA$_{\Delta351\text{-}405}$ integrity was calculated as:

$$100 \times \frac{NadA_{\Delta351\text{-}405}}{NadA_{\Delta351\text{-}405} + (C\text{-}del)}$$

This figure was consistently higher than 70%.

2.2 Enzymatic Peptide Map Generation and Matching to the Predicted Amino Acid Sequence NadA$_{\Delta351\text{-}405}$ was subjected to proteolytic digestion, followed by reverse phase HPLC coupled with ESI Q-ToF mass separation of trypsinized samples.

The samples underwent reduction and S-Carboxymethylation by treatment with the reducing agent dithiothreitol (DTT) followed by the alkylating agent iodoacetic acid, and were subsequently treated with sequencing grade modified trypsin, porcine Promega overnight at 37° C., at pH=8.5, in a ratio 1/50 (enzyme vs protein W/W).

RP-HPLC was carried out on HPLC system Alliance 2996 Waters, equipped with a Jupiter 5μ C4 Phenomenex column. Separation was obtained by gradient elution in H$_2$O+ HCOOH 0.1% and CH$_3$CN+HCOOH 0.1% at 0.2 ml/min flow rate.

The Micromass Q-ToF micro instrument source settings were typically 3000 V (including capillary voltage), cone voltage=30 V, extraction cone=1 V, source temperature=100° C., in positive mode.

The NadA$_{\Delta351\text{-}405}$ amino acid sequence was inserted onto Biolynx software provided by Waters Micromass which allowed the inventors to foresee the expected trypsin cuts on the protein molecule This resulted in a list of peptides characterized by a precise position, molecular mass and amino acid sequence, so that it was possible to correlate the theoretical peptides with the experimental masses resulting from LC-MS.

Table 21 shows the peptide mapping results obtained for phase I and II clinical phase lots. Selected peptides were submitted to ESI-Q-ToF MS/MS analysis, and confirmed the reported sequences (not shown).

TABLE 21

| Observed mass/charge Phase I lot | Observed mass/charge Phase II lot | Charge state | theoretical mass/charge ratio | Sequence | Residue |
|---|---|---|---|---|---|
| 246.29 | 246.30 | +1 | 246.18 | VK | 198-199 |
| | | | | | 85-86 |
| 405.35 | 405.38 | +1 | 405.21 | ETR | 306-308 |
| 421.40 | 421.43 | +1 | 421.26 | FVR | 262-264 |
| 462.44 | 462.48 | +1 | 462.29 | LTTK | 95-98 |
| 487.48 | 487.52 | +1 | 487.32 | GLGLK | 60-64 |
| 504.42 | 504.44 | +1 | 504.27 | IDEK | 141-144 |
| | | | | LDTR | 275-278 |
| 560.46 | 560.52 | +1 | 560.30 | DNIAK | 241-245 |
| 574.52 | 574.56 | +1 | 574.36 | TNIVK | 136-140 |
| 576.49 | 576.53 | +1 | 575.34 | VTDIK | 229-233 |
| 618.56 | 618.52 | +1 | 618.35 | LASAEK | 279-284 |
| 632.50 | 632.54 | +1 | 632.33 | ADEAVK | 173-178 |
| 633.50 | 633.54 | +1 | 633.32 | TANEAK | 179-184 |
| 659.55 | 659.60 | +1 | 659.37 | LNGLDK | 293-298 |
| | | | | AEAVAAK | 222-228 |
| 674.51 | 674.56 | +1 | 674.35 | QNVDAK | 79-84 |
| | | | | | 192-197 |
| 690.58 | 690.61 | +1 | 690.38 | TVSDLR | 299-304 |
| 694.46 | 694.53 | +1 | 694.29 | EESDSK | 256-261 |
| 704.52 | 704.59 | +1 | 704.36 | TVNENK | 73-78 |
| 718.54 | 718.60 | +1 | 718.37 | AAETAAGK | 200-207 |

TABLE 21-continued

| Observed mass/charge Phase I lot | Observed mass/charge Phase II lot | Charge state | theoretical mass/charge ratio | Sequence | Residue |
|---|---|---|---|---|---|
| 732.57 | 732.63 | +1 | 732.39 | ADIATNK | 234-240 |
| 774.67 | 774.71 | +1 | 774.47 | VVTNLTK | 66-72 |
| 806.57 | 806.63 | +1 | 806.39 | QTAEETK | 185-191 |
| 876.64 | 876.71 | +1 | 876.43 | AAESEIEK | 87-94 |
| 877.58 | 877.66 | +1 | 877.39 | ATNDDDVK | 1-8 |
| 914.62 | 914.72 | +1 | 914.43 | SIADHDTR | 285-292 |
| 996.69 | 996.79 | +1 | 996.48 | ANSADVYTR | 247-255 |
| 1060.78 | 1060.85 | +1 | 1060.55 | LEAVADTVDK | 145-154 |
| 1061.77 | 1061.84 | +1 | 1061.55 | IDGLNATTEK * | 265-274 |
| 631.45 | 631.49 | +2 | 631.30 | AEAAAGTANTAADK | 208-221 |
| 684.46 | 684.49 | +2 | 684.30 | DATAADVEADDFK * | 47-59 |
| 727.04 | 727.05 | +2 | 726.86 | LGENITTFAEETK | 123-135 |
| 871.12 | 871.14 | +2 | 870.91 | AGETIYDIDEDGTITK * | 30-45 |
| 982.25 | 982.30 | +2 | 982.00 | QGLAEQAALSGLFQPYNVG | 309-327 |
| 996.20 | 996.23 | +2 | 995.95 | HAEAFNDIADSLDETNTK | 155-172 |
| 675.19 | 675.22 | +3 | 675.01 | AATVAIAAAYNNGQEINGFK | 10-29 |
| 792.57 | 792.60 | +3 | 792.39 | LADTDAALADTDAALDATTNALNK * | 99-122 |

Tryptic digests of phase I and II DSs contained 4 out of 5 C-terminal peptides expected according to the predicted C-del sequences. These are shown in Table 22. Only the 27,605 Da sequence was not detected under these conditions.

TABLE 22

| Observed mass/charge clinical phase I | Observed mass/charge clinical phase II | Charge state | theoretical mass/charge ratio | Sequence | C-terminal peptide | MW Sequence (Da) |
|---|---|---|---|---|---|---|
| 987.80 | 987.84 | +1 | 987.51 | QGLAEQAALS | 309-318 | 33581.8 |
| 716.55 | 716.59 | +1 | 716.35 | QGLAEQA | 309-315 | 33310.4 |
| 432.39 | 432.43 | +1 | 432.20 | DNIA | 241-244 | 25448.8 |
| 389.37 | 389.42 | +1 | 389.20 | ADIA | 234-237 | 24692.0 |

The degree of integrity of NadA$_{\Delta 351-405}$ with respect to C-del was determined for the different lots by SDS-PAGE under denaturing conditions using Coomassie Blue staining.

2.3 In-Gel Digestion of SDS-PAGE Bands

Correspondence between mass-spectrometry and electrophoretic results was verified by protein band excision from a SDS-PAGE gel and determination of mass contribution by ESI Q-ToF.

Reducing SDS-PAGE was carried out according to the procedure described below. After electrophoretic separation, SDS was removed from the gel in several ammonium carbonate/acetonitrile washing steps, and the 4 bands were then excised and washed with water and acetonitrile, as shown in FIG. 87C. A tryptic digestion in NH$_4$HCO$_3$ 50 mM, overnight at 37°, was performed. After digestion the peptides were extracted from the gel with acid or basic solution, evaporated and analysed by RPLC-MS as described above. The tryptic peptide maps are presented in FIG. 88.

Detection results of C-terminal peptides are shown in Table 23. The main band (A+B) contains two different polypeptide chains, 1-327 and 1-315, corresponding to the entire NadA$_{\Delta 351-405}$ sequence and the heavier C-del, while the lower bands contain the sequence 1-263 (C) and the sequences 1-244 and 1-237 (D) respectively. The MW 33581.8 Da peptide could not be attributed because its C-terminal peptide had not been detected in the chromatograms, possibly due to the low concentration. While C-terminal peptides differed from one band to another, the same N-terminal peptide was detected in all bands, as expected.

(cod. B0631124), in a solution containing approximately 0.4 mg/ml (total proteins, Micro BCA determination). Before

TABLE 23

| Charge state | Theoretical M | C-terminal peptide | MW Sequence (Da) | Observed m/z | Band A | Band B | Band C | Band D |
|---|---|---|---|---|---|---|---|---|
| +2 | 982.00 | 309-327 | 34557.9 | 982.74 | D | ND | ND | ND |
| +1 | 716.35 | 309-315 | 33310.4 | 716.70 | ND | D | ND | ND |
| +2 | 551.77 | 306-315 |  | 552.07 |  |  |  |  |
| +2 | 470.71 | 256-263 | 27605.1 | 471.12 | ND | ND | D | ND |
| +2 | 573.29 | 234-244 | 25448.8 | 573.84 | ND | ND | ND | D |
| +2 | 473.26 | 229-237 | 24692.0 | 473.72 | ND | ND | ND | D |
| +2 | 439.2 | 1-8 | 877.39 | 438.7 | D | D | D | D |

D = detected
ND = not detected

3 Example 10C

Secondary Structure

Far-UV Circular Dichroism studies were performed on NadA$_{A351-405}$ at 260 and 180 nm and analyzed at RT on a Jasco 810 instrument, with 1 mm path length quartz cell (Hellma GmbH), with a band width of 1 nm, in a solution containing approximately 0.1 mg/ml protein (total protein, Micro BCA determination).

All CD spectra resulted from averaging three scans at scanning speed of 50 nm/min. The final spectra were corrected by subtracting a base-line spectrum of 10 mM sodium phosphate, pH 7.2, and are expressed as molar CD absorption ($\Delta\epsilon$) in $M^{-1}$ $cm^{-1}$. A mean residue molecular mass of 105.68 was used in calculations.

The fractional percentage of the secondary structure was calculated by computer fitting to a library of CD spectra of proteins of known structure (provided by Jasco), using Yang's algorithm.

FIG. 89 shows spectra of NadA$_{A351-405}$ clinical phase II and III lots, presenting negative Cotton effects (209 and 222 nm) and a positive band (191 nm) characteristic of α-helix secondary structures Spectrum deconvolution by the Yang algorithm (FIG. 89C) gave a further indication that a substantial portion of the DS material was in an α-helix conformation. Database homology studies conducted on native NadA also indicated an amino acid sequence with high α-helix forming propensity in the intermediate region of the molecule.

Thermal denaturation studies were conducted by far UV CD analysing samples after heating for 10 minutes at 70° C. As shown in FIG. 89, the spectrum deconvolution shows a disappearance of α-helix elements and a corresponding increase in the random coil content to about 52%, demonstrating the shift to a more disordered conformation.

4 Example 10D

Tertiary Structure

Tertiary structure organization was investigated on a Luminescence Spectrometer, at excitation wavelength of 280 nm. Emission was scanned between 290 and 390 nm at RT, and data were averaged on multiple analyses in order to minimize variability and lower background due to environmental noise.

Fluorescence spectra were recorded on a Perkin Elmer LS 50 B spectrofluorometer, at Room Temperature, in 1 cm path length quartz Perkin Elmer luminescence spectroscopy cell analytical sets, performance of the system was checked with the validation method provided in the FL WinLab 4.00.02 Perkin Elmer package.

Excitation wavelength of 280 nm was used, with a band pass of 5 and 10 nm for excitation and emission monochromator respectively. Emission spectra were registered between 290 and 390 nm; each spectra is the result of 3 different scans at a speed of 50 nm/min.

Fluorescence spectra were corrected by subtracting the corresponding base-line spectra of 10 mM sodium phosphate, pH 7.2. Fluorescence emission λmax (Fmax) values obtained are accurate to ±0.5 nm.

It was chosen to express fluorescence numerical data as λ of zero crossing for the spectrum first derivative, respect to spectrum maximum determination, to enhance precision of the measurement.

FIG. 90 shows normalized averaged spectra of native NadA$_{A351-405}$; clinical phase I-III lots were found to consistently present an emission maximum of 306 nm±0.5 nm.

Thermal denaturation studies monitored NadA$_{A351-405}$ fluorescence variations after heating treatment at 70° C. for 15 mins. As shown in FIG. 90, denaturation resulted in spectra maxima blue-shifted by only about 2 nm.

FLR spectrum of a free L-Tyrosine solution was acquired with the same analytical parameters as before: relative to native NadA$_{A351-405}$. The L-Tyr maximum was closer to that of the denatured protein, but the change of spectral shape was far more pronounced.

5 Example 10E

Quaternary Structure

SEC-HPLC coupled either to PDA monitoring UV absorption, or to RI-MALLS and Q-els (Refractive Index, Multi Angle Laser Light Scattering, Quasi Elastic Light Scattering) detectors was performed to investigate quaternary structure.

An Alliance 2996 Waters chromatographic system equipped with 996 PDA Waters detector was used for Size Exclusion Chromatography separation with UV detection and spectral analysis.

A TSK G3000SW×1 (Tosoh) column with a MW 10.000-500.000 Da separation range on globular proteins was used, together with the corresponding pre-column.

System suitability controls were performed before each analytical set to ensure system performance. 100 μl protein samples, at an approximate concentration of 0.2 mg/ml (total proteins, Micro BCA determination) were loaded onto the gel filtration column and eluted isocratically in 100 mM phosphate buffer+100 mM $Na_2SO_4$, pH 7.2 at a flow rate of 0.5 ml/min. UV absorbance was monitored at both 214 and 280 nm.

Spectral analyses were performed in the described conditions, but with UV scanning set between 240-300 nm. the Empower Waters software automatically subdivides a single peak in slices, and performs spectral comparison of all the spectra slices within the peak, with =a purity angle value lower than the purity threshold indicating spectral purity.

MALLS and Q-els analyses were performed in the same chromatographic conditions, but detection was made with Interferometric Refractometer Optilab Wyatt, Multi Angle Light Scattering Detector Dawn EOS Wyatt, and Quasi Elastic Light Scattering Detector Q-Els Wyatt. Dawn EOS Incident laser wavelength was 633 nm, and intensity of the scattered light was measured at 18 angles simultaneously; data elaboration was performed by the Software Astra 4.90.07 Wyatt. Zimm formalism was used to determine the weight-average molecular mass (Mw) in Da and polydispersity index (Mw/Mn) for each oligomer present in solution. Autocorrelation function was used to determine the oligomers hydrodynamic radius (Hr), expressed in nm. Uncertainties of measurements were directly calculated by Astra software.

Bovine Serum Albumin (Sigma) was used in each analytical set for signal normalization; the generic specific refractive index (dn/dc) value used for proteins in the literature was used for absolute MW determination. FIG. 91B shows the $NadA_{A351-405}$ SEC-HPLC analysis profile with spectral UV detection. 93-98% (depending on clinical phase lots) of the total chromatogram area eluted in a single peak both at 214 and 280 nm absorption. A minor peak was also present at a lower retention time.

Tailing of the major peak persisted to some extent in all lots, and was attributed to co-eluting C-terminal deleted forms of the protein. To verify this hypothesis, spectral analysis of the protein peaks was performed between 240 and 300 nm, to assess spectral homogeneity of peak composition.

FIG. 91A shows that the spectra constituting the $NadA_{A351-405}$ major peak, including those with a peak shoulder areas have a maximum absorption at 275.9 nm and are perfectly superimposed, that co-eluting substances are homogeneous from a spectral point of view. This finding is consistent with the presence of C-deleted, shorter forms of the same primary structure.

Spectra constituting the minor peak show the same trend, although with signal variability due to low protein concentration, and suggest that also this peak is $NadA_{A351-405}$ related.

Fractioning of the $NadA_{A351-405}$ main peak was performed during SEC-HPLC elution to identify its different components by means of an orthogonal method. 2 fractions were collected, the first fraction (F1) contained protein material which eluted between approximately 13.8 and 14.2 min, the second fraction (F2) contained material which eluted between 14.2 and 14.6 min The fractions were concentrated and analyzed by Coomassie SDS-PAGE.

FIG. 92A, shows the chromatographic superimposition of un-fractioned $NadA_{A351-405}$, F1 and F2 at 214 nm with respect to the entire sample, in F1 the main peak asymmetry is reduced, while in F2 the shoulder presence is emphasized.

FIG. 92B shows SDS-PAGE analysis of F1 and F2 in comparison with un-fractioned $NadA_{A351-405}$. In F1, the C-del bands are less evident, while in F2 the C-del bands are enriched, confirming their presence in the SEC peak's tail. The representation of SDS-PAGE lanes as electropherograms, in the same figure, shows the splitting of the main band and the different proportional amounts of C-deleted species in the different sections of the SEC main peak.

SEC separation, when coupled with RI-MALLS and Q-els detectors can provide absolute molecular dimensions for a sample: MW (Molecular Weight), calculated from the light scattered by the protein around the detector cell, and Rh (hydrodynamic radius), obtained by correlation with the molecular Brownian mobility, without the need for calibration and comparison with standard curves.

SEC-MALLS of $NadA_{A351-405}$ was carried out on different sessions and with different clinical phase lots, to monitor MW, MW/Mn (polydispersity), a measure of peak homogeneity, and Rh.

Normalization of the MALLS detectors was performed in each analytical session by use of BSA (Bovine Serum Albumin). FIG. 93A shows superimposition of the R1 traces for BSA and $NadA_{A351-405}$, the latter elutes earlier than BSA, suggesting larger molecular dimensions than those expected for a protein with a theoretical MW of 34.5 KDa.

The hydrodynamic radii, shown as horizontal lines through the peaks in FIG. 93A, of $NadA_{A351-405}$ has a value of 6.9 nm, higher than BSA (3.6 nm). Cumulative MW, shown in FIG. 93B indicates a MW of 96 KDa for $NadA_{A351-405}$ versus 68 KDa for BSA.

Table 24 shows averaged dimensional values for BSA and $NadA_{A351-405}$, obtained in multiple analyses. For every clinical phase lot analyzed, $NadA_{A351-405}$ experimental MW is consistent with a trimeric organization in solution, slightly lower than the theoretical 103.7 KDa, justified by the presence of the co-eluting C-deleted forms.

TABLE 24

| | | MW (Da) | Polydispersity MW/Mn | $Rh_{avg}$ (nm) |
|---|---|---|---|---|
| nomer | Average 3 det | 68.150 | 1.007 | 3.6 |
| | std. Dev. | 790 | 0.002 | 0.05 |
| | % RSD | 1.2 | 0.2 | 1.3 |
| $NadA\Delta_{351-405}$ clinical phase I | Average 6 det | 95.835 | 1.007 | 6.9 |
| | std. Dev. | 247 | 0.000 | 0.04 |
| | % RSD | 0.3 | 0.0 | 0.6 |
| $NadA\Delta_{351-405}$ clinical phase II | Average 6 det | 94.485 | 1.009 | 6.9 |
| | std. Dev. | 977 | 0.002 | 0.07 |
| | % RSD | 1.0 | 0.2 | 1.0 |
| $NadA\Delta_{351-405}$ clinical phase III | Average 3 det | 93.847 | 1.006 | 7.0 |
| | std. Dev. | 395 | 0.001 | 0.06 |
| | % RSD | 0.4 | 0.1 | 0.8 |

The minor peak present in DS chromatograms exhibited a higher MW with respect to trimeric $NadA_{A351-405}$ (about 230 kDa), but also a slightly higher polydispersity, MW/Mn 0.011 (data not shown) These data, together with spectral analysis findings, indicate it the minor peak represents an unstructured aggregate of $NadA_{A351-405}$.

Studies of thermal and chemical denaturation were conducted on $NadA_{A351-405}$ DS. 500 µl of protein solution in Eppendorf tubes was heated to 95° C. in a water bath for 60 seconds to provoke a complete disruption of $NadA_{A351-405}$, resulting in a shift of the peak's retention time to higher values in SEC-HPLC (same as seen in FIG. 94C).

The molecular form obtained was stable, with an unchanged chromatographic profile, and no more degradation occurred when the heating time was increased to 1.5 hours.

An identical result was obtained by 1:5 dilution of purified NadA$_{\Delta351\text{-}405}$ in denaturing buffer containing 6M Guanidine HCl. However, freezing NadA$_{\Delta351\text{-}405}$ in liquid N$_2$ for 30 minutes did not result in any change of the native chromatographic profile.

Comparison of the NadA$_{\Delta351\text{-}405}$ monomer peak with the denatured trimer results suggests that this result is caused by denaturation of the C-deleted enriched trimers.

Thermal denaturation was conducted on NadA$_{\Delta351\text{-}405}$ DS at a lower temperature and for different time intervals. FIG. 94 shows the kinetics of protein denaturation, partial after 8 or total after 14 minutes heating at 50° C. The chromatogram obtained after 8 minutes heating (FIG. 94B) suggests that preferential disassembly occurs for trimeric molecules containing C-deleted monomers. No disassembly through dimeric intermediates was detected in these experimental conditions.

SEC-MALLS results for NadA$_{\Delta351\text{-}405}$ before and after thermal denaturation are shown in FIG. 95. Upon disassembly, a new peak of Mw of 33.7 kDa appears, which is compatible with the theoretical expected value for the monomer, and its shoulder has a MW value of 26.7 kDa, an intermediate values among the NadA$_{\Delta351\text{-}405}$ C-deleted forms. At the same time, the remaining portion of the trimer peak appears slightly heavier than before disassembly. Interestingly, compared with BSA (both monomer and dimer), elution of the NadA$_{\Delta351\text{-}405}$ monomer happens much earlier, and its hydrodynamic radius value confirms that despite the lower Mw, the dimensional space that it occupies in solution is larger.

SDS-PAGE analysis was utilized to confirm the SEC-HPLC data. Electrophoretic migration of fractionated native and denatured NadA$_{\Delta351\text{-}405}$ SEC-HPLC peaks exhibited the same profile as un-fractioned NadA$_{\Delta351\text{-}405}$, with the principal band of the monomer at about 38 kDa and additional bands of the C-deleted forms spanning 34-30 kDa This demonstrated that only differences in conformation exist between the different fractions (not shown).

Finally, the ultimate proof that native NadA$_{\Delta351\text{-}405}$ is organized in a trimeric quaternary structure in solution is given by the fact that thermal disaggregation is a reversible reaction. After 72 hours at 4° C., the chromatographic profile of a sample denatured for 60 minutes at 95° C. reverts back to the oligomerized control.

Example 11

Neisseria Meningitidis SerogroupB 936-741 Antigen Characterisation

Drug substance antigen characterisation was performed was performed for MenB antigen 936-741 using a double approach:
i) bulk drug substance routine release analytic data by validated QC tests
ii) additional characterisation studies to address antigen specific issues and verify comparability of lots after manufacturing changes Table 25 illustrates the target parameters identified as important for recombinant proteins lot-to-lot physio-chemical comparability assessment. The choice of methodology was based on the particular features of the protein and the suitability of each technique to assess these characteristics.

TABLE 25

| | Target | Analytical method | Comparison Evaluation criteria |
|---|---|---|---|
| rMenB 936-741 | Molar Mass | ESI Q-TOF direct inj | MW consistent with the theoretical value and comparable among lots, in Daltons |
| | Primary Structure | Peptide Mapping | matching AA structure and sequence with the theoretical one and comparable among lots |
| | Secondary Structure | Circular Dichroism | superimposition CD spectra, comparison of spectral maxima, minima and crossover |
| | Tertiary Structure | FLR | superimposition FLR spectra, comparison of spectral max and min (as first derivative zero crossing) |
| | Quaternary Structure | SEC-MALLS, Q-ELS | absolute MW (Da), polydispersity and hydrodinamic radius (nm) equivalency |
| | Purity | Host Cell Protein WB | Number and intensity of HCP band contaminants on digitalized image comparable for different lots |
| | | SDS-PAGE | Number and intensity of protein bands on digitalized image comparable for different lots |
| | | RP-hplc | Chromatogram profiles, rT and Area % comparable |
| | Integrity | SEC-hplc (UV detection 214, 280 nm) | Chromatogram profiles, rT and Area % comparable |

Samples & Results

6 Example 11A

Protein Production

The chimeric protein 936-741 was generated by the fusion of antigen 741, a surface-exposed lipoprotein discovered by reverse vaccinology, to the accessory protein 936, to increase immunogenicity. The protein was expressed and purified from Escherichia coli using conventional centrifugation and column chromatography, which is well known in the art.

7 Example 11B

Primary Structure Analysis 7.1 Direct Infusion Mass Spectrometric Analysis

Experimental mass measurements of 936-741 were obtained by direct infusion on an ESI Q-ToF detector for clinical phase II and III lots. As shown in FIG. 96, molar mass results were comparable for all the lots. As shown in Table 26, a difference in MW of about 24 Da between the experimental and theoretical MW value was observed. This may be due to the presence of ionic antigen adducts.

TABLE 26

| Theoretical (Da) | Clinical phase II | Clinical phase III consistency | | |
|---|---|---|---|---|
| | | 806 | 807 | 808 |
| 46.122 | 46.156 | 46.154 | 46.156 | 46.156 |

7.2 Enzymatic Peptide Map Generation and Matching to the Predicted Amino Acid Sequence Peptide Mapping of trypsin digested proteins showed comparability between Phase II and Phase III material and with the theoretical fragmentation pattern. The analysis was carried out by LC-MS and the theoretical digestion pattern was obtained by Biolynx, MassLynx V 4.1, Waters.

8 Example 11C

Secondary Structure

Far-UV Circular Dichroism studies were performed on antigen 936-741 to compare protein secondary structure organisation of different lots. FIG. 97A shows the superimposition of phase II and III lots, which indicate the secondary structure similarity between lots.

9 Example 11D

Tertiary Structure

Tertiary structure organization was investigated on a Luminescence Spectrometer, at excitation wavelength of 280 and 295 nm. FIG. 98A shows a superimposition of emission spectra from different clinical phase lots. As the spectra almost perfectly superimpose, the tertiary structure seems to be comparable between the clinical phase lots.

10 Example 11E

Quaternary Structure

Figure 99:
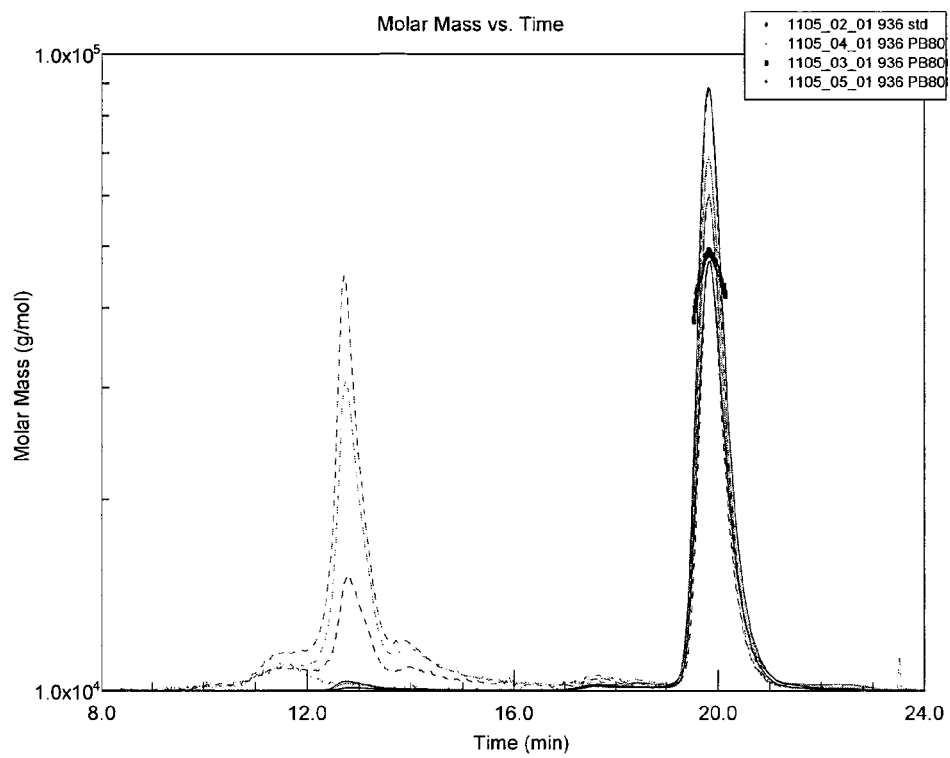

SEC-MALLS was used to determine Molecular Weight (Mw), polydispersity (Mw/Mn), and hydrodynamic radius (Rh). As shown in FIG. 99, these measurements were found to be comparable among lots, and were consistent with the theoretical monomeric organization. The MALLS detectors, enhancing the response for high Mw material, reveal the presence of very low concentrations of aggregates in all the considered lots. It therefore appears that 936-741 exists largely in monomeric form.

Figure 100:
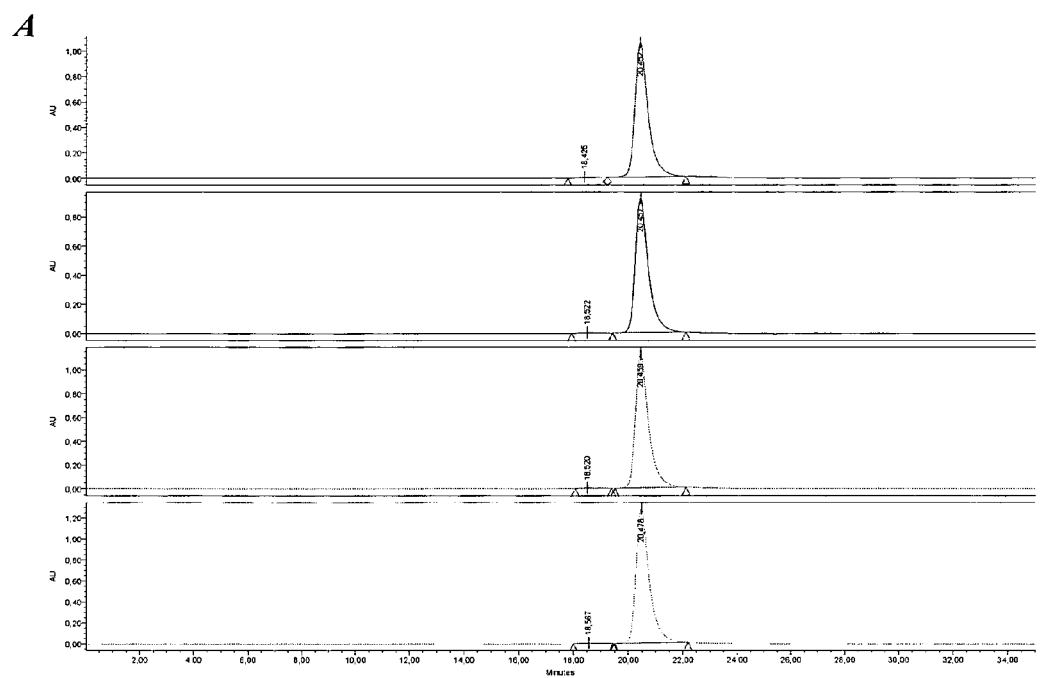

SEC-HPLC was performed, with detection at 214 nm. As shown in FIG. 100, this revealed no differences in profile between different clinical phase lots. This analysis revealed slightly higher integrity for phase II lots relative to phase III lots, and confirmed the results of the SEC-MALLS analysis.

11 Example 11F

Lot Purity

Coomassie SDS-PAGE and anti-HCP WB analysis was performed to analyse the relative purity of different clinical phase lots. As can be seen from FIGS. 101 and 102, lot purify was greater for phase III lots than for phase II lots As shown in FIG. 103, RP-HPLC showed comparable profiles between phase II and III lots, with a cleaner baseline value for phase III lots.

It will be understood that the invention has been described by way of Example only and modifications may be made whilst remaining within the scope and spirit of the invention.

REFERENCES

The Contents of which are Hereby Incorporated by Reference

[1] *Vaccines* (eds. Plotkin et al.) fourth edition, ISBN: 0721696880.
[2] Baker et al. (2003) *J Infect Dis* 188:66-73.
[3] Theilacker et al. (2003) *Infect Immun* 71:3875-84.
[4] Anonymous (2003) *Drugs R D* 4:383-5.
[5] Jones (2001) *Curr Opin Investig Drugs* 2:47-49.
[6] WO02/058737.
[7] WO03/007985.
[8] Rennels et al. (2002) *Pediatr Infect Dis J* 21:978-979.
[9] Campbell et al. (2002) *J Infect Dis* 186:1848-1851.
[10] Costantino et al. (1992) *Vaccine* 10:691-698.
[11] Lieberman et al. (1996) *JAMA* 275:1499-1503.
[12] Darkes & Plosker (2002) *Paediatr Drugs* 4:609-630.
[13] Ugozzoli (2002) *J Infect Dis* 186:1358-61.
[14] Granoff et al. (1997) *Infect Immun* 65:1710-5.
[15] Paradiso & Lindberg (1996) *Dev Biol Stand* 87:269-275.
[16] Corbel (1996) *Dev Biol Stand* 87:113-124.
[17] WO03/080678.
[18] Klug (1996) *Dev Biol Stand* 87:263-267.
[19] Plumb & Yost (1996) *Vaccine* 14:399-404.
[20] http://sbio.uctac.za/Sbio/documentation/ProbingProteinStructurebySpectroscopy.htm
[21] Ramsay et al. (2001) *Lancet* 357(9251):195-196.
[22] Lindberg (1999) *Vaccine* 17 Suppl 2:S28-36.
[23] Buttery & Moxon (2000) *J R Coll Physicians Lond* 34:163-168.
[24] Ahmad & Chapnick (1999) *Infect Dis Clin North Am* 13:113-133, vii.
[25] Goldblatt (1998) *J. Med. Microbiol.* 47:563-567.
[26] European patent 0477508.
[27] U.S. Pat. No. 5,306,492.
[28] WO98/42721.
[29] *Conjugate Vaccines* (eds. Cruse et al.) ISBN 3805549326, particularly vol. 10:48-114.
[30] Hermanson (1996) *Bioconjugate Techniques ISBN:* 0123423368 or 012342335X.
[31] U.S. Pat. No. 4,761,283
[32] U.S. Pat. No. 4,356,170
[33] WO00/10599
[34] Gever et al. *Med. Microbiol. Immunol*, 165: 171-288 (1979).
[35] U.S. Pat. No. 4,057,685.
[36] U.S. Pat. Nos. 4,673,574; 4,761,283; 4,808,700.
[37] U.S. Pat. No. 4,459,286.
[38] U.S. Pat. No. 4,965,338
[39] U.S. Pat. No. 4,663,160.
[40] Anonymous (January 2002) *Research Disclosure*, 453077.
[41] Anderson (1983) *Infect Immun* 39(1):233-238.
[42] Anderson et al. (1985) *J Clin Invest* 76(1):52-59.
[43] EP-A-0372501.
[44] EP-A-0378881.
[45] EP-A-0427347.
[46] WO93/17712
[47] WO94/03208.

[48] WO98/58668.
[49] EP-A-0471177.
[50] WO91/01146
[51] Falugi et al. (2001) *Eur J Immunol* 31:3816-3824.
[52] Baraldo et al, (2004) *Infect Immun.* 72:4884-7
[53] EP-A-0594610.
[54] WO00/56360.
[55] WO02/091998.
[56] WO01/72337
[57] WO00/61761.
[58] WO99/42130
[59] Bell (2000) *Pediatr Infect Dis J* 19:1187-1188.
[60] Iwarson (1995) *APMIS* 103:321-326.
[61] Gerlich et al. (1990) *Vaccine* 8 Suppl:S63-68 & 79-80.
[62] ProtParam Tool, Expasy: Gasteiger et al. *Protein Identification and Analysis Tools on the ExPASy Server*
[63] *The Proteomics Protocols Handbook* (John M. Walker (ed.)), Humana Press (2005): 571-607
[64] Hoist (2007) *Hum Vaccin* 3 (6)
[65] van Deuren (2000) *Clin. Microbiol. Rev.* 13: 144-166.
[66] Granoff *Meningococcal vaccines*. In: Plotkin, S. A., Offit, P. A., Orenstein, W. A., eds. *Vaccines, 5th ed.*
[67] Vedros (1987) *Development of meningococcal serogroups. Evolution of Meningococcal Disease.* N. A. Vedros, editor. CRC Press, Inc., Boca Raton, Fla. 33-37.
[68] Frasch (1989) *Clin. Microbiol. Rev.* 2:S134-S138
[69] Anonymous (1998). *Control of epidemic meningococcal disease. WHO practical guidelines* 2nd ed. World Health Organization
[70] Sparling (2002) *Am. J. Med.* 112, 72-74.
[71] Jodar (2002) *Lancet* 359:1499-1508
[72] Cartwright (2001) *Vaccine.* 19, 4347-4356.
[73] Miller (2001) *Vaccine.* 20, S58-67.
[74] Costantino (1992) *Vaccine* 10,691-698,
[75] Lepow (1986) *J. Infect. Dis.* 154:1033-1036
[76] Ramsay (2001) *Lancet* 357:195-196
[77] Finne (1983) *Lancet* 2, 355-7.
[78] Finne (1987) *J. Immunol.* 138:4402-4407
[79] Wyle (1972) *J Infect Dis.* 126, 514-21
[80] Hayrinen (1995) *J. Infect. Dis.* 171:1481-1490.
[81] Hoist (2005) *Vaccine.* 23, 2202-5.
[82] Pizza (2000) *Science.* March 10; 287(5459) 1816-20.
[83] Haneberg (1998) *Infect. Immun.* 66:334-1341
[84] Sacchi (1992-1998) *J. Infect. Dis.* 182:1169-1176.
[85] Giuliani (2006). *PNAS USA.* 103(29), 10834-9.
[86] Rappuoli (2003) *Science.* 302, 602.
[87] Tettelin *Science* 287, 1809-1815
[88] Rappuoli R (2000) *Curr. Opin. Microbiol.* 3, 445-450
[89] Kirsten (2005) *Expert Opinion on Biological Therapy* 5:12, 1611
[90] Litt (2004) *J Infect Dis.* 190 (8), 1488-97.
[91] Hoiczyk (2000) *EMBO J* 19: 5989-5999.
[92] Lafontaine (2000) *J Bacteriol* 182: 1364-1373.
[93] Roggenkamp, (2003) *J Bacteriol* 185: 3735-3744.
[94] Cornelis (1998) 62:1315-1352
[95] Comanducci (2002) *J Exp Med.* 195(11), 1445-54.
[96] Comanducci (2004) *Infect Immun.* 72 (7) 4217-23.
[97] Mazzon (2007) *J Immunol.* 179(6) 3904-16.
[98] de Cock (1997). *J. Mol. Biol.* 269:473-478
[99] Capecchi (2005) *Mol Microbiol.* 55 (3), 687-98.
[100] Hurme (1996). *J. Biol. Chem.* 271:12626-12631.
[101] O'Shea (1991) *Science.* 254:539-544.
[102] Barocchi (2005) *Nat Rev Microbiol.* 2005 3(4):349-58.
[103] Hoiczyk (2000) *EMBO J.* 19:5989-5999.
[104] Veniaminov (1996) *Determination of Protein Secondary Structure. In Circular Dichroism and the conformational analysis of biomolecules* (Fasman G. D. ed.), pp. 69-107, Plenum Press, NY and London.
[105] Eftink (2000) *Use of optical spectroscopic methods to study the thermodynamic stability of proteins. In: Spectrophotometry and spectrofluorimetry* (Gore, M. G. ed), 307-327, Oxford University Press.
[106] Wen (1996) *Anal Biochem.* 240(2), 155-66.
[107] Coligan (1997) *Current Protocols in Protein Science.* New York: Wiley pp. 6.0.1-6.7.14. pp. 9.4.1-9.4.16
[108] Sambrook (1989) *Molecular Cloning: A Laboratory Manual.* Cold Spring Harbor, N.Y.: Cold spring Harbor Laboratory Press.
[109] *Electrophoresis in Practice: A Guide to Methods and Applications of DNA and Protein Separations* R. Vestermeier, N. Barnes, S. Gronau-Czybulka and Habeck John Wiley & sons
[110] Yang (1986) *Methods Enzymol.* 130, 208-69.
[111] Schmitt (1977) *Derivative Spectroscopy: an introduction with practical examples* Bodenseewerk Perkin Elmer & co GmbH, Uberlingen, West Germany

The invention claimed is:

1. A method of analyzing the composition of a test sample including a protein comprising the steps of (i): analyzing the test sample by electromagnetic spectroscopy to obtain a spectrum of response intensity versus wavelength; (ii) derivatising the spectrum with respect to wavelength to obtain a derivative spectrum of the test sample; and (iii) comparing the derivative spectrum of the test sample with a derivative spectrum of a reference sample of a known purity.

2. The method of claim 1, wherein the electromagnetic spectroscopy is UV spectroscopy.

3. The method of claim 2 wherein the UV spectroscopy is UV absorption spectroscopy.

4. The method of claim 3 wherein analyzing the sample comprises analyzing at least part of the region of about 240 to about 340 nm.

5. The method of claim 4 wherein analyzing the sample comprises analyzing at least about 274 nm and/or 280 nm.

6. The method of claim 2 wherein the UV spectroscopy is fluorescence spectroscopy.

7. The method of claim 6 wherein analyzing the sample comprises analyzing at least part of the region of 300 to 390 nm.

8. The method of claim 6 wherein the test sample and the reference sample are excited at 280 nm.

9. The method of claim 6 wherein the test sample and the reference sample are excited at 295 nm.

10. The method of claim 1 wherein the test sample is drawn from a vaccine.

11. The method of claim 10 wherein the vaccine is glycoconjugate vaccine.

12. The method of claim 11 wherein the glycoconjugate vaccine contains $CRM_{197}$ diphtheria toxin derivative.

13. The method of claim 10 wherein the vaccine contains a protein antigen from serogroup B of *N. meningitidis*.

14. The method of claim 1 wherein the derivative spectrum of the test sample is between the first and fourth derivative.

15. The method of claim 1 comprising the step of smoothing the spectrum before or after the step of derivatising the spectrum.

* * * * *